United States Patent
Zheng et al.

(10) Patent No.: US 10,214,501 B2
(45) Date of Patent: Feb. 26, 2019

(54) 3-ALKYL BICYCLIC [4,5,0] HYDROXAMIC ACIDS AS HDAC INHIBITORS

(71) Applicant: Forma Therapeutics, Inc., Watertown, MA (US)

(72) Inventors: Xiaozhang Zheng, Lexington, MA (US); Pui Yee Ng, Waltham, MA (US); Bingsong Han, North Haven, CT (US); Jennifer R. Thomason, Clinton, MA (US); Mary-Margaret Zablocki, Revere, MA (US); Cuixian Liu, Madison, CT (US); Aleksandra Rudnitskaya, Roslindale, MA (US); David R. Lancia, Jr., Boston, MA (US); David S. Millan, Watertown, MA (US); Matthew W. Martin, Arlington, MA (US); Kenneth W. Bair, Wellesley, MA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 15/013,820

(22) Filed: Feb. 2, 2016

(65) Prior Publication Data
US 2016/0221972 A1 Aug. 4, 2016

Related U.S. Application Data

(60) Provisional application No. 62/110,716, filed on Feb. 2, 2015, provisional application No. 62/205,438, filed on Aug. 14, 2015.

(51) Int. Cl.
| | |
|---|---|
| A61K 31/553 | (2006.01) |
| C07D 267/14 | (2006.01) |
| C07D 413/06 | (2006.01) |
| C07D 413/12 | (2006.01) |
| C07D 413/04 | (2006.01) |
| C07D 243/14 | (2006.01) |
| C07D 291/08 | (2006.01) |
| C07D 401/06 | (2006.01) |
| C07D 401/10 | (2006.01) |
| C07D 403/06 | (2006.01) |
| C07D 403/10 | (2006.01) |
| C07D 405/06 | (2006.01) |
| C07D 413/14 | (2006.01) |
| C07D 417/04 | (2006.01) |
| C07D 471/04 | (2006.01) |
| C07D 498/04 | (2006.01) |
| C07D 498/08 | (2006.01) |
| C07D 493/08 | (2006.01) |
| C07D 413/08 | (2006.01) |
| C07D 491/107 | (2006.01) |

(Continued)

(52) U.S. Cl.
CPC ......... *C07D 267/14* (2013.01); *C07D 243/14* (2013.01); *C07D 267/12* (2013.01); *C07D 291/08* (2013.01); *C07D 401/06* (2013.01); *C07D 401/10* (2013.01); *C07D 403/06* (2013.01); *C07D 403/10* (2013.01); *C07D 405/06* (2013.01); *C07D 413/04* (2013.01); *C07D 413/06* (2013.01); *C07D 413/08* (2013.01); *C07D 413/12* (2013.01); *C07D 413/14* (2013.01); *C07D 417/04* (2013.01); *C07D 471/04* (2013.01); *C07D 491/107* (2013.01); *C07D 493/08* (2013.01); *C07D 495/10* (2013.01); *C07D 498/04* (2013.01); *C07D 498/08* (2013.01)

(58) Field of Classification Search
CPC ... A61K 31/553; C07D 267/14; C07D 413/06
USPC ..................... 514/211.09; 540/552
See application file for complete search history.

(56) References Cited

U.S. PATENT DOCUMENTS

| | | | |
|---|---|---|---|
| 4,332,802 A | 6/1982 | Schromm et al. | |
| 4,861,784 A | 8/1989 | Rauber et al. | |
| 5,153,185 A | 10/1992 | DiNinno et al. | |

(Continued)

FOREIGN PATENT DOCUMENTS

| | | |
|---|---|---|
| CN | 102558200 | 7/2012 |
| CN | 102838625 A | 12/2012 |

(Continued)

OTHER PUBLICATIONS

Blackburn "Potent Histone Deacetylase Inhibitors Derived from 4-(Aminomethyl)-N-hydroxybenzamide with High Selectivity for the HDAC6 Isoform", J.Medicinal Chemistry 56:18 2013.

(Continued)

*Primary Examiner* — Brenda L Coleman
(74) *Attorney, Agent, or Firm* — Choate, Hall & Stewart LLP; Brenda Herschbach Jarrell; John Rearick

(57) ABSTRACT

The present disclosure relates to inhibitors of zinc-dependent histone deacetylases (HDACs) useful in the treatment of diseases or disorders associated with an HDAC, e.g., HDAC6, having a Formula I:

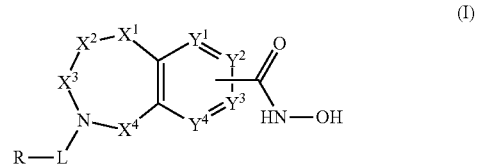

where R, L, $X^1$, $X^2$, $X^3$, $X^4$, $Y^1$, $Y^2$, $Y^3$, and $Y^4$ are described herein.

38 Claims, No Drawings

(51) Int. Cl.
*C07D 495/10* (2006.01)
*C07D 267/12* (2006.01)

(56) References Cited

U.S. PATENT DOCUMENTS

| | | |
|---|---|---|
| 5,244,911 A | 9/1993 | Booher et al. |
| 5,294,610 A | 3/1994 | DiNinno et al. |
| 5,384,317 A | 1/1995 | DiNinno et al. |
| 5,532,261 A | 7/1996 | DiNinno et al. |
| 5,612,356 A | 3/1997 | Yoshimura et al. |
| 5,714,518 A | 2/1998 | Reich et al. |
| 5,719,144 A | 2/1998 | Hartman et al. |
| 5,728,844 A | 3/1998 | Muller et al. |
| 5,807,854 A | 9/1998 | Bartroli et al. |
| 5,863,950 A | 1/1999 | Reich et al. |
| 6,001,823 A | 12/1999 | Hultgren et al. |
| 6,110,913 A | 8/2000 | Dorwald et al. |
| 6,153,396 A | 11/2000 | Hultgren et al. |
| 6,180,640 B1 | 1/2001 | Cuny et al. |
| 6,288,099 B1 | 9/2001 | Antane et al. |
| 6,403,632 B1 | 6/2002 | Duan et al. |
| 6,414,029 B1 | 7/2002 | Shechter et al. |
| 6,420,127 B1 | 7/2002 | Hultgren et al. |
| 6,476,019 B1 | 11/2002 | Radeke et al. |
| 6,762,177 B2 | 7/2004 | Radeke et al. |
| 6,787,554 B2 | 9/2004 | Gaudilliere |
| 6,872,542 B1 | 3/2005 | Hultgren et al. |
| 6,916,809 B2 | 7/2005 | Chen et al. |
| 6,962,791 B2 | 11/2005 | Hultgren et al. |
| 6,992,077 B2 | 1/2006 | Radeke et al. |
| 7,199,119 B2 | 4/2007 | Burkitt et al. |
| 7,214,690 B2 | 5/2007 | Higuchi et al. |
| 7,241,775 B2 | 7/2007 | Hofmeister et al. |
| 7,495,111 B2 | 2/2009 | Ramamoorthy et al. |
| 7,582,667 B2 | 9/2009 | Quagliato et al. |
| 7,622,582 B2 | 11/2009 | Kesteleyn et al. |
| 7,704,756 B2 | 4/2010 | Suich et al. |
| 7,705,017 B2 | 4/2010 | Cummings et al. |
| 7,943,608 B2 | 5/2011 | Schultz et al. |
| 7,951,795 B2 | 5/2011 | Bell et al. |
| 8,058,427 B2 | 11/2011 | Hsieh et al. |
| 8,119,655 B2 | 2/2012 | Dong et al. |
| 8,148,380 B2 | 4/2012 | Guiles et al. |
| 8,178,553 B2 | 5/2012 | Lavey et al. |
| 8,198,290 B2 | 6/2012 | Hodges |
| 8,324,221 B2 | 12/2012 | Banka et al. |
| 8,349,839 B2 | 1/2013 | Sturino et al. |
| 8,367,709 B2 | 2/2013 | Pinto et al. |
| 8,426,447 B2 | 4/2013 | White et al. |
| 8,436,005 B2 | 5/2013 | Liu et al. |
| 8,471,026 B2 | 6/2013 | Blackburn et al. |
| 8,513,433 B2 | 8/2013 | Panicker et al. |
| 8,518,964 B2 | 8/2013 | Truchon et al. |
| 8,524,732 B2 | 9/2013 | Schiemann et al. |
| 8,546,410 B2 | 10/2013 | Liu et al. |
| 8,569,336 B2 | 10/2013 | Tong et al. |
| 8,575,193 B2 | 11/2013 | Maier et al. |
| 8,598,342 B2 | 12/2013 | Kahne et al. |
| 8,629,272 B2 | 1/2014 | Fuchs et al. |
| 8,642,587 B2 | 2/2014 | Lange et al. |
| 8,642,615 B2 | 2/2014 | Wentland |
| 8,658,641 B2 | 2/2014 | Barvian et al. |
| 8,673,952 B2 | 3/2014 | Blaquiere et al. |
| 8,685,969 B2 | 4/2014 | Liu et al. |
| 8,686,032 B2 | 4/2014 | Davidson et al. |
| 8,703,936 B2 | 4/2014 | Jewett et al. |
| 8,765,773 B2 | 7/2014 | England et al. |
| 8,765,810 B2 | 7/2014 | Greene et al. |
| 8,778,931 B2 | 7/2014 | Gould |
| 8,785,626 B2 | 7/2014 | Blaquiere et al. |
| 8,815,891 B2 | 8/2014 | Kim et al. |
| 8,822,462 B2 | 9/2014 | Traynelis et al. |
| 8,822,488 B2 | 9/2014 | Deaver et al. |
| 8,871,759 B2 | 10/2014 | Coburn et al. |
| 9,630,922 B2 | 4/2017 | Ng et al. |
| 9,637,453 B2 | 5/2017 | Ng et al. |
| 2002/0034774 A1 | 3/2002 | Hultgren et al. |
| 2002/0045199 A1 | 4/2002 | Hultgren et al. |
| 2003/0171355 A1 | 9/2003 | Radeke et al. |
| 2003/0198992 A1 | 10/2003 | Hultgren et al. |
| 2003/0208066 A1 | 11/2003 | Levin et al. |
| 2004/0249147 A1 | 12/2004 | Sattigeri et al. |
| 2005/0038011 A1 | 2/2005 | Radeke et al. |
| 2006/0069083 A1 | 3/2006 | Steiner et al. |
| 2006/0194785 A1 | 8/2006 | Radeke et al. |
| 2006/0239909 A1 | 10/2006 | Anderson et al. |
| 2007/0155730 A1 | 7/2007 | Leit et al. |
| 2007/0185007 A1 | 8/2007 | Jin et al. |
| 2007/0197564 A1 | 8/2007 | Lavey et al. |
| 2007/0244154 A1 | 10/2007 | Brehm |
| 2007/0265299 A1 | 11/2007 | Lavey et al. |
| 2008/0004282 A1 | 1/2008 | Vohra et al. |
| 2008/0112889 A1 | 5/2008 | Buggy et al. |
| 2008/0113962 A1 | 5/2008 | Zimmermann et al. |
| 2008/0194638 A1 | 8/2008 | Dedhiya et al. |
| 2008/0255161 A1 | 10/2008 | Koltun et al. |
| 2008/0275029 A1 | 11/2008 | Berdini et al. |
| 2008/0280855 A1 | 11/2008 | Chiesa et al. |
| 2009/0093473 A1 | 4/2009 | Zimmermann et al. |
| 2009/0105283 A1 | 4/2009 | Koltun et al. |
| 2009/0136449 A1 | 5/2009 | Di Filippo et al. |
| 2009/0156586 A1 | 6/2009 | Lavey et al. |
| 2009/0221589 A1 | 9/2009 | Trieselmann et al. |
| 2009/0325948 A1 | 12/2009 | Hurley et al. |
| 2010/0076012 A1 | 3/2010 | Schiemann et al. |
| 2010/0120818 A1 | 5/2010 | Enderle |
| 2010/0173332 A1 | 7/2010 | Smaill et al. |
| 2010/0256082 A1 | 10/2010 | Schotzinger |
| 2010/0317678 A1 | 12/2010 | Moffat et al. |
| 2011/0039827 A1 | 2/2011 | Blackburn et al. |
| 2011/0039840 A1 | 2/2011 | Varasi et al. |
| 2011/0071136 A1 | 3/2011 | Haddach et al. |
| 2011/0076292 A1 | 3/2011 | Blaquiere et al. |
| 2011/0098267 A1 | 4/2011 | Babu et al. |
| 2011/0251184 A1 | 10/2011 | Blackburn et al. |
| 2011/0275762 A1 | 11/2011 | Cmiljanovic et al. |
| 2011/0288117 A1 | 11/2011 | Gould et al. |
| 2012/0015942 A1 | 1/2012 | Calderwood et al. |
| 2012/0015943 A1 | 1/2012 | Blackburn et al. |
| 2012/0083483 A1 | 4/2012 | Coburn et al. |
| 2012/0094997 A1 | 4/2012 | England et al. |
| 2012/0121502 A1 | 5/2012 | van Duzer et al. |
| 2012/0165316 A1 | 6/2012 | Gould |
| 2012/0244149 A1 | 9/2012 | Blaquiere et al. |
| 2012/0245144 A1 | 9/2012 | Heffron et al. |
| 2012/0245193 A1 | 9/2012 | Silverman et al. |
| 2012/0258949 A1 | 10/2012 | Varasi et al. |
| 2013/0029938 A1 | 1/2013 | Aquino et al. |
| 2013/0079331 A1 | 3/2013 | Blaquiere et al. |
| 2013/0281402 A1 | 10/2013 | Chen et al. |
| 2013/0289027 A1 | 10/2013 | De La Rosa et al. |
| 2013/0303567 A1 | 11/2013 | Panicker et al. |
| 2014/0018343 A1 | 1/2014 | Romero et al. |
| 2014/0018361 A1 | 1/2014 | Harriman et al. |
| 2014/0031302 A1 | 1/2014 | Winssinger et al. |
| 2014/0031340 A1 | 1/2014 | Dineen et al. |
| 2014/0038954 A1 | 2/2014 | Epstein et al. |
| 2014/0088101 A1 | 3/2014 | Ng et al. |
| 2014/0128371 A1 | 5/2014 | Barvian et al. |
| 2014/0194386 A1 | 7/2014 | Burns et al. |
| 2014/0239288 A1 | 8/2014 | Delcamp et al. |
| 2014/0241990 A1 | 8/2014 | Haydon et al. |
| 2014/0288047 A1 | 9/2014 | Blaquiere et al. |
| 2014/0296226 A1 | 10/2014 | White et al. |
| 2014/0323447 A1 | 10/2014 | Kley et al. |
| 2016/0221973 A1 | 8/2016 | Zheng et al. |
| 2016/0221997 A1 | 8/2016 | Zheng et al. |
| 2016/0222022 A1 | 8/2016 | Zheng et al. |
| 2016/0222028 A1 | 8/2016 | Zheng et al. |

(56) References Cited

U.S. PATENT DOCUMENTS

2016/0304456 A1 10/2016 Ng et al.
2016/0304462 A1 10/2016 Ng et al.

FOREIGN PATENT DOCUMENTS

| | | |
|---|---|---|
| EP | 2110377 A1 | 10/2009 |
| GB | 2503789 | 1/2014 |
| JP | 2000044562 | 2/2000 |
| JP | 2000357809 | 12/2000 |
| JP | 2001226269 | 8/2001 |
| JP | 2004210716 | 7/2004 |
| JP | 4162106 | 10/2008 |
| JP | 2009/191041 A | 8/2009 |
| JP | 2011148714 | 8/2011 |
| WO | WO-9503699 A1 | 2/1995 |
| WO | WO-9514028 A2 | 5/1995 |
| WO | WO 9748786 | 12/1997 |
| WO | WO 9901607 | 1/1999 |
| WO | WO-9967238 A2 | 12/1999 |
| WO | WO 2000034285 | 6/2000 |
| WO | WO-01/12630 A1 | 2/2001 |
| WO | WO-2010/092181 A1 | 12/2001 |
| WO | WO 2002036066 | 5/2002 |
| WO | WO 2002042273 | 5/2002 |
| WO | WO 2003087059 | 10/2003 |
| WO | WO 2004017950 | 3/2004 |
| WO | WO-2004/056182 A1 | 7/2004 |
| WO | WO 2004063156 | 7/2004 |
| WO | WO 2004111052 | 12/2004 |
| WO | WO-2005/123089 A2 | 12/2005 |
| WO | WO 2006065842 | 6/2006 |
| WO | WO 2006083869 | 8/2006 |
| WO | WO-2006/102557 A2 | 9/2006 |
| WO | WO-2006/138549 A1 | 12/2006 |
| WO | WO2007/022638 A1 | 3/2007 |
| WO | WO-2007/029035 A2 | 3/2007 |
| WO | WO 2007023135 | 3/2007 |
| WO | WO-2007/061880 A1 | 5/2007 |
| WO | WO-2007/079826 A1 | 7/2007 |
| WO | WO-2007/084451 A1 | 7/2007 |
| WO | WO-2007/100536 A1 | 9/2007 |
| WO | WO-2007/109178 A2 | 9/2007 |
| WO | WO-2007/143822 A1 | 12/2007 |
| WO | WO 2008011805 | 1/2008 |
| WO | WO 2008046155 | 4/2008 |
| WO | WO 2008048648 | 4/2008 |
| WO | WO-2008/055068 A2 | 5/2008 |
| WO | WO-2008/060721 A1 | 5/2008 |
| WO | WO-2008/061160 A1 | 5/2008 |
| WO | WO 2008071765 | 6/2008 |
| WO | WO 2008074858 | 6/2008 |
| WO | WO-2008/091349 A1 | 7/2008 |
| WO | WO-2008/101186 A1 | 8/2008 |
| WO | WO-2009/100045 A1 | 8/2009 |
| WO | WO-2009/123967 A1 | 10/2009 |
| WO | WO-2009127609 A1 | 10/2009 |
| WO | WO-2009/137503 A1 | 11/2009 |
| WO | WO-2010/028192 A1 | 3/2010 |
| WO | WO-2010/043893 A1 | 4/2010 |
| WO | WO 2010042475 | 4/2010 |
| WO | WO-2010/054278 A2 | 5/2010 |
| WO | WO 2010056230 | 5/2010 |
| WO | WO-2010/111483 A1 | 9/2010 |
| WO | WO 2010125469 | 11/2010 |
| WO | WO-2010/151317 A1 | 12/2010 |
| WO | WO2010/151318 A1 | 12/2010 |
| WO | WO-2010/151441 A1 | 12/2010 |
| WO | WO-2011/002520 A2 | 1/2011 |
| WO | WO-2011/011186 A2 | 1/2011 |
| WO | WO-2011/036280 A1 | 3/2011 |
| WO | WO-2011/039353 A1 | 4/2011 |
| WO | WO-2011/045265 A2 | 4/2011 |
| WO | WO-2011/079036 A1 | 6/2011 |
| WO | WO-2011/084991 A2 | 7/2011 |
| WO | WO-2011/088181 A1 | 7/2011 |
| WO | WO-2011/091213 A2 | 7/2011 |
| WO | WO-2011/106627 A1 | 9/2011 |
| WO | WO-2011/106632 A1 | 9/2011 |
| WO | WO-2011/137135 A1 | 11/2011 |
| WO | WO-2011/146591 A1 | 11/2011 |
| WO | WO-2012/016081 A2 | 2/2012 |
| WO | WO-2012/027564 A1 | 3/2012 |
| WO | WO-2012/031993 A1 | 3/2012 |
| WO | WO-2012/045804 A1 | 4/2012 |
| WO | WO-2012/054332 A1 | 4/2012 |
| WO | WO 2012045194 | 4/2012 |
| WO | WO-2012/088015 A2 | 6/2012 |
| WO | WO 2012085003 | 6/2012 |
| WO | WO-2012/106343 A2 | 8/2012 |
| WO | WO 2012110860 | 8/2012 |
| WO | WO-2012/126901 A1 | 9/2012 |
| WO | WO 2012117421 | 9/2012 |
| WO | WO-2012/178208 A2 | 12/2012 |
| WO | WO-2013/006408 A1 | 1/2013 |
| WO | WO-2013/008162 A1 | 1/2013 |
| WO | WO-2013/009827 A1 | 1/2013 |
| WO | WO-2013/013113 A2 | 1/2013 |
| WO | WO 2013033085 | 3/2013 |
| WO | WO-2013/052110 A1 | 4/2013 |
| WO | WO-2013/059582 A2 | 4/2013 |
| WO | WO-2013/090210 A1 | 6/2013 |
| WO | WO-2013/134467 A1 | 9/2013 |
| WO | WO 2014011753 | 1/2014 |
| WO | WO 2014018919 | 1/2014 |
| WO | WO 2014037342 | 3/2014 |
| WO | WO 2014048945 | 4/2014 |
| WO | WO-2014/110442 A1 | 7/2014 |
| WO | WO 2014127881 | 8/2014 |
| WO | WO 2014134127 | 9/2014 |
| WO | WO-2014/178606 A1 | 11/2014 |
| WO | WO-2015/054474 A1 | 4/2015 |
| WO | WO-2015/137750 A1 | 9/2015 |
| WO | WO-2016/126721 A1 | 8/2016 |
| WO | WO-2016/126722 A1 | 8/2016 |
| WO | WO-2016/126724 A1 | 8/2016 |
| WO | WO-2016/126725 A1 | 8/2016 |
| WO | WO-2016/126726 A1 | 8/2016 |
| WO | WO-2016/168598 A1 | 10/2016 |
| WO | WO-2016/168660 A1 | 10/2016 |
| WO | WO-2017/065473 A1 | 4/2017 |
| WO | WO-2017/218950 A1 | 12/2017 |

OTHER PUBLICATIONS

International Search Report from corresponding PCT International Application No. PCT/US2016/016197, dated Mar. 22, 2016.

Aldana-Masangkay, G.I. and Sakamoto, K.M. The Role of HDAC6 in Cancer, J. Biomed. Biotechnol., 875824: 1-10 (2011).

Amengual. J.E. et al, Dual Targeting of Protein Degradation Pathways with the Selective HDAC6 Inhibitor ACY-1215 and Bortezomib Is Synergistic in Lymphoma, Clin. Cancer Res., 21(20):4663-75 (2015).

Bazzaro M. et al, Ubiquitin Proteasome System Stress Underlies Synergistic Killing of Ovarian Cancer Cells by Bortezomib and a Novel HDAC6 Inhibitor, Clin. Cancer Res., 14(22):7340-7347 (2008).

Cha, T.L. et al, Dual degradation of aurora A and B kinases by the histone deacetylase inhibitor LBH589 induces G2-M arrest and apoptosis of renal cancer cells, Clin. Cancer Res., 15(3): 840-850 (2009).

Choi, S.Y. et al, Tubastatin A suppresses renal fibrosis via regulation of epigenetic histone modification and Smad3-dependent fibrotic genes, Vascul. Pharmacol., 72:130-140 (2015).

De Ruijter, A.J. et al, Histone deacetylases (HDACs): characterization of the classical HDAC family, Biochem. J., 370: 737-749 (2003).

Dhakal, B.K. and Mulve, M.A., Uropathogenic *Escherichia coli* invades host cells via an HDAC6-modulated microtubule-dependent pathway, J. Biol. Chem., 284(1):446-454 (2008).

Ding, G. et al, HDAC6 promotes hepatocellular carcinoma progression by inhibiting P53 transcriptional activity, FEBS Lett., 587:880-6 (2013).

(56) References Cited

OTHER PUBLICATIONS

Ding, N. et al, Histone deacetylase 6 activity is critical for the metastasis of Burkitt's lymphoma cells, Cancer Cell Int., 14:139 (2014).
Fiskus, W. et al, Molecular and biologic characterization and drug sensitivity of pan-histone deacetylase inhibitor-resistant acute myeloid leukemia cells, Blood, 112(7):2896-2905 (2008).
Hideshima, T. et al, Small-molecule inhibition of proteasome and aggresome function induces synergistic antitumor activity in multiple myeloma, Proc. Natl. Acad. Sci. USA, 102(24):8567-8572 (2005).
Kalin, J.H. et al, Second-generation histone deacetylase 6 inhibitors enhance the immunosuppressive effects of Foxp3+ T-regulatory cells, J. Med. Chem., 55:639-651 (2012).
Kamemura, K. et al, Effects of downregulated HDAC6 expression on the proliferation of lung cancer cells, Biochem. Biophys. Res. Commun., 374(1):84-89 (2008).
Kanno, K. et al, Overexpression of histone deacetylase 6 contributes to accelerated migration and invasion activity of hepatocellular carcinoma cells, Oncol. Rep., 28: 867-73 (2012).
Lee, Y-S. et al, The cytoplasmic deacetylase HDAC6 is required for efficient oncogenic tumorigenesis, Cancer Res., 68(18):7561-7569 (2008).
Li, Y. et al, Histone deacetylase 6 plays a role as a distinct regulator of diverse cellular processes, FEBS J., 280: 775-93 (2013).
Nawrocki, S.T. et al, Aggresome disruption: a novel strategy to enhance bortezomib-induced apoptosis in pancreatic cancer cells, Cancer Res., 66(7):3773-3781 (2006).
Park, S.Y. et al, Histone deacetylases 1, 6 and 8 are critical for invasion in breast cancer, Oncol. Rep. 2011, 25: 1677-1681 (2011).
Rey, M. et al, HDAC6 is required for invadopodia activity and invasion by breast tumor cells, Eur. J. Cell Biol., 90: 128-135 (2011).
Rivieccio, M.A. et al, HDAC6 is a target for protection and regeneration following injury in the nervous system, Proc. Natl. Acad. Sci. USA, 106(46):19599-195604 (2009).
Rodriguez-Gonzalez, R. et al, Multiple system organ response induced by hyperoxia in a clinically relevant animal model of sepsis, Blood 2008, 112(11): Abstract 1923 (2008).
Seidel, C. et al, 4-Hydroxybenzoic acid derivatives as HDAC6-specific inhibitors modulating microtubular structure and HSP90α chaperone activity against prostate cancer, Biochem. Pharmacol., 99: 31-52 (2016).
Simoes-Pires, C. et al, HDAC6 as a target for neurodegenerative diseases: what makes it different from the other HDACs?, Mol. Neurodegener., 8: 7 (2013).
Tannous, P. et al, Intracellular protein aggregation is a proximal trigger of cardiomyocyte autophagy, Circulation, 117(24):3070-3078 (2008).
Vishwakarma, S. et al, Tubastatin, a selective histone deacetylase 6 inhibitor shows anti-inflammatory and anti-rheumatic effects, Int. Immunopharmacol., 16:72-78 (2013).
Wang, L. et al, Immunomodulatory effects of deacetylase inhibitors: therapeutic targeting of FOXP3+ regulatory T cells, Nat. Rev. Drug Disc. 2009 8(12):969-981.
Zhang, L. et al, Proteomic identification and functional characterization of MYH9, Hsc70, and DNAJA1 as novel substrates of HDAC6 deacetylase activity, Protein Cell., 6(1): 42-54 (2015).
International Search Report for PCT/US2016/016194, 4 pages (dated Mar. 23, 2016).
International Search Report for PCT/US2016/016200, 4 pages (dated Mar. 22, 2016).
International Search Report for PCT/US2016/016201, 4 pages (dated Apr. 20, 2016).
International Search Report for PCT/US2016/016204, 4 pages (dated Mar. 22, 2016).
Bantscheff, M. et al., Chemoproteomics profiling of HDAC inhibitors reveal selective targeting of HDAC complexes, Nature Biotechnology, 29(3):255-265 (2011). Online Methods appended.
Benedetti R, Conte M, Altucci L. "Targeting Histone Deacetylases in Diseases: Where Are We?" Antioxidants & Redox Signaling, 23(1), pp. 99-126, 2015.
Bergman, J.A. et al., Selective histone deacetylase 6 inhibitors bearing substituted urea linkers inhibit melanoma cell growth, J. Med. Chem., 55:9891-9899 (2012).
Blackburn, C. et al., Histone deacetylase inhibitors derived from1,2,3,4-tetrahydropyrrolo[1,2-a]pyrazine and related heterocycles selective for the HDAC6 isoform, Bioorg Med Chem Lett., 24(23):5450-5454 (2014).
Bone, E.A. et al., Design and Development of HDAC6-Selective Inhibitors for Hematological Cancer Treatment and Solid Tumor Immunotherapy, Karus Therapeutics, Poster session presented at the AACR Annual Meeting, Philadelphia, PA, 1 page (2015). Abstract 3662.
Bradner, J.E. et al., Chemical phylogenetics of histone deacetylases, Nature Chemical Biology, 6:238-243 (2010). Supplemental Information appended, 26 pages.
Butler, K.V. and Kozikowski, A.P., Chemical Origins of Isoform Selectivity in Histone Deacetylase Inhibitors, Current Pharmaceutical Design, 14:505-528 (2008).
Butler, K.V. et al., Rational Design and Simple Chemistry Yield a Superior Neuroprotective HDAC6 Inhibitor, Tubastatin A, J. Am. Chem. Soc., 132:10842-10846 (2010).
Cancer, MedlinePlus, 10 pages. URL: http://www.nlm.nih.gov/medlineplus/cancer.html. [Retrieved Jul. 6, 2007].
Canet, E. and Touchon, P., Servier: Looking to the Future—Innovation-Driven Partnerships. Medicographia 120, vol. 36(3):267-429 (2014).
Choi, E. et al., Property-Based Optimization of Hydrozamate-Based γ-Lactam HDAC Inhibitors to Improve Their Metabolic Stability and Pharmacokinetic, J. Med. Chem., 55:10766-10770 (2012).
Choi, Y., Anti-Multiple Myeloma Activity of a Novel HDAC6 Inhibitor, DC-004, in Combination with Proteosomal Inhibitors, CKD Pharmaceutical Corporation, Presentation at the DOT Meeting, 26 pages, Sep. 24, 2015.
Chuang, M.J. et al., The HDAC Inhibitor LBH589 Induces ERK-Dependent Prometaphase Arrest in Prostate Cancer via HDAC6 Inactivation and Down-Regulation, PLOS One, 8(9):e73401 (2013).
D'Ydewalle, C. et al., HDAC6 inhibitors reverse axonal loss in a mouse model of mutant HSPB1-induced Charcot-Marie-Tooth disease, Nature Medicine, 8(17):968-974 (2011). Online Methods appended, 1 page.
Dallavalle S, Pisano C, Zunino F. "Development and therapeutic impact of HDAC6-selective inhibitors",Biochemical Pharmacology, Sep. 15, 2012; 84(6):756-65.
Di Micco, S. et al., Structural basis for the design and synthesis of selective HDAC inhibitors, Bioorganic & Medicinal Chemistry, 21:3795-3807 (2013).
Falkenberg, K.J. and Johnstone, R.W., Histone deacetylases and their inhibitors in cancer, neurological diseases and immune disorders, Nature Reviews, 13:673-691 (2014).
Feng, T. et al., Novel N-hydrozyfurylacrylamide-based histone deacetylase (HDAC) inhibitors with branched CAP group (Part 2), Bioorg. Med. Chem., 21(17):5339-5354 (2013).
Golub et al., Molecular Classification of Cancer: Class Discovery and Class Prediction by Gene Expression Monitoring, Science (1999), vol. 286, 531-537.
Gupta, P. et al., Towards Isozyme-Selective HDAC Inhibitors for Interrogating Disease, Current Topics in Medicinal Chemistry, 12:1479-1499 (2012).
Haakenson, J. and Zhang, X., HDAC6 and Ovarian Cancer, Int. J. Mol. Sci., 14:9514-9535 (2013).
Hadley, M. et al., In Vivo Evaluation of Ames Negative HDAC6 Inhibitor in Melanoma Model. The George Washington Cancer Center. AACR Annual Meeting, Presentation Poster (2017).
Hahnen, E. et al., Histone deacetylase inhibitors: possible implications for neurodegenerative disorders, Expert Opin. Investig. Drugs, 17(2):1-16 (2008).
Hajiagha Bozorgi, A. et al., A structure-activity relationship survey of histone deacetylase (HDAC) inhibitors, Chemometrics and Intelligent Laboratory Systems, 125:132-138 (2013).

(56) References Cited

OTHER PUBLICATIONS

Hanessian, S. et al., Vorinostat-Like Molecules as Structural, Stereochemical, and Pharmacological Tools, ACS Med. Chem. Lett., 1:70-74 (2010).
Holson, E., Design of inter-class selective inhibitors and discovery of endogenous "HDAC" substrates, The Stanley Center for Psychiatric Research, the Board Institute of Harvard and MIT, Presentation at the DOT Meeting in Boston, 44 pages, Oct. 7, 2014.
Inks, E.S. et al., A Novel Class of Small Molecule Inhibitors of HDAC6, ACS Chem. Biol., 7:331-339 (2012).
International Search Report for PCT/US2016/027755, 8 pages (dated Aug. 23, 2016).
International Search Report for PCT/US2016/027842, 8 pages (dated Aug. 12, 2016).
International Search Report for PCT/US2017/037970, 5 pages (dated Aug. 9, 2017).
Itoh, Y. et al., Design, Synthesis, Structure—Selectivity Relationship, and Effect on Human Cancer Cells of a Novel Series of Histone Deacetylase 6-Selective Inhibitors, J. Med. Chem., 50:5425-5438 (2007).
Jochems, J. et al., Antidepressant-Like Properties of Novel HDAC6-Selective Inhibitors with Improved Brain Bioavailability, Neuropsychopharmacology, 39:389-400 (2014).
Kalin JH, Bergman JA. "Development and therapeutic implications of selective histone deacetylase 6 inhibitors", J Med Chem. Aug. 22, 2013; 56(16):6297-313.
Kaliszczak, M. et al., A novel small molecule hydroxamate preferentially inhibits HDAC6 activity and tumour growth, British Journal of Cancer, 108:342-350 (2013).
Katharaj, E. and Jayaraman, R., Histone Deacetylase Inhibitors as Therapeutics Agents for Cancer Therapy: Drug Metabolism and Pharmacokinetic Propoerties, Drug Development—A Case Study Based Insight into Modern Strategies, InTech, 21 pages (2011).
Kee, H.J. et al., HDAC Inhibition Suppresses Cardiac Hypertrophy and Fibrosis in DOCA-Salt Hypertensive Rats via Regulation of HDAC6/HDAC8 Enzyme Activity, 37(4-5):229-239 (2013).
Kim, H.J. and Bae, S.C., Histone deacetylase inhibitors: molecular mechanisms of action and clinical trials as anti-cancer drugs, Am J Transl Res, 3(2):166-179 (2011).
Kim, J. et al., A Novel Regulatory Role of HDAC6 in the Functional Inflammatory Phenotype of Glia cells. The George Washington University Cancer Center. AACR Annual Meeting, Presentation Poster (2017).
Kim, Y.H. et al., A phase 1b Study in Cutaneous T-cell lymphoma (CTCL) with the novel topically applied skin-restricted histone deacetylase inhibitor (HDAC-i) SHP-141. Journal of Clinical Oncology 32:15_suppl, 8525-8525 (2014).
Konsoula, Z. et al., Pharmacokinetics-pharmacodynamics and anti-tumor activity of mercaptoacetamide-based histone deacetylase inhibitors, Mol Cancer Ther, 8(10):2844-2851 (2009).
Kozikowski, A.P. et al., Use of the Nitrile Oxide Cycloaddition (NOC) Reaction for Molecular Probe Generation: A New Class of Enzyme Selective Histone Deacetylase Inhibitors (HDACIs) Showing Picomolar Activity of HDAC6, J. Med. Chem., 51:4370-4373 (2008).
Kozikowski, A.P., Chemistry, the Brain, and Cancer—Ups and Downs on the Road to HDAC Drugs, Department of Medicinal Chemistry and Pharmacognosy, University of Illinois at Chicago, 61 pages, 2015.
Kroesen, K. et al., HDAC inhibitors and immunotherapy; a double edged sword?, Oncotarget, 5(16):6558-6572 (2014).
Krukowski, K. et al., Abstract 1612: An HDAC6 inhibitor for treatment of chemotherapy-induced peripheral numbness and pain in a mouse model, Abstracts/Brain, Behavior, and Immunity, 49:e28 (2015).
Kwon, S.H., Selective Inhibition of HDAC6 regulates preferential cytotoxicity in cancer cells by modulating p53 and Hsp90 stability, American Association for Cancer Research Annual Meeting, Philadelphia, Abstract 5324, 16 pages (Apr. 22, 2015).
Lai, M.J. et al., Synthesis and Biological Evaluation of 1-Arylsulfonyl-5-(N-hydroxyacrylamide)indoles as Potent Histone Deacetylase Inhibitors with Antitumor Activity in Vivo, J. Med. Chem., 55:3777-3791 (2012).
Lala et al., Role of nitric oxide in tumor progression: Lessons from experimental tumors, Cancer and Metastasis Reviews (1998), 17, 91-106.
Lee, J. and Huang, S.R., Cancer Epigenetics: Mechanisms and Crosstalk of HDAC Inhibitor, Vorinostat, Chemotherapy, 2(1):1000111 (2013).
Lee, J.H. et al., Anti-Multiple Myeloma Activity of a Novel HDAC6 Inhibitor, DC-004, in Combination with Proteosomal Inhibitors. CKD Research Institute (2015).
Lee, J.H. et al., Development of a histone deacetylase 6 inhibitor and its biological effects, PNAS Early Edition, 110(39):15704-15709 (2013).
Lim, H. et al., CKD-M134, a Novel HDAC6 Inhibitor, Ameliorates Experimental Colitis Models in Mice. CKD Research Institute, Presentation Poster, 1 page (Sep. 25, 2015).
Lin, X. et al., Design and Synthesis of Orally Bioavailable Aminopyrrolidinone Histone Deacetylase 6 Inhibitors, J. Med. Chem., 58:2809-2820 (2015).
Marek, L. et al., Histone Deacetylase (HDAC) Inhibitors with a Novel Connecting Unit Linker Region Reveal a Selectivity Profile for HDAC4 and HDAC5 with Improved Activity against Chemoresistant Cancer Cells, J. Med. Chem., 56(2):427-436 (2013).
Mishima, Y. et al., Ricolinostat (ACY-1215) induced inhibition of aggresome formation accelerates carfilzomib-induced multiple myeloma cell death, British Journal of Haematology, 169(9):423-434 (2015).
Molina, A. et al., Identification of ACY-1083: a Novel, Potent, and Highly Selective HDAC6 Inhibitor, Acetylon Pharmaceuticals, Inc., Poster presentation, 1 page, 2015.
Mottamal, M. et al., Histone Deacetylase Inhibitors in Clinical Studies as Templates for New Anticancer Agents, Molecules, 20:3898-3941 (2015).
New, M. et al., HDAC inhibitor-based therapies: Can we interpret the code?, Molecular Oncology, 6:637-656 (2012).
Olson, D.E. et al., Discovery of the First Histone Deacetylase 6/8 Dual Inhibitors, J. Med. Chem., 56:4816-4820 (2013).
Quartararo, C.E. et al., High-Throughput Screening of Patient-Derived Cultures Reveals Potential for Precision Medicine in Glioblastoma, ASC Med. Chem. Lett., 6:948-952 (2015).
Quayle, S.N. et al., Selective HDAC Inhibition by Ricolinostat (ACY-1215) or ACY-241 Synergizes with IMiD® Immunomodulatory Drugs in Multiple Myeloma (MM) and Mantle Cell Lymphoma (MCL) Cells, Acetylon Pharmaceuticals, Inc., AACR Poster Presentation in Boston, MA, 1 page (2015).
Raje, N. et al., Ricolinostat plus Lenalidomide and Dexamethasone in Patients with Relapsed & Refractory Multiple Myeloma: Phase 1B & Early Phase 2 Results, Acetylon Pharamceuticals Inc, Poster Presentation (2015).
Seki, H. et al., Synthesis/biological evaluation of hydrozamic acids and their prodrugs as inhibitors for Botulinum neurotoxin A light chain, Bioorganic & Medicinal Chemistry, 22:1208-1217 (2014).
Shen, S. et al., Bicyclic-Capped Histone Deacetylase 6 Inhibitors with Improved Activity in a Model of Axonal Charcot-Marie-Tooth Disease, ACS Chem Neurosci., 7(2):240-258 (2016).
Shon, S. et al., Abstract 1448: Therapeutic Role of a Novel Histone Deacetylase 6 Inhibitor, CKD-M808, in Rheumatoid Arthritis, ACR/ARHP Annual Meeting, 2 pages (2016). Accessed May 25, 2018. <http://acrabstracts.org/abstract/therapeutic-role-of-a-novel-histone-deacetylase-6-inhibitor-ckd-m808-in-rheumatoid-arthritis/>.
Suzuki, T. et al., Highly Potent and Selective Histone Deacetylase 6 Inhibitors Designed Based on a Small-Molecular Substrate, J. Med. Chem., 49:4809-4812 (2006).
Tang J, Yan H, Zhuang S. "Histone deacetylases as targets for treatment of multiple diseases", Clinical Science (Lond), Jun. 2013; 124(11):651-62.
Tang, G. et al., Identification of a Novel Aminotetralin Class of HDAC6 and HDAC8 Selective Inhibitors, J. Med. Chem., 57(19):8026-8034 (2014).
Tapadar, S. et al., Isoxazole moiety in the linker region of HDAC inhibitors adjacent to the Zn-chelating group: Effects on HDAC

(56) References Cited

OTHER PUBLICATIONS biology and antiproliferative activity, Bioorganic & Medicinal Chemistry Letters, 19:3023-3026 (2009).

Thaler, F. et al., Current trends in the development of histone deacetylase inhibitors: a review of recent patent applications, Pharm. Pat. Analyst, 1(1):75-90 (2012).

Thangapandian, S. et al., Molecular Modeling Study on Tunnel Behavior in Different Histone Deacetylase Isoforms, PLOS ONE, 7(11):e49327 (2012).

Valente, S. and Mai, A., Small-molecule inhibitors of histone deacetylase for the treatment of cancer and non-cancer diseases: a patent review (2011-2013), Expert Opin. Ther. Patents, 24(4):401-415 (2014).

Van Helleputte, L. et al., The role of histone deacetylase 6 (HDAC6) in neurodegeneration, Research and Reports in Biology, 5:1-13 (2014).

Varasi, M. et al., Discovery, Synthesis, and Pharmacological Evaluation of Spiropiperidine Hydroxamic Acid Based Derivatives as Structurally Novel Histone Deacetylase (HDAC) Inhibitors, Journal of Medicinal Chemistry, 54(8): 3051-3064 (2011).

Wagner, F.F. et al., Potent and Selective Inhibition of Histone Deacetylase 6 (HDAC6) Does Not Require a Surface-Binding Motif, J. Med. Chem., 56:1772-1776 (2013).

Wagner, F.F. et al., Small Molecule Inhibitors of Zinc-dependent Histone Deacetylases, Neurotherapeutics, 10(4):589-604 (2013).

Wang, Z. et al., HDAC6 promotes cell proliferation and confers resistance to temozolomide in glioblastoma. Cancer Letters 379:134-142 (2016).

West AC, Johnstone RW, "New and emerging HDAC inhibitors for cancer treatment", Journal of Clinical Investigation, Jan. 2, 2014; 124(1):30-9.

Wu, D. et al., Screening of selective histone deacetylase inhibitors by proteochemometric modeling, BMC Bioinformatics, 13:212 (2012).

Yang, M.H. et al., HDAC6 and SIRT2 regulate the acetylation state and oncogenic activity of mutant K-RAS, Mol Cancer Res, 11(9):1072-1077 (2013).

Yu, C.W. et al., Quinazolin-4-one Derivatives as Selective Histone Deacetylase-6 Inhibitors for the Treatment of Alzheimer's Disease, J. Med. Chem., 56(17):6775-6791 (2013).

Zhang, Y. et al., Discovery of a Tetrahydroisoquinoline-Based Hydroxamic Acid Derivative (ZYJ-34c) as Histone Deacetylase Inhibitor with Potent Oral Antitumor Activities, J. Med. Chem., 54:5532-5539 (2011).

Zhang, Y. et al., Two Catalytic Domains Are Required for Protein Deacetylation, The Journal of Biological Chemistry, 281(5):2401-2404 (2006).

3-ALKYL BICYCLIC [4,5,0] HYDROXAMIC ACIDS AS HDAC INHIBITORS

CROSS-REFERENCE TO RELATED APPLICATIONS

This application claims the benefit of priority of U.S. Provisional Application No. 62/110,716, filed Feb. 2, 2015 and U.S. Provisional Application No. 62/205,438, filed Aug. 14, 2015, both of which are incorporated herein by reference.

FIELD OF THE INVENTION

The present disclosure relates to inhibitors of zinc-dependent histone deacetylases (HDACs) useful in the treatment of diseases or disorders associated with HDACs including cell proliferation diseases (e.g., cancer), neurological and inflammatory diseases. Specifically, this disclosure is concerned with compounds and compositions inhibiting HDACs, methods of treating diseases associated with HDACs, and methods of synthesizing these compounds.

BACKGROUND OF THE INVENTION

Many members of the HDAC family require zinc (Zn) to function properly. For instance, the isozyme histone deacetylase 6 (HDAC6) is a zinc-dependent histone deacetylase that possesses histone deacetylase activity. Other family members include HDACs 1-5 and 7-11. (De Ruijter et al, *Biochem. J.* 2003. 370; 737-749).

HDAC6 is known to deacetylate and associate with α-tubulin, cortactin, heat shock protein 90, β-catenin, glucose-regulated protein 78 kDa, myosin heavy chain 9, heat shock cognate protein 70, and dnaJ homolog subfamily A member 1 (reviewed in Li et al, *FEBS J.* 2013, 280: 775-93; Zhang et al, *Protein Cell.* 2015, 6(1): 42-54). Diseases in which HDAC6 inhibition could have a potential benefit include cancer (reviewed in Aldana-Masangkay et al, *J. Biomed. Biotechnol.* 2011, 875824), specifically: multiple myeloma (Hideshima et al, *Proc. Natl. Acad. Sci. USA* 2005, 102(24):8567-8572); lung cancer (Kamemura et al, *Biochem. Biophys. Res. Commun.* 2008, 374(1):84-89); ovarian cancer (Bazzaro et al, *Clin. Cancer Res.* 2008, 14(22):7340-7347); breast cancer (Lee et al, *Cancer Res.* 2008, 68(18): 7561-7569; Park et al, *Oncol. Rep.* 2011, 25: 1677-81; Rey et al, *Eur. J Cell Biol.* 2011, 90: 128-35); prostate cancer (Seidel et al, *Biochem. Pharmacol.* 2015 (15)00714-5); pancreatic cancer (Nawrocki et al, *Cancer Res.* 2006, 66(7): 3773-3781); renal cancer (Cha et al, *Clin. Cancer Res.* 2009, 15(3): 840-850); hepatocellular cancer (Ding et al, *FEBS Lett.* 2013, 587:880-6; Kanno et al, *Oncol. Rep.* 2012, 28: 867-73); lymphomas (Ding et al, *Cancer Cell Int.* 2014, 14:139; Amengual et al, *Clin Cancer Res.* 2015, 21(20): 4663-75); and leukemias such as acute myeloid leukemia (AML) (Fiskus et al, *Blood* 2008, 112(7):2896-2905) and acute lymphoblastic leukemia (ALL) (Rodriguez-Gonzalez et al, *Blood* 2008, 1 12(1 1): Abstract 1923)).

Inhibition of HDAC6 may also have a role in cardiovascular disease, including pressure overload, chronic ischemia, and infarction-reperfusion injury (Tannous et al, *Circulation* 2008, 1 17(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Alzheimer's, Parkinson's and Huntington's disease (reviewed in Simoes-Pires et al, *Mol. Neurodegener.* 2013, 8: 7) or central nervous system trauma caused by tissue injury, oxidative-stress induced neuronal or axomal degeneration (Rivieccio et al, *Proc. Natl. Acad. Sci. USA* 2009, 106(46):19599-195604); and inflammation and autoimmune diseases through enhanced T cell-mediated immune tolerance at least in part through effects on regulatory T cells, including rheumatoid arthritis, psoriasis, spondylitis arthritis, psoriatic arthritis, multiple sclerosis, lupus, colitis and graft versus host disease (reviewed in Wang et al, *Nat. Rev. Drug Disc.* 2009 8(12):969-981; Vishwakarma et al, *Int Immunopharmacol.* 2013, 16:72-8; Kalin et al, *J. Med. Chem.* 2012, 55:639-51); and fibrotic disease, including kidney fibrosis (Choi et al, *Vascul. Pharmacol.* 2015 72:130-140).

Four HDAC inhibitors are currently approved for the treatment of some cancers. These are suberanilohydroxamic acid (Vorinostat; Zolinza®) for the treatment of cutaneous T cell lymphoma and multiple myeloma; Romidepsin (FK228; FR901228; Istodax®) for the treatment of peripheral T cell lymphoma; Panobinostat (LBH-589; Farydak®) for the treatment of multiple myeloma; and belinostat (PXD101; Beleodaq®) for the treatment of peripheral T cell lymphoma. However, these drugs are of limited effectiveness and can give rise to unwanted side effects. Thus there is a need for drugs with an improved safety-efficacy profile.

Given the complex function of HDAC6 and their potential utility in the treatment of proliferative diseases, neurological diseases, and inflammatory diseases, there is a need for HDAC inhibitors (e.g., HDAC6 inhibitors) with good therapeutic properties.

SUMMARY OF THE INVENTION

One aspect of the disclosure relates to compounds of Formula I:

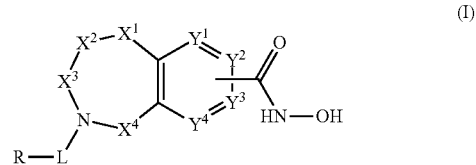

and pharmaceutically acceptable salts, prodrugs, solvates, hydrates, tautomers and isomers thereof, wherein:

$X^1$ is independently $CR^1R^2$, $NR^3$, O, or C=O;

$X^2$ and $X^4$ are each independently $CR^1R^2$, C=O, S(O) or $SO_2$;

$X^3$ is $CR^{1'}R^{2'}$; wherein $X^4$, $X^2$, and $X^1$ are not all simultaneously $CR^1R^2$;

$Y^1$ and $Y^4$ are not bonded to —C(O)NHOH and are each independently N or $CR^1$;

$Y^2$ and $Y^3$ are each independently N or $CR^1$ when not bonded to —C(O)NHOH and $Y^2$ and $Y^3$ are C when bonded to —C(O)NHOH;

L is a bond, —$(CR^1R^2)_n$—, —C(O)O—, —C(O)$NR^3$—, —S(O)$_2$—, —S(O)$_2NR^3$—, —S(O)—, or —S(O)$NR^3$—, wherein L is bound to the ring nitrogen through the carbonyl or sulfonyl group;

R is independently —H, —$C_1$-$C_6$ alkyl, —$C_2$-$C_6$ alkenyl, —$C_4$-$C_8$ cycloalkenyl, —$C_2$-$C_6$ alkynyl, —$C_3$-$C_8$ cycloalkyl, —$C_5$-$C_{12}$ spirocycle, heterocyclyl, spiroheterocyclyl, aryl, or heteroaryl containing 1-5 heteroatoms selected from the group consisting of N, S, P, and O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —$NO_2$, —CN, —$R^1$, —$R^2$, —$OR^3$, —$NHR^3$, —$NR^3R^4$, —$S(O)_2NR^3R^4$, —$S(O)_2R^1$, —$C(O)R^1$, or —$CO_2R^1$, —$NR^3S(O)_2R^1$, —$S(O)R^1$, —$S(O)NR^3R^4$, —$NR^3S(O)R^1$, heterocycle, aryl, or heteroaryl containing 1-5 heteroatoms selected from the group consisting of N, S, P, and O;

each $R^1$ and $R^2$ are independently, and at each occurrence, —H, —$R^3$, —$R^4$, —$C_1$-$C_6$ alkyl, —$C_2$-$C_6$ alkenyl, —$C_4$-$C_8$ cycloalkenyl, —$C_2$-$C_6$ alkynyl, —$C_3$-$C_8$ cycloalkyl, heterocyclyl, aryl, heteroaryl containing 1-5 heteroatoms selected from the group consisting of N, S, P, and O, —OH, halogen, —$NO_2$, —CN, —$NHC_1$-$C_6$ alkyl, —$N(C_1$-$C_6$ alkyl)$_2$, —$S(O)_2N(C_1$-$C_6$ alkyl)$_2$, —$N(C_1$-$C_6$ alkyl)$S(O)_2R^5$, —$S(O)_2(C_1$-$C_6$ alkyl), —$(C_1$-$C_6$ alkyl)$S(O)_2R^5$, —$C(O)C_1$-$C_6$ alkyl, —$CO_2C_1$-$C_6$ alkyl, —$N(C_1$-$C_6$ alkyl)$S(O)_2C_1$-$C_6$ alkyl, or —$(CHR^5)_nNR^3R^4$, wherein each alkyl, alkenyl, cycloalkenyl, alkynyl, cycloalkyl, heterocyclyl, aryl, or heteroaryl is optionally substituted with one or more substituents selected from —OH, halogen, —$NO_2$, oxo, —CN, —$R^5$, —$OR^3$, —$NHR^3$, $NR^3R^4$, —$S(O)_2N(R^3)_2$—, —$S(O)_2R^5$, —$C(O)R^5$, —$CO_2R^5$, —$NR^3S(O)_2R^5$, —$S(O)R^5$, —$S(O)NR^3R^4$, —$NR^3S(O)R^5$, heterocycle, aryl, or heteroaryl containing 1-5 heteroatoms selected from the group consisting of N, S, P, and O;

or $R^1$ and $R^2$ can combine with the carbon atom to which they are both attached to form a spirocycle, spiroheterocycle, or a spirocycloalkenyl;

or $R^1$ and $R^2$, when on adjacent atoms, can combine to form a heterocycle, cycloalkyl, aryl, heteroaryl containing 1-5 heteroatoms selected from the group consisting of N, S, P, and O, or cycloalkenyl;

or $R^1$ and $R^2$, when on non-adjacent atoms, can combine to form a bridging cycloalkyl or heterocycloalkyl;

$R^{1'}$ and $R^{2'}$ are independently, and at each occurrence, —H, —$C_1$-$C_6$ alkyl, —$C_2$-$C_6$ alkenyl, —$C_4$-$C_8$ cycloalkenyl, —$C_2$-$C_6$ alkynyl, —$C_3$-$C_8$ cycloalkyl, heterocyclyl, —OH, halogen, —$NO_2$, —CN, —$NHC_1$-$C_6$ alkyl, —$N(C_1$-$C_6$ alkyl)$_2$, —$S(O)_2N(C_1$-$C_6$ alkyl)$_2$, —$N(C_1$-$C_6$ alkyl)$S(O)_2R^5$, —$S(O)_2(C_1$-$C_6$ alkyl), —$(C_1$-$C_6$ alkyl)$S(O)_2R^5$, —$C(O)C_1$-$C_6$ alkyl, —$CO_2C_1$-$C_6$ alkyl, —$N(C_1$-$C_6$ alkyl)$S(O)_2C_1$-$C_6$ alkyl, or —$(CHR^5)_nNR^3R^4$, wherein each alkyl, alkenyl, cycloalkenyl, alkynyl, cycloalkyl, or heterocyclyl is optionally substituted with one or more substituents selected from —OH, halogen, —$NO_2$, oxo, —CN, —$R^5$, —$OR^3$, —$NHR^3$, $NR^3R^4$, —$S(O)_2N(R^3)_2$—, —$S(O)_2R^5$, —$C(O)R^5$, —$CO_2R^5$, —$NR^3S(O)_2R^5$, —$S(O)R^5$, —$S(O)NR^3R^4$, —$NR^3S(O)R^5$, heterocycle, aryl, or heteroaryl containing 1-5 heteroatoms selected from the group consisting of N, S, P, and O;

or $R^{1'}$ and $R^{2'}$ can combine with the carbon atom to which they are both attached to form a spirocycle, spiroheterocycle, or a spirocycloalkenyl;

or $R^{1'}$ and $R^{2'}$ can combine with $R^1$ or $R^2$ on adjacent atoms to form a heterocycle, cycloalkyl, aryl, heteroaryl containing 1-5 heteroatoms selected from the group consisting of N, S, P, and O, or cycloalkenyl;

or $R^{1'}$ and $R^{2'}$ can combine with $R^1$ or $R^2$ on non-adjacent atoms, to form a bridging cycloalkyl or heterocycloalkyl;

$R^3$ and $R^4$ are independently, at each occurrence, —H, —$C_1$-$C_6$ alkyl, —$C_2$-$C_6$ alkenyl, —$C_4$-$C_8$ cycloalkenyl, —$C_2$-$C_6$ alkynyl, —$C_3$-$C_8$ cycloalkyl, heterocyclyl, aryl, heteroaryl containing 1-5 heteroatoms selected from the group consisting of N, S, P, and O, —$S(O)_2N(C_1$-$C_6$ alkyl)$_2$, —$S(O)_2(C_1$-$C_6$ alkyl), —$(C_1$-$C_6$ alkyl)$S(O)_2R^5$, —$C(O)C_1$-$C_6$ alkyl, —$CO_2C_1$-$C_6$ alkyl, or —$(CHR^5)_nN(C_1$-$C_6$ alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —$NO_2$, Oxo, —CN, —$R^5$, —$O(C_1$-$C_6$ alkyl), —$NH(C_1$-$C_6$ alkyl), —$N(C_1$-$C_6$ alkyl)$_2$, —$S(O)_2N(C_1$-$C_6$ alkyl)$_2$, —$S(O)_2NH(C_1$-$C_6$ alkyl), —$C(O)C_1$-$C_6$ alkyl, —$CO_2C_1$-$C_6$ alkyl, —$N(C_1$-$C_6$ alkyl)$S(O)_2C_1$-$C_6$ alkyl, —$S(O)R^5$, —$S(O)N(C_1$-$C_6$ alkyl)$_2$, —$N(C_1$-$C_6$ alkyl)$S(O)R^5$, heterocycle, aryl, or heteroaryl containing 1-5 heteroatoms selected from the group consisting of N, S, P, and O;

or $R^3$ and R can combine with the nitrogen atom to which they are attached to form a heterocycle, wherein each heterocycle or heteroaryl is optionally substituted by —$R^1$, —$R^2$, —$R^4$, —$OR^4$, or —$NR^4R^5$;

$R^5$ is independently, and at each occurrence, —H, —$C_1$-$C_6$ alkyl, —$C_2$-$C_6$ alkenyl, —$C_4$-$C_8$ cycloalkenyl, —$C_2$-$C_6$ alkynyl, —$C_3$-$C_8$ cycloalkyl, heterocyclyl, aryl, heteroaryl containing 1-5 heteroatoms selected from the group consisting of N, S, P, and O, —OH, halogen, —$NO_2$, —CN, —$NHC_1$-$C_6$ alkyl, —$N(C_1$-$C_6$ alkyl)$_2$, —$S(O)_2NH(C_1$-$C_6$ alkyl), —$S(O)_2N(C_1$-$C_6$ alkyl)$_2$, —$S(O)_2C_1$-$C_6$ alkyl, —$C(O)C_1$-$C_6$ alkyl, —$CO_2C_1$-$C_6$ alkyl, —$N(C_1$-$C_6$ alkyl) $SO_2C_1$-$C_6$ alkyl, —$S(O)(C_1$-$C_6$ alkyl), —$S(O)N(C_1$-$C_6$ alkyl)$_2$, —$N(C_1$-$C_6$ alkyl)$S(O)(C_1$-$C_6$ alkyl) or —$(CH_2)_nN(C_1$-$C_6$ alkyl)$_2$; and n is independently, and at each occurrence, an integer from 0 to 6 and;

provided that when $X^2$ and $X^4$ are both C═O, $X^1$ is not $NR^3$.

Another aspect of the disclosure relates to a method of treating a disease or disorder associated with HDAC, e.g., HDAC6 modulation in a subject in need thereof, comprising administering to the subject an effective amount of a compound of Formula I.

Another aspect of the disclosure is directed to a method of inhibiting an HDAC, e.g., HDAC6. The method involves administering to a patient in need thereof an effective amount of a compound of Formula I.

Another aspect of the disclosure relates to a compound of Formula I, or a pharmaceutically acceptable salt, prodrug, solvate, hydrate, tautomer, or isomer thereof, for use in treating or preventing a disease associated with HDAC6 modulation.

Another aspect of the disclosure relates to the use of a compound of Formula I, or a pharmaceutically acceptable salt, prodrug, solvate, hydrate, tautomer, or isomer thereof, in the manufacture of a medicament for treating or preventing a disease associated with HDAC6 modulation.

Another aspect of the disclosure is directed to pharmaceutical compositions comprising a compound of Formula I and a pharmaceutically acceptable carrier. The pharmaceutically acceptable carrier can further include an excipient, diluent, or surfactant. The pharmaceutical composition can be effective for treating a disease or disorder associated with HDAC, e.g., HDAC6, modulation in a subject in need thereof. The pharmaceutical compositions can comprise the compounds of the present disclosure for use in treating diseases described herein. The compositions can contain at least one compound of the disclosure and a pharmaceutically acceptable carrier. The disclosure also provides the use of the compounds described herein in the manufacture of a medicament for the treatment of a disease associated with HDACs.

The present disclosure also provides methods for the treatment of human diseases or disorders including, without limitation, oncological, neurological, inflammatory, autoimmune, infectious, metabolic, hematologic, or cardiovascular diseases or disorders.

The present disclosure also provides compounds that are useful in inhibiting of zinc-dependent HDAC enzymes, for instance HDAC6. These compounds can also be useful in the treatment of diseases including cancer.

The present disclosure further provides compounds that can inhibit an HDAC, e.g., HDAC6. In some embodiments, the efficacy-safety profile of the compounds of the current disclosure can be improved relative to other known HDAC (e.g. HDAC6) inhibitors. Additionally, the present technology also has the advantage of being able to be used for a number of different types of diseases, including cancer and non-cancer indications. Additional features and advantages of the present technology will be apparent to one of skill in the art upon reading the Detailed Description of the Disclosure, below.

DETAILED DESCRIPTION OF THE INVENTION

HDAC6 is a zinc-dependent histone deacetylase that has two catalytic domains. HDAC6 can interact with and deacetylate non-histone proteins, including HSP90 and α-tubulin. Acetylation of HSP90 is associated with loss of function of HSP90. HDAC6 is also implicated in the degradation of misfolded proteins as part of the aggresome. Accordingly, inhibition of HDAC6 can have downstream effects that can play a role in the development of certain diseases such as cancer. The present disclosure provides inhibitors of HDACs, e.g., HDAC6 and methods for using the same to treat disease.

In a first aspect of the disclosure, compounds of the Formula I are described:

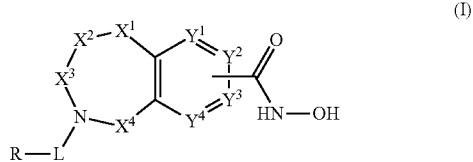

(I)

and pharmaceutically acceptable salts, prodrugs, solvates, hydrates, tautomers, and isomers thereof, wherein R, L, $X^1$, $X^2$, $X^3$, $X^4$, $Y^1$, $Y^2$, $Y^3$, and $Y^4$ are described as above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$ alkyl, —$C_1$-$C_6$ alkyl, —O$C_2$-$C_6$ alkenyl, —O$C_2$-$C_6$ alkynyl, —$C_2$-$C_6$ alkenyl, —$C_2$-$C_6$ alkynyl, —OH, —OP(O)(OH)$_2$, —OC(O)$C_1$-$C_6$ alkyl, —C(O)$C_1$-$C_6$ alkyl, —OC(O)O$C_1$-$C_6$ alkyl, —NH$_2$, —NH($C_1$-$C_6$ alkyl), —N($C_1$-$C_6$ alkyl)$_2$, —S(O)$_2$—$C_1$-$C_6$ alkyl, —S(O)NH$C_1$-$C_6$ alkyl, and —S(O)N($C_1$-$C_6$ alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 24 ring atoms or a polycyclic aromatic radical, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]

thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Alkyl" refers to a straight or branched chain saturated hydrocarbon. $C_1$-$C_6$ alkyl groups contain 1 to 6 carbon atoms. Examples of a $C_1$-$C_6$ alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon-carbon double bond and which may be straight or branched having about 2 to about 6 carbon atoms in the chain. Alkenyl groups can have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Alkynyl groups can have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, nitrogen, or sulfur and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heterocyclyl or heterocycloalkyl ring can also be fused or bridged, e.g., can be a bicyclic ring.

As used herein, the term "halo" or "halogen" means fluoro, chloro, bromo, or iodo.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A $C_3$-$C_{12}$ spirocycle is a spirocycle containing between 3 and 12 carbon atoms. One or more of the carbon atoms can be substituted with a heteroatom.

The term "spirocyclic heterocycle" or "spiroheterocycle" is understood to mean a spirocycle wherein at least one of the rings is a heterocycle (e.g., at least one of the rings is furanyl, morpholinyl, or piperadinyl).

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the disclosure.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (e.g., using an enzyme).

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula I may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

In another embodiment of the disclosure are described compounds of the Formula IA:

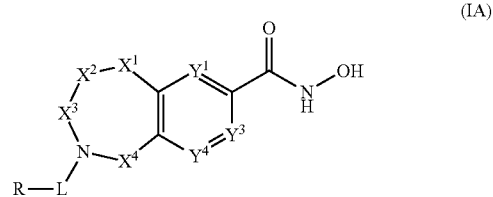

(IA)

and pharmaceutically acceptable salts, prodrugs, solvates, hydrates, tautomers or isomer thereof; where R, L, $X^1$, $X^2$, $X^3$, $X^4$, $Y^1$, $Y^3$, and $Y^4$ are defined as above in Formula I.

In another embodiment of the compounds of Formula IA, $X^4$ is $CR^1R^2$.

In another embodiment of the compounds of Formula IA, $X^1$ is $NR^3$, O, or C=O.

In another embodiment of the compounds of Formula IA, $X^1$ is O.

In another embodiment of the compounds of Formula IA, $X^1$ is O and $X^4$ is $CR^1R^2$.

In some embodiments of the disclosure, the compounds of Formula IA may be of the Formula IA-1:

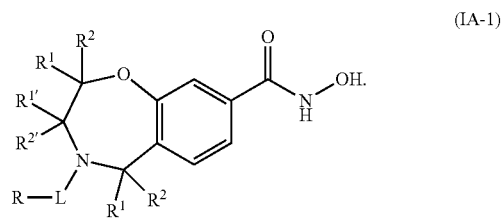

(IA-1)

For instance, in some embodiments of Formula IA-1, the compounds can be of the Formula IA-1a, Formula IA-1b, Formula IA-1c, Formula IA-1d, Formula IA-1e, or Formula IA-1f:

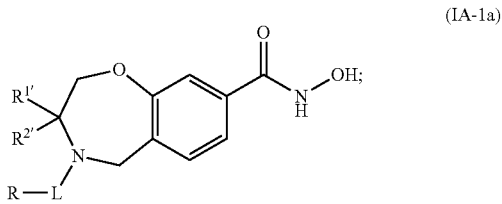

(IA-1a)

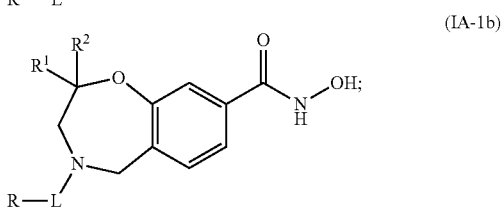

(IA-1b)

-continued

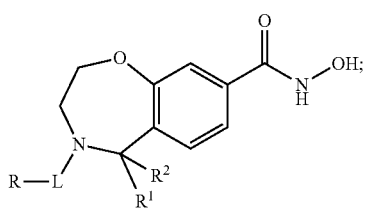
(IA-1c)

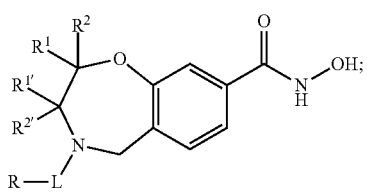
(IA-1d)

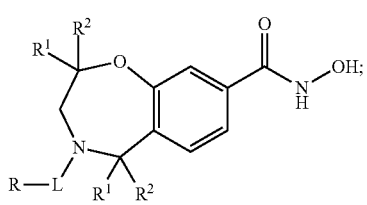
(IA-1e)

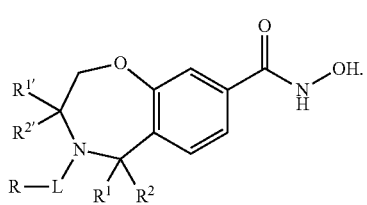
(IA-1f)

In other embodiments of the compounds of Formula IA, the compound is of the Formula IA-2:

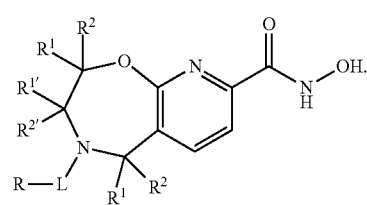
(IA-2)

In yet other another embodiments of the compounds of Formula IA, the compound is of the Formula IA-3:

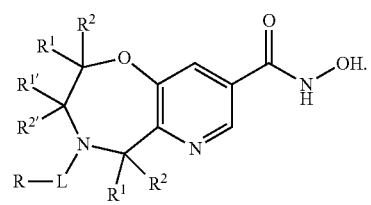
(IA-3)

In yet other embodiments of the compounds of Formula IA, the compound is of the Formula IA-4:

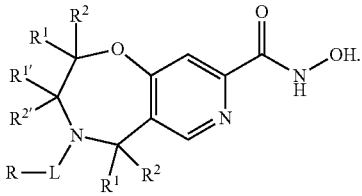
(IA-4)

In yet other another embodiments of the compounds of Formula IA, the compound is of the Formula IA-5:

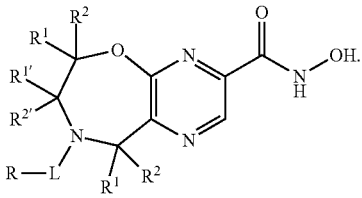
(IA-5)

In yet other another embodiments of the compounds of Formula IA, the compound is of the Formula IA-6:

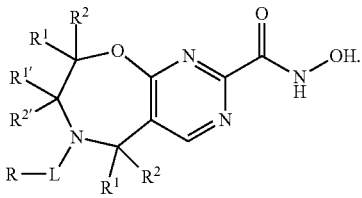
(IA-6)

In yet other another embodiments of the compounds of Formula IA, the compound is of the Formula IA-7:

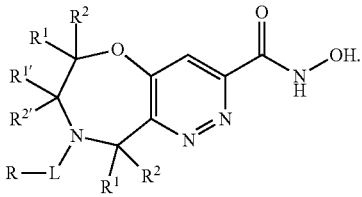
(IA-7)

In other embodiments of the compounds of Formula IA, the compound may also be of the Formula IA-8:

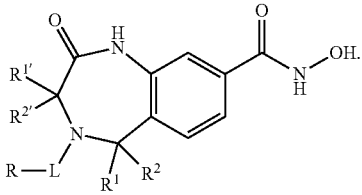
(IA-8)

In other embodiments of the compounds of Formula IA, the compound is of the Formula IA-9:

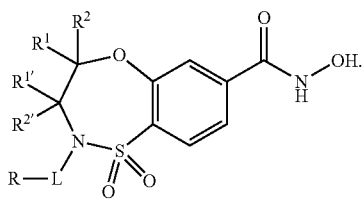

(IA-9)

In a further embodiment of the compounds of Formula IA, the compound is also of the Formula IA-10:

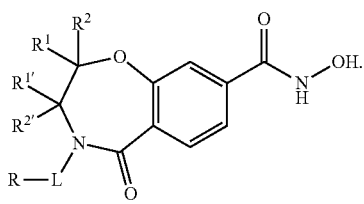

(IA-10)

In another embodiment of the compounds of Formula IA, the compound is of the Formula IA-11:

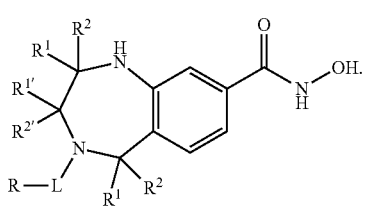

(IA-11)

In one embodiment of the disclosure are also disclosed compounds of the Formula IB:

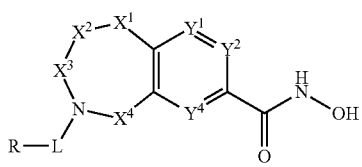

(IB)

and pharmaceutically acceptable salts, prodrugs, solvates, hydrates, enantiomers and isomers thereof where R, L, $X^1$, $X^2$, $X^3$, $X^4$, $Y^1$, $Y^2$, and $Y^4$ are defined as above in Formula I.

In one embodiment of the compounds of Formula IB, $X^4$ is $CR^1R^2$.

In another embodiment of the compounds of Formula IB, $X^1$ is $NR^3$, O, or C=O.

In another embodiment of the compounds of Formula IB, $X^1$ is O.

In another embodiment of the compounds of Formula IB, $X^1$ is O and $X^4$ is $CR^1R^2$.

In another embodiment of the compounds of Formula IB, $X^1$ is N, $X^2$ is C=O, and $X^4$ is $CR^1R^2$.

In some embodiments of the disclosure, the compounds of Formula IB, may be of the Formula IB-1:

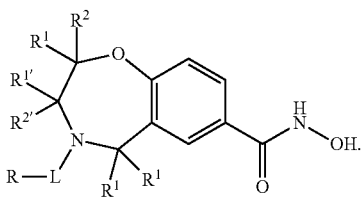

(IB-1)

In other embodiments of the compounds of Formula IB, the compound is of the Formula IB-2:

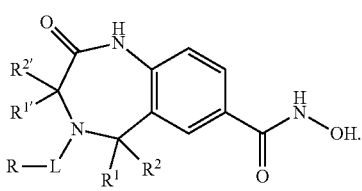

(IB-2)

For instance, in some embodiments, the compounds of the disclosure can be of the Formula IB-2a:

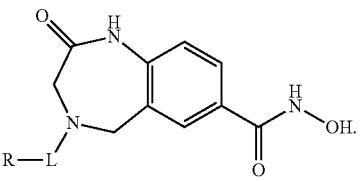

(IB-2a)

In yet other embodiments of the compounds of Formula IB, the compound is of the Formula (IB-3):

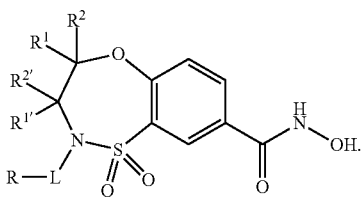

(IB-3)

In other embodiments of the compounds of Formula IB, the compound may also be of the Formula IB-4:

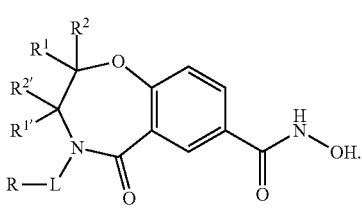

(IB-4)

In other embodiments of the compounds of Formula IB, the compound is of the Formula (IB-5):

(IB-5)

In some embodiments of Formula (I), $X^1$ is O. In another embodiment, $X^1$ is O and $X^2$ is $CR^1R^2$. In yet another embodiment, $X^1$ is O, $X^2$ is $CR^1R^2$, and $X^3$ is $CR^{1'}R^{2'}$. In another embodiment, $X^1$ is O, $X^2$ is $CR^1R^2$, $X^3$ is $CR^{1'}R^{2'}$, and $X^4$ is $CR^1R^2$. In yet another embodiment, $X^1$ is O, $X^2$ is $CR^1R^2$, $X^3$ is $CR^{1'}R^{2'}$, $X^4$ is $CR^1R^2$, and $Y^1$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is $CR^1$, and $Y^3$ is $CR^1$. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, and $Y^4$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, and $Y^2$ is C.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, and $Y^3$ is C. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, and $Y^4$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, and $Y^2$ is $CR^1$.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is a bond. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)O—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)NR$^3$—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —S(O)$_2$—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —S(O)$_2$NR$^3$—.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is a bond. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)O—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)NR$^3$—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —S(O)$_2$—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —S(O)$_2$NR$^3$—.

In another embodiment, $X^1$ is O, $X^2$ is $CR^1R^2$, $X^3$ is $CR^{1'}R^{2'}$, $X^4$ is $CR^1R^2$, and $Y^1$ is N. In yet another embodiment, $X^1$ is O, $X^2$ is $CR^1R^2$, $X^3$ is $CR^{1'}R^{2'}$, $X^4$ is $CR^1R^2$, $Y^1$ is N, and $Y^3$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, and $Y^4$ is $CR^1$. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, and $Y^2$ is C.

In another embodiment, $X^1$ is O, $X^2$ is $CR^1R^2$, $X^3$ is $CR^{1'}R^{2'}$, $X^4$ is $CR^1R^2$, $Y^1$ is N, and $Y^3$ is C. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, and $Y^4$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, and $Y^2$ is $CR^1$.

In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is a bond. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —C(O)O—. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —C(O)NR$^3$—. In another embodiment, $X^1$ is O, $X^2$ is $CR^1R^2$, $X^3$ is $CR^1R^2$, $X^4$ is $CR^1R^2$, $Y^1$ is N, $Y^3$ is $CR^1$, $Y^4$ is $CR^1$, $Y^2$ is C, and L is —S(O)$_2$—. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —S(O)$_2$NR$^3$—.

In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is a bond. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —C(O)O—. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —C(O)NR$^3$—. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —S(O)$_2$—. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —S(O)$_2$NR$^3$—.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, and $Y^4$ is N. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, and $Y^2$ is C. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, and $Y^4$ is N. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, and $Y^2$ is $CR^1$.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is a bond. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —C(O)O—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —C(O)NR$^3$—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —S(O)$_2$—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —S(O)$_2$NR$^3$—.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is a bond. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is —C(O)O—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is —C(O)NR$^3$—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is —S(O)$_2$—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is —S(O)$_2$NR$^3$—.

In some embodiments of Formula (I), $X^1$ is NR$^3$. In another embodiment, $X^1$ is NR$^3$ and $X^2$ is $CR^1R^2$. In yet another embodiment, $X^1$ is NR$^3$, $X^2$ is $CR^1R^2$, and $X^3$ is $CR^{1'}R^{2'}$. In another embodiment, $X^1$ is NR$^3$, $X^2$ is $CR^1R^2$, $X^3$ is $CR^{1'}R^{2'}$, and $X^4$ is $CR^1R^2$. In yet another embodiment, $X^1$ is NR$^3$, $X^2$ is $CR^1R^2$, $X^3$ is $CR^{1'}R^{2'}$, $X^4$ is $CR^1R^2$, and $Y^1$ is $CR^1$. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, and $Y^3$ is $CR^1$. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, and $Y^4$ is $CR^1$. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is $CR^1$, and $Y^2$ is C.

In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, and $Y^3$ is C. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, and $Y^4$ is $CR^1$. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is $CR^1$, and $Y^2$ is $CR^1$.

In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is $CR^1$, $Y^2$ is C, and L is a bond. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is $CR^1$, $Y^2$ is C, and L is —C(O)O—. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is $CR^1$, $Y^2$ is C, and L is —C(O)$NR^3$—. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is $CR^1$, $Y^2$ is C, and L is —S(O)$_2$—. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is $CR^1$, $Y^2$ is C, and L is —S(O)$_2$$NR^3$—.

In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is $CR^1$, $Y^2$ is $CR^1$, and L is a bond. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is $CR^1$, $Y^2$ is $CR^1$, and L is —C(O)O—. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is $CR^1$, $Y^2$ is $CR^1$, and L is —C(O)$NR^3$—. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is $CR^1$, $Y^2$ is $CR^1$, and L is —S(O)$_2$—. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is $CR^1$, $Y^2$ is $CR^1$, and L is —S(O)$_2$$NR^3$—.

In another embodiment, $X^1$ is $NR^3$, $X^2$ is $CR^1R^2$, $X^3$ is $CR^1R^{2'}$, $X^4$ is $CR^1R^2$, and $Y^1$ is N. In yet another embodiment, $X^1$ is $NR^3$, $X^2$ is $CR^1R^2$, $X^3$ is $CR^1R^{2'}$, $X^4$ is $CR^1R^2$, $Y^1$ is N, and $Y^3$ is $CR^1$. In another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is $CR^1$, and $Y^4$ is $CR^1$. In yet another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is $CR^1$, $Y^4$ is $CR^1$, and $Y^2$ is C.

In another embodiment, $X^1$ is $NR^3$, $X^2$ is $CR^1R^2$, $X^3$ is $CR^1R^{2'}$, $X^4$ is $CR^1R^2$, $Y^1$ is N, and $Y^3$ is C. In yet another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is C, and $Y^4$ is $CR^1$. In another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is C, $Y^4$ is $CR^1$, and $Y^2$ is $CR^1$.

In another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is $CR^1$, $Y^4$ is $CR^1$, $Y^2$ is C, and L is a bond. In yet another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is $CR^1$, $Y^4$ is $CR^1$, $Y^2$ is C, and L is —C(O)O—. In yet another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is C, $Y^4$ is $CR^1$, $Y^2$ is $CR^1$, and L is —C(O)$NR^3$—. In another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is C, $Y^4$ is $CR^1$, $Y^2$ is $CR^1$, and L is —S(O)$_2$—. In yet another embodiment, $X^1$ is $NR^3$, $X^2$ is $CR^1R^2$, $X^3$ is $CR^1R^{2'}$, $X^4$ is $CR^1R^2$, $Y^1$ is N, $Y^3$ is C, $Y^4$ is $CR^1$, $Y^2$ is $CR^1$, and L is —S(O)$_2$$NR^3$—.

In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, and $Y^4$ is N. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is N, and $Y^2$ is C. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, and $Y^4$ is N. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, and $Y^2$ is $CR^1$.

In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is a bond. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is —C(O)O—. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is —C(O)$NR^3$—. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is —S(O)$_2$—. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is —S(O)$_2$$NR^3$—.

In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is a bond. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —C(O)O—. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —C(O)$NR^3$—. In another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —S(O)$_2$—. In yet another embodiment, $X^1$ is $NR^3$, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —S(O)$_2$$NR^3$—.

In some embodiments of Formula (I), $X^1$ is $NR^3$. In another embodiment, $X^1$ is $NR^3$ and $X^2$ is C=O. In yet another embodiment, $X^1$ is $NR^3$, $X^2$ is C=O, and $X^3$ is $CR^1R^{2'}$. In another embodiment, $X^1$ is $NR^3$, $X^2$ is C=O, $X^3$ is $CR^1R^{2'}$, and $X^4$ is $CR^1R^2$. In yet another embodiment, $X^1$ is $NR^3$, $X^2$ is C=O, $X^3$ is $CR^1R^{2'}$, $X^4$ is $CR^1R^2$, and $Y^1$ is $CR^1$. In another embodiment, $X^1$ is $NR^3$, $X^2$ is C=O, $X^3$ is $CR^1R^{2'}$, $X^4$ is $CR^1R^2$, $Y^1$ is $CR^1$, and $Y^3$ is $CR^1$. In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, and $Y^4$ is $CR^1$. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is $CR^1$, and $Y^2$ is C.

In another embodiment, $X^1$ is $NR^3$, $X^2$ is C=O, $X^3$ is $CR^1R^{2'}$, $X^4$ is $CR^1R^2$, $Y^1$ is $CR^1$, and $Y^3$ is C. In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, and $Y^4$ is $CR^1$. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is $CR^1$, and $Y^2$ is CR.

In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is $CR^1$, $Y^2$ is C, and L is a bond. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)O—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)$NR^3$—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —S(O)$_2$—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —S(O)$_2NR^3$—.

In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is a bond. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)O—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)$NR^3$—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —S(O)$_2$—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —S(O)$_2NR^3$—.

In another embodiment, $X^1$ is $NR^3$, $X^2$ is C=O, $X^3$ is $CR^{1'}R^{2'}$, $X^4$ is $CR^1R^2$, and $Y^1$ is N. In yet another embodiment, $X^1$ is $NR^3$, $X^2$ is C=O, $X^3$ is $CR^{1'}R^{2'}$, $X^4$ is $CR^1R^2$, $Y^1$ is N, and $Y^3$ is $CR^1$. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, and $Y^4$ is $CR^1$. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, and $Y^2$ is C.

In another embodiment, $X^1$ is $NR^3$, $X^2$ is C=O, $X^3$ is $CR^{1'}R^{2'}$, $X^4$ is $CR^1R^2$, $Y^1$ is N, and $Y^3$ is C. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, and $Y^4$ is $CR^1$. In another embodiment, $X^1$ is $NR^3$, $X^2$ is C=O, $X^3$ is $CR^1R^2$, $X^4$ is $CR^1R^2$, $Y^1$ is N, $Y^3$ is C, $Y^4$ is $CR^1$, and $Y^2$ is $CR^1$.

In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is a bond. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —C(O)O—. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —C(O)$NR^3$—. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —S(O)$_2$—. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —S(O)$_2NR^3$—.

In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is a bond. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —C(O)O—. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —C(O)$NR^3$—. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —S(O)$_2$—. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —S(O)$_2NR^3$—.

In another embodiment, $X^1$ is $NR^3$, $X^2$ is C=O$^2$, $X^3$ is $CR^{1'}R^{2'}$, $X^4$ is $CR^1R^2$, $Y^1$ is $CR^1$, $Y^3$ is $CR^1$, and $Y^4$ is N. In yet another embodiment, $X^1$ is $NR^3$, $X^2$ is C=O, $X^3$ is $CR^1R^2$, $X^4$ is $CR^1R^2$, $Y^1$ is $CR^1$, $Y^3$ is $CR^1$, $Y^4$ is N, and $Y^2$ is C. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, and $Y^4$ is N. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is N, and $Y^2$ is $CR^1$.

In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is a bond. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —C(O)O—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —C(O)$NR^3$—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —S(O)$_2$—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is —S(O)$_2NR^3$—.

In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is a bond. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is —C(O)O—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is —C(O)$NR^3$—. In another embodiment, $X^1$ is $NR^3$, $X^2$ is C=O, $X^3$ is $CR^1R^2$, $X^4$ is $CR^1R^2$, $Y^1$ is $CR^1$, $Y^3$ is C, $Y^4$ is N, $Y^2$ is $CR^1$, and L is —S(O)$_2$—. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is —S(O)$_2NR^3$—.

In some embodiments of Formula (I), $X^2$ is $CR^1R^2$; $R^1$ is —H or —$C_1$-$C_6$ alkyl; and $R^2$ is —H, aryl, or —$C_1$-$C_6$ alkyl optionally substituted with one or more —OH, halogen, or —$OR^3$.

In some embodiments of Formula (I), $X^3$ is $CR^{1'}R^{2'}$; $R^{1'}$ is —H or —$C_1$-$C_6$ alkyl; and $R^{2'}$ is —H, or —$C_1$-$C_6$ alkyl optionally substituted with one or more halogen, —$OR^3$, or aryl.

In some embodiments of Formula (I), $X^3$ is $CR^{1'}R^{2'}$ and $R^{1'}$ and $R^{2'}$ combine with the carbon atom to which they are both attached to form a spirocycle.

In some embodiments of Formula (I), $R^1$ and $R^2$ combine with the atom to which they are both attached to form a spirocycle. In another embodiment, $R^1$ and $R^2$ combine with the atom to which they are both attached to form a spiroheterocycle. In another embodiment, $R^1$ and $R^2$ combine with the atom to which they are both attached to form a spirocycloalkenyl.

In some embodiments of Formula (I), $R^1$ and $R^2$, when on adjacent atoms, combine to form a heterocycle. In another embodiment, $R^1$ and $R^2$, when on adjacent atoms, combine to form a cycloalkyl. In yet another embodiment, $R^1$ and $R^2$, when on adjacent atoms, combine to form a cycloalkenyl. In another embodiment, $R^1$ and $R^2$, when on adjacent atoms, combine to form an aryl. In yet another embodiment, $R^1$ and $R^2$, when on adjacent atoms, combine to form a heteroaryl containing 1 to 5 heteroatoms selected from the group consisting of N, S, P, and O.

In some embodiments of Formula (I), $R^1$ and $R^2$, when on non-adjacent atoms, combine to form a bridging cycloalkyl. In yet another embodiment, $R^1$ and $R^2$, when on non-adjacent atoms, combine to form a heterocycloalkyl.

In some embodiments of Formula (I), $R^{1'}$ and $R^{2'}$ combine with the atom to which they are both attached to form a spirocycle. In another embodiment, $R^{1'}$ and $R^{2'}$ combine with the atom to which they are both attached to form a spiroheterocycle. In another embodiment, $R^1$ and $R^{2'}$ combine with the atom to which they are both attached to form a spirocycloalkenyl.

In some embodiments of Formula (I), $R^{1'}$ and $R^{2'}$, when on non-adjacent atoms, combine to form a bridging cycloalkyl. In yet another embodiment, $R^{1'}$ and $R^{2'}$, when on non-adjacent atoms, combine to form a heterocycloalkyl.

In some embodiments of Formula (I), $R^3$ and R combine with the nitrogen atom to which they are attached to form a heterocycle optionally substituted with —$R^4$, —$OR^4$, or —$NR^4R^5$. In some embodiments of Formula (I), $R^3$ and R combine with the nitrogen atom to which they are attached to form a heteroaryl containing 1 to 5 heteroatoms selected from the group consisting of N, S, P, and O, optionally substituted with —$R^4$, —$OR^4$, or —$NR^4R^5$.

In some embodiments of Formula (I), n is 1 to 6. In another embodiment, n is 0 to 5. In yet another embodiment, n is 0 to 4. In yet another embodiment, n is 1 to 4. In another embodiment, n is 0 to 3. In yet another embodiment, n is 0 to 2. In yet another embodiment, n is 0 or 1. In another embodiment, n is 1 or 2.

In some embodiments of Formula (I), $X^4$, $X^2$, and $X^1$ are not all simultaneously $CR^1R^{2'}$.

In some embodiments of Formula (I), $X^1$ is O, $X^2$ is $CR^1R^2$, and $X^4$ is $CR^1R^2$. In another embodiment, $X^2$ is C=O, $X^4$ is C=O, and $X^1$ is $CR^1R^2$. In yet another embodiment, $X^1$ is $NR^3$, $X^2$ is C=O, and $X^4$ is $CR^1R^2$.

In an illustrative embodiment, the compound of Formula I is:

4-(benzo[d]oxazol-2-yl)-N-hydroxy-2,3,4,5-tetrahydrobenzo[f][1,4]oxazepine-8-carboxamide;
4-(1-(cyclohexylmethyl)-1H-benzo[d]imidazol-2-yl)-N-hydroxy-2,3,4,5-tetrahydrobenzo[f][1,4]oxazepine-8-carboxamide;
4-(benzo[d]thiazol-2-yl)-N-hydroxy-2,3,4,5-tetrahydrobenzo[f][1,4]oxazepine-8-carboxamide;
4-cyclohexylmethyl)-N-hydroxy-2,3,4,5-tetrahydrobenzo[f][1,4]oxazepine-8-carboxamide;
N-hydroxy-4-phenyl-2,3,4,5-tetrahydrobenzo[f][1,4]oxazepine-8-carboxamide;
4-(4-cyano-3-(trifluoromethyl)phenyl)-N-hydroxy-2,3,4,5-tetrahydrobenzo[f][1,4]oxazepine-8-carboxamide;
4-(3,4-dichlorophenyl)-N-hydroxy-2,3,4,5-tetrahydrobenzo[f][1,4]oxazepine-8-carboxamide;
N-hydroxy-4-(pyridin-2-yl)-2,3,4,5-tetrahydrobenzo[f][1,4]oxazepine-8-carboxamide;
N-hydroxy-4-(pyridin-3-yl)-2,3,4,5-tetrahydrobenzo[f][1,4]oxazepine-8-carboxamide;
N-hydroxy-4-(pyridin-4-yl)-2,3,4,5-tetrahydrobenzo[f][1,4]oxazepine-8-carboxamide;
N-hydroxy-4-(p-tolyl)-2,3,4,5-tetrahydrobenzo[f][1,4]oxazepine-8-carboxamide;
N-hydroxy-4-(piperidine-1-carbonyl)-2,3,4,5-tetrahydrobenzo[f][1,4]oxazepine-8-carboxamide;
4-methoxyphenyl 8-(hydroxycarbamoyl)-2,3-dihydrobenzo[f][1,4]oxazepine-4(5H)-carboxylate;
cyclohexyl 8-(hydroxycarbamoyl)-2,3-dihydrobenzo[f][1,4]oxazepine-4(5H)-carboxylate;
N-hydroxy-4-(piperidin-1-yl sulfonyl)-2,3,4,5-tetrahydrobenzo[f][1,4]oxazepine-8-carboxamide;
N8-hydroxy-N4-methyl-N4-phenyl-2,3-dihydrobenzo[f][1,4]oxazepine-4,8(5H)-dicarboxamide;
4-cyclohexyl-N-hydroxy-2,3,4,5-tetrahydrobenzo[f][1,4]oxazepine-8-carboxamide;
4-(2-(dimethylamino)ethyl)-N-hydroxy-2,3,4,5-tetrahydrobenzo[f][1,4]oxazepine-8-carboxamide;
N-hydroxy-4-(2-methoxyethyl)-2,3,4,5-tetrahydrobenzo[f][1,4]oxazepine-8-carboxamide;
N-hydroxy-4-(1-((tetrahydro-2H-pyran-4-yl)methyl)-1H-benzo[d]imidazol-2-yl)-2,3,4,5-tetrahydrobenzo[f][1,4]oxazepine-8-carboxamide;
N-hydroxy-2,3,4,5-tetrahydrobenzo[f][1,4]oxazepine-8-carboxamide;
N-hydroxy-4-methyl-2,3,4,5-tetrahydrobenzo[f][1,4]oxazepine-8-carboxamide;
(R)—N-hydroxy-2-methyl-2,3,4,5-tetrahydrobenzo[f][1,4]oxazepine-8-carboxamide;
(R)—N8-hydroxy-N4-(4-methoxyphenyl)-2-methyl-2,3-dihydrobenzo[f][1,4]oxazepine-4,8(5H)-dicarboxamide;
(R)—N-hydroxy-4-((4-methoxyphenyl)sulfonyl)-2-methyl-2,3,4,5-tetrahydrobenzo[f][1,4]oxazepine-8-carboxamide;
(R)—N-hydroxy-4-(4-methoxybenzyl)-2-methyl-2,3,4,5-tetrahydrobenzo[f][1,4]oxazepine-8-carboxamide;
(R)—N-hydroxy-2-methyl-4-phenyl-2,3,4,5-tetrahydrobenzo[f][1,4]oxazepine-8-carboxamide;
(R)—N-hydroxy-2,4-dimethyl-2,3,4,5-tetrahydrobenzo[f][1,4]oxazepine-8-carboxamide;
(S)—N-hydroxy-2-methyl-2,3,4,5-tetrahydrobenzo[f][1,4]oxazepine-8-carboxamide;
(S)—N8-hydroxy-N4-(4-methoxyphenyl)-2-methyl-2,3-dihydrobenzo[f][1,4]oxazepine-4,8(5H)-dicarboxamide;
(S)—N-hydroxy-4-((4-methoxyphenyl)sulfonyl)-2-methyl-2,3,4,5-tetrahydrobenzo[f][1,4]oxazepine-8-carboxamide;
(S)—N-hydroxy-2-methyl-4-phenyl-2,3,4,5-tetrahydrobenzo[f][1,4]oxazepine-8-carboxamide;
(S)—N-hydroxy-2,4-dimethyl-2,3,4,5-tetrahydrobenzo[f][1,4]oxazepine-8-carboxamide;
(S)—N-hydroxy-4-(4-methoxybenzyl)-2-methyl-2,3,4,5-tetrahydrobenzo[f][1,4]oxazepine-8-carboxamide;
N-hydroxy-4-(4-methoxybenzyl)-3,3-dimethyl-2,3,4,5-tetrahydrobenzo[f][1,4]oxazepine-8-carboxamide;
N-hydroxy-3,3-dimethyl-2,3,4,5-tetrahydrobenzo[f][1,4]oxazepine-8-carboxamide;
N-hydroxy-3,3,4-trimethyl-2,3,4,5-tetrahydrobenzo[f][1,4]oxazepine-8-carboxamide;
(R)—N-hydroxy-3-isopropyl-4-(4-methoxybenzyl)-2,3,4,5-tetrahydrobenzo[f][1,4]oxazepine-8-carboxamide;
(R)—N-hydroxy-3-isopropyl-4-phenyl-2,3,4,5-tetrahydrobenzo[f][1,4]oxazepine-8-carboxamide;
(R)—N8-hydroxy-3-isopropyl-N4-(4-methoxyphenyl)-2,3-dihydrobenzo[f][1,4]oxazepine-4,8(5H)-dicarboxamide;
(R)—N-hydroxy-3-isopropyl-2,3,4,5-tetrahydrobenzo[f][1,4]oxazepine-8-carboxamide;
(R)—N-hydroxy-3-isopropyl-4-methyl-2,3,4,5-tetrahydrobenzo[f][1,4]oxazepine-8-carboxamide;
(S)—N-hydroxy-3-isopropyl-4-(4-methoxybenzyl)-2,3,4,5-tetrahydrobenzo[f][1,4]oxazepine-8-carboxamide;
(S)—N-hydroxy-3-isopropyl-4-phenyl-2,3,4,5-tetrahydrobenzo[f][1,4]oxazepine-8-carboxamide;
(S)—N8-hydroxy-3-isopropyl-N4-(4-methoxyphenyl)-2,3-dihydrobenzo[f][1,4]oxazepine-4,8(5H)-dicarboxamide;
(S)—N-hydroxy-3-isopropyl-2,3,4,5-tetrahydrobenzo[f][1,4]oxazepine-8-carboxamide;
(S)—N-hydroxy-3-isopropyl-4-methyl-2,3,4,5-tetrahydrobenzo[f][1,4]oxazepine-8-carboxamide;
(R)—N-hydroxy-3-methyl-2,3,4,5-tetrahydrobenzo[f][1,4]oxazepine-8-carboxamide;
(R)—N-hydroxy-3,4-dimethyl-2,3,4,5-tetrahydrobenzo[f][1,4]oxazepine-8-carboxamide;
(R)—N8-hydroxy-N4-(4-methoxyphenyl)-3-methyl-2,3-dihydrobenzo[f][1,4]oxazepine-4,8(5H)-dicarboxamide;

(R)—N-hydroxy-4-((4-methoxyphenyl)sulfonyl)-3-methyl-2,3,4,5-tetrahydrobenzo[f][1,4]oxazepine-8-carboxamide;
(R)—N-hydroxy-4-(4-methoxybenzyl)-3-methyl-2,3,4,5-tetrahydrobenzo[f][1,4]oxazepine-8-carboxamide;
(R)—N-hydroxy-3-methyl-4-phenyl-2,3,4,5-tetrahydrobenzo[f][1,4]oxazepine-8-carboxamide;
(S)—N8-hydroxy-N4-(4-methoxyphenyl)-3-methyl-2,3-dihydrobenzo[f][1,4]oxazepine-4,8(5H)-dicarboxamide;
(S)—N-hydroxy-4-((4-methoxyphenyl)sulfonyl)-3-methyl-2,3,4,5-tetrahydrobenzo[f][1,4]oxazepine-8-carboxamide;
(S)—N-hydroxy-4-(4-methoxybenzyl)-3-methyl-2,3,4,5-tetrahydrobenzo[f][1,4]oxazepine-8-carboxamide;
(S)—N-hydroxy-3-methyl-4-phenyl-2,3,4,5-tetrahydrobenzo[f][1,4]oxazepine-8-carboxamide;
(S)—N-hydroxy-3-methyl-2,3,4,5-tetrahydrobenzo[f][1,4]oxazepine-8-carboxamide;
(S)—N-hydroxy-3,4-dimethyl-2,3,4,5-tetrahydrobenzo[1,4]oxazepine-8-carboxamide;
(R)—N-hydroxy-4-(4-methoxybenzyl)-5-methyl-2,3,4,5-tetrahydrobenzo[f][1,4]oxazepine-7-carboxamide;
(S)—N-hydroxy-4-(4-methoxybenzyl)-5-methyl-2,3,4,5-tetrahydrobenzo[f][1,4]oxazepine-7-carboxamide;
N8-hydroxy-N4-(4-methoxyphenyl)-2,3-dihydropyrido[2,3-f][1,4]oxazepine-4,8(5H)-dicarboxamide;
N-hydroxy-4-((4-methoxyphenyl)sulfonyl)-2,3,4,5-tetrahydropyrido[2,3-f][1,4]oxazepine-8-carboxamide;
N-hydroxy-4-(4-methoxybenzyl)-2,3,4,5-tetrahydropyrido[2,3-f][1,4]oxazepine-8-carboxamide;
N8-hydroxy-N4-(4-methoxyphenyl)-2,3-dihydropyrido[3,2-f][1,4]oxazepine-4,8(5H)-dicarboxamide;
N-hydroxy-4-((4-methoxyphenyl)sulfonyl)-2,3,4,5-tetrahydropyrido[3,2-f][1,4]oxazepine-8-carboxamide;
N-hydroxy-4-(4-methoxybenzyl)-2,3,4,5-tetrahydropyrido[3,2-f][1,4]oxazepine-8-carboxamide;
N-hydroxy-4-(4-methoxybenzyl)-5-oxo-2,3,4,5-tetrahydrobenzo[f][1,4]oxazepine-8-carboxamide;
N-hydroxy-4-(4-methoxyphenethyl)-5-oxo-2,3,4,5-tetrahydrobenzo[f][1,4]oxazepine-8-carboxamide;
N-hydroxy-4-(4-methoxybenzyl)-5-oxo-2,3,4,5-tetrahydrobenzo[f][1,4]oxazepine-7-carboxamide;
N-hydroxy-4-(4-methoxyphenethyl)-5-oxo-2,3,4,5-tetrahydrobenzo[f][1,4]oxazepine-7-carboxamide;
N-hydroxy-4-(4-methoxyphenethyl)-2-oxo-2,3,4,5-tetrahydro-1H-benzo[e][1,4]diazepine-8-carboxamide;
4-((1H-benzo[d]imidazol-2-yl)methyl)-N-hydroxy-2-oxo-2,3,4,5-tetrahydro-1H-benzo[e][1,4]diazepine-8-carboxamide;
4-((1H-benzo[d]imidazol-2-yl)methyl)-N-hydroxy-2-oxo-2,3,4,5-tetrahydro-1H-benzo[e][1,4]diazepine-7-carboxamide;
N-hydroxy-4-(4-methoxyphenethyl)-2-oxo-2,3,4,5-tetrahydro-1H-benzo[e][1,4]diazepine-7-carboxamide;
N-hydroxy-2-oxo-4-(1-phenylethyl)-2,3,4,5-tetrahydro-1H-benzo[e][1,4]diazepine-7-carboxamide;
N-hydroxy-4-(4-methoxybenzyl)-2-oxo-2,3,4,5-tetrahydro-1H-benzo[e][1,4]diazepine-7-carboxamide;
N-hydroxy-4-((4-methoxyphenyl)sulfonyl)-2-oxo-2,3,4,5-tetrahydro-1H-benzo[e][1,4]diazepine-7-carboxamide;
N-hydroxy-2-oxo-4-phenyl-2,3,4,5-tetrahydro-1H-benzo[e][1,4]diazepine-7-carboxamide;
N-hydroxy-4-(4-methoxybenzyl)-1-methyl-2-oxo-2,3,4,5-tetrahydro-1H-benzo[e][1,4]diazepine-7-carboxamide;
N-hydroxy-4-(4-methoxybenzyl)-2,3,4,5-tetrahydro-1H-benzo[e][1,4]diazepine-7-carboxamide;
N-hydroxy-4-(4-methoxybenzyl)-1-methyl-2,3,4,5-tetrahydro-1H-benzo[e][1,4]diazepine-7-carboxamide;
2-benzyl-N-hydroxy-3,4-dihydro-2H-benzo[b][1,4,5]oxathiazepine-8-carboxamide 1,1-dioxide;
2-benzyl-N-hydroxy-3,4-dihydro-2H-benzo[b][1,4,5]oxathiazepine-7-carboxamide 1,1-dioxide;
N8-hydroxy-N4-(4-methoxyphenyl)-2,3-dihydrobenzo[f][1,4]oxazepine-4,8(5H)-dicarboxamide;
N7-hydroxy-N4-(4-methoxyphenyl)-2,3-dihydrobenzo[f][1,4]oxazepine-4,7(5H)-dicarboxamide;
N-hydroxy-4-((4-methoxyphenyl)sulfonyl)-2,3,4,5-tetrahydrobenzo[f][1,4]oxazepine-8-carboxamide;
N-hydroxy-4-((4-methoxyphenyl)sulfonyl)-2,3,4,5-tetrahydrobenzo[f][1,4]oxazepine-7-carboxamide;
4-((1H-benzo[d]imidazol-2-yl)methyl)-N-hydroxy-2,3,4,5-tetrahydrobenzo[f][1,4]oxazepine-8-carboxamide;
4-((1H-benzo[d]imidazol-2-yl)methyl)-N-hydroxy-2,3,4,5-tetrahydrobenzo[f][1,4]oxazepine-7-carboxamide;
N-hydroxy-4-((1-(2-methoxyethyl)-1H-benzo[d]imidazol-2-yl)methyl)-2,3,4,5-tetrahydrobenzo[f][1,4]oxazepine-8-carboxamide;
N-hydroxy-4-((1-(2-methoxyethyl)-1H-benzo[d]imidazol-2-yl)methyl)-2,3,4,5-tetrahydrobenzo[f][1,4]oxazepine-7-carboxamide;
N-hydroxy-4-(4-methoxyphenethyl)-2,3,4,5-tetrahydrobenzo[f][1,4]oxazepine-8-carboxamide;
N-hydroxy-4-(4-methoxyphenethyl)-2,3,4,5-tetrahydrobenzo[f][1,4]oxazepine-7-carboxamide;
N-hydroxy-4-(4-methoxybenzyl)-2,3,4,5-tetrahydrobenzo[f][1,4]oxazepine-8-carboxamide;
N-hydroxy-4-(4-methoxybenzyl)-2,3,4,5-tetrahydrobenzo[f][1,4]oxazepine-7-carboxamide;
4-(1H-benzo[d]imidazol-2-yl)-N-hydroxy-2,3,4,5-tetrahydrobenzo[f][1,4]oxazepine-8-carboxamide;
4-(1H-benzo[d]imidazol-2-yl)-N-hydroxy-2,3,4,5-tetrahydrobenzo[f][1,4]oxazepine-7-carboxamide;
N-hydroxy-4-(1-(2-methoxyethyl)-1H-benzo[d]imidazol-2-yl)-2,3,4,5-tetrahydrobenzo[f][1,4]oxazepine-8-carboxamide;
N-hydroxy-4-(1-(2-methoxyethyl)-1H-benzo[d]imidazol-2-yl)-2,3,4,5-tetrahydrobenzo[f][1,4]oxazepine-7-carboxamide;
N-hydroxy-4-((5-isopropylpyridin-2-yl)methyl)-2-oxo-2,3,4,5-tetrahydro-1H-benzo[e][1,4]diazepine-7-carboxamide;
N-hydroxy-2-oxo-4-(pyridin-4-ylmethyl)-2,3,4,5-tetrahydro-1H-benzo[e][1,4]diazepine-7-carboxamide;
N-hydroxy-2-oxo-4-(pyridin-2-ylmethyl)-2,3,4,5-tetrahydro-1H-benzo[e][1,4]diazepine-7-carboxamide;
N-hydroxy-2-oxo-4-(thiazol-2-ylmethyl)-2,3,4,5-tetrahydro-1H-benzo[e][1,4]diazepine-7-carboxamide;
N-hydroxy-4-(4-isopropoxybenzyl)-2-oxo-2,3,4,5-tetrahydro-1H-benzo[e][1,4]diazepine-7-carboxamide;
N-hydroxy-2-oxo-4-(4-(trifluoromethoxy)benzyl)-2,3,4,5-tetrahydro-1H-benzo[e][1,4]diazepine-7-carboxamide;
N-hydroxy-2-oxo-4-(3-phenoxybenzyl)-2,3,4,5-tetrahydro-1H-benzo[e][1,4]diazepine-7-carboxamide;
N-hydroxy-2-oxo-4-(4-phenoxybenzyl)-2,3,4,5-tetrahydro-1H-benzo[e][1,4]diazepine-7-carboxamide;
N-hydroxy-2-oxo-4-(3-(trifluoromethoxy)benzyl)-2,3,4,5-tetrahydro-1H-benzo[e][1,4]diazepine-7-carboxamide;
N-hydroxy-2-oxo-4-(2-(trifluoromethoxy)benzyl)-2,3,4,5-tetrahydro-1H-benzo[e][1,4]diazepine-7-carboxamide;
N-hydroxy-2-oxo-4-(4-(pyridin-2-yl)benzyl)-2,3,4,5-tetrahydro-1H-benzo[e][1,4]diazepine-7-carboxamide;
4-(4-(1H-pyrazol-1-yl)benzyl)-N-hydroxy-2-oxo-2,3,4,5-tetrahydro-1H-benzo[e][1,4]diazepine-7-carboxamide;

4-(4-cyanobenzyl)-N-hydroxy-2-oxo-2,3,4,5-tetrahydro-1H-benzo[e][1,4]diazepine-7-carboxamide;
N-hydroxy-2-oxo-4-(pyrimidin-5-ylmethyl)-2,3,4,5-tetrahydro-1H-benzo[e][1,4]diazepine-7-carboxamide;
N-hydroxy-4-(naphthalen-1-ylmethyl)-2-oxo-2,3,4,5-tetrahydro-1H-benzo[e][1,4]diazepine-7-carboxamide;
4-((2-(3-fluorophenyl)oxazol-4-yl)methyl)-N-hydroxy-2-oxo-2,3,4,5-tetrahydro-1H-benzo[e][1,4]diazepine-7-carboxamide;
4-(3-((dimethylamino)methyl)benzyl)-N-hydroxy-2-oxo-2,3,4,5-tetrahydro-1H-benzo[e][1,4]diazepine-7-carboxamide;
4-benzyl-N-hydroxy-2-oxo-2,3,4,5-tetrahydro-1H-benzo[e][1,4]diazepine-7-carboxamide;
N-hydroxy-4-(4-isopropylbenzyl)-2-oxo-2,3,4,5-tetrahydro-1H-benzo[e][1,4]diazepine-7-carboxamide;
4-(4-chlorobenzyl)-N-hydroxy-2-oxo-2,3,4,5-tetrahydro-1H-benzo[e][1,4]diazepine-7-carboxamide;
4-(2,5-difluorobenzyl)-N-hydroxy-2-oxo-2,3,4,5-tetrahydro-1H-benzo[e][1,4]diazepine-7-carboxamide;
4-(3,5-difluorobenzyl)-N-hydroxy-2-oxo-2,3,4,5-tetrahydro-1H-benzo[e][1,4]diazepine-7-carboxamide;
4-(3,5-dichlorobenzyl)-N-hydroxy-2-oxo-2,3,4,5-tetrahydro-1H-benzo[e][1,4]diazepine-7-carboxamide;
4-(2-fluoro-4-methoxybenzyl)-N-hydroxy-2-oxo-2,3,4,5-tetrahydro-1H-benzo[e][1,4]diazepine-7-carboxamide;
4-(2-chlorobenzyl)-N-hydroxy-2-oxo-2,3,4,5-tetrahydro-1H-benzo[e][1,4]diazepine-7-carboxamide;
4-((2,2-difluorobenzo[d][1,3]dioxol-4-yl)methyl)-N-hydroxy-2-oxo-2,3,4,5-tetrahydro-1H-benzo[e][1,4]diazepine-7-carboxamide;
N-hydroxy-2-oxo-4-(pyridin-3-ylmethyl)-2,3,4,5-tetrahydro-1H-benzo[e][1,4]diazepine-7-carboxamide;
N-hydroxy-4-((1-methyl-1H-imidazol-2-yl)methyl)-2-oxo-2,3,4,5-tetrahydro-1H-benzo[e][1,4]diazepine-7-carboxamide;
4-((1-acetylpiperidin-3-yl)methyl)-N-hydroxy-2-oxo-2,3,4,5-tetrahydro-1H-benzo[e][1,4]diazepine-7-carboxamide;
4-(imidazo[1,2-a]pyridin-2-ylmethyl)-N-hydroxy-2-oxo-2,3,4,5-tetrahydro-1H-benzo[e][1,4]diazepine-7-carboxamide;
4-(cyclopropylmethyl)-N-hydroxy-2-oxo-2,3,4,5-tetrahydro-1H-benzo[e][1,4]diazepine-7-carboxamide;
N-hydroxy-2-oxo-4-((tetrahydrofuran-3-yl)methyl)-2,3,4,5-tetrahydro-1H-benzo[e][1,4]diazepine-7-carboxamide;
4-((4,5-dimethylthiazol-2-yl)methyl)-N-hydroxy-2-oxo-2,3,4,5-tetrahydro-1H-benzo[e][1,4]diazepine-7-carboxamide;
4-(3-chlorobenzyl)-N-hydroxy-2-oxo-2,3,4,5-tetrahydro-1H-benzo[e][1,4]diazepine-7-carboxamide;
4-(4-(tert-butoxy)benzyl)-N-hydroxy-2-oxo-2,3,4,5-tetrahydro-1H-benzo[e][1,4]diazepine-7-carboxamide;
N-hydroxy-4-((1-isopropylpiperidin-4-yl)methyl)-2-oxo-2,3,4,5-tetrahydro-1H-benzo[e][1,4]diazepine-7-carboxamide;
4-(4-(1H-pyrrol-1-yl)benzyl)-N-hydroxy-2-oxo-2,3,4,5-tetrahydro-1H-benzo[e][1,4]diazepine-7-carboxamide;
N-hydroxy-4-(naphthalen-2-ylmethyl)-2-oxo-2,3,4,5-tetrahydro-1H-benzo[e][1,4]diazepine-7-carboxamide;
N-hydroxy-4-((2-morpholinopyridin-4-yl)methyl)-2-oxo-2,3,4,5-tetrahydro-1H-benzo[e][1,4]diazepine-7-carboxamide;
4-(imidazo[1,2-a]pyridin-7-ylmethyl)-N-hydroxy-2-oxo-2,3,4,5-tetrahydro-1H-benzo[e][1,4]diazepine-7-carboxamide;
N-hydroxy-2-oxo-4-(4-(thiazol-2-yl)benzyl)-2,3,4,5-tetrahydro-1H-benzo[e][1,4]diazepine-7-carboxamide;
N-hydroxy-4-((6-methoxypyridin-3-yl)methyl)-2,3,4,5-tetrahydrobenzo[f][1,4]oxazepine-8-carboxamide;
N-hydroxy-4-((6-methoxypyridin-3-yl)methyl)-2,3,4,5-tetrahydrobenzo[f][1,4]oxazepine-7-carboxamide;
N-hydroxy-4-((5-methoxypyridin-2-yl)methyl)-2,3,4,5-tetrahydrobenzo[f][1,4]oxazepine-8-carboxamide;
N-hydroxy-4-((5-methoxypyridin-2-yl)methyl)-2,3,4,5-tetrahydrobenzo[f][1,4]oxazepine-7-carboxamide;
(R)—N8-hydroxy-2-isopropyl-N4-(4-methoxyphenyl)-2,3-dihydrobenzo[f][1,4]oxazepine-4,8(5H)-dicarboxamide;
(R)—N8-hydroxy-2-(methoxymethyl)-N4-(4-methoxyphenyl)-2,3-dihydrobenzo[f][1,4]oxazepine-4,8(5H)-dicarboxamide;
(S)—N8-hydroxy-2-(methoxymethyl)-N4-(4-methoxyphenyl)-2,3-dihydrobenzo[f][1,4]oxazepine-4,8(5H)-dicarboxamide;
(R)—N8-hydroxy-N4-(4-methoxyphenyl)-2-phenyl-2,3-dihydrobenzo[f][1,4]oxazepine-4,8(5H)-dicarboxamide;
(S)—N8-hydroxy-N4-(4-methoxyphenyl)-2-phenyl-2,3-dihydrobenzo[f][1,4]oxazepine-4,8(5H)-dicarboxamide;
N-hydroxy-4-methyl-4,5-dihydro-2H-spiro[benzo[f][1,4]oxazepine-3,1'-cyclopropane]-8-carboxamide;
N-hydroxy-4-phenyl-4,5-dihydro-2H-spiro[benzo[f][1,4]oxazepine-3,1'-cyclopropane]-8-carboxamide;
N-hydroxy-4-(4-methoxybenzyl)-4,5-dihydro-2H-spiro[benzo[f][1,4]oxazepine-3,1'-cyclopropane]-8-carboxamide;
(S)-3-ethyl-N-hydroxy-4-methyl-2,3,4,5-tetrahydrobenzo[f][1,4]oxazepine-8-carboxamide;
(S)-3-ethyl-N-hydroxy-4-(4-methoxybenzyl)-2,3,4,5-tetrahydrobenzo[f][1,4]oxazepine-8-carboxamide;
(S)-3-ethyl-N-hydroxy-4-phenyl-2,3,4,5-tetrahydrobenzo[f][1,4]oxazepine-8-carboxamide;
(S)-3-ethyl-N-hydroxy-4-(o-tolyl)-2,3,4,5-tetrahydrobenzo[f][1,4]oxazepine-8-carboxamide;
(S)—N-hydroxy-3-isopropyl-4-(pyridin-3-yl)-2,3,4,5-tetrahydrobenzo[f][1,4]oxazepine-8-carboxamide;
(S)—N-hydroxy-3-isopropyl-4-(pyridin-2-yl)-2,3,4,5-tetrahydrobenzo[f][1,4]oxazepine-8-carboxamide;
(S)—N-hydroxy-3-isopropyl-4-(pyridin-4-yl)-2,3,4,5-tetrahydrobenzo[f][1,4]oxazepine-8-carboxamide;
(S)—N-hydroxy-3-methyl-4-(o-tolyl)-2,3,4,5-tetrahydrobenzo[f][1,4]oxazepine-8-carboxamide;
(S)—N-hydroxy-4-(2-methoxyphenyl)-3-methyl-2,3,4,5-tetrahydrobenzo[f][1,4]oxazepine-8-carboxamide;
(S)—N-hydroxy-3-methyl-4-(pyridin-2-yl)-2,3,4,5-tetrahydrobenzo[f][1,4]oxazepine-8-carboxamide;
(S)—N-hydroxy-3-methyl-4-(pyrrolidine-1-carbonyl)-2,3,4,5-tetrahydrobenzo[f][1,4]oxazepine-8-carboxamide;
(S)—N-hydroxy-3-methyl-4-(morpholine-4-carbonyl)-2,3,4,5-tetrahydrobenzo[f][1,4]oxazepine-8-carboxamide;
(S)—N-hydroxy-4-(isoindoline-2-carbonyl)-3-methyl-2,3,4,5-tetrahydrobenzo[f][1,4]oxazepine-8-carboxamide;
(S)—N-hydroxy-4-(4-methoxypiperidine-1-carbonyl)-3-methyl-2,3,4,5-tetrahydrobenzo[f][1,4]oxazepine-8-carboxamide;
(S)—N-hydroxy-3-methyl-4-(4-methylpiperazine-1-carbonyl)-2,3,4,5-tetrahydrobenzo[f][1,4]oxazepine-8-carboxamide;
(3S)—N-hydroxy-3-methyl-4-(2-methylpiperidine-1-carbonyl)-2,3,4,5-tetrahydrobenzo[f][1,4]oxazepine-8-carboxamide;
(3S)—N-hydroxy-3-methyl-4-(3-methylmorpholine-4-carbonyl)-2,3,4,5-tetrahydrobenzo[f][1,4]oxazepine-8-carboxamide;
(S)—N-hydroxy-3-methyl-4-(oxetan-3-ylmethyl)-2,3,4,5-tetrahydrobenzo[f][1,4]oxazepine-8-carboxamide;

(S)-4-(4-fluorophenyl)-N-hydroxy-3-methyl-2,3,4,5-tetrahydrobenzo[f][1,4]oxazepine-8-carboxamide;
(S)-4-(3-fluorophenyl)-N-hydroxy-3-methyl-2,3,4,5-tetrahydrobenzo[f][1,4]oxazepine-8-carboxamide;
(S)—N-hydroxy-3-methyl-4-(4-(trifluoromethyl)phenyl)-2,3,4,5-tetrahydrobenzo[f][1,4]oxazepine-8-carboxamide;
methyl (S)-8-(hydroxycarbamoyl)-3-methyl-2,3-dihydrobenzo[f][1,4]oxazepine-4(5H)-carboxylate;
isopropyl (S)-8-(hydroxycarbamoyl)-3-methyl-2,3-dihydrobenzo[f][1,4]oxazepine-4(5H)-carboxylate;
(S)—N-hydroxy-3-methyl-4-(methylsulfonyl)-2,3,4,5-tetrahydrobenzo[f][1,4]oxazepine-8-carboxamide;
(S)-4-(ethylsulfonyl)-N-hydroxy-3-methyl-2,3,4,5-tetrahydrobenzo[f][1,4]oxazepine-8-carboxamide;
(S)—N8-hydroxy-N4,N4,3-trimethyl-2,3-dihydrobenzo[f][1,4]oxazepine-4,8(5H)-dicarboxamide;
(S)—N-hydroxy-4-((2-methoxyethyl)sulfonyl)-3-methyl-2,3,4,5-tetrahydrobenzo[f][1,4]oxazepine-8-carboxamide;
(S)—N8-hydroxy-N4-(2-methoxyethyl)-3-methyl-2,3-dihydrobenzo[f][1,4]oxazepine-4,8(5H)-dicarboxamide;
(S)—N8-hydroxy-3-methyl-N4-phenyl-2,3-dihydrobenzo[f][1,4]oxazepine-4,8(5H)-dicarboxamide;
(S)—N-hydroxy-3-methyl-4-(piperidine-1-carbonyl)-2,3,4,5-tetrahydrobenzo[f][1,4]oxazepine-8-carboxamide;
(S)—N8-hydroxy-N4-(2-methoxyethyl)-N4,3-dimethyl-2,3-dihydrobenzo[f][1,4]oxazepine-4,8(5H)-dicarboxamide;
(S)—N-hydroxy-3-methyl-4-(pyridin-3-yl)-2,3,4,5-tetrahydrobenzo[f][1,4]oxazepine-8-carboxamide;
(S)—N-hydroxy-3-methyl-4-(pyridin-4-yl)-2,3,4,5-tetrahydrobenzo[f][1,4]oxazepine-8-carboxamide;
(S)—N-hydroxy-4-(3-methoxypropyl)-3-methyl-2,3,4,5-tetrahydrobenzo[f][1,4]oxazepine-8-carboxamide;
(3S)-4-(1-(4-fluorophenyl)ethyl)-N-hydroxy-3-methyl-2,3,4,5-tetrahydrobenzo[f][1,4]oxazepine-8-carboxamide;
(S)—N-hydroxy-3-methyl-4-(3-morpholinopropyl)-2,3,4,5-tetrahydrobenzo[f][1,4]oxazepine-8-carboxamide;
(3S)—N-hydroxy-3-methyl-4-(2-(tetrahydrofuran-2-yl)ethyl)-2,3,4,5-tetrahydrobenzo[f][1,4]oxazepine-8-carboxamide;
(S)-4-ethyl-N-hydroxy-3-methyl-2,3,4,5-tetrahydrobenzo[f][1,4]oxazepine-8-carboxamide;
(S)—N-hydroxy-4-isopropyl-3-methyl-2,3,4,5-tetrahydrobenzo[f][1,4]oxazepine-8-carboxamide;
(S)—N-hydroxy-4-isobutyl-3-methyl-2,3,4,5-tetrahydrobenzo[f][1,4]oxazepine-8-carboxamide;
(S)-4-(cyclobutylmethyl)-N-hydroxy-3-methyl-2,3,4,5-tetrahydrobenzo[f][1,4]oxazepine-8-carboxamide;
(S)-4-(cyclopropylmethyl)-N-hydroxy-3-methyl-2,3,4,5-tetrahydrobenzo[f][1,4]oxazepine-8-carboxamide;
(S)-4-(4-fluorobenzyl)-N-hydroxy-3-methyl-2,3,4,5-tetrahydrobenzo[f][1,4]oxazepine-8-carboxamide;
(S)-4-(cyclohexylmethyl)-N-hydroxy-3-methyl-2,3,4,5-tetrahydrobenzo[f][1,4]oxazepine-8-carboxamide;
(S)—N-hydroxy-3-methyl-4-(2-morpholinoethyl)-2,3,4,5-tetrahydrobenzo[f][1,4]oxazepine-8-carboxamide;
(S)—N-hydroxy-4-(2-methoxyethyl)-3-methyl-2,3,4,5-tetrahydrobenzo[f][1,4]oxazepine-8-carboxamide;
(S)-4-(cyclopentylmethyl)-N-hydroxy-3-methyl-2,3,4,5-tetrahydrobenzo[f][1,4]oxazepine-8-carboxamide;
(3S)—N-hydroxy-3-methyl-4-((tetrahydrofuran-2-yl)methyl)-2,3,4,5-tetrahydrobenzo[f][1,4]oxazepine-8-carboxamide;
(S)-4-cyclopentyl-N-hydroxy-3-methyl-2,3,4,5-tetrahydrobenzo[f][1,4]oxazepine-8-carboxamide;
(S)-4-((4-fluorophenyl)sulfonyl)-N-hydroxy-3-methyl-2,3,4,5-tetrahydrobenzo[f][1,4]oxazepine-8-carboxamide;
cyclopentyl (S)-8-(hydroxycarbamoyl)-3-methyl-2,3-dihydrobenzo[f][1,4]oxazepine-4(5H)-carboxylate;
cyclohexyl (S)-8-(hydroxycarbamoyl)-3-methyl-2,3-dihydrobenzo[f][1,4]oxazepine-4(5H)-carboxylate;
(S)—N8-hydroxy-N4,3-dimethyl-N4-phenyl-2,3-dihydrobenzo[f][1,4]oxazepine-4,8(5H)-dicarboxamide;
ethyl (S)-8-(hydroxycarbamoyl)-3-methyl-2,3-dihydrobenzo[f][1,4]oxazepine-4(5H)-carboxylate;
cyclobutyl (S)-8-(hydroxycarbamoyl)-3-methyl-2,3-dihydrobenzo[f][1,4]oxazepine-4(5H)-carboxylate;
tetrahydro-2H-pyran-4-yl (S)-8-(hydroxycarbamoyl)-3-methyl-2,3-dihydrobenzo[f][1,4]oxazepine-4(5H)-carboxylate;
4-fluorophenyl (S)-8-(hydroxycarbamoyl)-3-methyl-2,3-dihydrobenzo[f][1,4]oxazepine-4(5H)-carboxylate;
(S)—N-hydroxy-3-methyl-4-(oxetan-3-yl)-2,3,4,5-tetrahydrobenzo[f][1,4]oxazepine-8-carboxamide;
(R)—N-hydroxy-3-(methoxymethyl)-4-methyl-2,3,4,5-tetrahydrobenzo[f][1,4]oxazepine-8-carboxamide;
(R)—N-hydroxy-4-(4-methoxybenzyl)-3-(methoxymethyl)-2,3,4,5-tetrahydrobenzo[f][1,4]oxazepine-8-carboxamide;
(R)—N-hydroxy-3-(methoxymethyl)-4-phenyl-2,3,4,5-tetrahydrobenzo[f][1,4]oxazepine-8-carboxamide;
(R)—N-hydroxy-3-(methoxymethyl)-4-(o-tolyl)-2,3,4,5-tetrahydrobenzo[f][1,4]oxazepine-8-carboxamide;
(S)—N-hydroxy-3-(methoxymethyl)-4-methyl-2,3,4,5-tetrahydrobenzo[f][1,4]oxazepine-8-carboxamide;
(S)—N-hydroxy-4-(4-methoxybenzyl)-3-(methoxymethyl)-2,3,4,5-tetrahydrobenzo[f][1,4]oxazepine-8-carboxamide;
(S)—N-hydroxy-3-(methoxymethyl)-4-phenyl-2,3,4,5-tetrahydrobenzo[f][1,4]oxazepine-8-carboxamide;
(S)—N-hydroxy-3-(methoxymethyl)-4-(o-tolyl)-2,3,4,5-tetrahydrobenzo[f][1,4]oxazepine-8-carboxamid;
N-hydroxy-4-(pyrrolidine-1-carbonyl)-2,3,4,5-tetrahydrobenzo[f][1,4]oxazepine-8-carboxamide;
N-hydroxy-4-(morpholine-4-carbonyl)-2,3,4,5-tetrahydrobenzo[f][1,4]oxazepine-8-carboxamide;
N-hydroxy-4-(4-methylpiperazine-1-carbonyl)-2,3,4,5-tetrahydrobenzo[f][1,4]oxazepine-8-carboxamide;
N-hydroxy-4-(4-methoxypiperidine-1-carbonyl)-2,3,4,5-tetrahydrobenzo[f][1,4]oxazepine-8-carboxamide;
N-hydroxy-4-(isoindoline-2-carbonyl)-2,3,4,5-tetrahydrobenzo[f][1,4]oxazepine-8-carboxamide;
N-hydroxy-4-(2-methylpiperidine-1-carbonyl)-2,3,4,5-tetrahydrobenzo[f][1,4]oxazepine-8-carboxamide;
N-hydroxy-4-(3-methylmorpholine-4-carbonyl)-2,3,4,5-tetrahydrobenzo[f][1,4]oxazepine-8-carboxamide;
(R)—N-hydroxy-4-(4-methoxybenzyl)-5-methyl-2,3,4,5-tetrahydrobenzo[f][1,4]oxazepine-8-carboxamide;
(S)—N-hydroxy-4-(4-methoxybenzyl)-5-methyl-2,3,4,5-tetrahydrobenzo[f][1,4]oxazepine-8-carboxamide;
(S)—N-hydroxy-3-methyl-4-(3-(trifluoromethyl)phenyl)-2,3,4,5-tetrahydrobenzo[f][1,4]oxazepine-8-carboxamide;
(S)—N-hydroxy-3-methyl-4-(4-(trifluoromethoxy)phenyl)-2,3,4,5-tetrahydrobenzo[f][1,4]oxazepine-8-carboxamide;
(S)-4-(4-chlorophenyl)-N-hydroxy-3-methyl-2,3,4,5-tetrahydrobenzo[f][1,4]oxazepine-8-carboxamide;
(S)-4-(2-chlorophenyl)-N-hydroxy-3-methyl-2,3,4,5-tetrahydrobenzo[f][1,4]oxazepine-8-carboxamide;
(S)-4-(2-fluorophenyl)-N-hydroxy-3-methyl-2,3,4,5-tetrahydrobenzo[f][1,4]oxazepine-8-carboxamide;
(S)-4-(azetidine-1-carbonyl)-N-hydroxy-3-methyl-2,3,4,5-tetrahydrobenzo[f][1,4]oxazepine-8-carboxamide;

(S)—N-hydroxy-4-(3-methoxyazetidine-1-carbonyl)-3-methyl-2,3,4,5-tetrahydrobenzo[f][1,4]oxazepine-8-carboxamide;
(3S)—N-hydroxy-4-(3-methoxypyrrolidine-1-carbonyl)-3-methyl-2,3,4,5-tetrahydrobenzo[f][1,4]oxazepine-8-carboxamide;
(S)—N8-hydroxy-3-methyl-N4-(pyridin-3-yl)-2,3-dihydrobenzo[f][14]oxazepine-4,8(5H)-dicarboxamide;
(S)—N4-cyclohexyl-N8-hydroxy-3-methyl-2,3-dihydrobenzo[f][1,4]oxazepine-4,8(5H)-dicarboxamide;
(S)—N8-hydroxy-3-methyl-N4-(pyridin-2-yl)-2,3-dihydrobenzo[f][1,4]oxazepine-4,8(5H)-dicarboxamide;
(S)—N8-hydroxy-3-methyl-N4-(tetrahydro-2H-pyran-4-yl)-2,3-dihydrobenzo[f][1,4]oxazepine-4,8(5H)-dicarboxamide;
(S)—N8-hydroxy-N4,3-dimethyl-N4-(tetrahydro-2H-pyran-4-yl)-2,3-dihydrobenzo[f][1,4]oxazepine-4,8(5H)-dicarboxamide;
(S)—N8-hydroxy-3-methyl-N4-(pyridin-4-yl)-2,3-dihydrobenzo[f][1,4]oxazepine-4,8(5H)-dicarboxamide;
(S)-4-((1R,5R)-8-oxa-3-azabicyclo[3.2.1]octane-3-carbonyl)-N-hydroxy-3-methyl-2,3,4,5-tetrahydrobenzo[f][1,4]oxazepine-8-carboxamide;
(S)-4-((1S,5S)-8-oxa-3-azabicyclo[3.2.1]octane-3-carbonyl)-N-hydroxy-3-methyl-2,3,4,5-tetrahydrobenzo[f][1,4]oxazepine-8-carboxamide;
(S)-4-(3,4-dihydro-2H-benzo[b][1,4]oxazine-4-carbonyl)-N-hydroxy-3-methyl-2,3,4,5-tetrahydrobenzo[f][1,4]oxazepine-8-carboxamide;
N-hydroxy-2-oxo-4-(piperidine-1-carbonyl)-2,3,4,5-tetrahydro-1H-benzo[e][1,4]diazepine-7-carboxamide;
(S)-3-benzyl-N-hydroxy-4-(morpholine-4-carbonyl)-2,3,4,5-tetrahydrobenzo[f][1,4]oxazepine-8-carboxamide;
In another embodiment, non-limiting illustrative compounds of the disclosure include:
N8-hydroxy-N4-(tetrahydro-2H-pyran-4-yl)-N4-(3-(trifluoromethyl)phenyl)-2,3-dihydrobenzo[f][1,4]oxazepine-4,8(5H)-dicarboxamide;
(R)—N-hydroxy-4-(morpholine-4-carbonyl)-3-((trifluoromethoxy)methyl)-2,3,4,5-tetrahydrobenzo[f][1,4]oxazepine-8-carboxamide;
(3S)—N-hydroxy-3,5-dimethyl-4-(morpholine-4-carbonyl)-2,3,4,5-tetrahydrobenzo[f][1,4]oxazepine-8-carboxamide; or
(S)-6-fluoro-N-hydroxy-3-methyl-4-(morpholine-4-carbonyl)-2,3,4,5-tetrahydrobenzo[f][1,4]oxazepine-8-carboxamide.

In another embodiment of the disclosure, the compounds of Formula I are enantiomers. In some embodiments the compounds are the (S)-enantiomer. In other embodiments the compounds are the (R)-enantiomer. In yet other embodiments, the compounds of Formula I may be (+) or (−) enantiomers.

It should be understood that all isomeric forms are included within the present disclosure, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Methods of Synthesizing the Disclosed Compounds

The compounds of the present disclosure may be made by a variety of methods, including standard chemistry. Suitable synthetic routes are depicted in the schemes given below.

The compounds of Formula I may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. These methods include, but are not limited, to those methods described below. Compounds of the present disclosure can be synthesized by following the steps outlined in General Schemes 1, 2, 3, 4, and 5 which comprise different sequences of assembling intermediates 2a, 2b, 2c, 2d, 2e, 2f, 2g, 2h, 2i, 2j, 2k, 2m, 2n, 2o, 2p, 2q, 2r, 2s, 2t, 2u, 2v, 2w, 2x, 2y, 2z, 2aa, 2bb, and 2cc. Starting materials are either commercially available or made by known procedures in the reported literature or as illustrated.

Scheme 1. General synthesis of ethers, thioethers, or sulfones described in the disclosure.

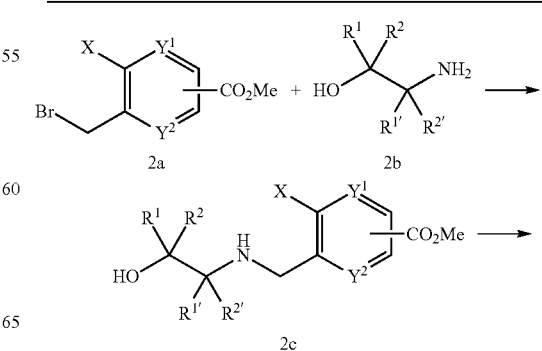

-continued

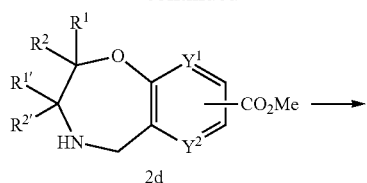

2d

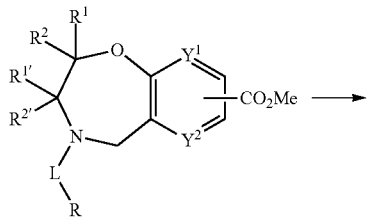

2e

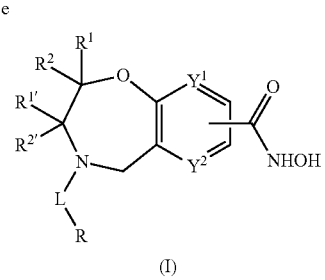

(I)

X = Halogen wherein L, R, $R^1$, $R^2$, $R^{1'}$, $R^{2'}$, $Y^1$ and $Y^2$ are defined as in Formula (I).

The general way of preparing target molecules of Formula (I) by using intermediates 2a, 2b, 2c, 2d, and 2e is outlined in General Scheme 1. Nucleophilic addition of alcohol 2b to Intermediate 2a using a base, e.g., potassium carbonate ($K_2CO_3$), in a solvent, e.g., acetonitrile (MeCN), provides Intermediate 2c. Cyclization of Intermediate 2c in the presence of a catalytic amount of a metal catalyst, e.g., copper iodide (CuI), palladium acetate (Pd(OAc)$_2$), etc., and a base, e.g., potassium carbonate ($K_2CO_3$), in a solvent, e.g., isopropanol (i-PrOH), optionally at elevated temperature provides Intermediate 2d. Addition of the R-L moiety can be achieved, for instance, via alkylation, reductive amination, arylation, urea formation, or sulfonation. For example, alkylation of Intermediate 2d with an alkyl halide in the presence of a base, e.g., sodium hydride (NaH), and optionally at elevated temperatures provides Intermediate 2e. Treatment of Intermediate 2e with hydroxylamine and a base, e.g., aqueous sodium hydroxide (aq. NaOH) in a solvent, e.g., tetrahydrofuran (THF) and/or methanol (MeOH), provides compounds of Formula (I).

Scheme 2. General synthesis of amides described in the disclosure.

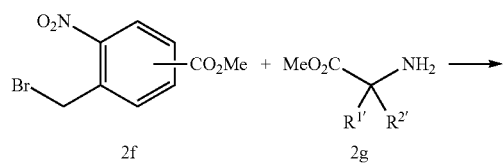

2f                2g

-continued

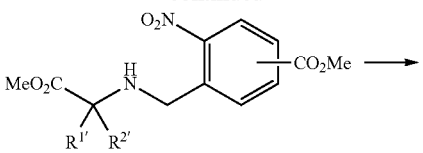

2h

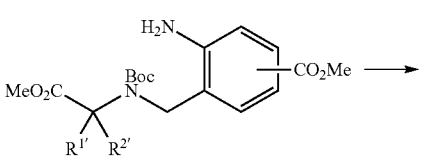

2i

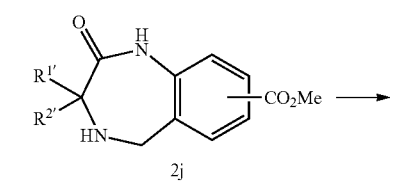

2j

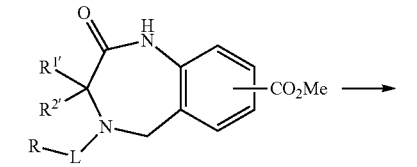

2k

[structure]

(I)

wherein L, R, $R^{1'}$, and $R^{2'}$ are defined as in Formula (I).

The general way of preparing target molecules of Formula (I) by using intermediates 2f, 2g, 2h, 2i, 2j, and 2k is outlined in General Scheme 2. Nucleophilic addition of amine 2g to Intermediate 2f using a base, e.g., N,N-diisopropylethylamine (DIEA), and in a solvent, e.g., MeCN, dichloromethane (DCM), or DMF, provides Intermediate 2h. Protection of the amine group in intermediate 2h with a typical acid labile protecting group (e.g., t-butoxycarbonyl (Boc)) using aprotecting group precursor and 4-Dimethylaminopyridine (DMAP), in a solvent e.g., DCM or tetrahydrofuran (THF), followed by hydrogenation in the presence of a metal catalyst, e.g., palladium on carbon, and hydrogen ($H_2$) gas in a solvent, e.g., DCM, provides Intermediate 2i. Cyclization of Intermediate 2i in the presence of a base, e.g., potassium carbonate ($K_2CO_3$), and in a solvent, e.g., isopropanol (i-PrOH), optionally at elevated temperatures provides Intermediate 2j. Addition of the R-L moiety can be achieved via alkylation, reductive amination, arylation, urea formation, or sulfonation. For example, alkylation of Intermediate 2j with an alkyl halide in the presence of a base, e.g., sodium hydride (NaH), and optionally at elevated temperatures provides Intermediate 2k. Treatment of Intermediate 2k with hydroxylamine and a base, e.g., aqueous sodium hydroxide (aq. NaOH) in a solvent, e.g., tetrahydrofuran (THF) and/or methanol (MeOH), provides compounds of Formula (I).

Scheme 3. General synthesis of sulfonamides described in the disclosure.

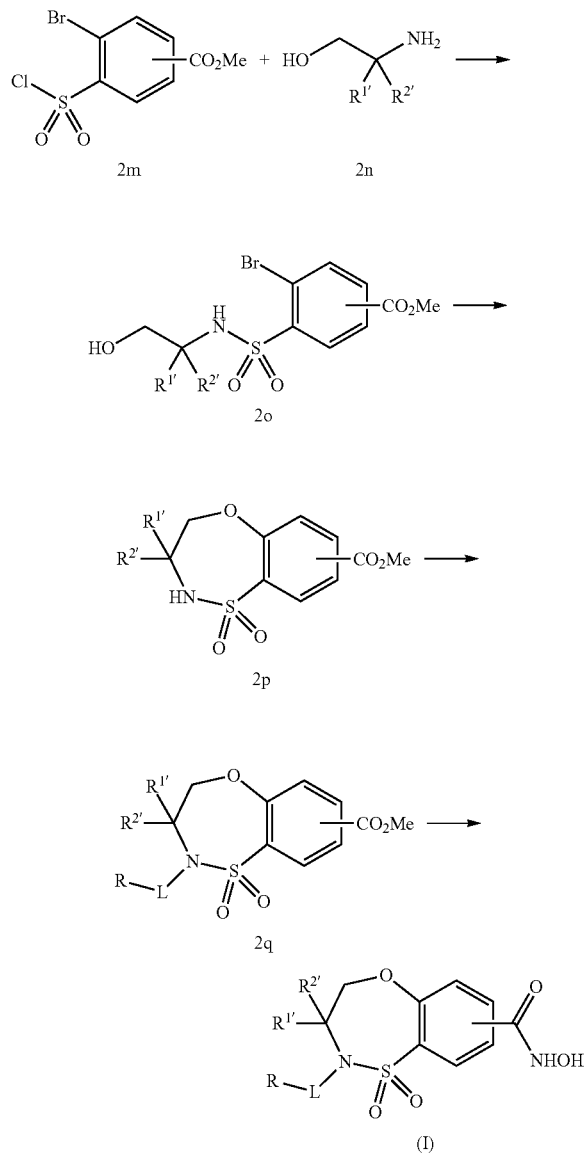

Scheme 4. General synthesis of amides described in the disclosure.

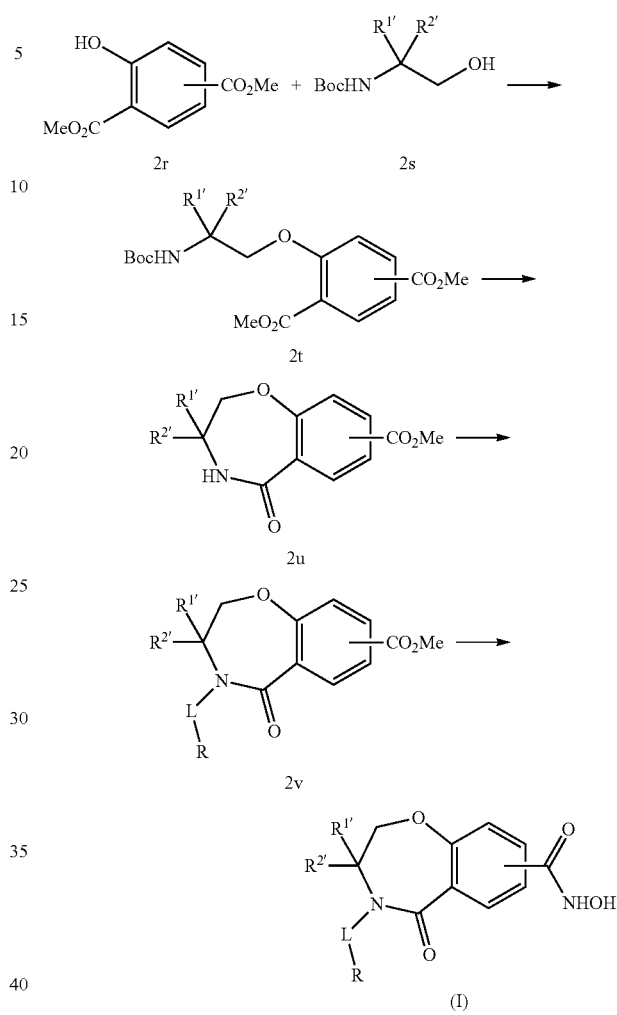

wherein L, R, $R^{1'}$, and $R^{2'}$ are defined as in Formula (I).

The general way of preparing target molecules of Formula (I) by using intermediates 2m, 2n, 2o, 2p, and 2q, is outlined in General Scheme 3. Sulfonylation of alcohol 2n with Intermediate 2m in the presence of a metal oxide, e.g., MgO, and in a solvent, e.g., THF, provides Intermediate 2o. Cyclization of Intermediate 2o in the presence of a base, e.g., sodium methoxide (NaOMe), and in a solvent, e.g., methanol (MeOH), i-PrOH, etc., provides Intermediate 2p. Addition of the R-L moiety can be achieved via alkylation, reductive amination, arylation, urea formation, or sulfonation. For example, alkylation of Intermediate 2p with an alkyl halide in the presence of a base, e.g., sodium hydride (NaH), and optionally at elevated temperatures provides Intermediate 2q. Treatment of Intermediate 2q with hydroxylamine and a base, e.g., aqueous sodium hydroxide (aq. NaOH), in a solvent, e.g., tetrahydrofuran (THF) and/or methanol (MeOH), provides compounds of Formula (I).

wherein L, R, $R^{1'}$, and $R^{2'}$ are defined as in Formula (I).

The general way of preparing target molecules of Formula (I) by using intermediates 2r, 2s, 2t, 2u, and 2v, is outlined in General Scheme 4. Intermediate 2t can be obtained by alkylation of 2s with phenol 2r using a Mitsunobu reagent (e.g., diethyl azodicarboxylate (DEAD) or diisopropyl azodicarboxylate (DIAD)), and triphenyl phosphine in a solvent, e.g., tetrahydrofuran (THF), dichloromethane (DCM). Deprotection of intermediate 2t using a strong acid such as trifluoroacetic acid (TFA) in a solvent, e.g., dichloromethane (DCM), followed by cyclization in the presence of a base, e.g., triethylamine ($Et_3N$), and optionally in a solvent, e.g., THF, MeOH, etc., at elevated temperature provides Intermediate 2u. Addition of the R-L moiety can be achieved via alkylation, reductive amination, arylation, urea formation, or sulfonation. For example, alkylation of Intermediate 2u with an alkyl halide in the presence of a base, e.g., sodium hydride (NaH), and optionally at elevated temperatures provides Intermediate 2v. Treatment of Intermediate 2v with hydroxylamine and a base, e.g., aqueous sodium hydroxide (aq. NaOH) in a solvent, e.g., tetrahydrofuran (THF) and/or methanol (MeOH), provides compounds of Formula (I).

Scheme 5. General synthesis of chiral compounds described in the disclosure.

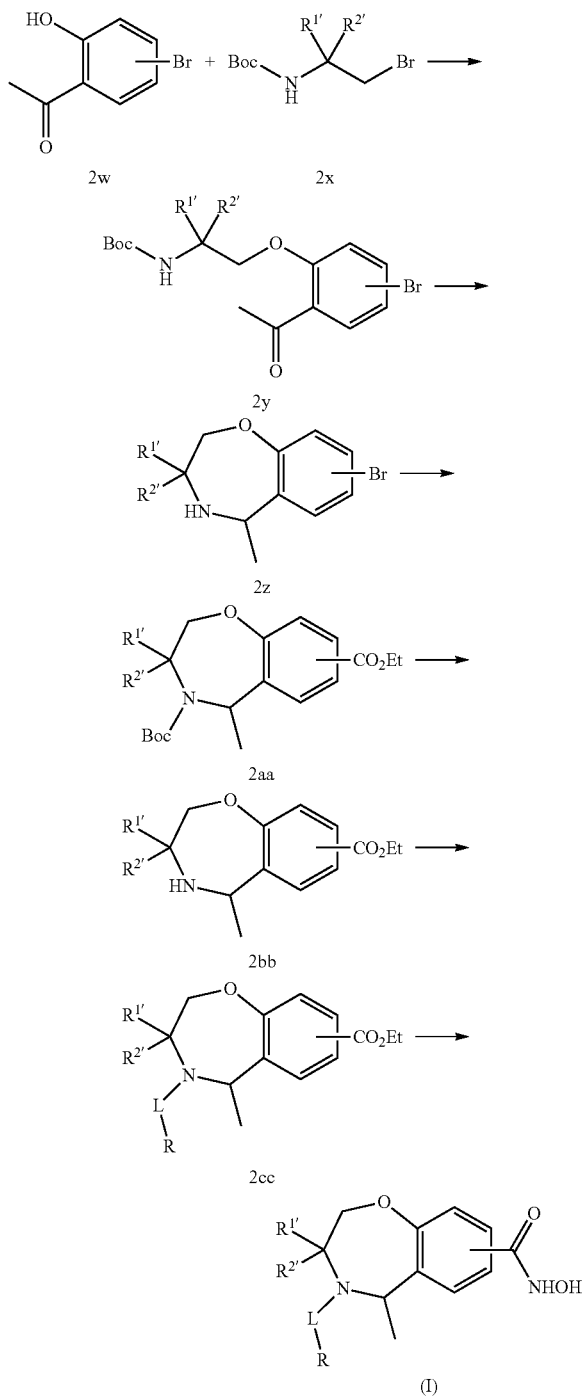

wherein L, R, $R^{1'}$, and $R^{2'}$ are defined as in Formula (I).

The general way of preparing target molecules of Formula (I) by using intermediates 2w, 2x, 2y, 2z, 2aa, 2bb, and 2cc, is outlined in General Scheme 5. Alkylation of phenol 2w with Intermediate 2x using potassium iodide (KI) and a base, e.g., potassium carbonate ($K_2CO_3$), in a solvent, e.g., MeCN, THF, etc., provides Intermediate 2y. Deprotection of Intermediate 2y using a strong acid such as trifluoroacetic acid (TFA) in a solvent, e.g., dichloromethane (DCM) followed by cyclization via intramolecular reductive amination in the presence of sodium borohydride or sodium cyanoborohydride in a solvent, e.g., THF, MeOH, etc., provides Intermediate 2z. Protection of the amine group in intermediate 2z with a typical acid labile protecting group (e.g., t-butoxycarbonyl (Boc)) using a protecting group precursor and optionally 4-DMAP in a solvent e.g., DCM or tetrahydrofuran (THF), followed by carbonylation in the presence of a metal catalyst, e.g., [1,1'-Bis(diphenylphosphino)ferrocene]palladium(II) dichloride, and carbon monoxide (CO) gas in a solvent, e.g., DCM, provides Intermediate 2aa. Deprotection of intermediate 2aa using a strong acid such as trifluoroacetic acid (TFA) in a solvent, e.g., dichloromethane (DCM) provides Intermediate 2bb. Addition of the R-L moiety can be achieved via alkylation, reductive amination, arylation, urea formation, or sulfonation. For example, alkylation of Intermediate 2bb with an alkyl halide in the presence of a base, e.g., sodium hydride (NaH), and optionally at elevated temperatures provides Intermediate 2cc. Treatment of Intermediate 2cc with hydroxylamine and a base, e.g., aqueous sodium hydroxide (aq. NaOH), in a solvent, e.g., tetrahydrofuran (THF) and/or methanol (MeOH), provides compounds of Formula (I).

Methods of Using the Disclosed Compounds

Another aspect of the disclosure relates to a method of treating a disease associated with HDAC, e.g., HDAC6, modulation in a subject in need thereof. The method involves administering to a patient in need of treatment for diseases or disorders associated with HDAC, e.g., HDAC6, modulation an effective amount of a compound of Formula I. In an embodiment, the disease can be, but is not limited to, cancer, neurodegenerative disease, neurodevelopmental disease, inflammatory or autoimmune disease, infection, metabolic disease, hematologic disease, or cardiovascular disease.

Another aspect of the disclosure is directed to a method of inhibiting an HDAC, e.g., HDAC6. The method involves administering to a patient in need thereof an effective amount of Formula I.

The present disclosure relates to compositions capable of modulating the activity of (e.g., inhibiting) HDACs, for instance HDAC6. The present disclosure also relates to the therapeutic use of such compounds.

One therapeutic use of the compounds of the present disclosure is to treat proliferative diseases or disorders such as cancer. Cancer can be understood as abnormal or unregulated cell growth within a patient and can include but is not limited to lung cancer, ovarian cancer, breast cancer, prostate cancer, pancreatic cancer, hepatocellular cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), and multiple myeloma.

One therapeutic use of the compounds of the present disclosure is to treat neurological diseases or disorders or neurodegeneration. Neurological disorders are understood as disorders of the nervous system (e.g., the brain and spinal cord). Neurological disorders or neurodegenerative diseases can include but are not limited to epilepsy, attention deficit disorder (ADD), Alzheimer's disease, Parkinson's Disease, Huntington's Disease, amyotrophic lateral sclerosis, spinal muscular atrophy, essential tremor, central nervous system trauma caused by tissue injury, oxidative stress-induced neuronal or axomal degeneration, and multiple sclerosis.

Another therapeutic use of the compounds of the present disclosure is to treat neurodevelopmental disorders. Neurodevelopmental disorders can include, but are not limited to, Rett syndrome.

Another therapeutic use of the compounds of the present disclosure is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-1β, and increased expression of the FOXP3 transcription factor.

Another therapeutic use of the compounds of the present disclosure is also to treat autoimmune diseases or disorders. Autoimmune disorders are understood as disorders wherein a host's own immune system responds to tissues and substances occurring naturally in the host's body. Autoimmune diseases can include but are not limited to Rheumatoid arthritis, spondylitis arthritis, psoriatic arthritis, multiple sclerosis, systemic lupus erythematosus, inflammatory bowel disease, graft versus host disease, transplant rejection, fibrotic disease, Crohn's Disease, type-1 diabetes, Eczema, and psoriasis.

Another therapeutic use of the compounds of the present disclosure is also to treat infectious diseases or disorders. Infections or infectious diseases are caused by the invasion of a foreign pathogen. The infection may be caused by, for instance, a bacteria, a fungus, or virus.

For example, a bacterial infection may be caused by a $E.$ $coli.$

Yet another therapeutic use of the compounds of the present disclosure is also to treat metabolic diseases or disorders. Metabolic diseases can be characterized as abnormalities in the way that a subject stores energy. Metabolic disorders can include but are not limited to metabolic syndrome, diabetes, obesity, high blood pressure, and heart failure.

Yet another therapeutic use of the compounds of the present disclosure is also to treat hematologic disorders. Hematologic diseases primarily affect the blood. Hematologic disorders can include but are not limited to anemia, lymphoma, and leukemia.

Yet another therapeutic use of the compounds of the present disclosure is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, atherosclerosis, peripheral artery disease, and heart failure.

Another aspect of the present disclosure relates to a compound of Formula (I), or a pharmaceutically acceptable salt, hydrate, solvate, prodrug, stereoisomer, or tautomer thereof, for use in treating or preventing a disease associated with HDAC6 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase.

In another aspect, the present disclosure relates to the use of a compound of Formula (I), or a pharmaceutically acceptable salt, hydrate, solvate, prodrug, stereoisomer, or tautomer thereof, in the manufacture of a medicament for treating or preventing a disease associated with HDAC6 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase.

In some embodiments, the cancer is cutaneous T-cell lymphoma, peripheral T-cell lymphoma, multiple myeloma, leukemia, lung, ovarian, breast, prostate, pancreatic, hepatocellular or renal cancer. In other embodiments, the neurodegenerative disease is Alzheimer's, Huntington's, Parkinson's, Amyotrophic Lateral Sclerosis, or spinal muscular atrophy. In other embodiments, the neurodevelopmental disorder is Rett syndrome. In yet other embodiments, the inflammatory or autoimmune disease is rheumatoid arthritis, spondylitis arthritis, psoriatic arthritis, psoriasis, multiple sclerosis, systemic lupus erythematosus, inflammatory bowel diseases, graft versus host disease, transplant rejection or fibrotic disease.

The disclosed compound can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanami dephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure relates to a pharmaceutical composition comprising a compound of Formula I and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present disclosure can inhibit HDACs such as HDAC6 by interacting with the zinc ($Zn^{2+}$) ion in the protein's active site via the hydroxamic acid group bound to the aromatic ring of the compound. The binding can prevent the zinc ion from interacting with its natural substrates, thus inhibiting the enzyme.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The present disclosure includes a number of unique features and advantages compared with other inhibitors of HDAC enzymes, for instance HDAC6. For instance, the present disclosure features a unique class of small molecule therapeutic agents of Formula I. The compounds were designed by using crystal structure information of HDAC ligand-protein complexes as well as advanced computational chemistry tools. These techniques led to the development of new chemical scaffolds that were iteratively refined to optimize key recognition features between the ligand and receptor known to be necessary for potency.

Definitions used in the following examples and elsewhere herein are:
BINAP 2,2'-bis(diphenylphosphino)-1,1'-binaphthalene
Boc: t-butoxycarbonyl
$CCl_4$: carbon tetrachloride
$CDCl_3$: deuterated chloroform
$CH_2Cl_2$: methylene chloride, dichloromethane
CO (g): carbon monoxide gas
$Cs_2CO_3$: cesium carbonate
$Cu(OAc)_2$ copper (II) acetate
CuI: copper (I) iodide
DEAD: diethyl azodicarboxylate
DIEA: diisopropylethylamine
DMA: dimethylacetamide
DMF: N,N-dimethylformamide
DMSO: dimethylsulfoxide
$Et_3N$: triethylamine
$Et_2O$: diethyl ether
EtOAc: EtOAc
h: hours
$H_2O$: water
HCl: hydrochloric acid
$H_4NHCO_3$: ammonium bicarbonate
Johnphos: (2-biphenyl)di-tert-butylphosphine
$K_2CO_3$: potassium carbonate
$KH_2PO_4$ potassium dihydrogen phosphate
MeCN: acetonitrile
MeOH: methanol MgSO$_4$: magnesium sulfate
NaBH(OAc)$_3$: sodium triacetoxyborohydride
min: minutes
Na(CN)BH$_3$: sodium cyanoborohydride
Na$_2$SO$_4$: sodium sulfate
NaHCO$_3$: sodium bicarbonate
NaOH: sodium hydroxide
NBS: N-bromosuccinimide
NH$_2$OH: hydroxylamine
NH$_4$Cl: ammonium chloride
NH$_4$HCO$_3$: ammonium bicarbonate
Pd(dppf)Cl$_2$: [1,1'-bis(diphenylphosphino)ferrocene]dichloropalladium(II)
Pd(dppf)Cl$_2$.CH$_2$Cl$_2$: [1,1'-bis(diphenylphosphino)ferrocene]dichloropalladium(II)-dichloromethane adduct
Pd(OAc)$_2$: palladium(II) acetate
Pd$_2$(dba)$_3$ tris(dibenzylideneacetone)dipalladium(0)
Pd$_2$(dba)$_3$.CHCl$_3$ tris(dibenzylideneacetone)dipalladium(0)-chloroform adduct
pet. ether: petroleum ether
prep-HPLC: preparatory high pressure liquid chromatography
prep-TLC: preparatory thin layer chromatography
RuPhos 2-dicyclohexylphosphino-2',6'-diisopropoxybiphenyl
RuPhos-Pd-G2 chloro(2-dicyclohexylphosphino-2',6'-diisopropoxy-1,1'-biphenyl)[2-(2'-amino-1,1'-biphenyl)]palladium(II)
TFA: trifluoroacetic acid
THF: tetrahydrofuran
Xantphos 4,5-bis(diphenylphosphino)-9,9-dimethylxanthene
XPhos-Pd-G3 (2-dicyclohexylphosphino-2',4',6'-triisopropyl-1,1'-biphenyl)[2-(2'-amino-1,1'-biphenyl)]palladium(II) methanesulfonate Example 1—Preparation of 4-(benzo[d]oxazol-2-yl)-N-hydroxy-2,3,4,5-tetrahydrobenzo[f][1,4]oxazepine-8-carboxamide

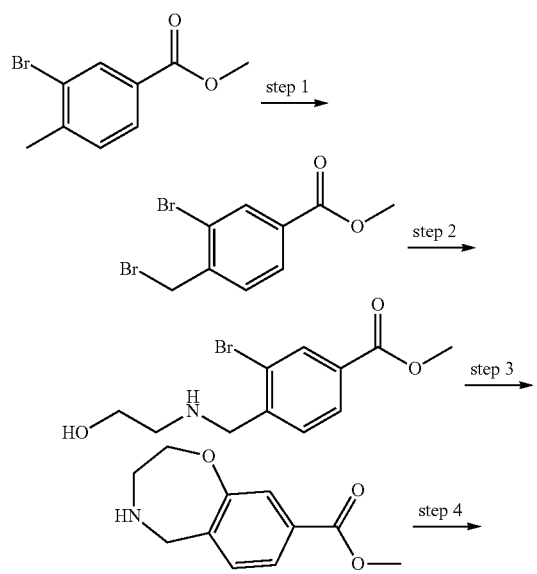

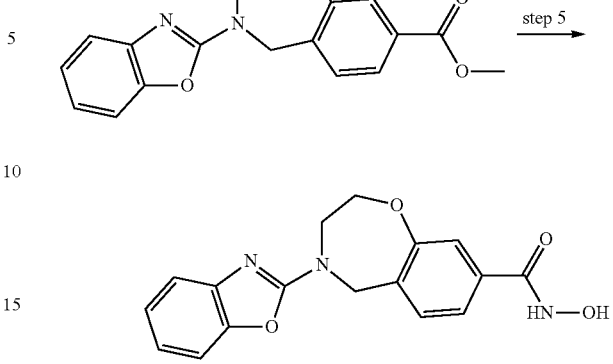

Step-1: Methyl 3-bromo-4-(bromomethyl)benzoate

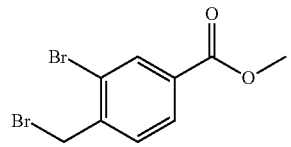

Methyl 3-bromo-4-methylbenzoate (25 g, 109.14 mmol, 1 equiv), NBS (21.5 g, 120.80 mmol, 1.11 equiv), benzoyl peroxide (146 mg, 0.57 mmol, 0.01 equiv), and CCl$_4$ (120 mL) were placed in a 250-mL round-bottom flask. The resulting solution was stirred overnight at 85° C. in an oil bath. The resulting mixture was cooled and concentrated under vacuum. The residue was purified by silica gel chromatography (EtOAc/pet. ether, 1:10) to afford the title compound as a white solid (20 g) and used without further purification.

Step-2: Methyl 3-bromo-4-((2-hydroxyethylamino)methyl)benzoate

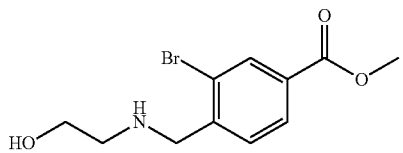 [SMILES: COC(=O)c1ccc(CNCCO)c(Br)c1]

Methyl 3-bromo-4-(bromomethyl)benzoate (20 g, 64.94 mmol, 1 equiv), K$_2$CO$_3$ (26.9 g, 194.63 mmol, 3 equiv), MeCN (100 mL), and 2-aminoethan-1-ol (4.76 g, 77.93 mmol, 1.20 equiv) were placed in a 250-mL round-bottom flask. The resulting solution was stirred for 2 h at −5° C. The resulting mixture was concentrated under vacuum, washed with water (50 mL) and EtOAc (50 mL). The organic layer was concentrated under vacuum and were placed in a 250-mL round-bottom flask. (MeOH/CH$_2$Cl$_2$, 1:20) to afford the title compound as a light yellow oil (16 g, 56% yield over 2 steps). MS: (ES, m/z): 288 [M+H]$^+$.

Step-3: Methyl 2,3,4,5-tetrahydrobenzo[f][1,4]oxazepine-8-carboxylate

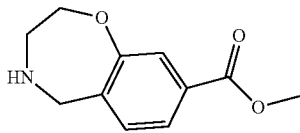

Methyl 3-bromo-4-((2-hydroxyethylamino)methyl)benzoate (7 g, 24.29 mmol, 1 equiv), $K_2CO_3$ (6.6 g, 47.75 mmol, 1.97 equiv), CuI (912 mg, 4.79 mmol, 0.20 equiv), and isopropanol (100 mL) were placed in a 250-mL round-bottom flask. The resulting solution was stirred overnight at 110° C. in an oil bath. The solution was cooled and the solids were filtered out. The filtrate was concentrated under vacuum and purified by silica gel chromatography (EtOAc/pet. ether, 1:1) to afford the title compound as a yellow oil (3 g, 60% yield). $^1$H-NMR (300 MHz, CDCl$_3$) δ(ppm): 7.70-7.68 (t, 2H), 7.26-7.22 (t, 1H), 4.13-4.09 (t, 2H), 4.05 (s, 2H), 3.93 (s, 3H), 3.50 (s, 1H), 3.30-3.28 (t, 2H). MS: (ES, m/z): 208 [M+H]$^+$.

Step-4: Methyl 4-(benzo[d]oxazol-2-yl)-2,3,4,5-tetrahydrobenzo[f][1,4]oxazepine-8-carboxylate

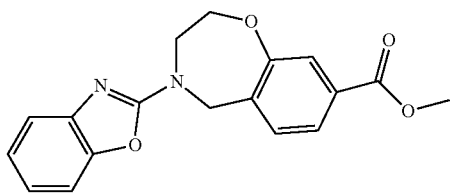 [SMILES: COC(=O)c1ccc2c(c1)OCCN(c1nc3ccccc3o1)C2]

Into a 100-mL round-bottom flask purged and maintained with an inert atmosphere of nitrogen, was placed methyl 2,3,4,5-tetrahydrobenzo[f][1,4]oxazepine-8-carboxylate (200 mg, 0.97 mmol, 1 equiv), 2-bromo-1H-1,3-benzoxazole (285 mg, 1.45 mmol, 1.5 equiv), CuI (37 mg, 0.19 mmol, 0.2 equiv), ethane-1,2-diol (0.1 mL) and phosphoperoxol potassium (263 mg, 1.95 mmol, 2 equiv). The resulting solution was stirred overnight at 110° C. in an oil bath. The resulting mixture was cooled and concentrated under vacuum. The residue was purified by silica gel chromatography (EtOAc/pet. ether, 1:5) to afford the title compound as a yellow oil (197 mg, 63% yield). MS: (ES, m/z): 325 [M+H]$^+$.

Step-5: 4-(Benzo[d]oxazol-2-yl)-N-hydroxy-2,3,4,5-tetrahydrobenzo[f][1,4]oxazepine-8-carboxamide

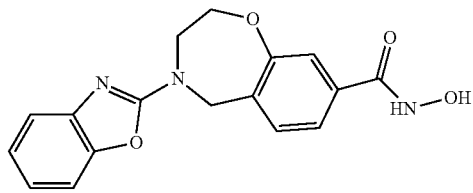 [SMILES: O=C(NO)c1ccc2c(c1)OCCN(c1nc3ccccc3o1)C2]

Into a 100-mL round-bottom flask, was placed methyl 4-(benzo[d]oxazol-2-yl)-2,3,4,5-tetrahydrobenzo[f][1,4]oxazepine-8-carboxylate (100 mg, 0.31 mmol, 1 equiv), NH$_2$OH (50% in water, 1 mL), aq. 1N NaOH (0.62 mL, 2 equiv), and THF (3 mL). The resulting solution was stirred overnight at 40° C. in an oil bath. The crude product (80 mg) was purified by Prep-HPLC (Column: Sunfire Prep C18 OBD, 5 μm, 19×150 mm; Mobile Phase A: Water/0.05% Formic Acid; Mobile Phase B: MeCN; Flow rate: 25 mL/min; Gradient: 5% B to 50% B in 9 min; Detector: UV 254, 220 nm) to afford the title compound as a pink solid (29 mg, 29% yield). $^1$H-NMR (400 MHz, DMSO-d$_6$) δ(ppm): 11.16 (s, 1H), 9.03 (s, 1H), 7.50-6.98 (t, 7H), 4.84 (s, 2H), 4.26-4.24 (t, 2H), 4.08-4.06 (t, 2H). MS: (ES, m/z): 326 [M+H]$^+$.

TABLE 1

The following compounds were prepared according to the method of Example 1.

| Structure | Found M + H | $^1$H-NMR (300 MHz, DMSO-d$_6$) δ(ppm) |
|---|---|---|
| 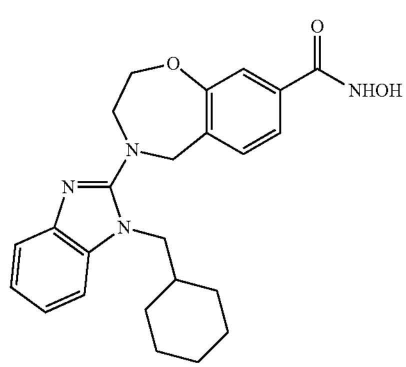 | (ES, m/z): 421 [M + H]$^+$ | 11.18 (s, 1H), 9.06 (s, 1H), 7.50-7.34 (m, 5H), 7.06-7.03 (m, 2H), 4.55-4.47 (t, 1H), 4.35 (s, 1H), 4.02 (d, 1H, ), 3.73 (s, 1H), 1.79 (s, 1H), 1.16-1.47 (m, 3H), 1.23-1.10 (m, 2H), 0.98-0.78 (m, 5H) |

TABLE 1-continued
The following compounds were prepared according to the method of Example 1.
| Structure | Found M + H | ¹H-NMR (300 MHz, DMSO-$d_6$) δ(ppm) |
|---|---|---|
| | (ES, m/z): 342 [M + H]⁺ | 10.98 (s, 1H), 9.04 (s, 1H), 7.75 (d, J = 7.8 Hz, 1H), 7.52-7.22 (m, 5H), 7.08-7.02 (m, 1H), 4.83 (s, 2H), 4.27-4.11 (m, 4H) |
| | (ES, m/z): 305 [M + H]⁺ | 11.16 (s, 1H), 9.03 (s, 1H), 8.18 (s, 1H), 7.39-7.20 (m, 3H), 3.99 (s, 2H), 3.75-3.73 (d, J = 8 Hz, 2H), 2.96 (s, 2H), 2.20-2.18 (d, J = 5.6 Hz, 2H), 1.70-1.63 (m, 4H), 1.47-1.46 (d, J = 8 Hz, 1H), 1.24-1.11 (m, 4H), 0.85-0.77 (m, 2H) |
| | (ES, m/z): 423 [M + H]⁺ | 11.25 (s, 1H), 9.06 (br s, 1H), 7.70-7.72 (m, 1H), 7.24-7.51 (m, 6H), 4.88 (s, 2H), 4.50 (s, 2H), 4.08-4.10 (d, J = 7.2 Hz, 2H), 3.91 (s, 2H), 3.53-3.59 (d, J = 24.4 Hz, 2H), 2.87-2.94 (m, 2H), 1.80-1.91 (m, 1H), 0.92 (s, 4H) |
Example 2—Preparation of N-hydroxy-4-phenyl-2,3,4,5-tetrahydrobenzo[f][1,4]oxazepine-8-carboxamide
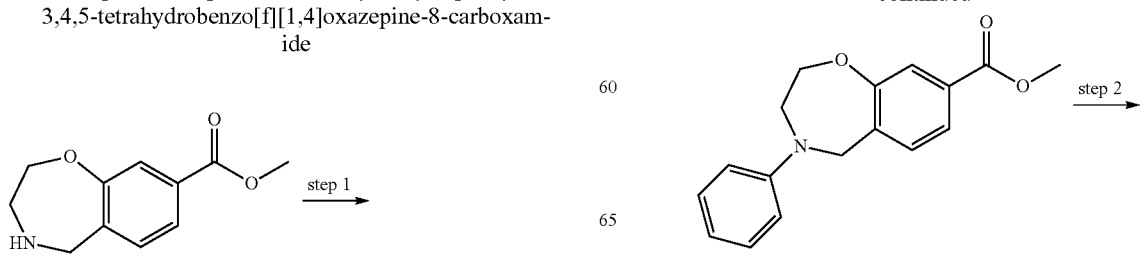

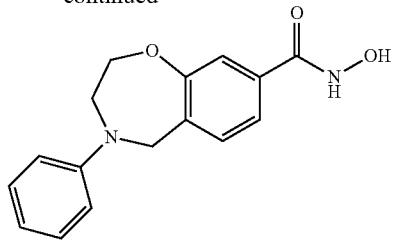

Step-1: Methyl 4-phenyl-2,3,4,5-tetrahydrobenzo[f][1,4]oxazepine-8-carboxylate

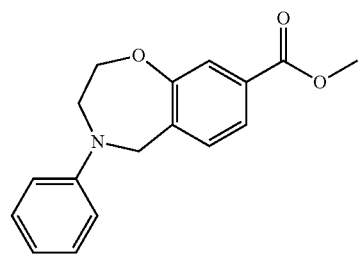 [SMILES: COC(=O)c1ccc2c(c1)OCCN(c1ccccc1)C2]

Into a 50-mL round-bottom flask, was placed methyl 2,3,4,5-tetrahydrobenzo[f][1,4]oxazepine-8-carboxylate (100 mg, 0.48 mmol, 1 equiv), Pd$_2$(dba)$_3$ (50 mg, 0.05 mmol, 0.11 equiv), Xantphos (14 mg, 0.02 mmol, 0.05 equiv), Cs$_2$CO$_3$ (326 mg, 1 mmol, 2.08 equiv), dioxane (10 mL) and bromobenzene (117 mg, 0.75 mmol, 1.54 equiv). The resulting mixture was stirred overnight at 100° C. in an oil bath. After cooling, the solids were filtered out and the filtrate was concentrated under vacuum. The residue was purified by prep-TLC (EtOAc/pet. ether, 1:5) to afford the title compound as a light yellow oil (50 mg, 37% yield). MS: (ES, m/z): 284 [M+H]$^+$.

Step-2: N-Hydroxy-4-phenyl-2,3,4,5-tetrahydrobenzo[f][1,4]oxazepine-8-carboxamide

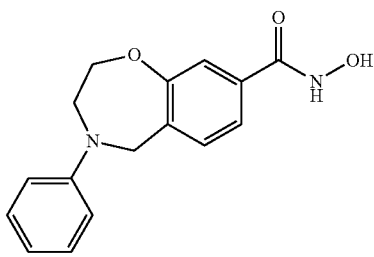 [SMILES: O=C(NO)c1ccc2c(c1)OCCN(c1ccccc1)C2]

Into a 100-mL round-bottom flask, was placed methyl 4-phenyl-2,3,4,5-tetrahydrobenzo[f][1,4]oxazepine-8-carboxylate (50 mg, 0.18 mmol, 1 equiv), NH$_2$OH (50% in water, 1 mL, 50 equiv), aq. 1N NaOH (0.36 mL, 2 equiv) and THF (3 mL). The resulting solution was stirred overnight at 40° C. in an oil bath. The crude product was purified by Prep-HPLC (Column: Sunfire Prep C18 ODB, 5 μm, 19×150 mm; Mobile Phase A: Water/0.05% Formic Acid; Mobile Phase B: MeCN; Flow rate: 25 mL/min; Gradient: 5% B to 55% B in 8 min; Detector: UV 254, 220 nm) to afford the title compound as a pink oil (2.5 mg, 5% yield). $^1$H-NMR (400 MHz, DMSO-d$_6$) δ(ppm): 11.12 (s, 1H), 9.03 (s, 1H), 7.56-6.56 (m, 8H), 4.66 (s, 2H), 4.17-4.10 (t, 2H), 3.91-3.80 (t, 2H). MS: (ES, m/z): 326 [M+H]$^+$.

TABLE 2

| | | |
|---|---|---|
| The following compounds were prepared according to the method of Example 2. | | |
| Structure | Found M + H | $^1$H-NMR (400 MHz, DMSO-d$_6$) δ(ppm) |
| [structure: 4-(3-trifluoromethyl-4-cyanophenyl)-N-hydroxy-2,3,4,5-tetrahydrobenzo[f][1,4]oxazepine-8-carboxamide] | (ES, m/z): 378 [M + H]$^+$ | 11.15 (s, 1H), 9.02 (s, 1H), 7.79-7.76 (t, 1H), 7.60-7.58 (t, 1H), 7.41-7.39 (t, 1H), 7.30-7.22 (t, 3H), 4.86 (s, 2H), 4.20-4.19 (t, 2H), 4.06-4.05 (t, 2H) |
| [structure: 4-(3,4-dichlorophenyl)-N-hydroxy-2,3,4,5-tetrahydrobenzo[f][1,4]oxazepine-8-carboxamide] | (ES, m/z): 353 [M + H]$^+$ | 11.11 (s, 1H), 9.04 (s, 1H), 7.59-7.57 (t, 1H), 7.50-7.43 (t, 1H), 7.30-7.28 (t, 2H), 7.09-7.08 (t, 1H), 6.90-6.87 (t, 1H), 4.69 (s, 2H), 4.13-4.11 (t, 2H), 3.90-3.88 (t, 2H) |

TABLE 2-continued

The following compounds were prepared according to the method of Example 2.

| Structure | Found M + H | $^{1}$H-NMR (400 MHz, DMSO-$d_6$) δ(ppm) |
|---|---|---|
| 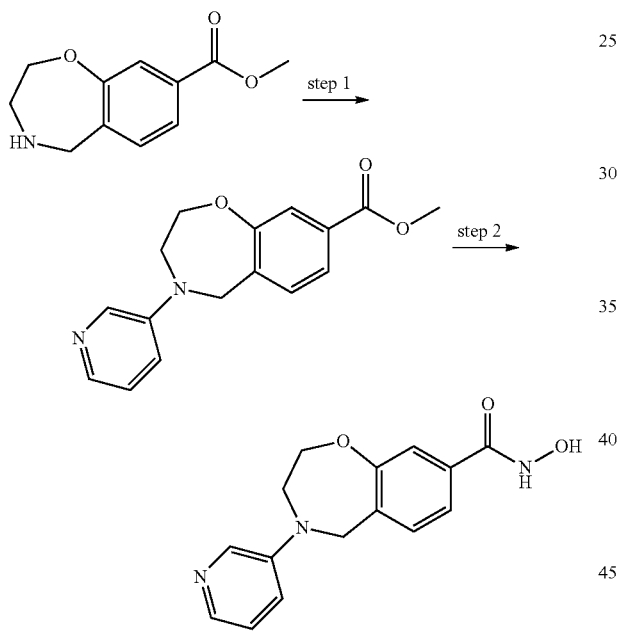 | (ES, m/z): 286 [M + H]$^{+}$ | 11.06 (s, 1H), 9.03 (s, 1H), 8.04-8.05 (t, J = 1.5 Hz, 1H), 7.29-7.49 (m, 4H), 6.86-6.89 (d, J = 8.7 Hz, 1H), 6.53-6.57 (m, 1H), 4.77 (s, 2H), 4.10 (s, 4H) |

Example 3—Preparation of N-hydroxy-4-(pyridin-3-yl)-2,3,4,5-tetrahydrobenzo[f][1,4]oxazepine-8-carboxamide

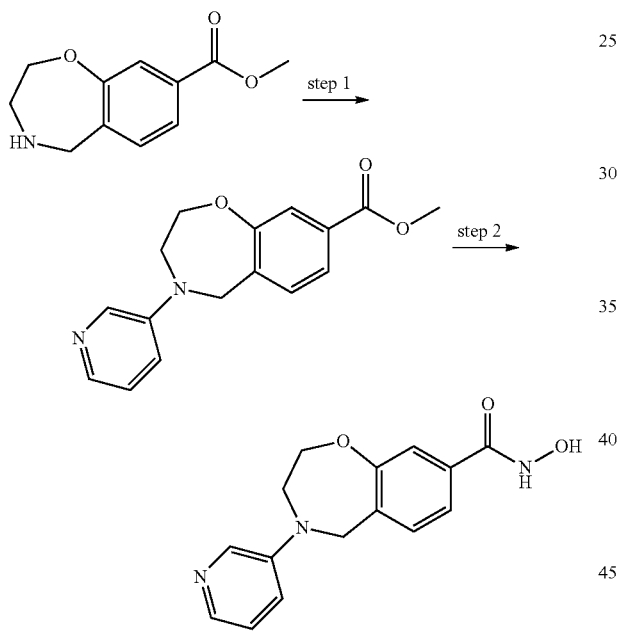

Step-1: Methyl 4-(pyridin-3-yl)-2,3,4,5-tetrahydrobenzo[f][1,4]oxazepine-8-carboxylate

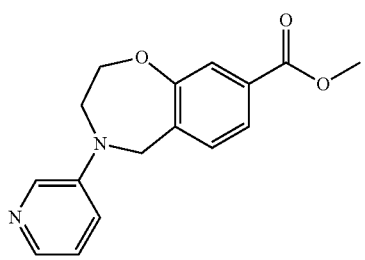 [SMILES: COC(=O)c1ccc2c(c1)OCCN(c1cccnc1)C2]

Into a 25-mL sealed tube, was placed a solution of methyl 2,3,4,5-tetrahydrobenzo[f][1,4]oxazepine-8-carboxylate (200 mg, 0.97 mmol, 1 equiv) in 1,4-dioxane (10 mL), 3-bromopyridine (171 mg, 1.08 mmol, 1.5 equiv), Pd$_2$(dba)$_3$*CHCl$_3$ (15 mg, 0.02 equiv), BINAP (20 mg, 0.03 mmol, 0.03 equiv) and Cs$_2$CO$_3$ (489 mg, 1.50 mmol, 2 equiv). The resulting mixture was stirred for 1.5 h at 150° C. in a microwave reactor. The reaction mixture was concentrated under vacuum. The residue was diluted with H$_2$O (30 mL) and then extracted with EtOAc (3×100 mL). The organic layer was concentrated and the residue was purified by silica gel chromatography (MeOH/CH$_2$Cl$_2$, 1:10) to afford the title compound as a light yellow oil (50 mg, 18% yield). MS: (ES, m/z): 285 [M+H]$^{+}$.

Step-2: N-Hydroxy-4-(pyridin-3-yl)-2,3,4,5-tetrahydrobenzo[f][1,4]oxazepine-8-carboxamide

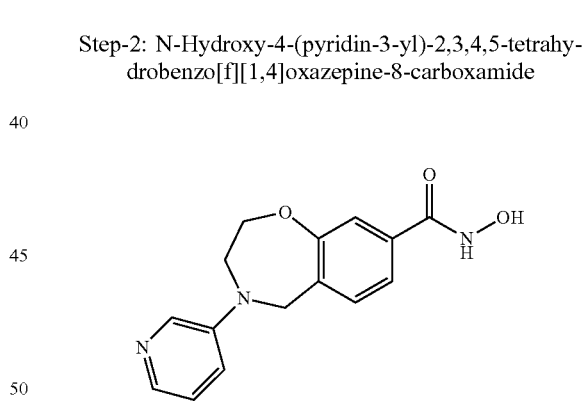

Into a 100-mL round-bottom flask, was placed a solution of methyl 4-(pyridin-3-yl)-2,3,4,5-tetrahydrobenzo[f][1,4]oxazepine-8-carboxylate (50 mg, 0.18 mmol, 1 equiv) in THF/MeOH (4:1, 2.5 mL), NH$_2$OH (50% in water, 1 mL, 60 equiv), aq. 1N NaOH (0.5 mL, 2 equiv). The resulting solution was stirred overnight at room temperature. The mixture was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector: UV 254 nm) to afford the title compound as a yellow solid (3.3 mg, 6% yield). $^{1}$H-NMR (400 MHz, DMSO-$d_6$) δ(ppm): 8.33 (b, 1H), 8.26 (s, 1H), 7.83 (b, 1H), 7.62 (s, 1H), 7.39-7.09 (m, 4H), 4.72 (s, 1H), 4.13 (b, 2H), 3.93 (s, 2H). MS: (ES, m/z): 286 [M+H]$^{+}$.

TABLE 3

The following compound was prepared according to the method of Example 3.

| Structure | Found M + H | ¹H-NMR (400 MHz, DMSO-d$_6$) δ(ppm) |
|---|---|---|
| (structure: N-hydroxy-4-(pyridin-4-yl)-2,3,4,5-tetrahydrobenzo[f][1,4]oxazepine-8-carboxamide) | (ES, m/z): 286 [M + H]⁺ | 8.30-8.08 (m, 3H), 7.58-7.30 (m, 3H), 6.81 (s, 2H), 4.70 (s, 2H), 4.13 (s, 2H), 3.92 (s, 2H) |

Example 4—Preparation of N-hydroxy-4-(p-tolyl)-2,3,4,5-tetrahydrobenzo[f][1,4]oxazepine-8-carboxamide

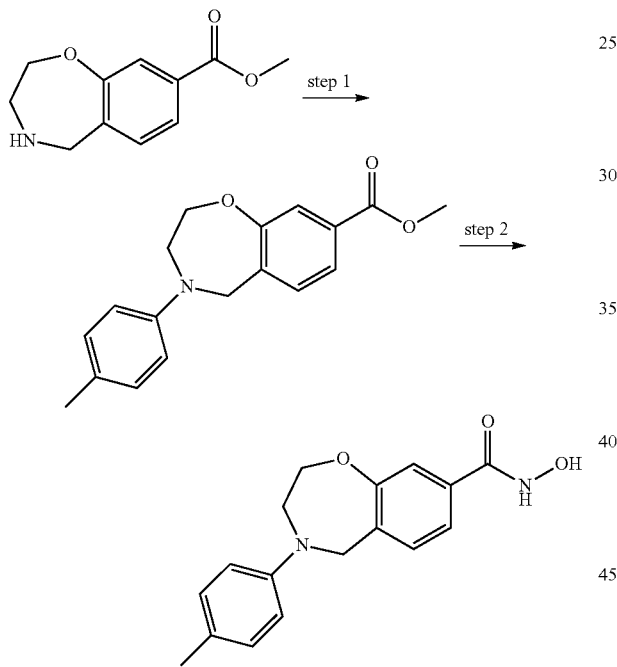

Step-1: Methyl 4-(p-tolyl)-2,3,4,5-tetrahydrobenzo[f][1,4]oxazepine-8-carboxylate Into a 100-mL round-bottom flask, was placed methyl 2,3,4,5-tetrahydrobenzo[f][1,4]oxazepine-8-carboxylate (200 mg, 0.97 mmol, 1 equiv), p-tolylboronic acid (162 mg, 1.19 mmol, 1.24 equiv), Cu(OAc)$_2$ (18 mg, 0.10 mmol, 0.1 equiv), pyridine (16 mg, 0.20 mmol, 0.21 equiv), CH$_2$Cl$_2$ (10 mL). The resulting solution was stirred for 2 h at room temperature, then concentrated under vacuum. The residue was purified by silica gel chromatography (EtOAc/pet. ether, 1:5) to afford the title compound as a light yellow solid (120 mg, 42% yield). MS: (ES, m/z): 298 [M+H]⁺.

Step-2: N-Hydroxy-4-(p-tolyl)-2,3,4,5-tetrahydrobenzo[f][1,4]oxazepine-8-carboxamide Into a 100-mL round-bottom flask was placed methyl 4-(p-tolyl)-2,3,4,5-tetrahydrobenzo[f][1,4]oxazepine-8-carboxylate (120 mg, 0.40 mmol, 1 equiv), NH$_2$OH (50% in water, 1 mL, 38 equiv), aq. 1N NaOH (1 mL, 2.5 equiv), and THF/MeOH (4:1, 3 mL). The resulting solution was stirred overnight at 40° C. in an oil bath. The mixture was purified by Prep-HPLC (Column: Sunfire Prep C18 OBD, 5 μm, 19×150 mm; Mobile Phase A: Water/0.05% Formic Acid; Mobile Phase B: MeCN; Flow rate: 25 mL/min; Gradient: 5% B to 60% B in 10 min; Detector: UV 254, 220 nm) to afford the title compound as a pink solid (31 mg, 26% yield). ¹H-NMR (400 MHz, DMSO-d$_6$) δ(ppm): 11.11 (s, 1H), 9 (s, 1H), 7.55-7.52 (t, 1H), 7.37-7.34 (t, 1H), 7.27-7.27 (t, 1H), 6.93-6.90 (t, 2H), 6.78-6.79 (t, 2H), 4.62 (s, 2H), 4.11-4.09 (t, 2H), 3.85-3.83 (t, 2H), 2.11 (s, 3H). MS: (ES, m/z): 299 [M+H]⁺.

Example 5—Preparation of N-hydroxy-4-(piperidine-1-carbonyl)-2,3,4,5-tetrahydrobenzo[f][1,4]oxazepine-8-carboxamide

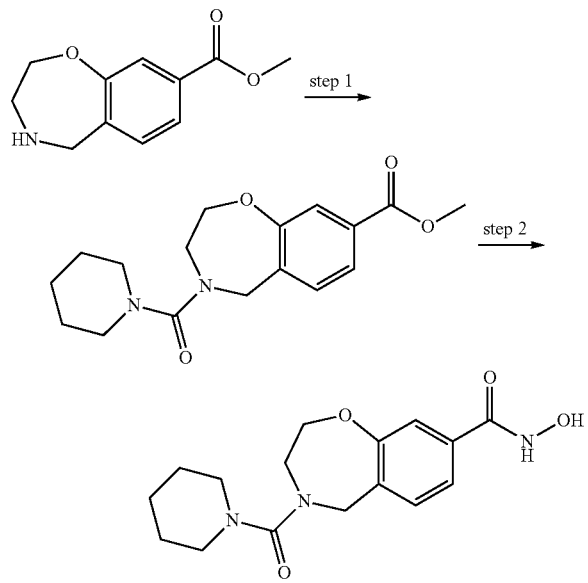

Step-1: Methyl 4-(piperidine-1-carbonyl)-2,3,4,5-tetrahydrobenzo[f][1,4]oxazepine-8-carboxylate

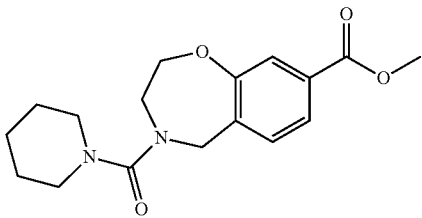 [SMILES: COC(=O)c1ccc2c(c1)OCCN(C(=O)N1CCCCC1)C2]

Into a 10-mL round-bottom flask, was placed a solution of methyl 2,3,4,5-tetrahydrobenzo[f][1,4]oxazepine-8-carboxylate (104 mg, 0.50 mmol, 1 equiv) in $CH_2Cl_2$ (2 mL), $Et_3N$ (101.5 mg, 1 mmol, 2 equiv) and piperidine-1-carbonyl chloride (82 mg, 0.56 mmol, 1.1 equiv). The resulting solution was stirred overnight at room temperature. The reaction was then quenched by the addition of water (20 mL) and extracted with $CH_2Cl_2$ (3×20 mL). The combined organic layers were washed with brine (30 mL), dried over anhydrous $Na_2SO_4$, filtered, and concentrated under vacuum. The residue was purified by silica gel chromatography (EtOAc/pet. ether, 1:3) to afford the title compound as a white solid (133 mg, 83% yield). MS: (ES, m/z): 319 $[M+H]^+$.

Step-2: N-Hydroxy-4-(piperidine-1-carbonyl)-2,3,4,5-tetrahydrobenzo[f][1,4]oxazepine-8-carboxamide

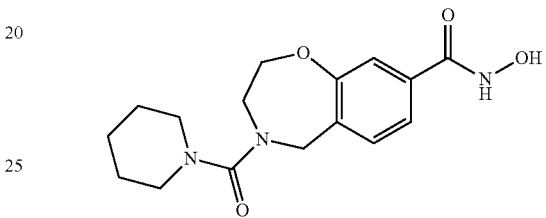

Into a 25-mL round-bottom flask, was placed a solution of methyl 4-(piperidine-1-carbonyl)-2,3,4,5-tetrahydrobenzo[f][1,4]oxazepine-8-carboxylate (133 mg, 0.42 mmol, 1 equiv) in THF/MeOH (4:1, 2 mL), aq. 1N NaOH (0.836 mL, 2 equiv) and $NH_2OH$ (50% in water, 828 mg, 25 mmol, 30 equiv). The resulting solution was stirred for 2 h at room temperature. The pH value of the solution was adjusted to 6 with 2N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector: UV 254, 220 nm) to afford the title compound as a pink solid (49 mg, 27% yield). $^1$H-NMR (400 MHz, DMSO-$d_6$) δ(ppm): 11.18 (s, 1H), 7.36-7.39 (m, 1H), 7.28-7.31 (t, J=1.6 Hz, 2H), 4.37 (s, 2H), 4.17-4.20 (t, J=4.4 Hz, 2H), 3.55-3.57 (t, J=4.8 Hz, 2H), 3.06-3.07 (d, J=5.2 Hz, 2H), 1.49-1.51 (d, J=6 Hz, 6H). MS: (ES, m/z): 320 $[M+H]^+$.

TABLE 4

The following compounds were prepared according to the method of Example 5.

| Structure | Found M + H | $^1$H-NMR (400 MHz, DMSO-$d_6$) δ(ppm) |
|---|---|---|
| 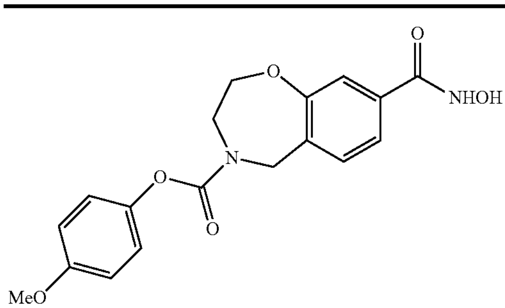 | (ES, m/z): 359 $[M + H]^+$ | 11.20 (s, 1H), 7.30-7.46 (m, 3H), 6.99-7.01 (d, J = 8.8 Hz, 1H), 6.87-6.89 (t, J = 2.4 Hz, 3H), 4.72 (s, 1H), 4.61 (s, 1H), 4.25 (s, 1H), 4.16 (s, 1H), 3.98 (s, 1H), 3.83 (s, 1H), 3.72 (s, 3H) |

TABLE 4-continued

The following compounds were prepared according to the method of Example 5.

| Structure | Found M + H | ¹H-NMR (400 MHz, DMSO-$d_6$) δ(ppm) |
|---|---|---|
| | (ES, m/z): 335 [M + H]⁺ | 11.17 (s, 1H), 7.40-7.42 (d, J = 7.2 Hz, 1H), 7.28-7.33 (t, J = 8 Hz, 2H), 4.51 (s, 3H), 4.07 (s, 2H), 3.76 (s, 2H), 1.59-1.67 (m, 4H), 1.28-281.42 (m, 6H) |
| | (ES, m/z): 356 [M + H]⁺ | 11.22 (s, 1H), 9.02-9.06 (br s, 1H), 7.31-7.42 (m, 3H), 4.47 (s, 2H), 4.14-4.17 (m, 2H), 3.64-3.66 (m, 2H), 3.01-3.02 (m, 4H), 1.44 (m, 6H) |

Example 6—Preparation of N8-hydroxy-N4-methyl-N4-phenyl-2,3,7,8-tetrahydrobenzo[f][1,4]oxazepine-4,8(5H)-dicarboxamide

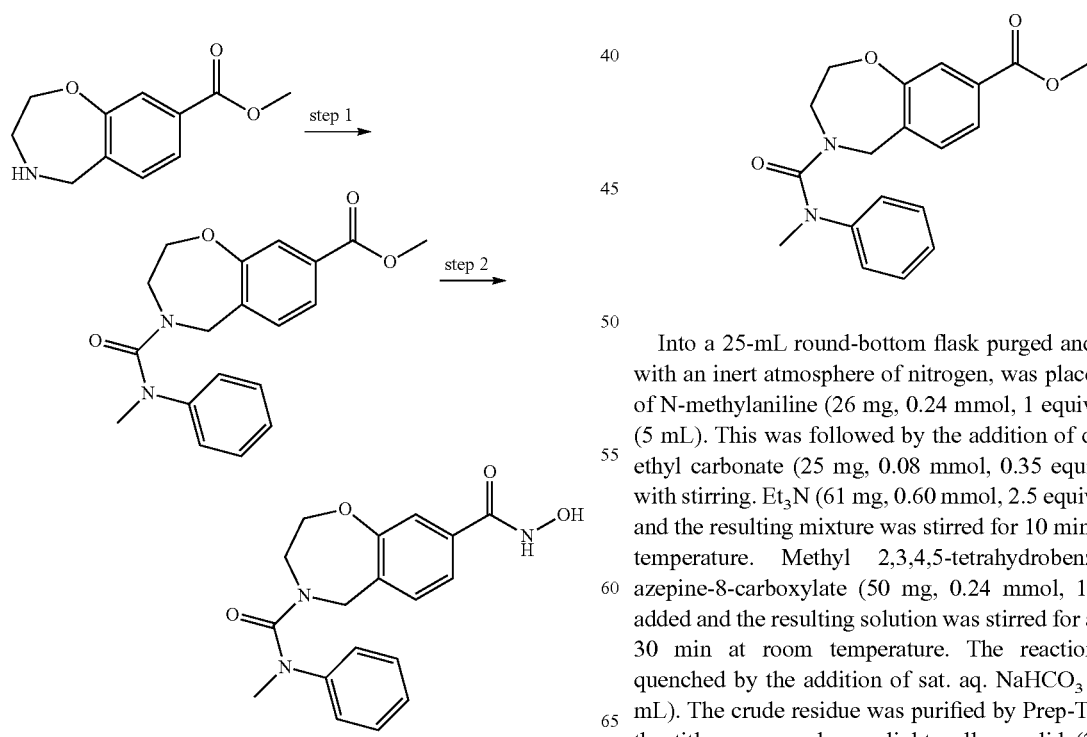

Step-1: Methyl 4-(methyl(phenyl)carbamoyl)-2,3,4,5-tetrahydrobenzo[f][1,4]oxazepine-8-carboxylate Into a 25-mL round-bottom flask purged and maintained with an inert atmosphere of nitrogen, was placed a solution of N-methylaniline (26 mg, 0.24 mmol, 1 equiv) in $CH_2Cl_2$ (5 mL). This was followed by the addition of ditrichloromethyl carbonate (25 mg, 0.08 mmol, 0.35 equiv) dropwise with stirring. $Et_3N$ (61 mg, 0.60 mmol, 2.5 equiv) was added and the resulting mixture was stirred for 10 minutes at room temperature. Methyl 2,3,4,5-tetrahydrobenzo[f][1,4]oxazepine-8-carboxylate (50 mg, 0.24 mmol, 1 equiv) was added and the resulting solution was stirred for an additional 30 min at room temperature. The reaction was then quenched by the addition of sat. aq. $NaHCO_3$ solution (10 mL). The crude residue was purified by Prep-TLC to afford the title compound as a light yellow solid (25 mg, 30% yield). MS: (ES, m/z): 340 [M+H]⁺.

Step-2: N8-Hydroxy-N4-methyl-N4-phenyl-2,3,7,8-tetrahydrobenzo[f][1,4]oxazepine-4,8(5H)-dicarboxamide

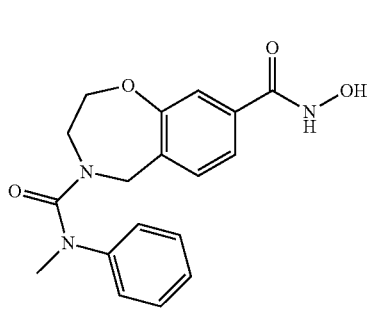 [SMILES: CN(C(=O)N1CCOc2cc(C(=O)NO)ccc2C1)c1ccccc1]

Into a 25-mL round-bottom flask was placed a solution of methyl 4-(methyl(phenyl)carbamoyl)-2,3,4,5-tetrahydrobenzo[f][1,4]oxazepine-8-carboxylate (65 mg, 0.19 mmol, 1 equiv) in THF/MeOH (4:1, 2 mL). This was followed by the addition of NH$_2$OH (50% in water, 0.35 mL, 30 equiv) dropwise with stirring. To this was added aq. 1N NaOH (0.57 mL, 3 equiv). The resulting solution was stirred for 30 min at room temperature. The pH value of the solution was adjusted to 5-6 with 1N HCl. The crude product was purified by Prep-HPLC (Column: XBridge RP C18 OBD, 5 μm, 19×150 mm; Mobile Phase A: Water/0.05% TFA; Mobile Phase B: MeCN; Flow rate: 25 mL/min; Gradient: 5% B to 44% B in 7 min; Detector: UV 254 nm) to afford the title compound as a pink solid (61 mg, 94% yield). $^1$H-NMR (400 MHz, DMSO-d$_6$) δ(ppm): 11.16 (s, 1H), 7.23-7.33 (m, 3H), 7.14 (s, 1H), 7.01-7.09 (m, 3H), 6.99 (d, 1H), 4.35 (s, 2H), 4.04-4.07 (s, 2H), 3.40-3.43 (s, 2H), 3.03 (s, 3H). MS: (ES, m/z): 341 [M+H]$^+$.

Example 7—Preparation of 4-cyclohexyl-N-hydroxy-2,3,4,5-tetrahydrobenzo[f][1,4]oxazepine-8-carboxamide

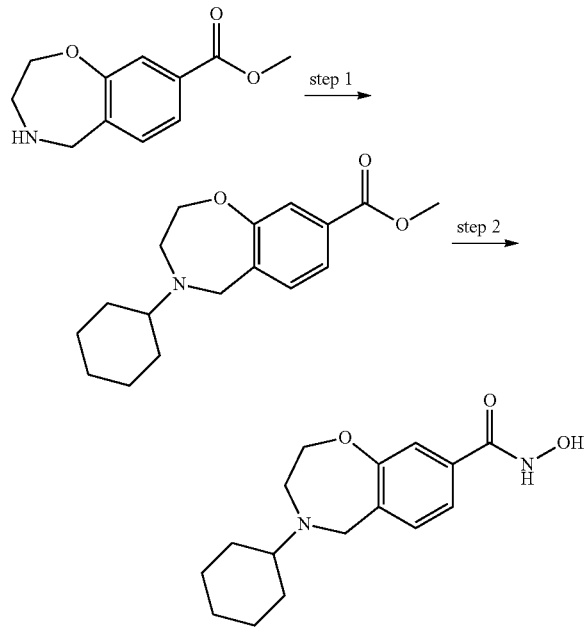

Step-1: Methyl 4-cyclohexyl-2,3,4,5-tetrahydrobenzo[f][1,4]oxazepine-8-carboxylate

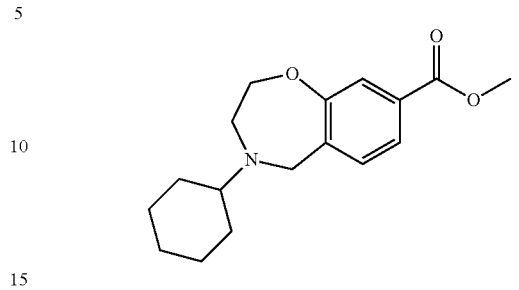

Into a 25-mL round-bottom flask, was placed methyl 2,3,4,5-tetrahydrobenzo[f][1,4]oxazepine-8-carboxylate (206 mg, 0.99 mmol, 1 equiv), CH$_2$Cl$_2$ (8 mL) and cyclohexanone (106 mg, 1.08 mmol, 1.1 equiv). The solution was stirred for 1 h at room temperature. Then to this was added NaBH(OAc)$_3$ (2.15 g, 10.14 mmol, 10 equiv). The resulting solution was stirred for 4 h at room temperature. The reaction mixture was cooled to 0° C. with a water/ice bath. The reaction was then quenched by the addition of water (20 mL) and extracted with CH$_2$Cl$_2$ (3×50 mL). The organic phase was washed with sat. aq. NaHCO$_3$ solution (50 mL), dried over anhydrous Na$_2$SO$_4$, filtered and concentrated under vacuum to afford the title compound as brown oil (80 mg) which was used without further purification. MS: (ES, m/z): 289 [M+H]$^+$.

Step-2: 4-Cyclohexyl-N-hydroxy-2,3,4,5-tetrahydrobenzo[f][1,4]oxazepine-8-carboxamide

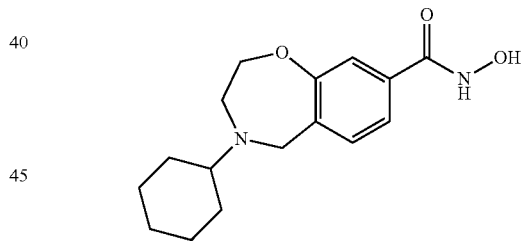

Into a 25-mL round-bottom flask, was placed a solution of methyl 4-cyclohexyl-2,3,4,5-tetrahydrobenzo[f][1,4]oxazepine-8-carboxylate (140 mg, 0.48 mmol, 1 equiv) in THF/MeOH (4:1, 2 mL), aq. 1N NaOH (0.969 mL, 2 equiv) and NH$_2$OH (50% in water, 959 mg, 30 equiv). The resulting solution was stirred for 2 h at room temperature. The pH value of the solution was adjusted to 6 with 2N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector: UV 254, 220 nm) to afford the title compound as an orange solid (35 mg, 18% yield). $^1$H-NMR (400 MHz, DMSO-d$_6$) δ(ppm): 11.33 (s, 1H), 9.98 (s, 1H), 9.15 (s, 1H), 7.54 (s, 2H), 7.44 (s, 1H), 4.49-4.64 (m, 2H), 4.09-4.14 (t, J=12.8 Hz, 1H), 3.65-3.70 (d, J=20.4 Hz, 2H), 3.39 (s, 1H), 2.02-2.12 (m, 2H), 1.83-1.85 (d, J=11.6 Hz, 2H), 1.46-1.64 (m, 3H), 1.21-1.31 (m, 3H). MS: (ES, m/z): 290 [M+H]$^+$.

TABLE 5

The following compounds were prepared according to the method of Example 7.

| Structure | Found M + H | ¹H-NMR (400 MHz, DMSO-$d_6$) δ(ppm) |
|---|---|---|
| 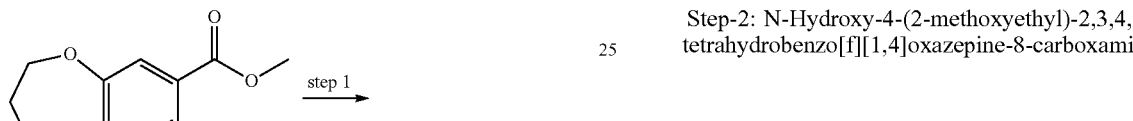 | (ES, m/z): 280 [M + H]⁺ | 11.21 (s, 1H), 10.10 (s, 1H), 7.37-7.45 (m, 3H), 4.05-4.15 (d, J = 37.2 Hz, 2H), 3.94 (s, 2H), 3.21-3.24 (m, 2H), 3.14 (s, 2H), 2.74-2.78 (m, 8H) |

Example 8—Preparation of N-hydroxy-4-(2-methoxyethyl)-2,3,4,5-tetrahydrobenzo[f][1,4]oxazepine-8-carboxamide

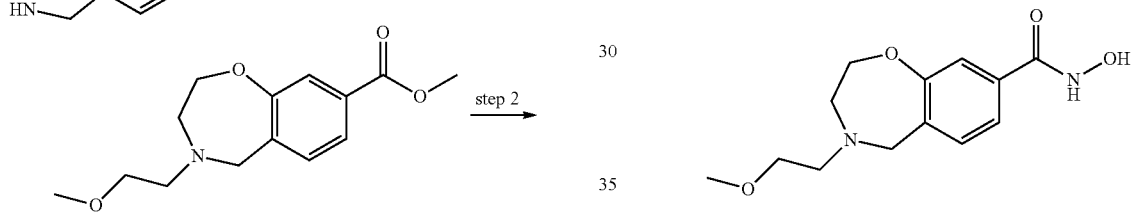

Step-1: Methyl 4-(2-methoxyethyl)-2,3,4,5-tetrahydrobenzo[f][1,4]oxazepine-8-carboxylate

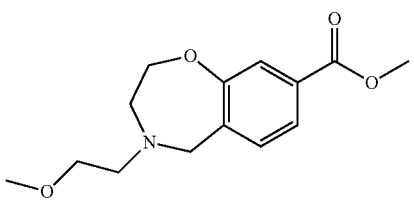

Into a 10-mL round-bottom flask, was placed a solution of methyl 2,3,4,5-tetrahydrobenzo[f][1,4]oxazepine-8-carboxylate (104 mg, 0.50 mmol, 1 equiv) in DMF (2 mL), $K_2CO_3$ (138.1 mg, 1 mmol, 2 equiv) and 1-iodo-2-methoxyethane (102.8 mg, 0.55 mmol, 1.1 equiv). The resulting solution was stirred overnight at room temperature. The reaction was then quenched by the addition of water (20 mL) and extracted with $CH_2Cl_2$ (3×20 mL). The combined organic layers were washed with brine (30 mL), dried over anhydrous $Na_2SO_4$, filtered, and concentrated under vacuum. The residue was purified by silica gel chromatography (MeOH/$CH_2Cl_2$, 1:10) to afford the title compound as a yellow oil (46 mg). MS: (ES, m/z): 266 [M+H]⁺.

Step-2: N-Hydroxy-4-(2-methoxyethyl)-2,3,4,5-tetrahydrobenzo[f][1,4]oxazepine-8-carboxamide Into a 25-mL round-bottom flask, was placed a solution of methyl 4-(2-methoxyethyl)-2,3,4,5-tetrahydrobenzo[f][1,4]oxazepine-8-carboxylate (46 mg, 0.17 mmol, 1 equiv) in THF/MeOH (4:1, 2 mL), aq. 1N NaOH (0.347 mL, 2 equiv) and $NH_2OH$ (50% in water, 343.7 mg, 10.42 mmol, 30 equiv). The resulting solution was stirred for 2 h at room temperature. The pH value of the solution was adjusted to 6 with 2N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector: UV 254, 220 nm) to afford the title compound as an orange solid (29 mg, 44% yield). ¹H-NMR (400 MHz, DMSO-$d_6$) δ(ppm): 11.31 (s, 1H), 10.29 (s, 1H), 9.15 (s, 1H), 7.50-7.55 (m, 2H), 7.44 (s, 1H), 4.24-4.51 (m, 4H), 3.69 (s, 4H), 3.34 (s, 3H). MS: (ES, m/z): 267[M+H]⁺.

Example 9—Preparation of N-hydroxy-2,3,4,5-tetrahydrobenzo[f][1,4]oxazepine-8-carboxamide 2,2,2-trifluoroacetate

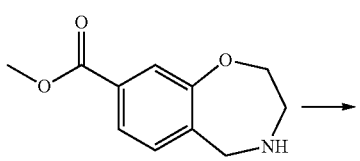

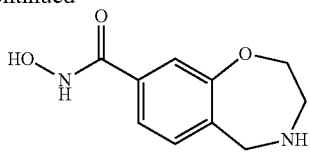

Into a 8-mL vial, was placed methyl 2,3,4,5-tetrahydrobenzo[f][1,4]oxazepine-8-carboxylate (60 mg, 0.29 mmol, 1 equiv) in THF/MeOH (4:1, 1.5 mL), aq. 1N NaOH (0.58 mL, 0.58 mmol, 2 equiv) and NH₂OH (50% in water, 0.58 mL, 8.69 mmol, 30 equiv). The resulting solution was stirred for 2 h at room temperature. The crude product was purified by Prep-HPLC (Column: XBridge RP C18 OBD, 5 μm, 19×150 mm; Mobile Phase A: Water/0.05% TFA; Mobile Phase B: MeCN; Flow rate: 25 mL/min; Gradient: 4% B to 58% B in 7 min; Detector: UV 254, 220 nm) to afford the title compound as a pink solid (21 mg, 23% yield). $^1$H-NMR (400 MHz, DMSO-d$_6$) δ(ppm): 11.29 (s, 1H), 9.42 (br s, 2H), 9.11 (s, 1H), 7.48-7.52 (m, 2H), 7.42-7.45 (s, 1H), 4.37 (s, 2H), 4.21-4.23 (m, 2H), 3.49-3.51 (m, 2H). MS: (ES, m/z): 209 [M+H]$^+$.

Example 10—Preparation of N-hydroxy-4-methyl-2,3,4,5-tetrahydrobenzo[f][1,4]oxazepine-8-carboxamide 2,2,2-trifluoroacetate

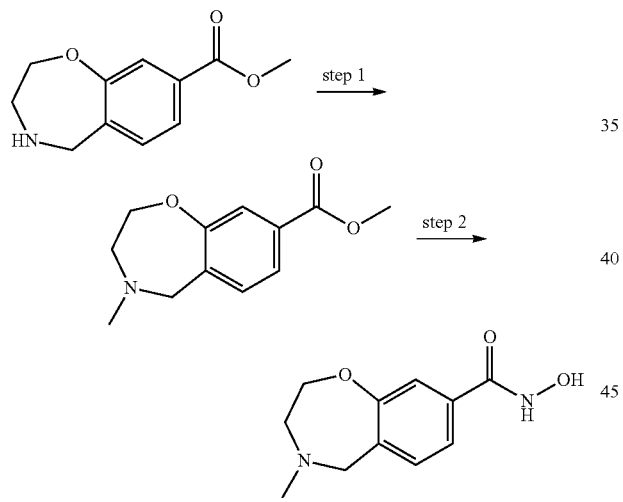

Step-1: Methyl 4-methyl-2,3,4,5-tetrahydrobenzo[f][1,4]oxazepine-8-carboxylate

Into a 25-mL round-bottom flask, was placed methyl 2,3,4,5-tetrahydrobenzo[f][1,4]oxazepine-8-carboxylate (100 mg, 0.31 mmol, 1 equiv), acetic acid (3 mL) and paraformaldehyde (28 mg, 0.93 mmol, 3 equiv). The resulting mixture was stirred for 2 h at room temperature. Then acetyl ethaneperoxoate sodioboranyl acetate (327 mg, 1.54 mmol, 5 equiv) was added and the reaction was stirred for an additional 18 h at room temperature. The resulting mixture was concentrated under vacuum, diluted with EtOAc (50 mL), washed with H₂O (3×25 mL), dried over anhydrous MgSO₄, filtered and concentrated to afford the title compound as a yellow solid (100 mg) which was used without further purification. MS: (ES, m/z): 222 [M+H]$^+$.

Step-2: N-Hydroxy-4-methyl-2,3,4,5-tetrahydrobenzo[f][1,4]oxazepine-8-carboxamide 2,2,2-trifluoroacetate

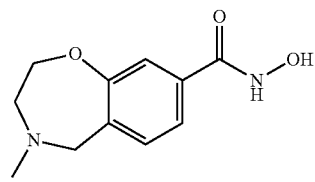 [SMILES: CN1CCOc2cc(C(=O)NO)ccc2C1]

Into a 8-mL vial, was placed methyl 4-methyl-2,3,4,5-tetrahydrobenzo[f][1,4]oxazepine-8-carboxylate (100 mg, 0.45 mmol, 1 equiv) in THF/MeOH (4:1, 1 mL), aq. 1N NaOH (0.9 mL, 0.90 mmol, 2 equiv) and NH₂OH (50% in water, 0.9 mL, 13.56 mmol, 30 equiv). The resulting solution was stirred for 1 h at room temperature. The crude product was purified by Prep-HPLC (Column: XBridge RP C18 OBD, 5 μm, 19×150 mm; Mobile Phase A: Water/0.05% TFA; Mobile Phase B: MeCN; Flow rate: 25 mL/min; Gradient: 4% B to 58% B in 7 min; Detector: UV 254, 220 nm) to afford the title compound as a yellow oil (45 mg, 29% yield). $^1$H-NMR (400 MHz, DMSO-d$_6$) δ(ppm): 11.31 (s, 1H), 10.54 (s, 1H), 9.91 (s, 1H), 7.42-7.54 (m, 3H), 4.48 (s, 1H), 4.26 (s, 2H), 3.62 (s, 2H), 3.88 (s, 3H). MS: (ES, m/z): 223 [M+H]$^+$.

Example 11—Preparation of (R)—N-hydroxy-2-methyl-2,3,4,5-tetrahydrobenzo[f][1,4]oxazepine-8-carboxamide

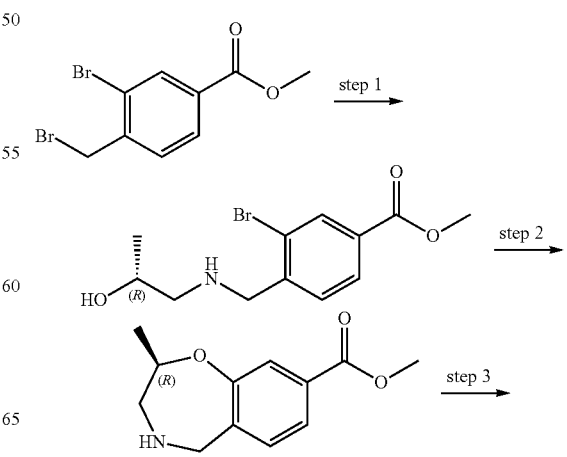

-continued

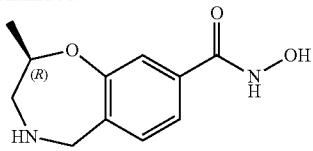

Step-1: Methyl (R)-3-bromo-4-(((2-hydroxypropyl) amino)methyl)benzoate

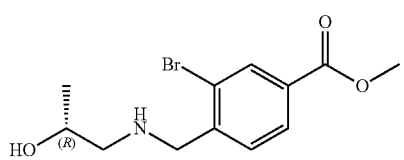

Into a 250-mL round-bottom flask, was placed a solution of methyl 3-bromo-4-(bromomethyl)benzoate (7 g, 22.73 mmol, 1 equiv) in MeCN (80 mL), potassium carbonate (4.69 g, 33.93 mmol, 1.50 equiv) and (2R)-1-aminopropan-2-ol (1.7 g, 22.63 mmol, 1 equiv). The resulting mixture was stirred for 3 h at room temperature and then concentrated under vacuum. The residue was diluted with EtOAc (80 mL) and the resulting solution was washed with water (3×30 mL). The organic phase was concentrated under vacuum to afford the title compound as an off-white solid (3 g) which was used without further purification. MS: (ES, m/z): 302 [M+H]$^+$.

Step-2: Methyl (R)-2-methyl-2,3,4,5-tetrahydrobenzo[f][1,4]oxazepine-8-carboxylate

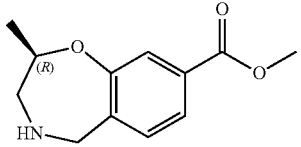

Into a 100-mL round-bottom flask purged and maintained with an inert atmosphere of nitrogen, was placed a solution of methyl (R)-3-bromo-4-(((2-hydroxypropyl)amino) methyl)benzoate (2.75 g, 9.10 mmol, 1 equiv) in isopropanol (32 mL), potassium carbonate (2.53 g, 18.31 mmol, 2 equiv) and CuI (520 mg, 2.73 mmol, 0.30 equiv). The resulting solution was stirred for 21 h at 110° C. in an oil bath. The resulting mixture was concentrated under vacuum and the residue was diluted with EtOAc (100 mL). The resulting mixture was washed with water (3×150 mL) and the organic phase was concentrated, then the residue was purified by silica gel chromatography (CH$_2$Cl$_2$/MeOH, 99:1) to afford the title compound as a brown oil (1.1 g, 55% yield). MS: (ES, m/z): 222 [M+H]$^+$.

Step-3: (R)—N-Hydroxy-2-methyl-2,3,4,5-tetrahydrobenzo[f][1,4]oxazepine-8-carboxamide

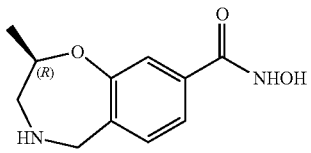

Into a 8-mL vial, was placed a solution of methyl (R)-2-methyl-2,3,4,5-tetrahydrobenzo[f][1,4]oxazepine-8-carboxylate (50 mg, 0.23 mmol, 1 equiv) in THF/MeOH (4:1, 1 mL), NH$_2$OH (50% in water, 0.44 mL, 30 equiv) and aq. 1N NaOH (0.45 mL, 2 equiv). The resulting solution was stirred for 14 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 4% B to 18% B in 6 min; Detector: UV 254, 220 nm) to afford the title compound as a brown oil (15 mg, 21% yield). $^1$H-NMR (400 MHz, DMSO-d$_6$) δ(ppm): 11.28 (s, 1H), 9.24 (br s, 2H), 7.56-7.33 (m, 3H), 4.45-4.38 (d, J=7.2 hz, 1H), 4.31-4.28 (d, J=7.2 hz, 1H), 4.18-4.11 (m, 1H), 3.53-3.49 (d, J=6.4 Hz, 1H), 3.29-3.28 (m, 1H), 1.39-1.37 (m, 3H). MS: (ES, m/z): 223 [M+H]$^+$.

Example 12—Preparation of (R)—N8-hydroxy-N4-(4-methoxyphenyl)-2-methyl-2,3-dihydrobenzo[f][1,4]oxazepine-4,8(5H)-dicarboxamide

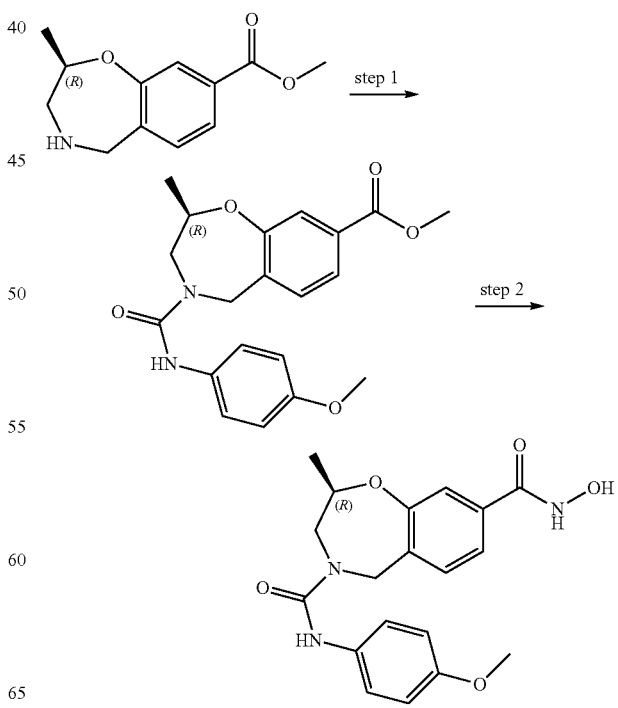

Step-1: Methyl (R)-4-((4-methoxyphenyl)carbamoyl)-2-methyl-2,3,4,5-tetrahydrobenzo[f][1,4]oxazepine-8-carboxylate

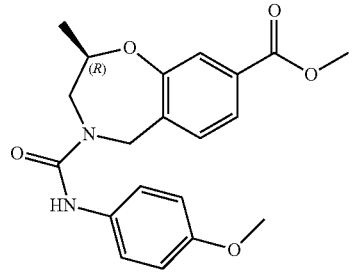

Into a 8-mL vial, were placed a solution of methyl (R)-2-methyl-2,3,4,5-tetrahydrobenzo[f][1,4]oxazepine-8-carboxylate (150 mg, 0.68 mmol, 1 equiv) in CH$_2$Cl$_2$ (4 mL), Et$_3$N (81 mg, 0.80 mmol, 3 equiv) and 1-isocyanato-4-methoxybenzene (167 mg, 1.12 mmol, 1.5 equiv). The resulting mixture was stirred for 16 h at room temperature and then washed with water (2×10 mL). The organic phase was concentrated and the residue was purified by silica gel chromatography (EtOAc/pet. ether, 1:3) to afford the title compound as a light yellow oil (40 mg, 16% yield). MS: (ES, m/z): 371 [M+H]$^+$.

Step-2: (R)—N8-Hydroxy-N4-(4-methoxyphenyl)-2-methyl-2,3-dihydrobenzo[f][1,4]oxazepine-4,8 (5H)-dicarboxamide

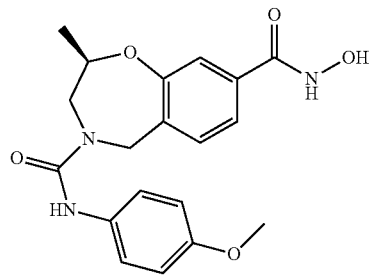 [SMILES: COc1ccc(NC(=O)N2Cc3ccc(C(=O)NO)cc3O[C@H](C)C2)cc1]

Into a 8-mL vial, was placed methyl (R)-4-((4-methoxyphenyl)carbamoyl)-2-methyl-2,3,4,5-tetrahydrobenzo[f][1,4]oxazepine-8-carboxylate (40 mg, 0.11 mmol, 1 equiv) in THF/MeOH (4:1, 2 mL). To this was added aq. 1N NaOH (0.22 mL, 2 equiv) and NH$_2$OH (50% in water, 0.22 mL, 30 equiv). The resulting solution was stirred for 3 h at room temperature. The crude product was purified by Prep-HPLC (Column:Column:XBridge XP C18 OBD, 5 μm, 19×150 mm; Mobile Phase A: Water/0.05% TFA; Mobile Phase B: MeCN; Flow rate: 0.7 mL/min; Gradient: 5% B to 80% B in 7 min; Detector: UV 254, 220 nm) to afford the title compound as an off-white solid (21 mg, 52% yield). $^1$H-NMR (400 MHz, DMSO-d$_6$) δ(ppm): 11.14 (s, 1H), 9 (br s, 1H), 8.35 (s, 1H), 7.42-7.39 (m, 2H), 7.37-7.33 (m, 1H), 7.27-7.20 (m, 2H), 6.79-7.77 (m, 2H), 4.84-4.80 (d, J=15.6 Hz, 1H), 4.42-4.39 (d, J=15.6 Hz, 1H), 4.03-4 (d, J=12.4 Hz, 2H), 3.67 (s, 3H), 3.32-3.28 (m, 1H), 1.32-1.30 (d, J=6.0 Hz, 3H). MS: (ES, m/z): 372 [M+H]$^+$.

Example 13—Preparation of (R)—N-Hydroxy-4-(4-methoxyphenylsulfonyl)-2-methyl-2,3,4,5-tetrahydrobenzo[f][1,4]oxazepine-8-carboxamide

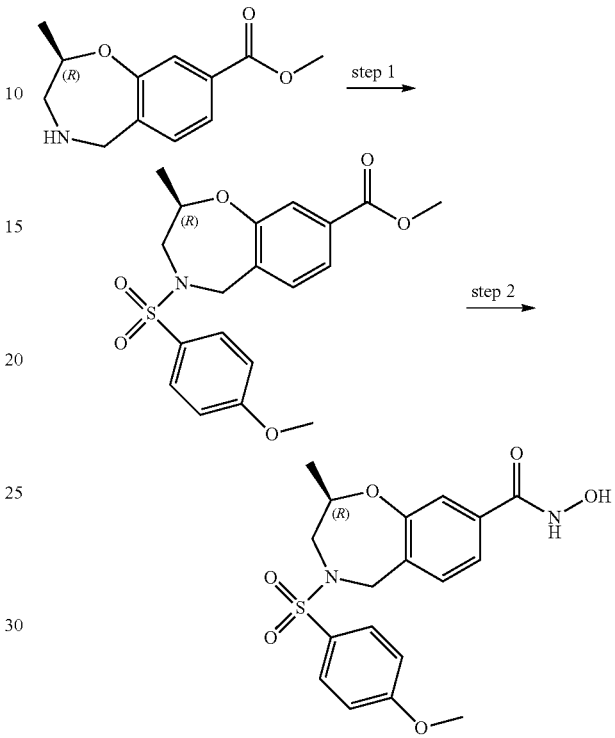

Step-1: Methyl (R)-4-((4-methoxyphenyl)sulfonyl)-2-methyl-2,3,4,5-tetrahydrobenzo[f][1,4]oxazepine-8-carboxylate

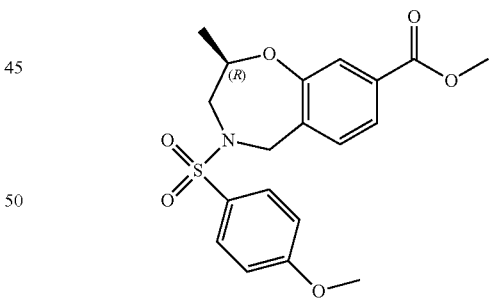

Into a 40-mL round-bottom flask, was placed a solution of methyl (R)-2-methyl-2,3,4,5-tetrahydrobenzo[f][1,4]oxazepine-8-carboxylate (100 mg, 0.45 mmol, 1 equiv) in CH$_2$Cl$_2$ (20 mL), 4-methoxybenzene-1-sulfonyl chloride (140 mg, 0.68 mmol, 1.5 equiv), Et$_3$N (140 mg, 1.38 mmol, 3 equiv) and 4-dimethylaminopyridine (55 mg, 0.45 mmol, 1 equiv). The resulting mixture was stirred for 10 h at room temperature. The above mixture was concentrated under vacuum. The residue was purified by silica gel chromatography (EtOAc/pet. ether, 1:1) to afford the title compound as a light yellow oil (80 mg, 45% yield). MS: (ES, m/z): 392 [M+H]$^+$.

Step-2: (R)—N-Hydroxy-4-((4-methoxyphenyl)sulfonyl)-2-methyl-2,3,4,5-tetrahydrobenzo[f][1,4]oxazepine-8-carboxamide

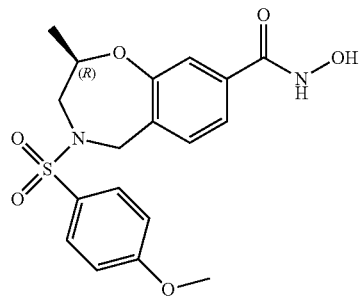

Into a 10-mL vial, was placed a solution of methyl (R)-4-((4-methoxyphenyl)sulfonyl)-2-methyl-2,3,4,5-tetrahydrobenzo[f][1,4]oxazepine-8-carboxylate (80 mg, 0.21 mmol, 1 equiv) in THF/MeOH (4:1, 2 mL). This was followed by the addition of aq. 1N NaOH (10.42 mL, 2 equiv) and NH$_2$OH (50% in water, 0.42 mL, 30 equiv). The resulting solution was stirred for 2 h at room temperature. The crude product was purified by Prep-HPLC (Column: XBridge XP C18 OBD, 5 µm, 19×150 mm; Mobile Phase A: Water/0.05% TFA; Mobile Phase B: MeCN; Flow rate: 0.7 mL/min; Gradient: 8% B to 45% B in 7 min; Detector: UV 254 nm) to afford the title compound as a pink solid (78 mg, 97% yield). $^1$H-NMR (400 MHz, DMSO-d$_6$) δ(ppm): 11.17 (br s, 1H), 7.69-7.68 (m, 2H), 7.42-7.40 (m, 1H), 7.33-7.31 (m, 1H), 7.25-7.24 (m, 1H), 7.05-7.02 (m, 2H), 4.57-4.53 (m, 1H), 4.25-4.21 (m, 1H), 4.03-3.98 (m, 1H), 3.81 (s, 3H), 3.68-3.65 (m, 1H), 3.24-3.18 (m, 1H), 1.26-1.24 (d, J=6.4 Hz, 3H). MS: (ES, m/z): 393 [M+H]$^+$.

Example 14—Preparation of (R)—N-hydroxy-4-(4-methoxybenzyl)-2-methyl-2,3,4,5-tetrahydrobenzo[f][1,4]oxazepine-8-carboxamide

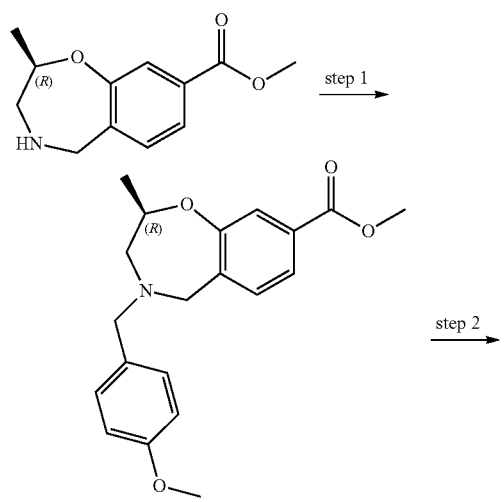

Step-1: Methyl (R)-4-(4-methoxybenzyl)-2-methyl-2,3,4,5-tetrahydrobenzo[f][1,4]oxazepine-8-carboxylate

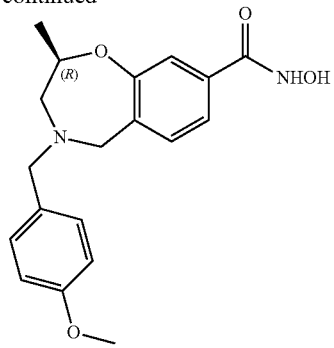

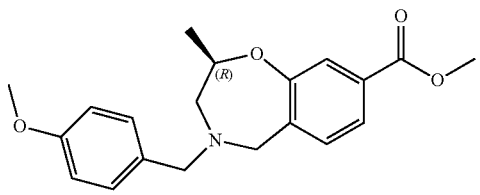

Into a 50-mL flask, was placed a solution of methyl (R)-2-methyl-2,3,4,5-tetrahydrobenzo[f][1,4]oxazepine-8-carboxylate (100 mg, 0.45 mmol, 1 equiv) in THF (10 mL). This was followed by the addition of sodium hydride (60%, 50 mg, 2.08 mmol, 3 equiv). To this was added 1-(bromomethyl)-4-methoxybenzene (90 mg, 0.45 mmol, 1 equiv). The resulting mixture was stirred for 4 h at room temperature. The reaction was then quenched by the addition of water (3 mL). The organic layer was concentrated under vacuum to afford the title compound as a light yellow oil (80 mg) which was used without further purification. MS: (ES, m/z): 342 [M+H]$^+$.

Step-2: (R)—N-Hydroxy-4-(4-methoxybenzyl)-2-methyl-2,3,4,5-tetrahydrobenzo[f][1,4]oxazepine-8-carboxamide

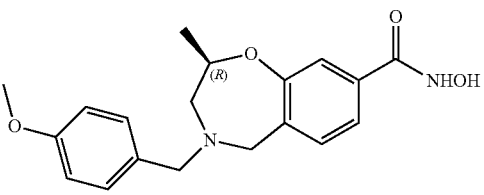

Into a 10-mL vial, was placed a solution of methyl (R)-4-(4-methoxybenzyl)-2-methyl-2,3,4,5-tetrahydrobenzo[f][1,4]oxazepine-8-carboxylate (70 mg, 0.21 mmol, 1 equiv) in THF/MeOH (4:1, 2 mL). To the above mixture was added aq. 1N NaOH (0.42 mL, 2 equiv) and NH$_2$OH (50% in water, 0.42 mL, 30 equiv). The resulting solution was stirred for 3 h at room temperature. The crude product was purified by Prep-HPLC (Column: XBridge XP C18 OBD, 5 µm, 19×150 mm; Mobile Phase A: Water/ 0.05% TFA; Mobile Phase B: MeCN; Flow rate: 0.7 mL/min; Gradient: 7% B to 55% B in 7 min; Detector: UV 254 nm) to afford the title compound as a pink solid (34 mg, 49% yield). $^1$H-NMR (400 MHz, DMSO-$d_6$) δ(ppm): 11.30 (br s, 1H), 9.12 (br s, 1H), 7.53-7.44 (m, 5H), 7.03 (m, 2H), 4.49-3.97 (m, 5H), 3.79 (s, 3H), 3.60-3.35 (m, 2H), 1.34-1.33 (d, J=5.2 Hz, 3H). MS: (ES, m/z): 343 [M+H]$^+$.

Example 15—Preparation of (R)—N-hydroxy-2-methyl-4-phenyl-2,3,4,5-tetrahydrobenzo[f][1,4]oxazepine-8-carboxamide

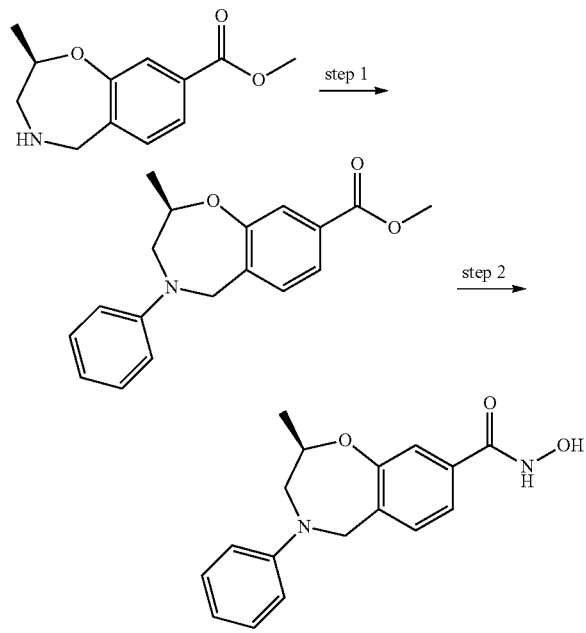

Step-1: Methyl (R)-2-methyl-4-phenyl-2,3,4,5-tetrahydrobenzo[f][1,4]oxazepine-8-carboxylate

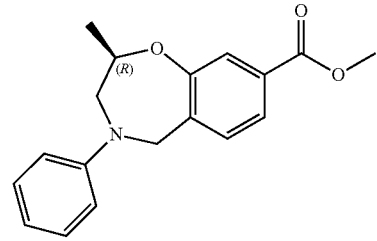

Into a 8-mL vial purged and maintained with nitrogen, placed a solution of methyl (R)-2-methyl-2,3,4,5-tetrahydrobenzo[f][1,4]oxazepine-8-carboxylate (300 mg, 1.36 mmol, 1 equiv) in dioxane (8 mL), iodobenzene (827 mg, 4.05 mmol, 3 equiv), Xantphos (312 mg, 0.54 mmol, 0.4 equiv), Cs$_2$CO$_3$ (1.33 g, 4.05 mmol, 3 equiv) and Pd(OAc)$_2$ (61 mg, 0.27 mmol, 0.2 equiv). The resulting mixture was stirred for 20 h at 110° C. in an oil bath. The resulting mixture was concentrated under vacuum. The residue was diluted with EtOAc (20 mL), washed with water (3×15 mL), dried and concentrated. The residue was purified by silica gel chromatography (EtOAc/pet. ether, 1:3) to afford the title compound as a brown oil (270 mg, 67% yield). MS: (ES, m/z): 298 [M+H]$^+$.

Step-2: (R)—N-hydroxy-2-methyl-4-phenyl-2,3,4,5-tetrahydrobenzo[f][1,4]oxazepine-8-carboxamide

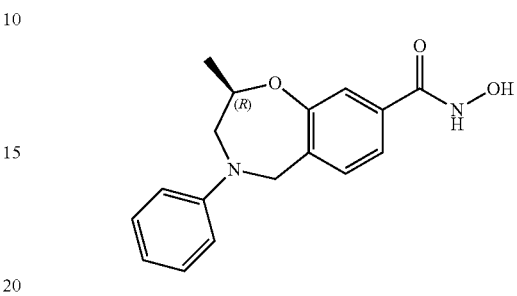

Into a 8-mL vial, was placed methyl (R)-2-methyl-4-phenyl-2,3,4,5-tetrahydrobenzo[f][1,4]oxazepine-8-carboxylate (270 mg, 0.91 mmol, 1 equiv) in THF/MeOH (4:1, 3 mL). To the above mixture was added aq. 1N NaOH (1.82 mL, 1.82 mmol, 2 equiv) and NH$_2$OH (50% in water, 1.83 mL, 27.18 mmol, 30 equiv). The resulting mixture was stirred for 3 h at room temperature. The crude product was purified by Prep-HPLC (Column: XBridge XP C18 OBD, 5 µm, 19×150 mm; Mobile Phase A: Water/0.05% TFA; Mobile Phase B: MeCN; Flow rate: 0.7 mL/min; Gradient: 5% B to 62% B in 7 min; Detector: UV 254 nm) to afford the title compound as a brown solid (134 mg, 49% yield). $^1$H-NMR (400 MHz, DMSO-$d_6$) δ(ppm): 11.29 (br s, 1H), 7.55-7.52 (d, J=7.5 Hz, 1H), 7.37-7.28 (m, 2H), 7.12-7.07 (m, 2H), 6.87-6.84 (m, 2H), 6.59-6.54 (m, 1H), 4.84-4.79 (d, J=16.2 Hz, 1H), 4.48-4.36 (d, J=15.6 Hz, 1H), 4.07-3.87 (m, 3H), 1.37-1.35 (d, J=6.3 Hz, 3H). MS: (ES, m/z): 299 [M+H]$^+$.

Example 16—Preparation of (R)—N-hydroxy-2,4-dimethyl-2,3,4,5-tetrahydrobenzo[f][1,4]oxazepine-8-carboxamide

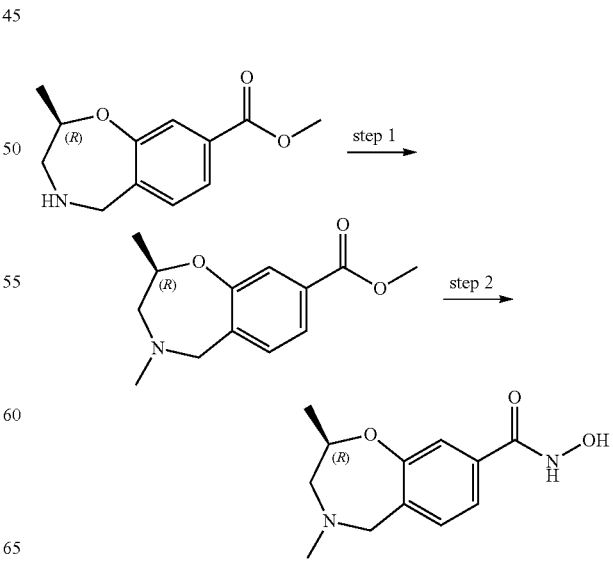

Step-1: Methyl (R)-2,4-dimethyl-2,3,4,5-tetrahydrobenzo[f][1,4]oxazepine-8-carboxylate

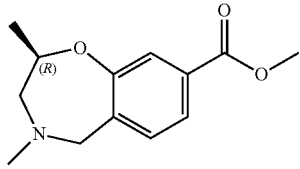

Into a 8-mL vial, was placed a solution of methyl (2R)-2-methyl-2,3,4,5-tetrahydro-1,4-benzoxazepine-8-carboxylate (70 mg, 0.32 mmol, 1 equiv) in acetic acid (1.5 mL). This was followed by the addition of formaldehyde (40% in water, 28 mg, 0.93 mmol, 3 equiv) in portions. The mixture was stirred for 2 h at room temperature. To this was added NaBH(OAc)₃ (334 mg, 1.58 mmol, 5 equiv), in portions at 0° C. The resulting solution was stirred for 18 h at room temperature. The reaction mixture was diluted with EtOAc (40 mL), then washed with water (2×20 mL). The combined organic layers were dried over anhydrous Na₂SO₄, filtered, and concentrated under vacuum to afford the title compound as a yellow solid (63 mg) which was used without further purification. MS: (ES, m/z): 236 [M+H]⁺.

Step-2: (R)—N-hydroxy-2,4-dimethyl-2,3,4,5-tetrahydrobenzo[f][1,4]oxazepine-8-carboxamide

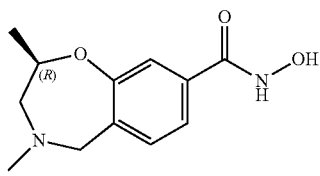

Into a 8-mL vial, was placed a solution of methyl (R)-2,4-dimethyl-2,3,4,5-tetrahydrobenzo[f][1,4]oxazepine-8-carboxylate (134 mg, 0.57 mmol, 1 equiv) in THF/MeOH (4:1, 2 mL). aq. 1N NaOH (1.71 mL, 3 equiv) and NH₂OH (50% in water, 1.13 mL, 30 equiv) were added. The resulting solution was stirred for 15 h at room temperature. The crude product was purified by Prep-HPLC (Column: T3 C18 OBD, 5 μm, 19×150 mm; Mobile Phase A: Water/0.05% TFA; Mobile Phase B: MeCN; Flow rate: 25 mL/min; Gradient: 3% B to 30% B in 10 min; Detector: UV 254, 220 nm) to afford the title compound as a TFA salt as an off-white solid (5 mg, 4% yield). ¹H-NMR (400 MHz, DMSO-d₆) δ(ppm): 7.32-7.17 (m, 2H), 7.06-7.01 (s, 1H), 4.56-3.91 (m, 1H), 3.79-3.71 (t, J=17.2 hz, 1H), 3.67-3.51 (t, J=33.2 hz, 1H), 2.89-2.84 (m, 1H), 2.69-2.61 (m, 1H), 2.27-2.25 (d, J=3.6 Hz, 3H), 1.24-1.20 (d, J=8.0 Hz, 3H). MS: (ES, m/z): 237 [M+H]⁺.

Example 17—Preparation of (S)—N-hydroxy-2-methyl-2,3,4,5-tetrahydrobenzo[f][1,4]oxazepine-8-carboxamide

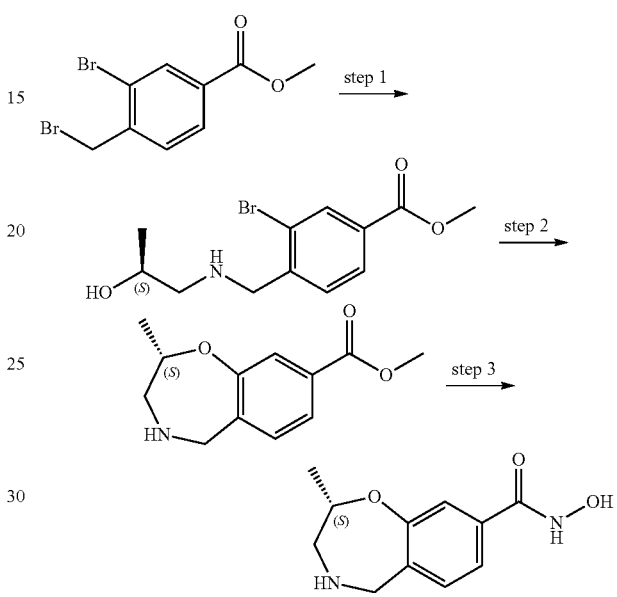

Step-1: Methyl (S)-3-bromo-4-(((2-hydroxypropyl)amino)methyl)benzoate

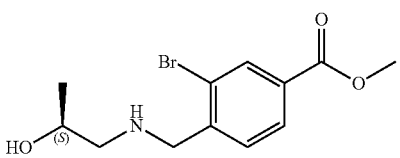

Into a 500-mL round-bottom flask, was placed (2S)-1-aminopropan-2-ol (2.98 g, 39.68 mmol, 1 equiv), MeCN (150 mL) and K₂CO₃ (8.24 g, 59.62 mmol, 1.5 equiv). This was followed by the addition of a solution of methyl 3-bromo-4-(bromomethyl)benzoate (12.3 g, 39.94 mmol, 1 equiv) in MeCN (20 mL) dropwise with stirring at room temperature over 1 h. The resulting solution was stirred for 3 h at room temperature. The resulting mixture was concentrated under vacuum. The residue was diluted with EtOAc (300 mL) and washed with water (3×300 mL). The combined organic layers were dried and concentrated. The residue was purified by silica gel chromatography (EtOAc/pet. ether, 1:5) to afford the title compound as an off-white solid (5.1 g, 42% yield). MS: (ES, m/z): 302 [M+H]⁺.

Step-2: Methyl (S)-2-methyl-2,3,4,5-tetrahydrobenzo[f][1,4]oxazepine-8-carboxylate

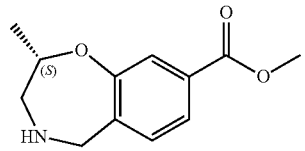

Into a 150-mL pressure tank reactor purged and maintained with an inert atmosphere of nitrogen, was placed methyl (S)-3-bromo-4-(((2-hydroxypropyl)amino)methyl) benzoate (5.1 g, 16.88 mmol, 1 equiv), isopropanol (120 mL), $K_2CO_3$ (3.510 g, 25.40 mmol, 1.5 equiv) and CuI (966 mg, 5.07 mmol, 0.3 equiv). The resulting solution was stirred for 17 h at 110° C. in an oil bath. The resulting mixture was concentrated under vacuum. The residue was diluted with $CH_2Cl_2$ (200 mL), washed with water (2×200 mL), dried and concentrated. The residue was purified by silica gel chromatography (EtOAc/pet. ether, 1:2) to afford the title compound as a yellow oil (2.2 g, 59% yield). $^1$H-NMR (DMSO, 400 MHz) δ(ppm): 7.57-7.53 (m, 1H), 7.46-7.44 (m, 1H), 7.30-7.27 (m, 1H), 3.84-3.76 (m, 5H), 3.09-3.05 (d, J=13.6 Hz, 1H), 2.75-2.66 (s, 1H), 1.30-1.29 (d, J=6.4 Hz, 2H). 1.23-1.22 (d, J=6.4 Hz, 3H). MS: (ES, m/z): 222 [M+H]$^+$.

Step-3: (S)—N-Hydroxy-2-methyl-2,3,4,5-tetrahydrobenzo[f][1,4]oxazepine-8-carboxamide

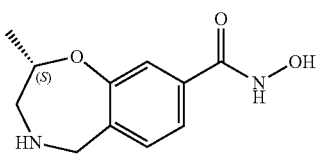

Into a 8-mL vial, was placed a solution of methyl (S)-2-methyl-2,3,4,5-tetrahydrobenzo[f][1,4]oxazepine-8-carboxylate (50 mg, 0.23 mmol, 1 equiv) in THF/MeOH (4:1, 1 mL), $NH_2OH$ (50% in water, 0.44 mL, 30 equiv) and aq. 1N NaOH (0.45 mL, 2 equiv) were added. The resulting solution was stirred for 14 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 4% B to 18% B in 6 min; Detector: UV 254, 220 nm) to afford the title compound as a brown oil (23.5 mg, 31% yield). $^1$H-NMR (400 MHz, DMSO-d$_6$) δ(ppm): 11.29 (s, 1H), 9.11 (s, 3H), 7.52-7.44 (m, 3H), 4.43-4.39 (d, J=7.2 hz, 1H), 4.32-4.29 (d, J=7.2 hz, 1H), 4.19-4.12 (m, 1H), 3.53-3.50 (d, J=6.4 Hz, 1H), 3.29-3.25 (d, J=6.8 Hz, 1H), 1.38-1.37 (m, 3H). MS: (ES, m/z): 223 [M+H]$^+$.

Example 18—Preparation of (S)—N8-hydroxy-N4-(4-methoxyphenyl)-2-methyl-2,3-dihydrobenzo[f][1,4]oxazepine-4,8(5H)-dicarboxamide

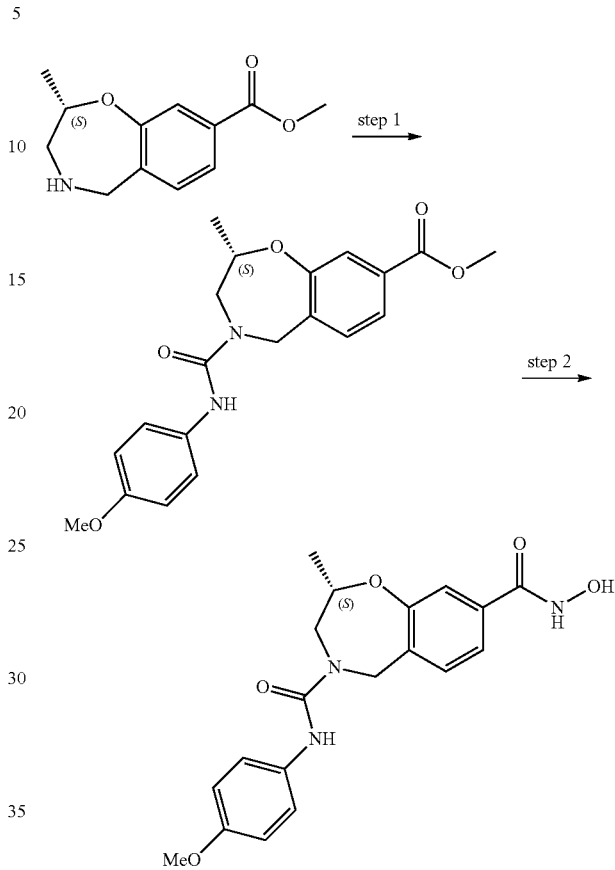

Step-1: Methyl (S)-4-((4-methoxyphenyl)carbamoyl)-2-methyl-2,3,4,5-tetrahydrobenzo[f][1,4]oxazepine-8-carboxylate

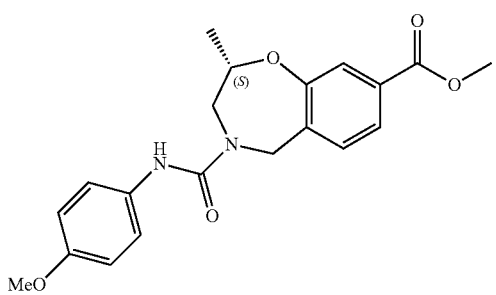

Into a 20-mL vial, was placed a solution of methyl (S)-2-methyl-2,3,4,5-tetrahydrobenzo[f][1,4]oxazepine-8-carboxylate (150 mg, 0.68 mmol, 1 equiv) in $CH_2Cl_2$ (10 mL), 1-isocyanato-4-methoxybenzene (150 mg, 1.01 mmol, 1.2 equiv) and $Et_3N$ (0.18 mg, 3 equiv). The resulting solution was stirred for 10 h at room temperature. The resulting mixture was concentrated under vacuum. The residue was purified by silica gel chromatography (EtOAc/pet. ether, 1:1) to afford the title compound as a light yellow oil (150 mg, 60% yield). MS: (ES, m/z): 371 [M+H]$^+$.

Step-2: (S)—N8-Hydroxy-N4-(4-methoxyphenyl)-2-methyl-2,3-dihydrobenzo[f][1,4]oxazepine-4,8(5H)-dicarboxamide

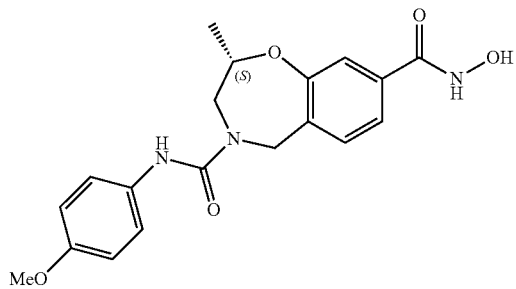

Into a 10-mL vial, was placed a solution of methyl (S)-4-((4-methoxyphenyl)carbamoyl)-2-methyl-2,3,4,5-tetrahydrobenzo[f][1,4]oxazepine-8-carboxylate (370 mg, 1 mmol, 1 equiv) in THF/MeOH (4:1, 4 mL). This was followed by the addition of aq. 1N NaOH (1 mL, 2 equiv). To this was added NH$_2$OH (50% in water, 1 mL, 30 equiv). The resulting solution was stirred for 3 h at room temperature. The crude product was purified by Prep-HPLC (Column: XBridge XP C18 OBD, 5 μm, 19×150 mm; Mobile Phase A: Water/0.05% TFA; Mobile Phase B: MeCN; Flow rate: 0.7 mL/min; Gradient: 10% B to 60% B in 7 min; Detector: UV 254 nm) to afford the title compound as a light brown solid (106 mg, 73% yield). $^1$H-NMR (400 MHz, DMSO-d$_6$) δ(ppm): 11.14 (br s, 1H), 8.36 (br s, 1H), 7.43-7.38 (m, 2H), 7.28-7.24 (m, 2H), 6.81-6.80 (m, 2H), 4.85-4.81 (d, J=15.6 Hz, 1H), 4.43-4.39 (d, J=15.6 Hz, 1H), 4.04-4.01 (d, J=12.8 Hz, 1H), 3.76 (s, 3H), 3.43-3.37 (m, 2H), 1.32-1.31 (d, J=6.4 Hz, 3H). MS: (ES, m/z): 372 [M+H]$^+$.

Example 19—Preparation of (S)—N-hydroxy-4-((4-methoxyphenyl)sulfonyl)-2-methyl-2,3,4,5-tetrahydrobenzo[f][1,4]oxazepine-8-carboxamide

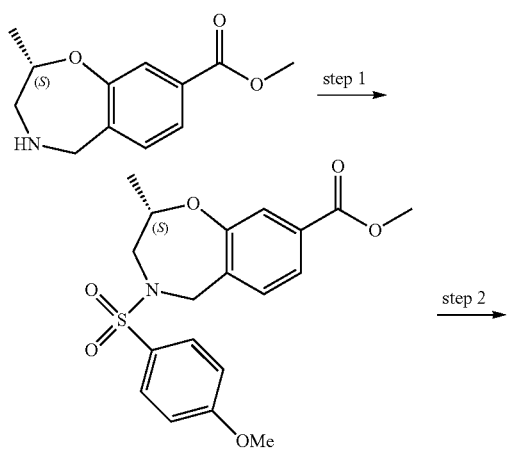

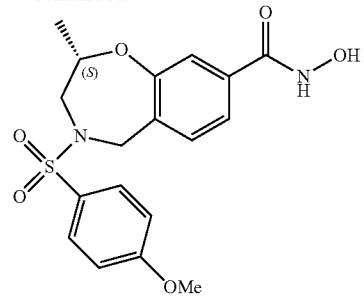

Step-1: Methyl (S)-4-((4-methoxyphenyl)sulfonyl)-2-methyl-2,3,4,5-tetrahydrobenzo[f][1,4]oxazepine-8-carboxylate

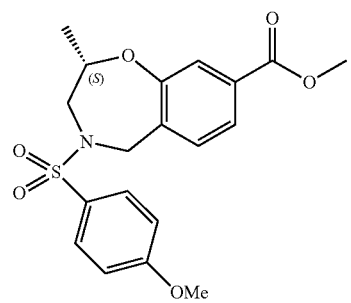

Into a 50-mL flask, was placed a solution of methyl (S)-2-methyl-2,3,4,5-tetrahydrobenzo[f][1,4]oxazepine-8-carboxylate (100 mg, 0.45 mmol, 1 equiv) in CH$_2$Cl$_2$ (20 mL), Et$_3$N (140 mg, 1.38 mmol, 3 equiv) and 4-dimethylaminopyridine (55 mg, 0.45 mmol, 1 equiv), then 4-methoxybenzene-1-sulfonyl chloride (140 mg, 0.68 mmol, 1.5 equiv) was added at 0° C. The resulting solution was stirred for 4 h at room temperature and concentrated under vacuum. The residue was purified by silica gel chromatography (EtOAc/pet. ether, 1:1) to afford the title compound as a yellow solid (80 mg, 45% yield). MS: (ES, m/z): 392 [M+H]$^+$.

Step-2: (S)—N-Hydroxy-4-((4-methoxyphenyl)sulfonyl)-2-methyl-2,3,4,5-tetrahydrobenzo[f][1,4]oxazepine-8-carboxamide Into a 10-mL vial, was placed a solution of methyl (S)-4-((4-methoxyphenyl)sulfonyl)-2-methyl-2,3,4,5-tetrahydrobenzo[f][1,4]oxazepine-8-carboxylate (80 mg, 0.20 mmol, 1 equiv) in THF/MeOH (4:1, 2 mL). This was followed by the addition of aq. 1N NaOH (0.41 mL, 2 equiv) and NH$_2$OH (50% in water, 0.41 mL, 30 equiv). The resulting solution was stirred for 2 h at room temperature. The crude product was purified by Prep-HPLC (Column: XBridge XP C18 OBD, 5 µm, 19×150 mm; Mobile Phase A: Water/0.05% TFA; Mobile Phase B: MeCN; Flow rate: 0.7 mL/min; Gradient: 9% B to 60% B in 9 min; Detector: UV 254 nm) to afford the title compound as a pink solid (34 mg, 43% yield). $^1$H-NMR (400 MHz, DMSO-d$_6$) δ(ppm): 11.17 (br s, 1H), 9.01 (br s, 1H), 7.70-7.66 (m, 2H), 7.42-7.39 (m, 1H), 7.33-7.31 (m, 1H), 7.24 (s, 1H), 7.06-7.02 (m, 2H), 4.57-4.53 (d, J=16 Hz, 1H), 4.25-4.21 (d, J=16 Hz, 1H), 4.04-3.91 (m, 1H), 3.82 (s, 3H), 3.68-3.65 (m, 1H), 3.21-3.18 (m, 1H), 1.26-1.25 (m, J=6.4 Hz, 3H). MS: (ES, m/z): 393 [M+H]$^+$.

Example 20—Preparation of (S)—N-hydroxy-2-methyl-4-phenyl-2,3,4,5-tetrahydrobenzo[f][1,4]oxazepine-8-carboxamide

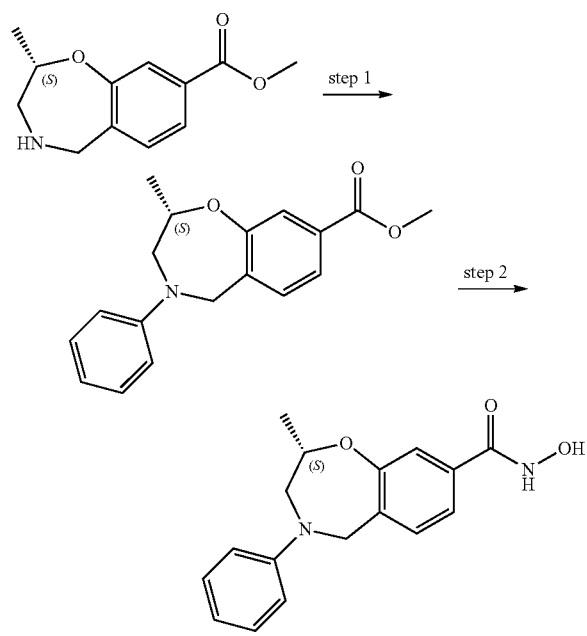

Step-1: Methyl (S)-2-methyl-4-phenyl-2,3,4,5-tetrahydrobenzo[f][1,4]oxazepine-8-carboxylate Into a 10-mL vial purged and maintained with Nitrogen, was placed a solution of methyl (S)-2-methyl-2,3,4,5-tetrahydrobenzo[f][1,4]oxazepine-8-carboxylate (100 mg, 0.45 mmol, 1 equiv) in 1,4-dioxane (5 mL), iodobenzene (180 mg, 0.88 mmol, 2 equiv), Pd(OAc)$_2$ (10 mg, 0.04 mmol, 0.1 equiv), Xantphos (50 mg, 0.09 mmol, 0.2 equiv) and Cs$_2$CO$_3$ (450 mg, 1.38 mmol, 3 equiv). The resulting solution was stirred for 10 h at 100° C. and then concentrated under vacuum. The residue was purified by silica gel chromatography (EtOAc/pet. ether, 1:5) to afford the title compound as a light yellow solid (50 mg, 37% yield). MS: (ES, m/z): 298 [M+H]$^+$.

Step-2: (S)—N-Hydroxy-2-methyl-4-phenyl-2,3,4,5-tetrahydrobenzo[f][1,4]oxazepine-8-carboxamide

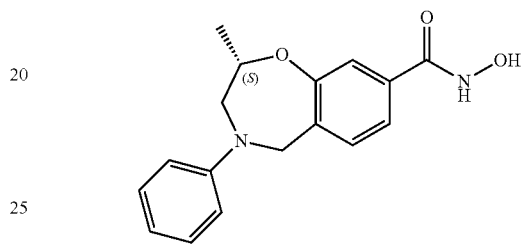

Into a 10-mL vial, was placed a solution of methyl (S)-2-methyl-4-phenyl-2,3,4,5-tetrahydrobenzo[f][1,4]oxazepine-8-carboxylate (50 mg, 0.17 mmol, 1 equiv) in THF/MeOH (4:1, 3 mL). This was followed by the addition of aq. 1N NaOH (0.34 mL, 2 equiv) and NH$_2$OH (50% in water, 0.34 mL, 30 equiv). The resulting solution was stirred for 3 h at room temperature. The crude product was purified by Prep-HPLC (Column: XBridge XP C18 OBD, 5 µm, 19×150 mm; Mobile Phase A: Water/0.05% TFA; Mobile Phase B: MeCN; Flow rate: 0.7 mL/min; Gradient: 12% B to 48% B in 11 min; Detector: UV 254 nm) to afford the title compound as a brown solid (12 mg, 25% yield). $^1$H-NMR (400 MHz, DMSO-d$_6$) δ(ppm): δ11.09 (br s, 1H), 7.54-7.52 (m, 1H), 7.37-7.35 (m, 1H), 7.34 (s, 1H), 7.29-7.28 (m, 2H), 6.95-6.85 (m, 2H), 6.59-6.55 (m, 1H), 4.83-4.79 (d, J=16 Hz, 1H), 4.62-4.58 (d, J=16 Hz, 1H), 4.08-4.02 (m, 2H), 3.47-3.41 (m, 1H), 1.36-1.24 (m, J=6.4 Hz, 3H). MS: (ES, m/z): 299 [M+H]$^+$.

Example 21—Preparation of (S)—N-hydroxy-2,4-dimethyl-2,3,4,5-tetrahydrobenzo[f][1,4]oxazepine-8-carboxamide

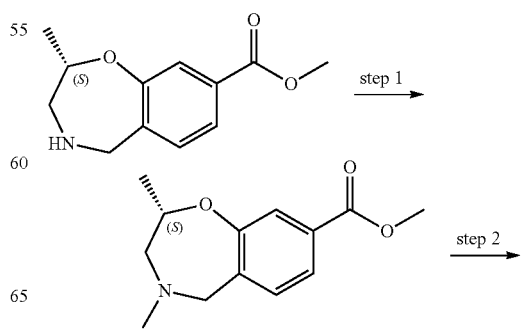

-continued

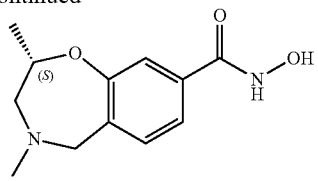

Step-1: Methyl (S)-2,4-dimethyl-2,3,4,5-tetrahydrobenzo[f][1,4]oxazepine-8-carboxylate

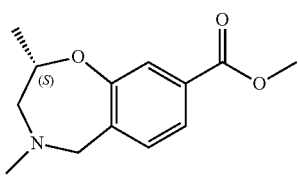

Into a 8-mL vial, was placed methyl (S)-2-methyl-2,3,4,5-tetrahydrobenzo[f][1,4]oxazepine-8-carboxylate (190 mg, 0.86 mmol, 1 equiv), formaldehyde (78 mg, 2.60 mmol, 3 equiv), acetic acid (2.5 mL) and NaBH(OAc)$_3$ (907 mg, 4.30 mmol, 5 equiv). The resulting solution was stirred for 16 h at room temperature. The reaction was quenched with water (20 mL). The resulting solution was extracted with EtOAc (2×20 mL), washed with H$_2$O (2×15 mL) and concentrated to afford the title compound as yellow oil (100 mg, 49% yield) which was used without further purification. MS: (ES, m/z): 236 [M+H]$^+$.

Step-2: (S)—N-hydroxy-2,4-dimethyl-2,3,4,5-tetrahydrobenzo[f][1,4]oxazepine-8-carboxamide

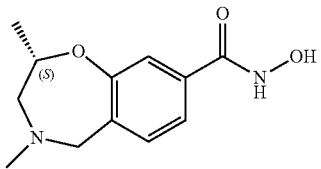

Into a 8-mL vial, was placed methyl (S)-2,4-dimethyl-2,3,4,5-tetrahydrobenzo[f][1,4]oxazepine-8-carboxylate (100 mg, 0.43 mmol, 1 equiv), THF/MeOH (4:1, 2.5 mL). To this was added aq. 1N NaOH (0.85 mL, 0.85 mmol, 2 equiv) and NH$_2$OH (50% in water, 0.86 mL, 12.73 mmol, 30 equiv). The resulting solution was stirred for 3 h at room temperature. The crude product was purified by Prep-HPLC (Column: XBridge RP C18 OBD, 5 µm, 19×150 mm; Mobile Phase A: Water/0.05% formic acid; Mobile Phase B: MeCN/0.05% TFA; Flow rate: 0.7 mL/min; Gradient: 5% B to 40% B in 7 min; Detector: UV 254 nm) to afford the title compound as a light brown solid (37 mg, 37% yield). $^1$H-NMR (400 MHz, DMSO-d$_6$) δ(ppm): 11.30 (s, 1H), 10.16 (br s, 1H), 9.19 (s, 1H), 7.54-7.52 (m, 1H), 4.46-7.44 (m, 2H), 4.63-4.49 (m, 2H), 3.75-3.48 (m, 2H), 3.11-2.70 (m, 3H), 1.37-1.35 (d, J=6.4 Hz, 3H). MS: (ES, m/z): 237 [M+H]$^+$.

Example 22—Preparation of (S)—N-hydroxy-4-(4-methoxybenzyl)-2-methyl-2,3,4,5-tetrahydrobenzo[f][1,4]oxazepine-8-carboxamide

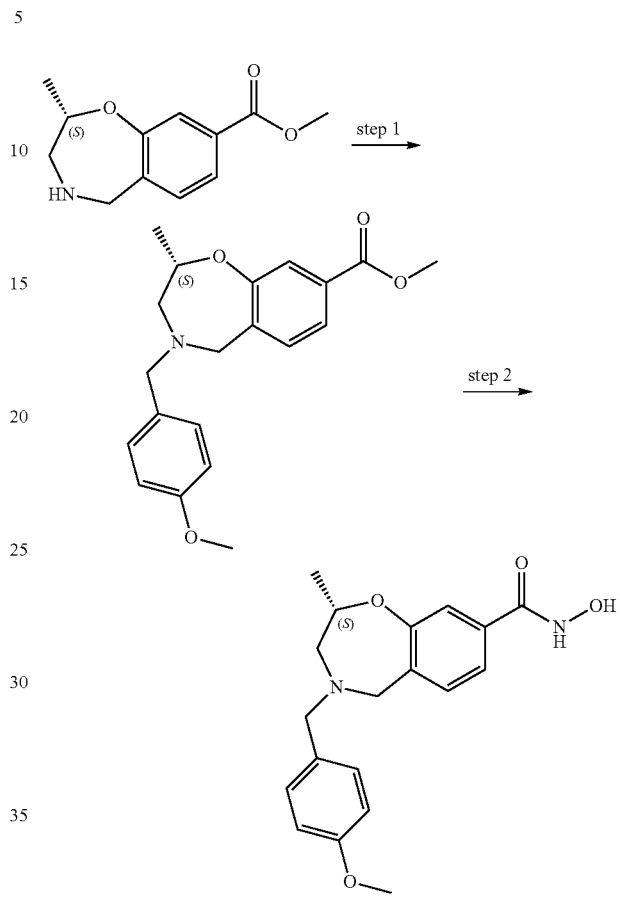

Step-1: Methyl (S)-4-(4-methoxybenzyl)-2-methyl-2,3,4,5-tetrahydrobenzo[f][1,4]oxazepine-8-carboxylate

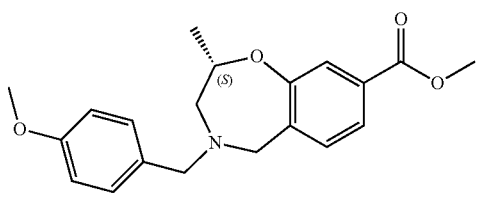

Into a 8-mL vial, was placed methyl (S)-2-methyl-2,3,4,5-tetrahydrobenzo[f][1,4]oxazepine-8-carboxylate (100 mg, 0.45 mmol, 1 equiv). This was followed by the addition of sodium hydride (60% in oil, 55 mg, 2.29 mmol, 3 equiv) at 0° C. The mixture was stirred at room temperature for 1 h and then 1-(bromomethyl)-4-methoxybenzene (91 mg, 0.45 mmol, 1 equiv) was added. The mixture was stirred for 19 h at room temperature. The reaction was then quenched with water (20 mL). The resulting solution was extracted with EtOAc (20 mL) and washed with H$_2$O (2×15 mL). The organic phase was concentrated and the residue was purified by silica gel chromatography (EtOAc/pet. ether, 1:3) to afford the title compound as a yellow oil (60 mg, 39% yield). MS: (ES, m/z): 342 [M+H]+.

Step-2: (S)—N-hydroxy-4-(4-methoxybenzyl)-2-methyl-2,3,4,5-tetrahydrobenzo[f][1,4]oxazepine-8-carboxamide

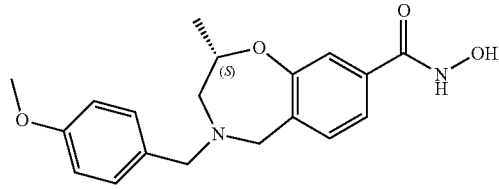

Into a 8-mL vial, was placed methyl (S)-4-(4-methoxybenzyl)-2-methyl-2,3,4,5-tetrahydrobenzo[f][1,4]oxazepine-8-carboxylate (60 mg, 0.18 mmol, 1 equiv) in THF/MeOH (4:1, 2 mL). To this was added aq. 1N NaOH (0.35 mL, 0.35 mmol, 2 equiv). To the mixture was added NH$_2$OH (50% in water, 0.36 mL, 5.27 mmol, 30 equiv). The resulting solution was stirred for 3 h at room temperature. The crude product was purified by Prep-HPLC (Column Sunfire Prep C18 OBD, 5 μm, 19×150 mm; Mobile Phase A: Water/0.05% TFA; Mobile Phase B: MeCN; Flow rate: 0.7 mL/min; Gradient: 5% B to 30% B in 6 min; Detector: UV 254 nm) to afford the title compound as an off-white solid (21 mg, 26% yield). $^1$H-NMR (400 MHz, DMSO-d$_6$) δ(ppm): 11.17 (s, 1H), 9.13-9.11 (br s, 1H), 7.57-7.28 (m, 5H), 4.67-4.11 (m, 5H), 3.89-3.87 (m, 3H), 3.78-3.56 (m, 2H), 1.34 (s, 3H). MS: (ES, m/z): 343 [M+H]+.

Example 23—Preparation of (R)—N8-hydroxy-2-isopropyl-N4-(4-methoxyphenyl)-2,3-dihydrobenzo[f][1,4]oxazepine-4,8(5H)-dicarboxamide

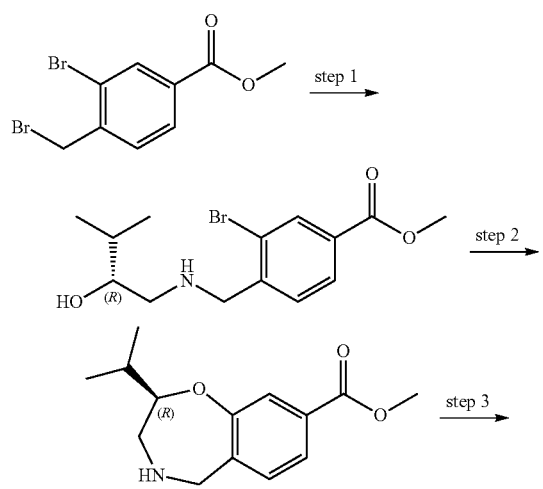

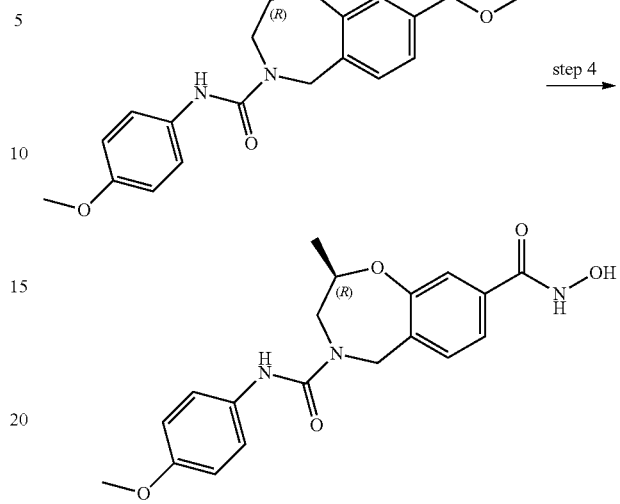

Step-1: Methyl (R)-3-bromo-4-(((2-hydroxy-3-methylbutyl)amino)methyl)benzoate

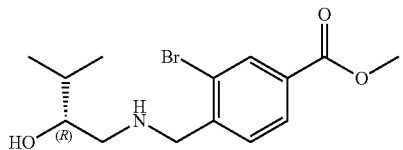

Into a 500-mL round-bottom flask, was placed (R)-1-amino-3-methylbutan-2-ol (6.41 g, 62.13 mmol, 2 equiv), MeCN (100 mL) and K$_2$CO$_3$ (6.44 g, 46.60 mmol, 1.5 equiv). This was followed by the addition of methyl 3-bromo-4-(bromomethyl)benzoate (9.52 g, 30.91 mmol, 1 equiv) in several batches. The resulting solution was stirred for 16 h at room temperature. The resulting mixture was concentrated under vacuum. The residue was dissolved in EtOAc (200 mL) and washed with H$_2$O (2×100 mL). The organic layer was dried over anhydrous Na$_2$SO$_4$, filtered, and concentrated. The residue was purified by silica gel chromatography (EtOAc/pet. ether, 3:2) to afford the title compound as a yellow solid (6.48 g, 63% yield). MS: (ES, m/z): 330 [M+H]+.

Step-2: Methyl (R)-2-isopropyl-2,3,4,5-tetrahydrobenzo[f][1,4]oxazepine-8-carboxylate

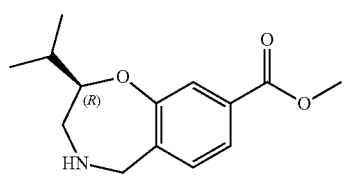

Into a 100-mL pressure tank reactor purged and maintained with an inert atmosphere of nitrogen, was placed methyl (R)-3-bromo-4-(((2-hydroxy-3-methylbutyl)amino)methyl)benzoate (4.91 g, 14.87 mmol, 1 equiv), isopropanol (50 mL), $K_2CO_3$ (3.09 g, 22.36 mmol, 1.5 equiv) and CuI (1.42 g, 7.46 mmol, 0.5 equiv). The resulting solution was stirred for 16 h at 110° C. in an oil bath. The resulting mixture was concentrated under vacuum. The residue was dissolved in $CH_2Cl_2$ (200 mL) and washed with $H_2O$ (3×100 mL). The organic layer was dried over anhydrous $MgSO_4$, filtered, and concentrated. The residue was purified by silica gel chromatography ($H_2O$/MeCN, 3:1) to afford the TFA salt of the title compound as a green solid (1.5 g, 40% yield). MS: (ES, m/z): 250 $[M+H]^+$.

Step-3: Methyl (R)-2-isopropyl-4-((4-methoxyphenyl)carbamoyl)-2,3,4,5-tetrahydrobenzo[f][1,4]oxazepine-8-carboxylate

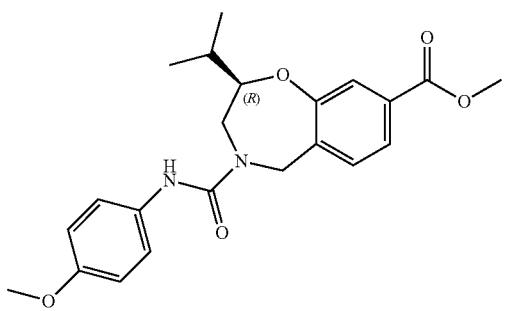

Into a 8-mL vial, was placed methyl (R)-2-isopropyl-2,3,4,5-tetrahydrobenzo[f][1,4]oxazepine-8-carboxylate (100 mg, 0.40 mmol, 1 equiv), $CH_2Cl_2$ (1.5 mL) and $Et_3N$ (121 mg, 1.20 mmol, 3 equiv). This was followed by the addition of 1-isocyanato-4-methoxybenzene (90 mg, 0.60 mmol, 1.5 equiv) at 0° C. The resulting solution was stirred for 4 h at room temperature, then concentrated under vacuum. The residue was purified by silica gel chromatography (EtOAc/pet. ether, 1:2) to afford the title compound as a red oil (110 mg, 69% yield). MS: (ES, m/z): 399 $[M+H]^+$.

Step-4: (R)—N8-Hydroxy-2-isopropyl-N4-(4-methoxyphenyl)-2,3-dihydrobenzo[f][1,4]oxazepine-4,8(5H)-dicarboxamide

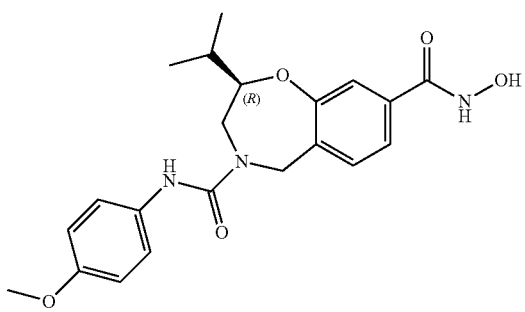

Into a 8-mL vial, was placed methyl (R)-2-isopropyl-4-((4-methoxyphenyl)carbamoyl)-2,3,4,5-tetrahydrobenzo[f][1,4]oxazepine-8-carboxylate (110 mg, 0.28 mmol, 1 equiv) in THF/MeOH (4:1, 1.5 mL). Then $NH_2OH$ (50% in water, 0.56 mL, 8.48 mmol, 30 equiv) and aq. 1N NaOH (0.56 mL, 0.55 mmol, 2 equiv) were added at the same time. The resulting solution was stirred for 16 h at room temperature. The crude product was purified by Prep-HPLC (Column: Sunfire Prep C18 OBD, 5 µm, 19×50 mm; Mobile Phase A: Water/0.05% formic acid; Mobile Phase B: MeCN; Flow rate: 25 mL/min; Gradient: 23% B to 40% B in 7 min; Detector: UV 254, 220 nm) to afford the title compound as a light pink solid (20.2 mg, 18% yield). $^1$H-NMR (400 MHz, DMSO-$d_6$) δ(ppm): 11.87 (br s, 1H), 8.40 (s, 1H), 7.45-7.41 (m, 2H), 7.39-7.33 (m, 1H), 7.28-7.26 (m, 2H), 6.80-6.78 (d, J=9.2 hz, 2H), 4.89-4.85 (d, J=16.0 Hz, 1H), 4.46-4.42 (d, J=16.0 Hz, 1H), 4.11-4.08 (d, J=13.6 Hz, 1H), 3.68 (s, 3H), 3.59-3.55 (m, 1H), 3.48-3.42 (m, 1H), 1.96-1.88 (m, 1H), 1.09-1.06 (m, 6H). MS: (ES, m/z): 400 $[M+H]^+$.

Example 24—Preparation of (R)—N8-hydroxy-2-(methoxymethyl)-N4-(4-methoxyphenyl)-2,3-dihydrobenzo[f][1,4]oxazepine-4,8(5H)-dicarboxamide

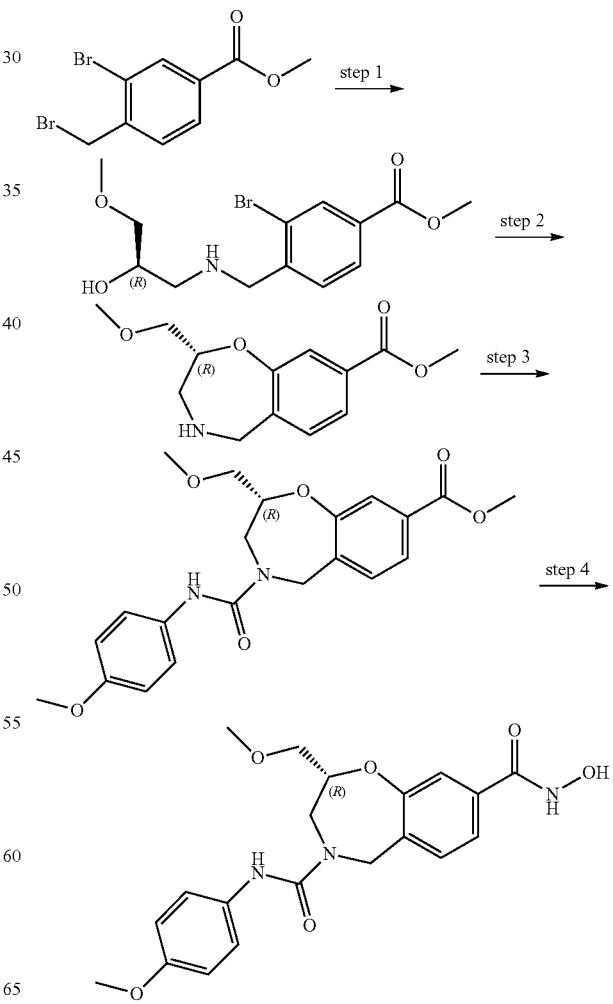

Step-1: Methyl (R)-3-bromo-4-(((2-hydroxy-3-methoxypropyl)amino)methyl)benzoate

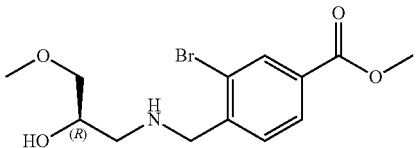

Into a 500-mL round-bottom flask, was placed a solution of (R)-1-amino-3-methoxypropan-2-ol (5.7 g, 54.22 mmol, 1.1 equiv) in MeCN (150 mL) and $K_2CO_3$ (10 g, 72.46 mmol, 1.5 equiv). This was followed by the addition of a solution of methyl 3-bromo-4-(bromomethyl)benzoate (15.2 g, 49.36 mmol, 1 equiv) in MeCN (100 mL) dropwise with stirring at room temperature. The resulting mixture was stirred for 16 h at room temperature. The resulting mixture was concentrated under vacuum. The residue was diluted with $H_2O$ (100 mL) and extracted with EtOAc (3×100 mL). The organic layer was washed with $H_2O$ (2×100 mL) and concentrated under vacuum. The residue was purified by silica gel chromatography (EtOAc/pet. ether, 1:4) to afford the title compound as a yellow solid (6.4 g, 39% yield). MS: (ES, m/z): 332 $[M+H]^+$.

Step-2: Methyl (R)-2-(methoxymethyl)-2,3,4,5-tetrahydrobenzo[f][1,4]oxazepine-8-carboxylate

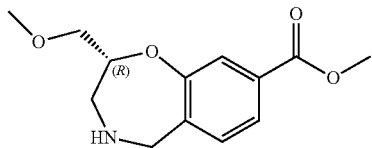

Into a 150-mL pressure tank reactor purged and maintained with an inert atmosphere of nitrogen, was placed a solution of methyl (R)-3-bromo-4-(((2-hydroxy-3-methoxypropyl)amino)methyl)benzoate (6.4 g, 19.27 mmol, 1 equiv) in isopropanol (130 mL), $K_2CO_3$ (4.01 g, 29.06 mmol, 1.5 equiv) and CuI (1.47 g, 7.74 mmol, 0.4 equiv). The resulting solution was stirred for 16 h at 110° C. in an oil bath. The resulting mixture was concentrated under vacuum. The residue was diluted with $H_2O$ (100 mL) and extracted with $CH_2Cl_2$ (3×100 mL). The organic layer was washed with $H_2O$ (2×100 mL) and concentrated under vacuum. The residue was purified by C18 chromatography (MeCN/$H_2O$+ 0.05% TFA, 88:12) to afford the TFA salt of the title compound as a yellow solid (3.5 g, 50% yield). MS: (ES, m/z): 252 $[M+H]^+$.

Step-3: Methyl (R)-2-(methoxymethyl)-4-((4-methoxyphenyl)carbamoyl)-2,3,4,5-tetrahydrobenzo[f][1,4]oxazepine-8-carboxylate

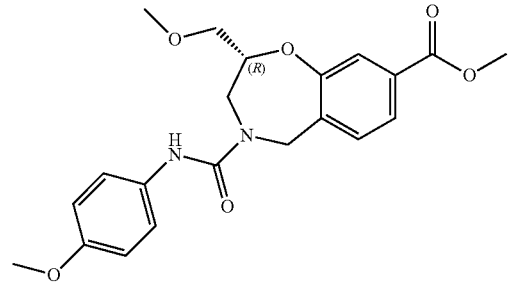

Into a 8-mL vial, was placed a solution of methyl (R)-2-(methoxymethyl)-2,3,4,5-tetrahydrobenzo[f][1,4]oxazepine-8-carboxylate*TFA (100 mg, 0.27 mmol, 1 equiv) in $CH_2Cl_2$ (2 mL), $Et_3N$ (111 mg, 1.10 mmol, 4 equiv), a solution of 1-isocyanato-4-methoxybenzene (61 mg, 0.41 mmol, 1.5 equiv) in $CH_2Cl_2$ (0.5 mL). The resulting mixture was stirred for 6 h at room temperature. The resulting solution was diluted with $CH_2Cl_2$ (10 mL) and washed with $H_2O$ (2×15 mL). The combined organic layers were dried over anhydrous $MgSO_4$, filtered, and concentrated under vacuum. The residue was purified by silica gel chromatography (EtOAc/pet. ether, 1:2) to afford the title compound as a colorless oil (100 mg, 91% yield). MS: (ES, m/z): 401 $[M+H]^+$.

Step-4: (R)—N8-Hydroxy-2-(methoxymethyl)-N4-(4-methoxyphenyl)-2,3-dihydrobenzo[f][1,4]oxazepine-4,8(5H)-dicarboxamide

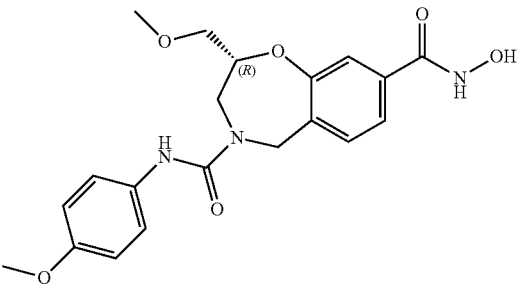

Into a 8-mL vial, was placed a solution of methyl (R)-2-(methoxymethyl)-4-((4-methoxyphenyl)carbamoyl)-2,3,4,5-tetrahydrobenzo[f][1,4]oxazepine-8-carboxylate (100 mg, 0.25 mmol, 1 equiv) in THF/MeOH (4:1, 3 mL). Then aq. 1N NaOH (0.50 mL, 2 equiv) and $NH_2OH$ (50% in $H_2O$, 0.50 mL, 30 equiv) were added simultaneously. The resulting solution was stirred for 2 h at room temperature. The crude product was purified by Prep-HPLC (Column: Xbridge Prep C18 OBD, 5 μm, 19×50 mm; Mobile Phase A: Water/0.05% formic acid; Mobile Phase B: MeCN; Flow rate: 23 mL/min; Gradient: 5% B to 39% B in 7 min; Detector: UV 254, 220 nm) to afford the title compound as a light pink solid (62.7 mg, 63% yield). $^1$H-NMR (400 MHz, DMSO-$d_6$) δ(ppm): 11.15 (br s, 1H), 9.03 (br s, 1H), 8.40 (s, 1H), 7.44-7.7.39 (m, 2H), 7.36-7.35 (m, 1H), 7.28-7.24 (m, 2H), 6.81-6.77 (m, 2H), 4.87-4.83 (m, 1H), 4.48-4.44 (m, 1H), 4.08-4.03 (m, 2H), 3.68 (s, 3H), 3.61-3.48 (m, 3H), 3.35-3.33 (m, 3H). MS: (ES, m/z): 402 $[M+H]^+$.

TABLE 6

The following compounds were prepared according to the method of Example 24, using (S)-1-amino-3-methoxypropan-2-ol.

| Structure | Found M + H | $^1$H-NMR (400 MHz, DMSO-$d_6$) δ(ppm) |
|---|---|---|
| 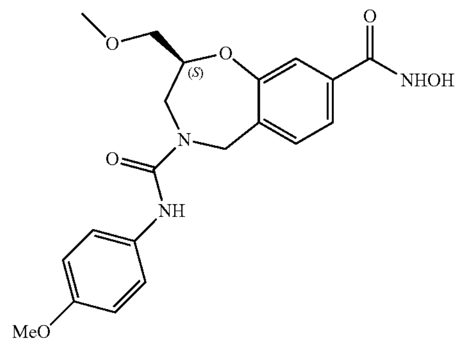 | (ES, m/z): 402 [M + H]$^+$ | 11.17 (s, 1H), 9.02 (s, 1H), 8.04 (s, 1H), 7.45-7.41 (m, 2H), 7.40-7.36 (m, 1H), 7.28-7.24 (m, 2H), 6.81-6.77 (m, 2H), 4.87-4.83 (d, J = 15.6 Hz, 1H), 4.48-4.44 (d, J = 15.6 Hz, 1H), 4.08-4.03 (m, 2H), 3.68 (s, 3H), 3.61-3.48 (m, 3H), 3.35-3.33 (d, J = 9.2 hz, 2H) |

Example 25—Preparation of (R)—N8-hydroxy-N4-(4-methoxyphenyl)-2-phenyl-2,3-dihydrobenzo[f][1,4]oxazepine-4,8(5H)-dicarboxamide

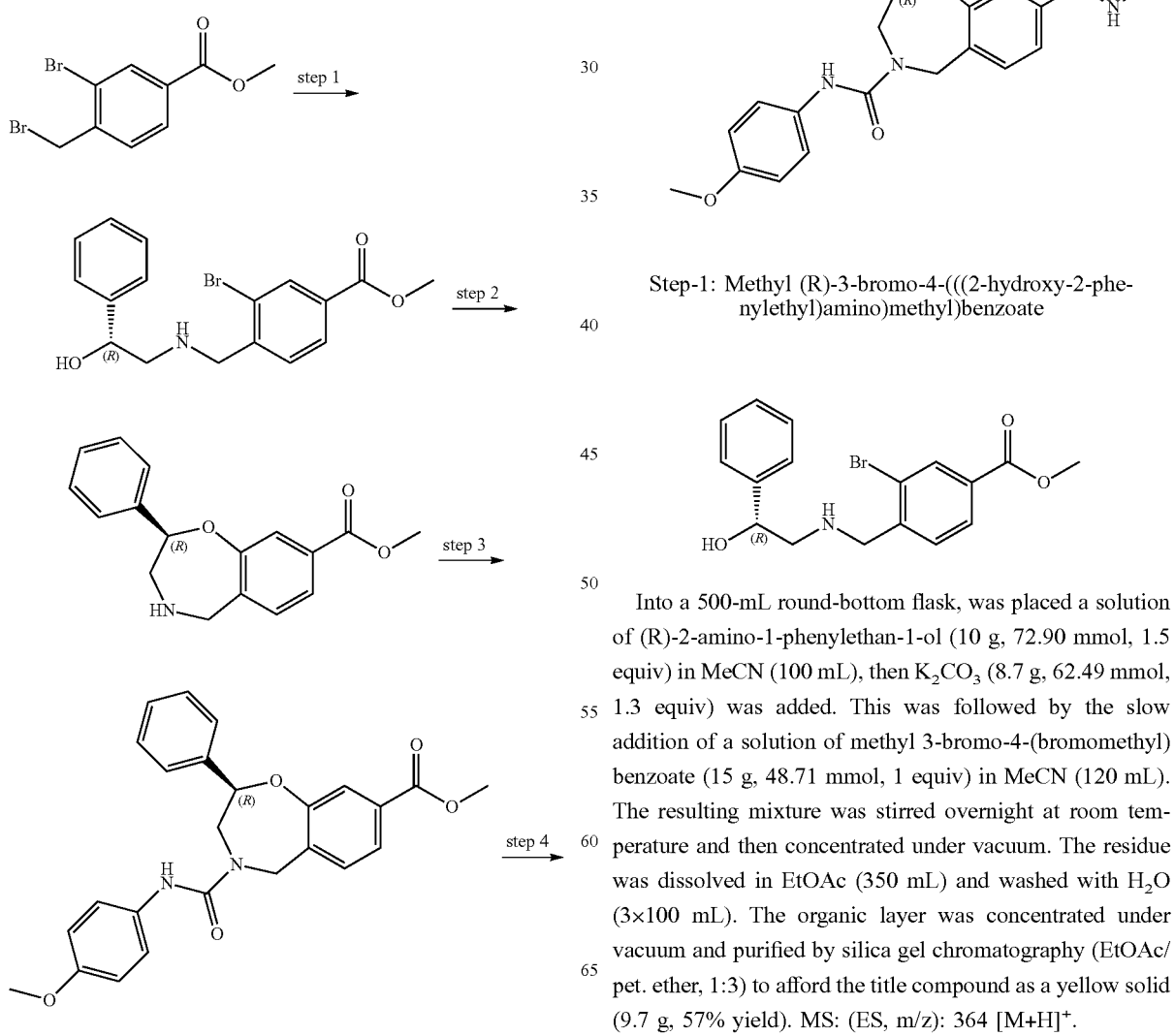

Step-1: Methyl (R)-3-bromo-4-(((2-hydroxy-2-phenylethyl)amino)methyl)benzoate

Into a 500-mL round-bottom flask, was placed a solution of (R)-2-amino-1-phenylethan-1-ol (10 g, 72.90 mmol, 1.5 equiv) in MeCN (100 mL), then K$_2$CO$_3$ (8.7 g, 62.49 mmol, 1.3 equiv) was added. This was followed by the slow addition of a solution of methyl 3-bromo-4-(bromomethyl)benzoate (15 g, 48.71 mmol, 1 equiv) in MeCN (120 mL). The resulting mixture was stirred overnight at room temperature and then concentrated under vacuum. The residue was dissolved in EtOAc (350 mL) and washed with H$_2$O (3×100 mL). The organic layer was concentrated under vacuum and purified by silica gel chromatography (EtOAc/pet. ether, 1:3) to afford the title compound as a yellow solid (9.7 g, 57% yield). MS: (ES, m/z): 364 [M+H]$^+$.

Step-2: Methyl (R)-2-phenyl-2,3,4,5-tetrahydrobenzo[f][1,4]oxazepine-8-carboxylate

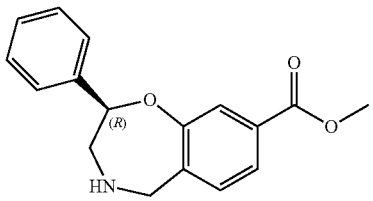

Into a 100-mL sealed tube, was placed a solution of methyl (R)-3-bromo-4-(((2-hydroxy-2-phenylethyl)amino)methyl)benzoate (4.0 g, 10.98 mmol, 1 equiv) in isopropanol (80 mL), then $K_2CO_3$ (3.1 g, 22.43 mmol, 2 equiv) was added. This was followed by the addition of CuI (630 mg, 3.31 mmol, 0.3 equiv). The resulting mixture was stirred overnight at 110° C. in an oil bath. The solids were filtered out and the filtrate was concentrated under vacuum. The residue was dissolved in EtOAc (300 mL) and washed with $H_2O$ (3×150 mL). The organic layer was concentrated under vacuum. The residue was dissolved in DMF and purified by Flash-Prep-HPLC (Mobile Phase A: Water/0.05% TFA, Mobile Phase B: MeCN; Gradient: 5% B to 20% B in 15 min; Detector: 220, 254 nm) to afford the TFA salt of the title compound as a white solid (1.9 g, 61% yield). MS: (ES, m/z): 284 [M+H]$^+$.

Step-3: Methyl (R)-4-((4-methoxyphenyl)carbamoyl)-2-phenyl-2,3,4,5-tetrahydrobenzo[f][1,4]oxazepine-8-carboxylate

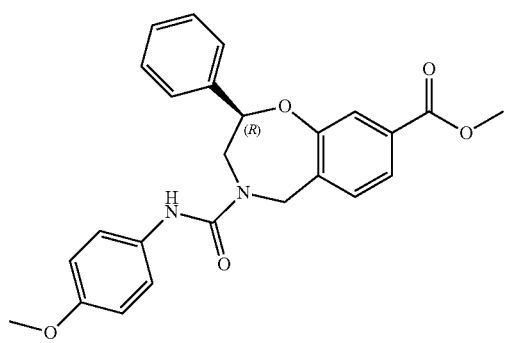

Into a 8-mL vial, was placed a solution of methyl (R)-2-phenyl-2,3,4,5-tetrahydrobenzo[f][1,4]oxazepine-8-carboxylate.TFA (100 mg, 0.35 mmol, 1 equiv) in $CH_2Cl_2$ (2.0 mL). This was followed by the addition of $Et_3N$ (76.13 mg, 0.75 mmol, 3 equiv) at 0° C. To this was added 1-isocyanato-4-methoxybenzene (56.2 mg, 0.38 mmol, 1.5 equiv). The resulting mixture was stirred for 6 h at room temperature and diluted with $CH_2Cl_2$ (20 mL). The resulting mixture was washed with $H_2O$ (3×15 mL) and the combined organic layers were concentrated under vacuum. The residue was purified by silica gel chromatography (EtOAc/pet. ether, 1:1) to afford the title compound as a yellow oil (105 mg, 69% yield). MS: (ES, m/z): 433 [M+H]$^+$.

Step-4: (R)—N8-Hydroxy-N4-(4-methoxyphenyl)-2-phenyl-2,3-dihydrobenzo[f][1,4]oxazepine-4,8(5H)-dicarboxamide

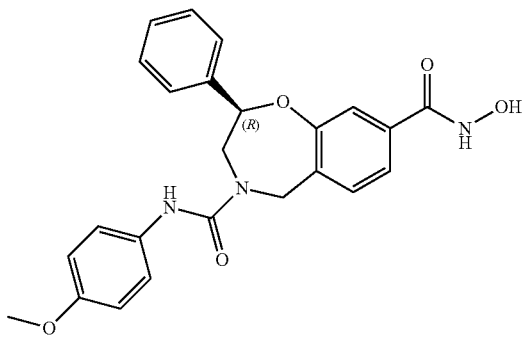

Into a 8-mL vial, was placed a solution of methyl (R)-4-((4-methoxyphenyl)carbamoyl)-2-phenyl-2,3,4,5-tetrahydrobenzo[f][1,4]oxazepine-8-carboxylate (105 mg, 0.24 mmol, 1 equiv) in THF/MeOH (4:1, 2.5 mL). Then aq. 1N NaOH (0.48 mL, 2 equiv) and $NH_2OH$ (50% in $H_2O$, 0.48 mL, 30 equiv) were added simultaneously. The resulting solution was stirred for 2 h at room temperature. The crude product was purified by Prep-HPLC (Column: Xbridge Prep C18 OBD, 5 µm, 19×50 mm; Mobile Phase A: Water/0.05% formic acid; Mobile Phase B: MeCN; Flow rate: 25 mL/min; Gradient: 30% B to 70% B in 10 min; Detector: UV 254, 220 nm) to afford the title compound as a pink solid (48.6 mg, 46% yield). $^1$H-NMR (400 MHz, DMSO-$d_6$) δ(ppm): 11.13 (br s, 1H), 9.02 (s, 1H), 8.51 (s, 1H), 7.55-7.28 (m, 10H), 6.81-6.79 (d, 2H), 5.02-4.94 (m, 2H), 4.58-4.54 (d, 1H), 4.26-4.22 (d, 1H), 3.71-3.65 (m, 4H). MS: (ES, m/z): 434 [M+H]$^+$.

TABLE 7

The following compounds were prepared according to the method of Example 25, using (S)-2-amino-1-phenylethan-1-ol.

| Structure | Found M + H | $^1$H-NMR (400 MHz, DMSO-$d_6$) δ(ppm) |
|---|---|---|
| 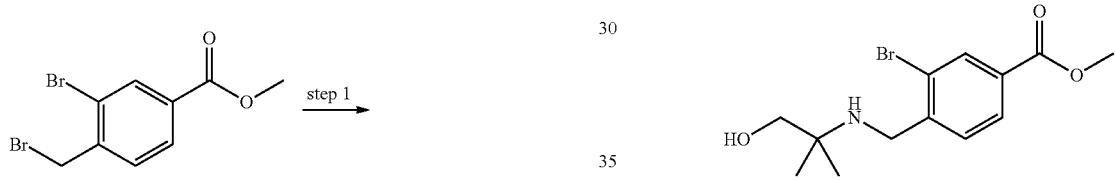 | (ES, m/z): 434 [M + H]$^+$ | 11.12 (s, 1H), 9.02 (s, 1H), 8.51 (s, 1H), 7.57-7.51 (m, 3H), 7.51-7.43 (m, 3H), 7.42-7.33 (m, 2H), 7.32-7.26 (m, 2H), 6.81-6.79 (d, J = 8.8 Hz, 2H), 5.02-4.94 (m, 2H), 4.58-4.54 (d, J = 15.6 Hz, 1H), 4.23-4.22 (d, J = 14.0 Hz, 1H), 3.71-3.64 (m, 4H) |

Example 26—Preparation of N-hydroxy-4-(4-methoxybenzyl)-3,3-dimethyl-2,3,4,5-tetrahydrobenzo[f][1,4]oxazepine-8-carboxamide

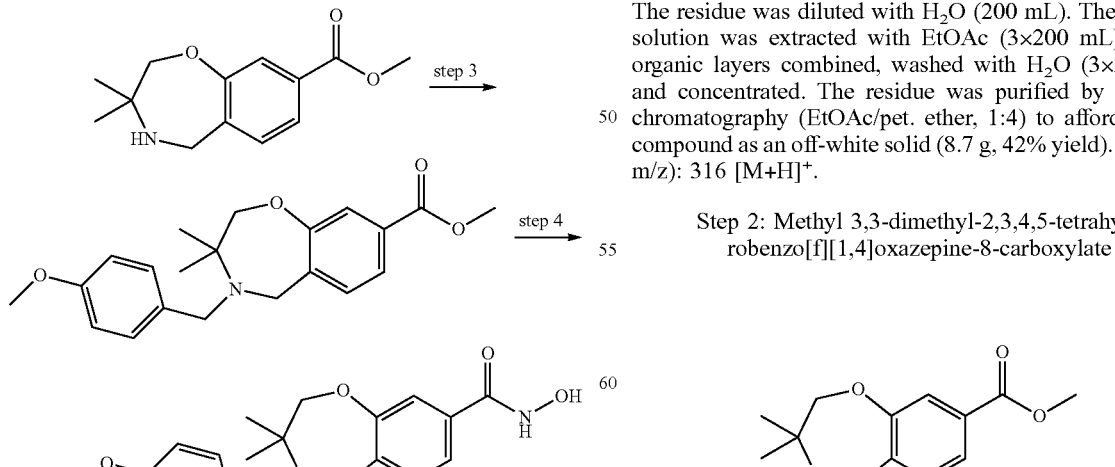

Step-1: Methyl 3-bromo-4-[[(1-hydroxy-2-methylpropan-2-yl)amino]methyl]benzoate

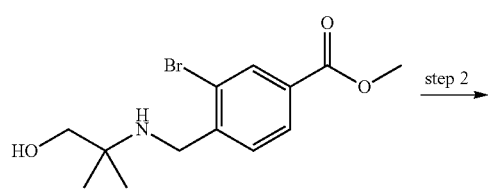

Into a 500-mL round-bottom flask, were placed a solution of 2-amino-2-methylpropan-1-ol (11.52 g, 129.24 mmol, 2 equiv) in MeCN (150 mL), K$_2$CO$_3$ (13.40 g, 97.10 mmol, 1.5 equiv). This was followed by the addition of a solution of methyl 3-bromo-4-(bromomethyl)benzoate (20 g, 64.94 mmol, 1 equiv) in MeCN (50 mL) dropwise with stirring at room temperature. The resulting solution was stirred for 16 h at room temperature, then concentrated under vacuum. The residue was diluted with H$_2$O (200 mL). The resulting solution was extracted with EtOAc (3×200 mL) and the organic layers combined, washed with H$_2$O (3×200 mL), and concentrated. The residue was purified by silica gel chromatography (EtOAc/pet. ether, 1:4) to afford the title compound as an off-white solid (8.7 g, 42% yield). MS: (ES, m/z): 316 [M+H]$^+$.

Step 2: Methyl 3,3-dimethyl-2,3,4,5-tetrahydrobenzo[f][1,4]oxazepine-8-carboxylate Into a 250-mL pressure tank reactor purged and maintained with an inert atmosphere of nitrogen, were placed a solution of methyl 3-bromo-4-[[(1-hydroxy-2-methylpropan-2-yl)amino]methyl]benzoate (8.7 g, 27.52 mmol, 1 equiv) in isopropanol (150 mL), $K_2CO_3$ (5.7 g, 41.30 mmol, 1.5 equiv) and CuI (1.57 g, 8.26 mmol, 0.3 equiv). The resulting solution was stirred overnight at 110° C. in an oil bath, then concentrated under vacuum. The residue was diluted with $H_2O$ (200 mL). The resulting solution was extracted with EtOAc (3×200 mL) and the combined organic layers was washed with $H_2O$ (3×200 mL) and concentrated. The residue was purified by silica gel chromatography (EtOAc/pet. ether, 1:2) to afford the title compound as a green oil (3.9 g, 60% yield). 1H-NMR (400 MHz, DMSO-d6) δ(ppm): 7.63-7.60 (d, J=12.8 Hz, 1H), 7.54-7.52 (s, 1H), 7.25-7.23 (d, J=7.6 Hz, 1H), 4.01 (s, 2H), 3.94-3.89 (m, 5H), 1.23 (s, 6H). MS: (ES, m/z): 236 [M+H]⁺.

Step-3: Methyl 4-(4-methoxybenzyl)-3,3-dimethyl-2,3,4,5-tetrahydrobenzo[f][1,4]oxazepine-8-carboxylate

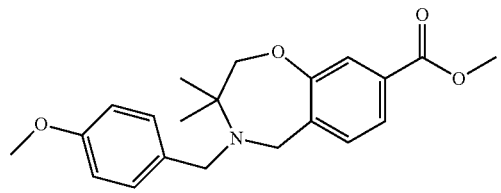

Into a 8-mL vial, was placed a solution of methyl 3,3-dimethyl-2,3,4,5-tetrahydrobenzo[f][1,4]oxazepine-8-carboxylate (100 mg, 0.43 mmol, 1 equiv) in THF (2 mL). This was followed by the addition of sodium hydride (60%, 51 mg, 2.12 mmol, 3 equiv). To this was added 1-(bromomethyl)-4-methoxybenzene (86 mg, 0.43 mmol, 1 equiv). The resulting solution was stirred for 22 h at room temperature. The reaction was then quenched with water (3 mL). The resulting solution was extracted with EtOAc (3×10 mL), washed with water (3×10 mL) and concentrated. The residue was purified by silica gel chromatography (EtOAc/pet. ether, 1:4) to afford the title compound as a light yellow oil (100 mg, 66% yield). MS: (ES, m/z): 356 [M+H]⁺.

Step-4: N-Hydroxy-4-(4-methoxybenzyl)-3,3-dimethyl-2,3,4,5-tetrahydrobenzo[f][1,4]oxazepine-8-carboxamide

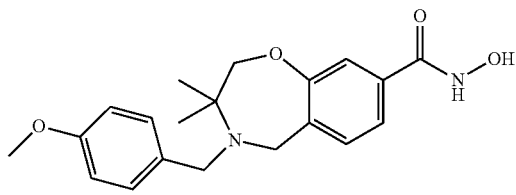 [SMILES: COc1ccc(CN2Cc3ccc(C(=O)NO)cc3OCC2(C)C)cc1]

Into a 8-mL vial, was placed a solution of methyl 4-(4-methoxybenzyl)-3,3-dimethyl-2,3,4,5-tetrahydrobenzo[f][1,4]oxazepine-8-carboxylate (100 mg, 0.28 mmol, 1 equiv) in THF/MeOH (4:1, 2.5 mL). This was followed by the addition of $NH_2OH$ (50% in water, 0.56 mL, 30 equiv). To this was added aq. 1N NaOH (0.55 mL, 2 equiv). The resulting solution was stirred for 2 h at room temperature. The crude product was purified by Prep-HPLC (Column: XBridge C18 OBD, 5 μm, 19×150 mm; Mobile Phase A: Water/0.05% TFA; Mobile Phase B: MeCN; Flow rate: 20 mL/min; Gradient: 30% B to 70% B in 10 min; Detector: UV 254, 220 nm) to afford the title compound as a TFA salt as a light pink solid (27 mg, 20% yield). ¹H-NMR (400 MHz, DMSO-d₆) δ(ppm): 11.30 (s, 1H), 9.80 (s, 1H), 9.52-8.61 (br, 1H), 7.47-7.39 (m, 4H), 7.29-7.03 (m, 3H), 5.02-4.51 (m, 2H), 4.51-4.16 (m, 3H) 4.32-4.28 (m, 3H) 3.60-3.45 (m, 1H), 1.75-1.41 (m, 6H). MS: (ES, m/z): 357 [M+H]⁺.

Example 27—Preparation of N-hydroxy-3,3-dimethyl-2,3,4,5-tetrahydrobenzo[f][1,4]oxazepine-8-carboxamide

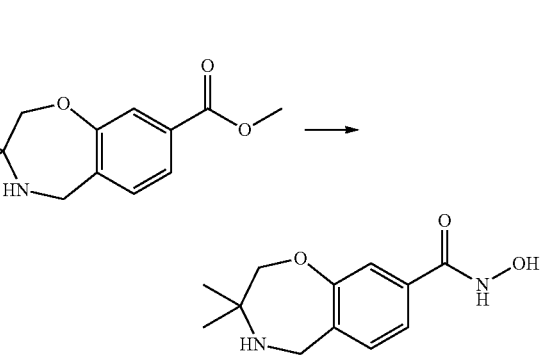

Into a 8-mL vial, was placed a solution of methyl 3,3-dimethyl-2,3,4,5-tetrahydrobenzo[f][1,4]oxazepine-8-carboxylate (100 mg, 0.43 mmol, 1 equiv) in THF/MeOH (4:1, 2 mL), followed by the addition of aq. 1N NaOH (0.85 mL, 2 equiv) and $NH_2OH$ (50% in $H_2O$, 0.84 mL, 30 equiv). The resulting solution was stirred for 3 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 2% B to 8% B in 7 min; Detector: UV 254, 220 nm) to afford the title compound as the TFA salt as an off-white solid (57 mg, 39% yield). ¹H-NMR (400 MHz, DMSO-d₆) δ(ppm): 11.30 (br, 1H), 9.32 (m, 2H), 9.12 (br, 1H), 7.51 (s, 2H), 7.42 (s, 1H), 4.42 (s, 2H), 4.03 (s, 2H), 1.39 (s, 6H) MS: (ES, m/z): 237 [M+H]⁺.

Example 28—Preparation of N-hydroxy-3,3,4-trimethyl-2,3,4,5-tetrahydrobenzo[f][1,4]oxazepine-8-carboxamide

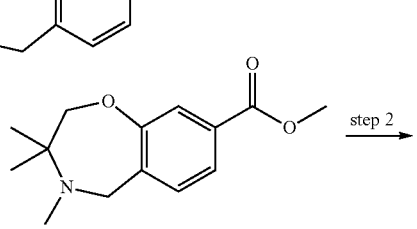

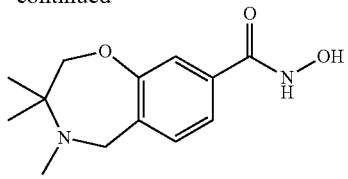

Step-1: Methyl 3,3,4-trimethyl-2,3,4,5-tetrahydrobenzo[f][1,4]oxazepine-8-carboxylate

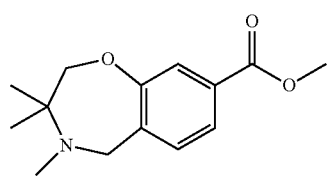

Into a 8-mL vial, was placed a solution of methyl 3,3-dimethyl-2,3,4,5-tetrahydrobenzo[f][1,4]oxazepine-8-carboxylate (100 mg, 0.43 mmol, 1 equiv) in acetic acid (2 mL). This was followed by the addition of formaldehyde (38 mg, 1.27 mmol, 3 equiv) and NaBH(OAc)$_3$ (449 mg, 2.13 mmol, 5 equiv). The resulting mixture was stirred for 16 h at room temperature. H$_2$O (20 mL) was added, then the resulting solution was extracted with EtOAc (3×30 mL), washed with H$_2$O (3×20 mL), dried over anhydrous Na$_2$SO$_4$, filtered and concentrated under vacuum. The residue was purified by silica gel chromatography (EtOAc/pet. ether, 1:1) to afford the title compound as a yellow oil (28 mg, 27% yield). MS: (ES, m/z): 250 [M+H]$^+$.

Step-2: N-Hydroxy-3,3,4-trimethyl-2,3,4,5-tetrahydrobenzo[f][1,4]oxazepine-8-carboxamide

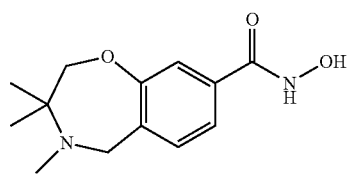 [SMILES: CN1Cc2ccc(C(=O)NO)cc2OCC1(C)C]

Into a 8-mL vial, was placed a solution of methyl 3,3,4-trimethyl-2,3,4,5-tetrahydrobenzo[f][1,4]oxazepine-8-carboxylate (28.4 mg, 0.11 mmol, 1 equiv) in THF/MeOH (4:1, 1 mL), followed by aq. 1N NaOH (0.23 mL, 2 equiv) and NH$_2$OH (50% in H$_2$O, 0.23 mL, 30 equiv). The resulting solution was stirred for 3 h at room temperature. The crude product was purified by Prep-HPLC (Column: XBridge RP C18 OBD, 5 μm, 19×150 mm; Mobile Phase A: Water/ 0.05% TFA; Mobile Phase B: MeCN; Flow rate: 25 mL/min; Gradient: 5% B to 13% B in 4 min; Detector: UV 254, 220 nm) to afford the title compound as the TFA salt as a brown oil (18 mg, 44% yield). $^1$H-NMR (300 MHz, DMSO-d$_6$) δ(ppm): 11.30 (br s, 1H), 10.17-10.08 (br s, 1H), 9.12 (br, 1H), 7.53-7.41 (m, 3H), 4.74-4.70 (d, J=12.0 Hz, 1H), 4.50-4.28 (m, 2H), 4.07-4.03 (d, J=12.0 Hz, 1H), 2.77-2.73 (s, 3H), 1.53 (s, 3H), 1.40 (s, 3H). MS: (ES, m/z): 251 [M+H]$^+$.

Example 29—Preparation of (S)—N-hydroxy-3-isopropyl-4-(4-methoxybenzyl)-2,3,4,5-tetrahydrobenzo[f][1,4]oxazepine-8-carboxamide

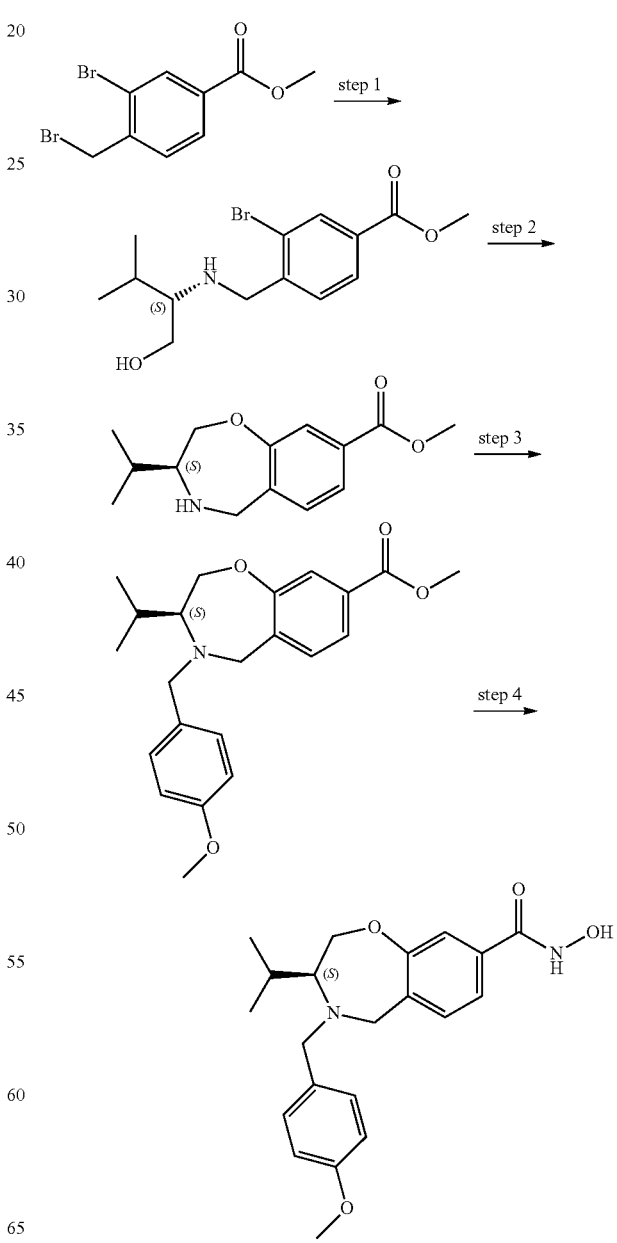

Step-1: Methyl (S)-3-bromo-4-(((1-hydroxy-3-methylbutan-2-yl)amino)methyl)benzoate

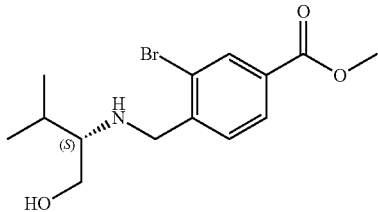

Into a 1-L round-bottom flask, was placed a solution of (S)-2-amino-3-methylbutan-1-ol (23.33 g, 226.15 mmol, 2 equiv) in MeCN (300 mL). This was followed by the addition of a solution of methyl 3-bromo-4-(bromomethyl)benzoate (35 g, 113.65 mmol, 1 equiv) in MeCN (200 mL) dropwise with stirring. The resulting solution was stirred for 17 h at room temperature, then concentrated under vacuum. The residue was diluted with H$_2$O (300 mL), extracted with EtOAc (3×300 mL) and the combined organic layers were concentrated. The residue was purified by silica gel chromatography (EtOAc/pet. ether, 1:2) to afford the title compound as an off-white solid (20 g, 53% yield). MS: (ES, m/z): 330 [M+H]$^+$.

Step-2: Methyl (S)-3-isopropyl-2,3,4,5-tetrahydrobenzo[f][1,4]oxazepine-8-carboxylate

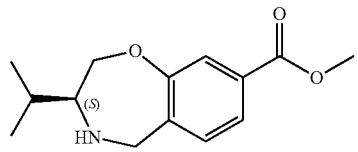

Into a 500-mL pressure tank reactor purged and maintained with an inert atmosphere of nitrogen, were placed a solution of methyl (S)-3-bromo-4-(((1-hydroxy-3-methylbutan-2-yl)amino)methyl)benzoate (20 g, 60.57 mmol, 1 equiv) in isopropanol (350 mL), K$_2$CO$_3$ (12.9 g, 93.48, 1.5 equiv) and CuI (3.6 g, 18.95 mmol, 0.3 equiv). The resulting mixture was stirred for 23 h at 110° C. in an oil bath and then concentrated under vacuum. The residue was diluted with H$_2$O (300 mL), extracted with CH$_2$Cl$_2$ (3×300 mL). The combined organic layers were washed with H$_2$O (3×300 mL) and concentrated. The residue was purified by silica gel chromatography (EtOAc/pet. ether, 1:1) to afford the title compound as a yellow oil (5.3 g, 35% yield). 1H-NMR (400 MHz, DMSO-d6) δ(ppm): 7.66-7.64 (d, J=8.0 Hz, 1H), 7.57 (s, 1H), 7.31-7.29 (d, J=8.0 Hz, 1H), 4.43-4.40 (m, 1H), 4.09-3.95 (m, 2H), 3.94-3.81 (s 3H), 3.72-3.69 (m, 1H), 2.89-2.86 (m, 1H), 1.88-1.80 (m, 1H), 1.03-0.99 (m, 6H). MS: (ES, m/z): 250 [M+H]$^+$.

Step-3: Methyl (S)-3-isopropyl-4-(4-methoxybenzyl)-2,3,4,5-tetrahydrobenzo[f][1,4]oxazepine-8-carboxylate

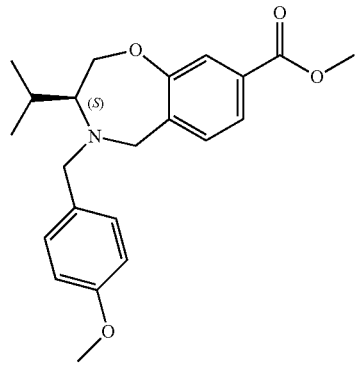

Into a 8-mL vial, was placed a solution of methyl (S)-3-isopropyl-2,3,4,5-tetrahydrobenzo[f][1,4]oxazepine-8-carboxylate (100 mg, 0.40 mmol, 1 equiv) in THF (2 mL), followed by the addition of sodium hydride (60% dispersion in oil, 49 mg, 2.04 mmol, 3 equiv) at 0° C. To this was added 1-(bromomethyl)-4-methoxybenzene (81 mg, 0.40 mmol, 1 equiv). The resulting solution was stirred for 16 h at room temperature, then quenched with water (3 mL). The resulting mixture was concentrated under vacuum and diluted with H$_2$O (10 mL). The resulting solution was extracted with EtOAc (3×10 mL), washed with H$_2$O (3×10 mL), and concentrated. The residue was purified by silica gel chromatography (EtOAc/pet. ether, 1:4) to afford the title compound as a yellow oil (70 mg, 47% yield). MS: (ES, m/z): 370 [M+H]$^+$.

Step-4: (S)—N-hydroxy-3-isopropyl-4-(4-methoxybenzyl)-2,3,4,5-tetrahydrobenzo[f][1,4]oxazepine-8-carboxamide

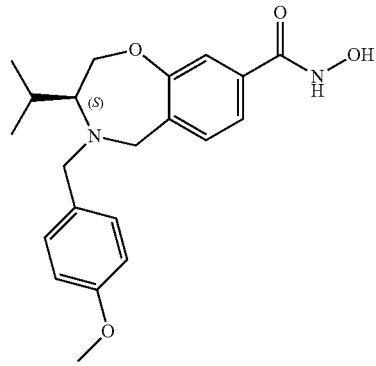

Into a 8-mL vial, was placed a solution of methyl (S)-3-isopropyl-4-(4-methoxybenzyl)-2,3,4,5-tetrahydrobenzo[f][1,4]oxazepine-8-carboxylate (70 mg, 0.19 mmol, 1 equiv) in THF/MeOH (4:1, 2 mL), followed by the addition of NH$_2$OH (50% in water, 0.38 mL, 30 equiv) and aq. 1N NaOH (0.38 mL, 2 equiv). The resulting solution was stirred for 2 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 20 mL/min; Gradient: 5% B to 70% B in 7 min; Detector: UV 254, 220 nm) to afford the title compound as the TFA salt as a light brown solid (42 mg, 48% yield). 1H-NMR (400 MHz, DMSO-d6) δ(ppm): 11.40-10.89 (s, 1H), 9.44-8.65 (br, 1H), 7.50-6.68 (m, 7H), 4.98-3.89 (m, 7H), 3.75-3.71 (m, 3H), 2.21-1.91 (s, 1H). 1.09-0.89 (s, J=6.4 Hz, 6H). MS: (ES, m/z): 371 [M+H]$^+$.

TABLE 8

The following compound was prepared according to the method of Example 29, using (R)-2-amino-3-methylbutan-1-ol.

| Structure | Found M + H | $^1$H-NMR (400 MHz, DMSO-d$_6$) δ(ppm) |
|---|---|---|
| 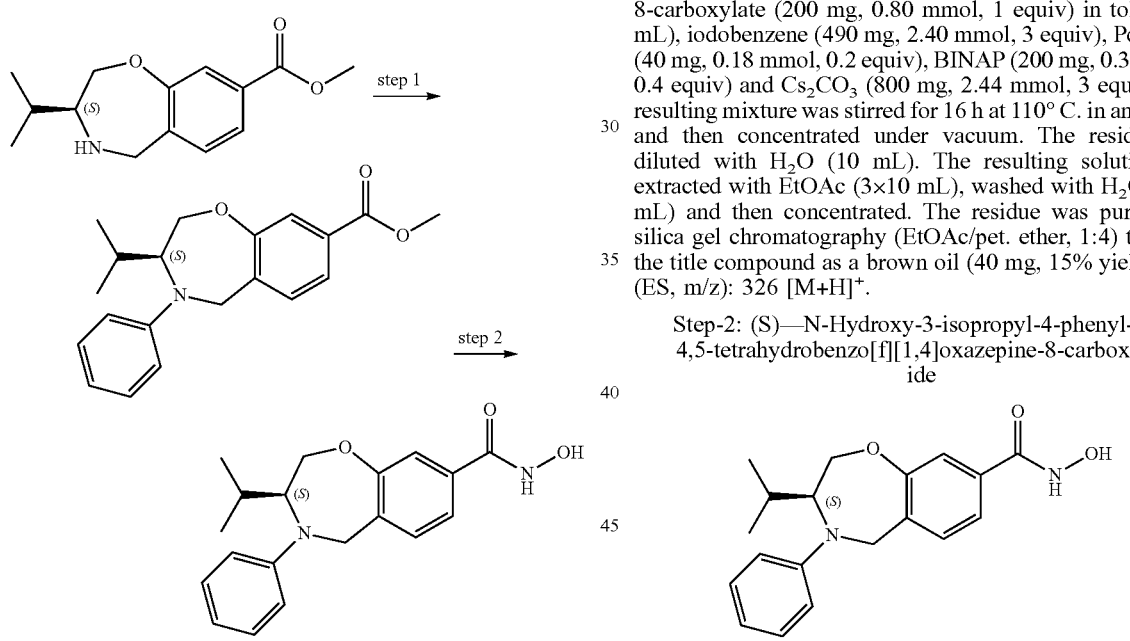 | (ES, m/z): 371 [M + H]$^+$ | 11.51-10.85 (br, 1H), 9.71-8.92 (br, 1H), 7.51-7.22 (m, 3H), 7.19-6.79 (m, 4H), 4.99-4.09 (m, 5H), 3.86-3.67 (m, 3H), 2.27-1.71 (m, 1H), 1.21-0.56 (d, J = 6.0 Hz, 6H) |

Example 30—Preparation of (S)—N-hydroxy-3-isopropyl-4-phenyl-2,3,4,5-tetrahydrobenzo[f][1,4]oxazepine-8-carboxamide Step-1: Methyl (S)-3-isopropyl-4-phenyl-2,3,4,5-tetrahydrobenzo[f][1,4]oxazepine-8-carboxylate

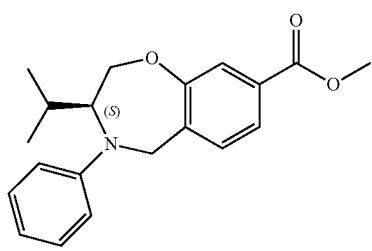

Into a 8-mL vial purged and maintained with an inert atmosphere of nitrogen, were placed a solution of methyl (S)-3-isopropyl-2,3,4,5-tetrahydrobenzo[f][1,4]oxazepine-8-carboxylate (200 mg, 0.80 mmol, 1 equiv) in toluene (3 mL), iodobenzene (490 mg, 2.40 mmol, 3 equiv), Pd(OAc)$_2$ (40 mg, 0.18 mmol, 0.2 equiv), BINAP (200 mg, 0.32 mmol, 0.4 equiv) and Cs$_2$CO$_3$ (800 mg, 2.44 mmol, 3 equiv). The resulting mixture was stirred for 16 h at 110° C. in an oil bath and then concentrated under vacuum. The residue was diluted with H$_2$O (10 mL). The resulting solution was extracted with EtOAc (3×10 mL), washed with H$_2$O (3×10 mL) and then concentrated. The residue was purified by silica gel chromatography (EtOAc/pet. ether, 1:4) to afford the title compound as a brown oil (40 mg, 15% yield). MS: (ES, m/z): 326 [M+H]$^+$.

Step-2: (S)—N-Hydroxy-3-isopropyl-4-phenyl-2,3,4,5-tetrahydrobenzo[f][1,4]oxazepine-8-carboxamide

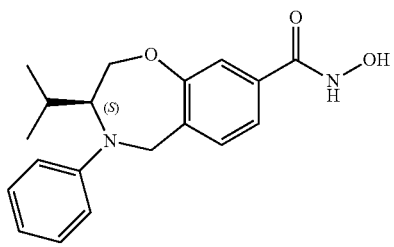

Into a 8-mL vial, was placed a solution of methyl (S)-3-isopropyl-4-phenyl-2,3,4,5-tetrahydrobenzo[f][1,4]oxazepine-8-carboxylate (40 mg, 0.12 mmol, 1 equiv) in THF:MeOH (2 mL, 4:1). This was followed by the addition of NH$_2$OH (50% in water, 0.25 mL, 30 equiv) and aq. 1N NaOH (0.25 mL, 2 equiv). The resulting solution was stirred for 2 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 5% B to 78% B in 7 min; Detector, UV 254, 220 nm) to afford the title compound as an off-white solid (7.5 mg, 14% yield). $^1$H-NMR (400 MHz, DMSO-d$_6$) δ(ppm): 11.08 (s, 1H), 8.97 (s, 1H), 7.49-7.47 (d, J=8.0 Hz, 1H), 7.35-7.33 (d, J=8.0 Hz, 1H), 7.08-7.01 (m, 3H), 6.71-6.69 (d, J=8.0 Hz, 2H), 6.53-6.50 (m, 1H), 4.93-4.80 (m, 1H), 4.50-4.23 (m, 3H), 3.98-3.79 (m, 1H), 2.11-1.95 (m, 1H), 1.07-0-96 (m, 6H). MS: (ES, m/z): 327 [M+H]$^+$.

TABLE 9

The following compound was prepared according to the method of Example 30, using methyl (R)-3-isopropyl-2,3,4,5-tetrahydrobenzo[f][1,4]oxazepine-8-carboxylate.

| Structure | Found M + H | ¹H-NMR (400 MHz, DMSO-d₆) δ(ppm) |
|---|---|---|
| 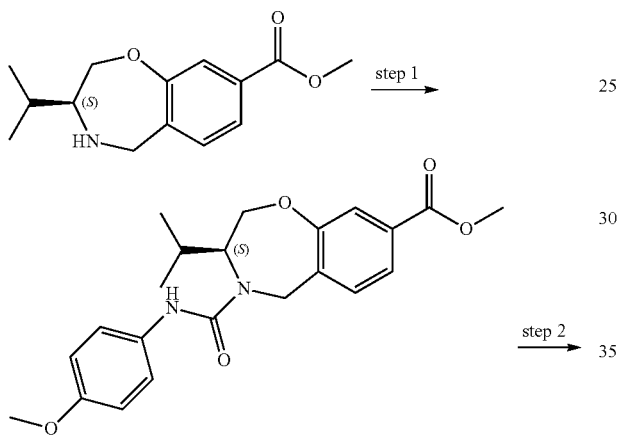 | (ES, m/z): 327 [M + H]⁺ | 11.08-11.05 (s, 1H), 9.03-8.95 (br, 1H), 7.49-7.47 (d, J = 8.0 Hz, 1H), 7.35-7.33 (d, J = 8.0 Hz, 1H), 7.11-6.94 (m, 3H), 6.79-6.63 (m, 2H), 6.52-6.41 (m, 1H), 4.94-4.90 (d, J = 17.6 Hz, 1H), 4.49-4.32 (m, 3H), 3.94-3.84 (m, 1H), 2.08-1.98 (m, 1H), 1.08-0.97 (m, 6H) |

Example 31—Preparation of (S)—N8-hydroxy-3-isopropyl-N4-(4-methoxyphenyl)-2,3-dihydrobenzo[f][1,4]oxazepine-4,8(5H)-dicarboxamide

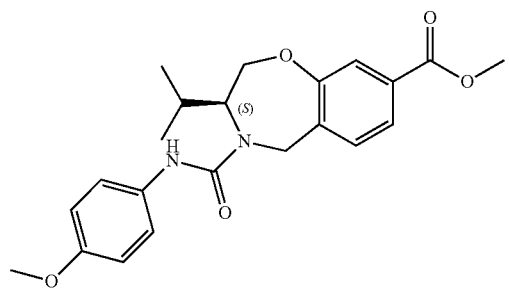

Step-1: Methyl (S)-3-isopropyl-4-((4-methoxyphenyl)carbamoyl)-2,3,4,5-tetrahydrobenzo[f][1,4]oxazepine-8-carboxylate

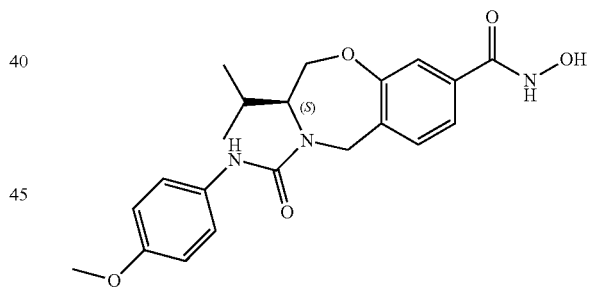

Into a 8-mL vial, were placed a solution of methyl (S)-3-isopropyl-2,3,4,5-tetrahydrobenzo[f][1,4]oxazepine-8-carboxylate (150 mg, 0.60 mmol, 1 equiv) in CH₂Cl₂ (2.5 mL), Et₃N (183 mg, 1.81 mmol, 3 equiv) and 1-isocyanato-4-methoxybenzene (135 mg, 0.91 mmol, 1.5 equiv). The resulting mixture was stirred overnight at room temperature and then concentrated. The residue was purified by silica gel chromatography (EtOAc/pet. ether, 1:2) to afford the title compound as a pink solid (250 mg) which was used without further purification. MS: (ES, m/z): 399 [M+H]⁺.

Step-2: (S)—N8-Hydroxy-3-isopropyl-N4-(4-methoxyphenyl)-2,3-dihydrobenzo[f][1,4]oxazepine-4,8(5H)-dicarboxamide Into a 8-mL vial, was placed a solution of methyl (S)-3-isopropyl-4-((4-methoxyphenyl)carbamoyl)-2,3,4,5-tetrahydrobenzo[f][1,4]oxazepine-8-carboxylate (100 mg, 0.25 mmol, 1 equiv) in THF:MeOH (2.0 mL, 4:1), then aq. 1N NaOH (0.75 mL, 2 equiv) and NH₂OH (50% in H₂O, 0.75 mL, 30 equiv) were added. The resulting solution was stirred for 2 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 4% B to 32% B in 7 min; Detector, UV 254, 220 nm) to afford the title compound as a pink solid (75 mg, 75% yield). ¹H-NMR (400 MHz, DMSO-d₆) δ(ppm): 11.12 (s, 1H), 9 (s, 1H), 8.14 (s, 1H), 7.32-6.76 (m, 7H), 4.91-4.87 (d, 1H), 4.58-4.54 (d, 1H), 4.35-4.26 (m, 3H), 3.69-3.67 (s, 3H), 2-1.97 (s, 1H), 0.99-0.97 (d, 3H, J=8.0 Hz), 0.95-0.93 (d, 3H, J=8.0 Hz). MS: (ES, m/z): 400 [M+H]⁺.

TABLE 10

The following compound was prepared according to the method of Example 31, using methyl (R)-3-isopropyl-2,3,4,5-tetrahydrobenzo[f][1,4]oxazepine-8-carboxylate.

| Structure | Found M + H | $^1$H-NMR (400 MHz, DMSO-d$_6$) δ(ppm) |
|---|---|---|
| 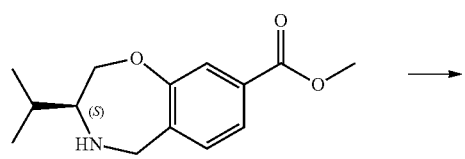 | (ES, m/z): 400 [M + H]$^+$ | 11.12 (br s, 1H), 8.14 (s, 1H), 7.39-7.30 (s, 2H), 7.29-7.12 (m, 3H), 6.83-6.71 (m, 2H), 4.96-4.82 (d, J = 23.2 Hz, 1H), 4.62-4.48 (d, J = 23.2 Hz, 1H), 4.41-4.21 (m, 3H), 3.67 (s, 3H), 2.09-1.84 (m, 1H), 1.04-0.87 (m, 6H) |

Example 32—Preparation of (S)—N-hydroxy-3-isopropyl-2,3,4,5-tetrahydrobenzo[f][1,4]oxazepine-8-carboxamide

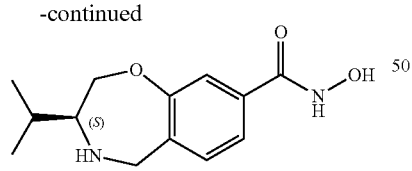

Into a 8-mL vial, was placed a solution of methyl (S)-3-isopropyl-2,3,4,5-tetrahydrobenzo[f][1,4]oxazepine-8-carboxylate (100 mg, 0.40 mmol, 1 equiv) in THF:MeOH (2 mL, 4:1). This was followed by the addition of NH$_2$OH (50% in H$_2$O, 398 mg, 12.05 mmol, 30 equiv) and aq. 1N NaOH (32 mg, 0.80 mmol, 2 equiv). The resulting solution was stirred for 2 h at room temperature. The crude product was purified by Prep-HPLC (Column: XBridge RP C18 OBD, 5 μm, 19×50 mm; Mobile Phase A: Water/0.05% formic acid; Mobile Phase B: MeCN/0.05% formic acid; Flow rate: 23 mL/min; Gradient: 2% B to 10% B in 7 min; Detector, UV 254, 220 nm) to afford the title compound as a pink solid (99 mg, 68% yield). $^1$H-NMR (400 MHz, DMSO-d$_6$) δ(ppm): 11.30 (s, 1H), 9.31 (s, 1H), 7.53-7.40 (m, 3H), 4.55-4.34 (m, 3H), 4-3.95 (m, 1H), 3.51 (s, 1H), 2.10-2.06 (m, 1H), 1.03-1.02 (d, J=4.0 Hz, 3H), 0.98-0.96 (d, J=8.0 Hz, 3H). MS: (ES, m/z): 250 [M+H]$^+$.

TABLE 11

The following compound was prepared according to the method of Example 32, using methyl (R)-3-isopropyl-2,3,4,5-tetrahydrobenzo[f][1,4]oxazepine-8-carboxylate.

| Structure | Found M + H | $^1$H-NMR (400 MHz, DMSO-d$_6$) δ(ppm) |
|---|---|---|
| 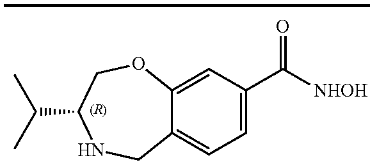 | (ES, m/z): 250 [M + H]$^+$ | 11.31 (br s, 1H), 9.42-9.31 (br s, 1H), 9.11-9.04 (m, 2H), 7.54-7.49 (m, 2H), 7.41 (s, 1H), 4.56-4.35 (m, 3H), 4.01-3.96 (m, 1H), 3.52 (s, 1H), 2.13-2.05 (m, 1H), 1.04-0.97 (m, 6H) |

-continued

Example 33—Preparation of (S)—N-hydroxy-3-isopropyl-4-methyl-2,3,4,5-tetrahydrobenzo[f][1,4]oxazepine-8-carboxamide

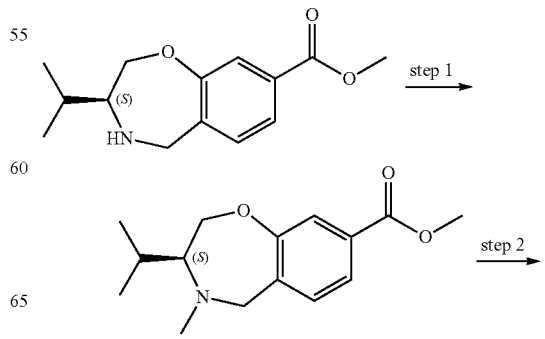

-continued

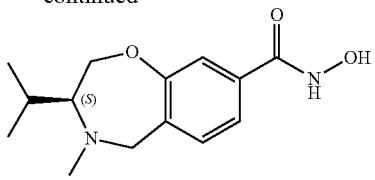

Step-1: Methyl (S)-3-isopropyl-4-methyl-2,3,4,5-tetrahydrobenzo[f][1,4]oxazepine-8-carboxylate

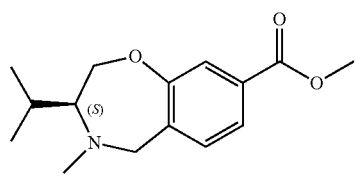

Into a 8-mL vial, were placed a solution of methyl (S)-3-isopropyl-2,3,4,5-tetrahydrobenzo[f][1,4]oxazepine-8-carboxylate (150 mg, 0.60 mmol, 1 equiv) in acetic acid (3.0 mL) and paraformaldehyde (180 mg, 5.62 mmol, 10 equiv). The resulting solution was stirred for 2 h at room temperature. Then NaBH(OAc)₃ (2.54 g, 20 equiv) was added at 0° C. The reaction was stirred for an additional 1 day at room temperature and then concentrated under vacuum to afford the title compound as light yellow oil (190 mg) which was used without purification. MS: (ES, m/z): 264 [M+H]⁺.

Step-2: (S)—N-Hydroxy-3-isopropyl-4-methyl-2,3,4,5-tetrahydrobenzo[f][1,4]oxazepine-8-carboxamide

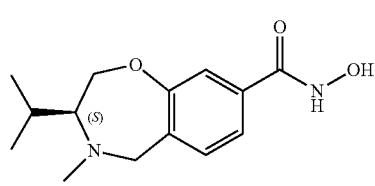

Into a 8-mL vial, was placed a solution of methyl (S)-3-isopropyl-4-methyl-2,3,4,5-tetrahydrobenzo[f][1,4]oxazepine-8-carboxylate (90 mg, 0.34 mmol, 1 equiv) in THF:MeOH (2 mL, 4:1), followed by the addition of NH₂OH (50% in water, 0.67 mL, 10.27 mmol, 30 equiv) and aq. 1N NaOH (0.68 mL, 2 equiv). The resulting solution was stirred for 2 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 3% B to 10% B in 7 min; Detector, UV 254, 220 nm) to afford the title compound as an orange semi-solid (35 mg, 27% yield). ¹H-NMR (400 MHz, DMSO-d₆) δ(ppm): 11.31 (s, 1H), 10.25-9.78 (s, 1H), 9.14-9.05 (s, 1H), 7.56-7.33 (m, 3H), 4.91-4.73 (s, 0.5H), 4.68-4.60 (d, 2.5H), 4.60-4.33 (m, 0.4H), 4.30-4.16 (m, 0.6H), 3.99-3.22 (m, 2H), 3.67-2.64 (s, 2H), 2.51-2.33 (m, 0.7H), 2.11-1.88 (m, 0.3H), 1.10-0.89 (m, 6H). MS: (ES, m/z): 265 [M+H]⁺.

TABLE 12

The following compound was prepared according to the method of Example 33, using methyl (R)-3-isopropyl-2,3,4,5-tetrahydrobenzo[f][1,4]oxazepine-8-carboxylate.

| Structure | Found M + H | ¹H-NMR (400 MHz, DMSO-d₆) δ(ppm) |
|---|---|---|
| 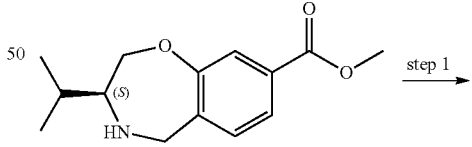 | (ES, m/z): 265 [M + H]⁺ | 11.30 (br s, 1H), 9.13 (br s, 1H), 7.58-7.27 (m, 3H), 4.84-4.80 (d, J = 12.0 Hz, 1H), 4.49-4.32 (m, 3H), 4.13-3.81 (m, 1H), 2.99-2.88 (s, 2H), 2.61-2.54 (s, 1H), 2.36 (s, 1H), 1.10-1.09 (d, J = 3.0 Hz, 6H) |

Example 34—Preparation of (S)—N-hydroxy-3-isopropyl-4-(pyridin-4-yl)-2,3,4,5-tetrahydrobenzo[f][1,4]oxazepine-8-carboxamide

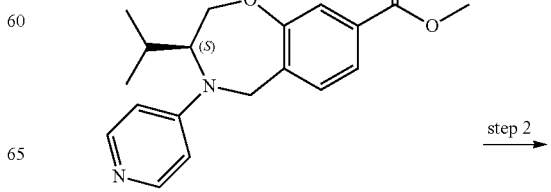

-continued

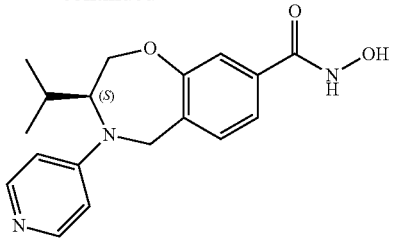

Step-1: Methyl (S)-3-isopropyl-4-(pyridin-4-yl)-2,3,4,5-tetrahydrobenzo[f][1,4]oxazepine-8-carboxylate

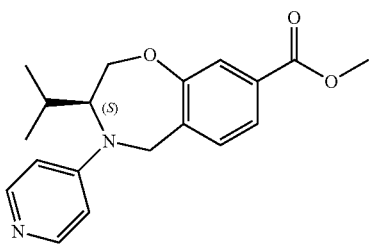

Into a 40-mL sealed tube purged and maintained with an inert atmosphere of nitrogen, was placed a solution of methyl (S)-3-isopropyl-2,3,4,5-tetrahydrobenzo[f][1,4]oxazepine-8-carboxylate (250 mg, 1.00 mmol, 1 equiv) in toluene (15 mL), 4-bromopyridine (1.56 g, 8.00 mmol, 8 equiv), RuPhos (187 mg, 0.40 mmol, 0.4 equiv), Pd$_2$(dba)$_3$ (189 mg, 0.18 mmol, 0.2 equiv) and sodium tert-butoxide (480 mg, 5.00 mmol, 5 equiv). The resulting solution was stirred for 20 h at 110° C. in an oil bath. The resulting solution was diluted with H$_2$O (10 mL) and extracted with EtOAc (3×10 mL). The combined organic layers were washed with H$_2$O (3×10 mL) and concentrated under vacuum. The residue was purified by silica gel chromatography (EtOAc/pet. ether, 1:1) to afford the title compound as a brown oil (15 mg, 5% yield). MS: (ES, m/z): 327[M+H]$^+$ Step-2: (S)—N-Hydroxy-3-isopropyl-4-(pyridin-4-yl)-2,3,4,5-tetrahydrobenzo[f][1,4]oxazepine-8-carboxamide

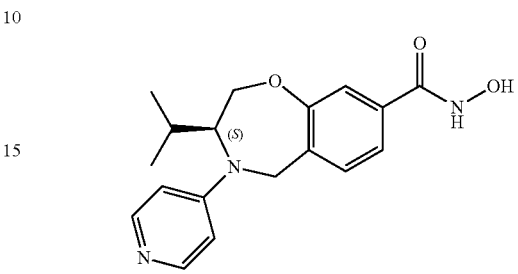

Into a 8-mL vial, was placed a solution of methyl (S)-3-isopropyl-4-(pyridin-4-yl)-2,3,4,5-tetrahydrobenzo[f][1,4]oxazepine-8-carboxylate (15 mg, 0.05 mmol, 1 equiv) in THF/MeOH (4:1, 1.5 mL). This was followed by the addition of NH$_2$OH (50% in water, 0.1 mL, 30 equiv). To this was added aq. 1N NaOH (0.1 mL, 2 equiv). The resulting solution was stirred for 3 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 5% B to 45% B in 8 min; Detector: UV 254, 220 nm) to afford the title compound as a brown oil (2 mg, 12% yield). $^1$H-NMR (400 MHz, DMSO-d$_6$) δ(ppm): 11.18 (br s, 1H), 9.05 (br s, 1H), 8.25-8.16 (m, 2H), 7.65-7.63 (m, 1H), 7.51-7.40 (m, 2H), 7.32 (s, 1H), 7.29-7.17 (m, 2H), 7.07-7.04 (m, 1H), 6.93-6.91 (m, 1H), 5.23-5.18 (m, 1H), 4.92-4.79 (m, 1H), 4.58-4.44 (m, 3H), 2.15-2.12 (m, 1H), 1.06-1.04 (d, J=3.2 Hz, 3H), 0.94-0.92 (d, J=3.2 Hz, 3H). MS: (ES, m/z): 328[M+H]$^+$.

TABLE 13

The following compounds were prepared according to the method of Example 34.

| Structure | Found M + H | $^1$H-NMR (400 MHz, DMSO-d$_6$) δ(ppm) |
|---|---|---|
|  | (ES, m/z): 328 [M + H]$^+$ | 11.28 (br s, 1H), 8.29 (s, 1H), 8.04-8.02 (d, J = 2.6 Hz, 1H), 7.96-7.94 (d, J = 3.6 Hz, 1H), 7.74-7.71 (m, 1H), 7.62-7.56 (m, 1H), 7.42-7.40 (m, 1H), 7.18-7.14 (m, 1H), 5.13-5.08 (m, 1H), 4.72-4.68 (m, 1H), 4.51-41 (m, 2H), 4.32-4.19 (m, 1H), 2.12-2.07 (m, 1H), 0.98-0.96 (d, J = 3.2 hz, 3H), 0.89-0.87 (d, J = 3.6 Hz, 3H) |
|  | (ES, m/z): 328 [M + H]$^+$ | 11.17 (br s. 1H), 8.02-8.01 (br s, 1H), 7.96-7.84 (m, 1H), 7.71-7.68 (m, 1H), 7.60-7.58 (d, J = 3.6 Hz, 1H), 7.16 (s, 2H), 6.96-6.85 (m, 1H), 5.21-4.97 (m, 2H), 4.84-4.72 (m, 1H), 4.63-4.48 (m, 2H), 2.15-2.13 (m, 1H), 1.07-1.05 (d, J = 3.2 hz, 3H), 0.97-0.96 (d, J = 3.2 hz, 3H) |

Example 35—Preparation of (S)—N8-hydroxy-N4-(4-methoxyphenyl)-3-methyl-2,3-dihydrobenzo[f][1,4]oxazepine-4,8(5H)-dicarboxamide

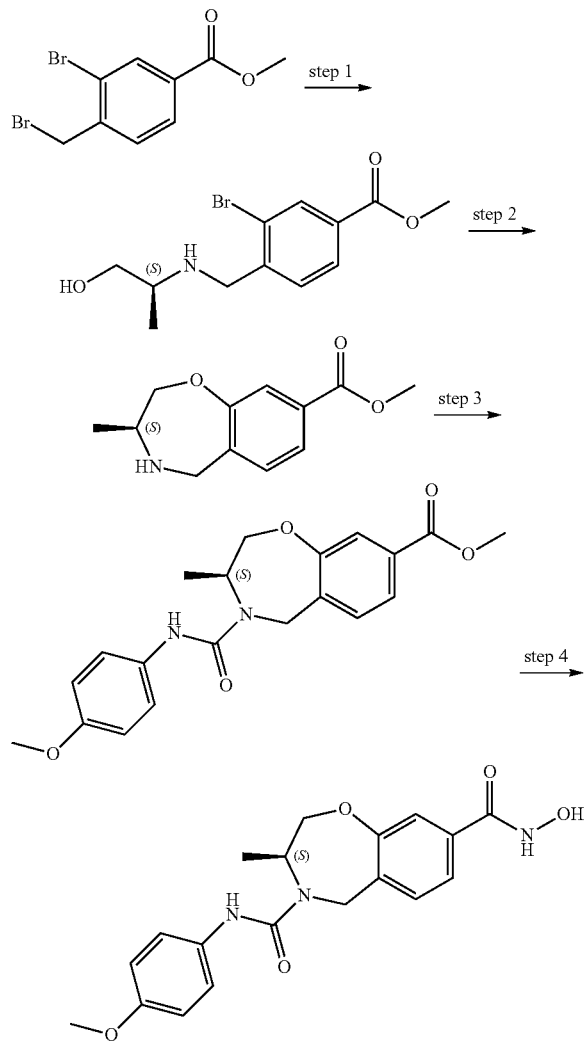

Step-1: Methyl (S)-3-bromo-4-(((1-hydroxypropan-2-yl)amino)methyl)benzoate

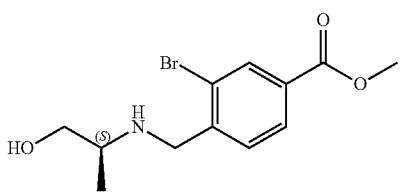

Into a 500-mL round-bottom flask, was placed a solution of methyl 3-bromo-4-(bromomethyl)benzoate (10 g, 32.47 mmol, 1 equiv) in THF (150 mL), (S)-2-aminopropan-1-ol (2.4 g, 31.95 mmol, 1 equiv) and $K_2CO_3$ (6.7 g, 1.5 equiv). The resulting solution was stirred for 3 h at room temperature, then concentrated under vacuum. The residue was washed with EtOAc/pet. ether (1:10, 20 mL) to afford the title compound as an off-white solid (5 g, 51% yield). MS: (ES, m/z): 302 [M+H]$^+$.

Step-2: Methyl (S)-3-methyl-2,3,4,5-tetrahydrobenzo[f][1,4]oxazepine-8-carboxylate

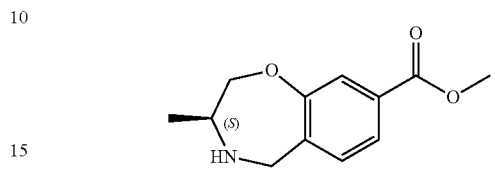

Into a 100-mL round-bottom flask purged and maintained with an inert atmosphere of nitrogen, was placed a solution of methyl (S)-3-bromo-4-(((1-hydroxypropan-2-yl)amino)methyl)benzoate (3.2 g, 10.59 mmol, 1 equiv) in isopropanol (35 mL), $K_2CO_3$ (2.20 g, 15.92 mmol, 1.5 equiv) and CuI (610 mg, 3.20 mmol, 0.3 equiv). The resulting solution was stirred for 19 h at 110° C. in an oil bath. The resulting mixture was concentrated under vacuum, diluted with EtOAc (300 mL), and washed with $H_2O$ (3×100 mL). The organic phase was concentrated and the residue was purified by silica gel chromatography (EtOAc/pet. ether, 1:4) to afford the title compound as a light yellow oil (1 g, 43% yield). $^1$H-NMR (400 MHz, DMSO-d$_6$) δ(ppm): 7.57-7.50 (m, 1H), 7.45 (s, 1H), 7.35-7.29 (m, 1H), 4.27-4.19 (m, 1H), 3.99-3.81 (m, 5H), 3.37-3.21 (m, 2H), 3.17-3.10 (s, 1H), 1.05-0.94 (d, J=6.4 Hz, 3H). MS: (ES, m/z): 222 [M+H]$^+$.

Step-3: Methyl (S)-4-((4-methoxyphenyl)carbamoyl)-3-methyl-2,3,4,5-tetrahydrobenzo[f][1,4]oxazepine-8-carboxylate

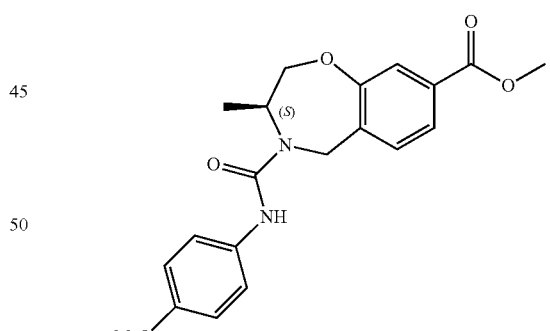

Into a 25-mL flask, was placed a solution of methyl (S)-3-methyl-2,3,4,5-tetrahydrobenzo[f][1,4]oxazepine-8-carboxylate (100 mg, 0.45 mmol, 1 equiv) in $CH_2Cl_2$ (10 mL), 1-isocyanato-4-methoxybenzene (100 mg, 0.67 mmol, 1.5 equiv), Et$_3$N (150 mg, 1.48 mmol, 3 equiv) and 4-dimethylaminopyridine (50 mg, 0.41 mmol, 1 equiv). The resulting solution was stirred for 10 h at room temperature. The resulting mixture was concentrated under vacuum. The residue was purified by silica gel chromatography (EtOAc/pet. ether, 1:1) to afford the title compound as a light yellow oil (30 mg, 18% yield). MS: (ES, m/z): 371 [M+H]$^+$.

Step-4: (S)—N8-hydroxy-N4-(4-methoxyphenyl)-3-methyl-2,3-dihydrobenzo[f][1,4]oxazepine-4,8(5H)-dicarboxamide

Example 36—Preparation of (S)—N-hydroxy-4-((4-methoxyphenyl)sulfonyl)-3-methyl-2,3,4,5-tetrahydrobenzo[f][1,4]oxazepine-8-carboxamide

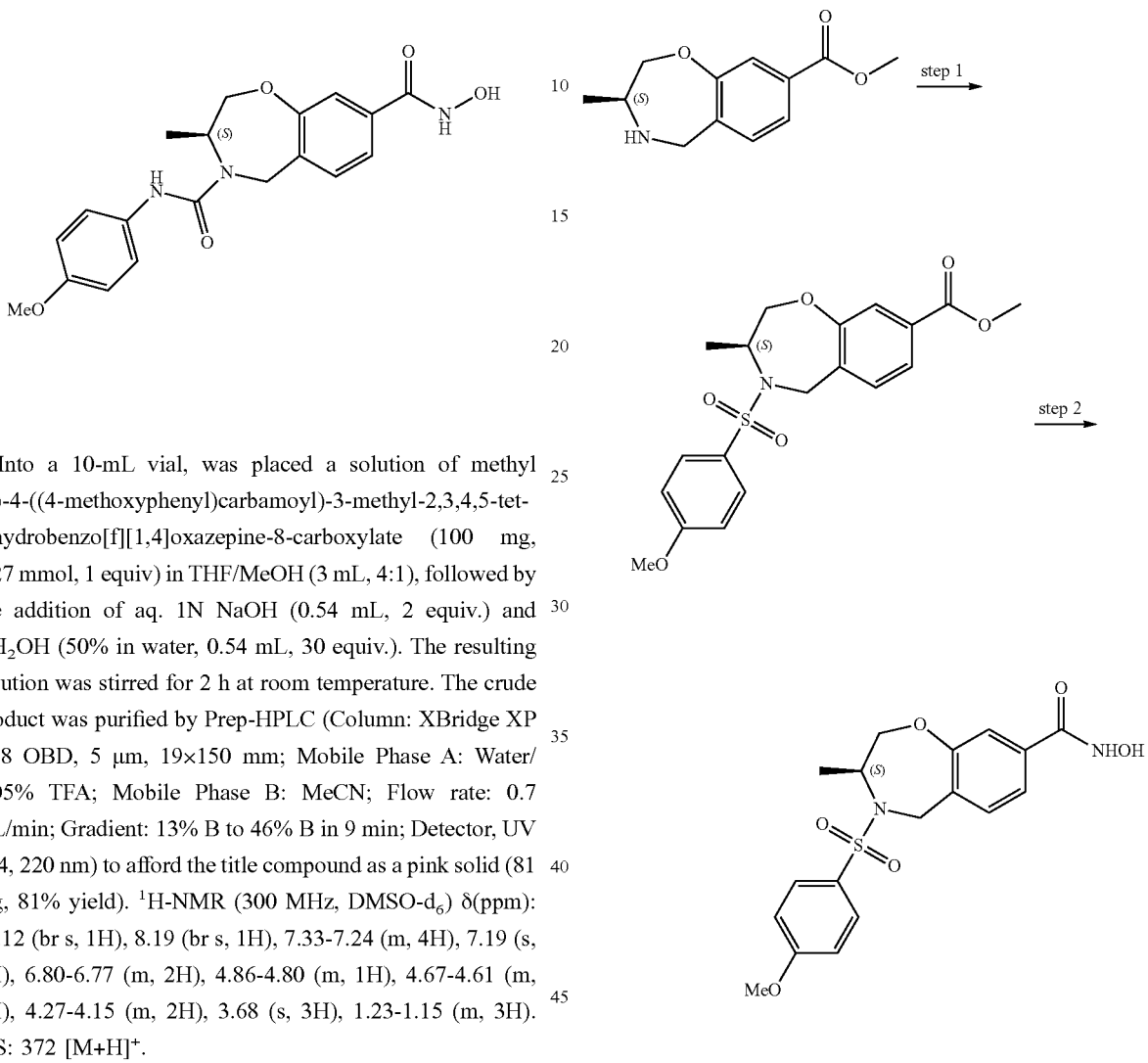

Into a 10-mL vial, was placed a solution of methyl (S)-4-((4-methoxyphenyl)carbamoyl)-3-methyl-2,3,4,5-tetrahydrobenzo[f][1,4]oxazepine-8-carboxylate (100 mg, 0.27 mmol, 1 equiv) in THF/MeOH (3 mL, 4:1), followed by the addition of aq. 1N NaOH (0.54 mL, 2 equiv.) and NH$_2$OH (50% in water, 0.54 mL, 30 equiv.). The resulting solution was stirred for 2 h at room temperature. The crude product was purified by Prep-HPLC (Column: XBridge XP C18 OBD, 5 μm, 19×150 mm; Mobile Phase A: Water/0.05% TFA; Mobile Phase B: MeCN; Flow rate: 0.7 mL/min; Gradient: 13% B to 46% B in 9 min; Detector, UV 254, 220 nm) to afford the title compound as a pink solid (81 mg, 81% yield). $^1$H-NMR (300 MHz, DMSO-d$_6$) δ(ppm): 11.12 (br s, 1H), 8.19 (br s, 1H), 7.33-7.24 (m, 4H), 7.19 (s, 1H), 6.80-6.77 (m, 2H), 4.86-4.80 (m, 1H), 4.67-4.61 (m, 2H), 4.27-4.15 (m, 2H), 3.68 (s, 3H), 1.23-1.15 (m, 3H). MS: 372 [M+H]$^+$.

TABLE 14

The following compound was prepared according to the method of Example 35, using (R)-2-aminopropan-1-ol.

| Structure | Found M + H | $^1$H-NMR (400 MHz, DMSO-d$_6$) δ(ppm) |
|---|---|---|
| 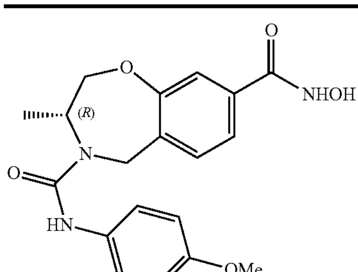 | (ES, m/z): 372 [M + H]$^+$ | 11.11 (br s, 1H), 8.18 (s, 1H), 7.33-7.24 (m, 4H), 7.18 (s, 1H), 6.80-6.76 (m, 2H), 4.85-4.80 (m, 1H), 4.69-4.61 (m, 2H), 4.27-4.15 (m, 2H), 3.68 (s, 3H), 1.16-1.15 (m, 3H) |

Step-1: Methyl (S)-4-((4-methoxyphenyl)sulfonyl)-3-methyl-2,3,4,5-tetrahydrobenzo[f][1,4]oxazepine-8-carboxylate

Step-2: (S)—N-Hydroxy-4-((4-methoxyphenyl)sulfonyl)-3-methyl-2,3,4,5-tetrahydrobenzo[f][1,4]oxazepine-8-carboxamide

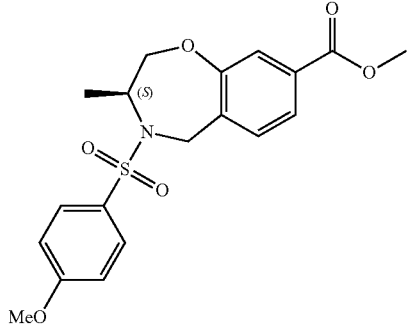

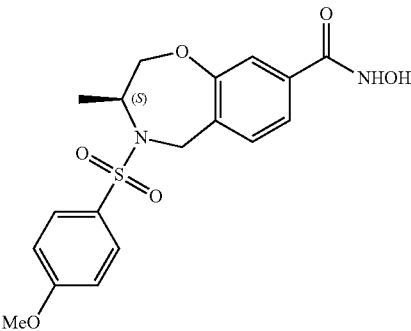

Into a 8-mL vial, was placed a solution of methyl (S)-3-methyl-2,3,4,5-tetrahydrobenzo[f][1,4]oxazepine-8-carboxylate (100 mg, 0.45 mmol, 1 equiv) in $CH_2Cl_2$ (3 mL), $Et_3N$ (137 mg, 1.35 mmol, 3 equiv), 4-dimethylaminopyridine (110 mg, 0.90 mmol, 2 equiv) and 4-methoxybenzene-1-sulfonyl chloride (234 mg, 1.13 mmol, 2.50 equiv). The resulting solution was stirred for 17 h at room temperature and then concentrated under vacuum. The residue was diluted with $H_2O$ (10 mL), extracted with EtOAc (20 mL) and the organic layer concentrated under vacuum. The residue was purified by silica gel chromatography (EtOAc/pet. ether, 1:2) to afford the title compound as a light yellow oil (90 mg, 51% yield). MS: (ES, m/z): 392 $[M+H]^+$.

Into a 8-mL vial, was placed methyl (S)-4-((4-methoxyphenyl)sulfonyl)-3-methyl-2,3,4,5-tetrahydrobenzo[f][1,4]oxazepine-8-carboxylate (90 mg, 0.23 mmol, 1 equiv) in THF/MeOH (4:1, 2 mL). To this was added aq. 1N NaOH (0.46 mL, 2 equiv) and $NH_2OH$ (50% in water, 0.46 mL, 30 equiv). The resulting solution was stirred for 3 h at room temperature. The crude product was purified by Prep-HPLC (Column: XBridge XP C18 OBD, 5 μm, 19×150 mm; Mobile Phase A: Water/0.05% TFA; Mobile Phase B: MeCN; Flow rate: 0.7 mL/min; Gradient: 5% B to 55% B in 7 min; Detector, UV 254, 220 nm) to afford the title compound as an off-white solid (64 mg, 71% yield). $^1$H-NMR (300 MHz, DMSO-$d_6$) δ(ppm): 11.07 (br s, 1H), 7.36-7.33 (m, 2H), 7.28-7.25 (m, 1H), 7.21-7.18 (m, 1H), 6.80 (s, 1H), 6.75-6.72 (m, 2H), 4.90-4.84 (d, J=17.4 Hz, 1H), 4.60-4.54 (d, J=17.4 Hz, 1H), 4.32-4.29 (m, 1H), 4.17-4.13 (m, 1H), 4.09-3.99 (m, 1H), 3.71 (m, 4H), 1.13-1.11 (m, J=6.6 Hz, 3H). MS: (ES, m/z): 393 $[M+H]^+$.

TABLE-15

The following compound was prepared according to the method of Example 36, using methyl (R)-3-methyl-2,3,4,5-tetrahydrobenzo[f][1,4]oxazepine-8-carboxylate.

| Structure | Found M + H | $^1$H-NMR (400 MHz, DMSO-$d_6$) δ(ppm) |
|---|---|---|
| 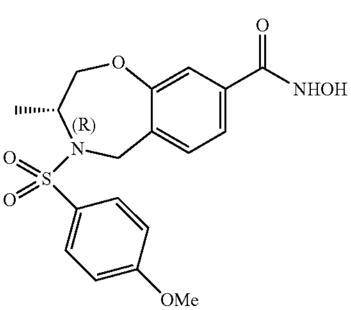 | (ES, m/z): 393 $[M+H]^+$ | 11.07 (br s, 1H), 8.98 (s, 1H), 7.36-7.33 (m, 2H), 7.28-7.25 (m, 1H), 7.20-7.18 (m, 1H), 6.80 (s, 1H), 6.79-6.72 (m, 2H), 4.89-4.85 (m, 1H), 4.59-4.55 (m, 1H), 4.31-4.26 (l, 2H), 4.16-4.10 (m, 1H), 4.02-3.98 (m, 1H), 3.71 (s, 3H), 1.13-1.06 (m, 3 H) |

Example 37—Preparation of (S)—N-hydroxy-4-(4-methoxybenzyl)-3-methyl-2,3,4,5-tetrahydrobenzo[f][1,4]oxazepine-8-carboxamide

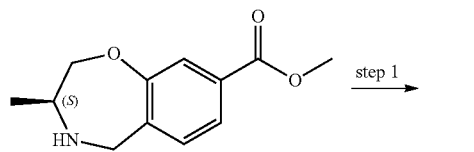

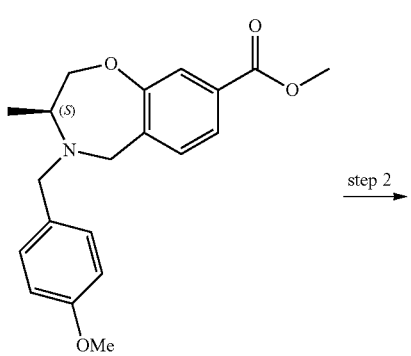

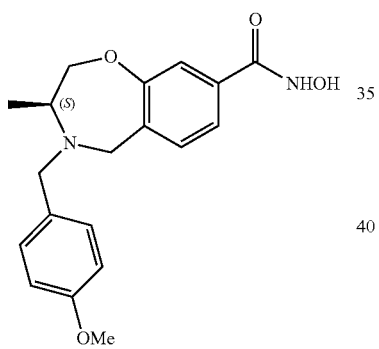

Step-1: Methyl (S)-4-(4-methoxybenzyl)-3-methyl-2,3,4,5-tetrahydrobenzo[f][1,4]oxazepine-8-carboxylate Into a 8-mL vial, was placed a solution of methyl (S)-3-methyl-2,3,4,5-tetrahydrobenzo[f][1,4]oxazepine-8-carboxylate (100 mg, 0.45 mmol, 1 equiv) in THF (3 mL). This was followed by the addition of sodium hydride (90 mg, 3.75 mmol, 5 equiv, 60% dispersion in oil) and 1-(bromomethyl)-4-methoxybenzene (91 mg, 0.45 mmol, 1 equiv). The resulting solution was stirred for 17 h at room temperature. The reaction was then quenched by the addition of $H_2O$ (2 mL). The resulting mixture was concentrated under vacuum. The residue was purified by silica gel chromatography (EtOAc/pet. ether, 1:3) to afford the title compound as a light yellow oil (68 mg, 44% yield). MS: (ES, m/z): 342 $[M+H]^+$.

Step-2: (S)—N-Hydroxy-4-(4-methoxybenzyl)-3-methyl-2,3,4,5-tetrahydrobenzo[f][1,4]oxazepine-8-carboxamide

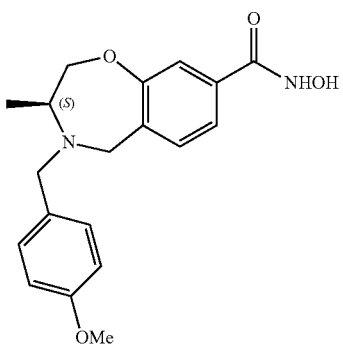

Into a 8-mL vial, was placed methyl (S)-4-(4-methoxybenzyl)-3-methyl-2,3,4,5-tetrahydrobenzo[f][1,4]oxazepine-8-carboxylate (67.6 mg, 0.20 mmol, 1 equiv) in THF/MeOH (4:1, 2 mL). To this was added aq. 1N NaOH (0.40 ml, 2 equiv) and $NH_2OH$ (50% in water, 0.40 mL, 30 equiv). The resulting solution was stirred for 3 h at room temperature. The crude product was purified by Prep-HPLC (Column: XBridge XP C18 OBD, 5 µm, 19×150 mm; Mobile Phase A: Water/0.05% TFA; Mobile Phase B: MeCN; Flow rate: 0.7 mL/min; Gradient: 5% B to 25% B in 7 min; Detector, UV 254, 220 nm) to afford the title compound as a brown solid (58 mg, 85% yield). $^1$H-NMR (300 MHz, DMSO-$d_6$) δ(ppm): 11.35 (br, 1H), 10.65 (br, 1H), 7.52-7.25 (m, 5H), 7.02-6.99 (m, 2H), 4.89-4.28 (m, 6H), 3.86-3.67 (m, 4H), 1.48-1.46 (d, J=6 Hz, 3H). MS: (ES, m/z): 343 $[M+H]^+$.

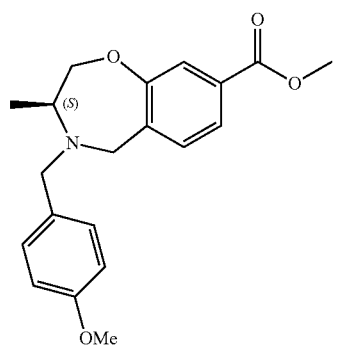

TABLE-16

The following compound was prepared according to the method of Example 37, using methyl (R)-3-methyl-2,3,4,5-tetrahydrobenzo[f][1,4]oxazepine-8-carboxylate.

| Structure | Found M + H | $^1$H-NMR (400 MHz, DMSO-d$_6$) δ(ppm) |
|---|---|---|
| 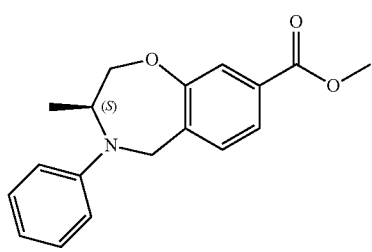 | (ES, m/z): 343 [M + H]$^+$ | 11.31 (s, 1H), 10.83-10.06 (br, 1H), 9.73-8.57 (br, 1H), 7.51-7.33 (m, 5H), 7.13-6.92 (m, 2H), 5.13-3.96 (m, 7H), 3.78 (s, 3H), 1.47 (s, 3H) |

Example 38—Preparation of (S)—N-hydroxy-3-methyl-4-phenyl-2,3,4,5-tetrahydrobenzo[f][1,4]oxazepine-8-carboxamide

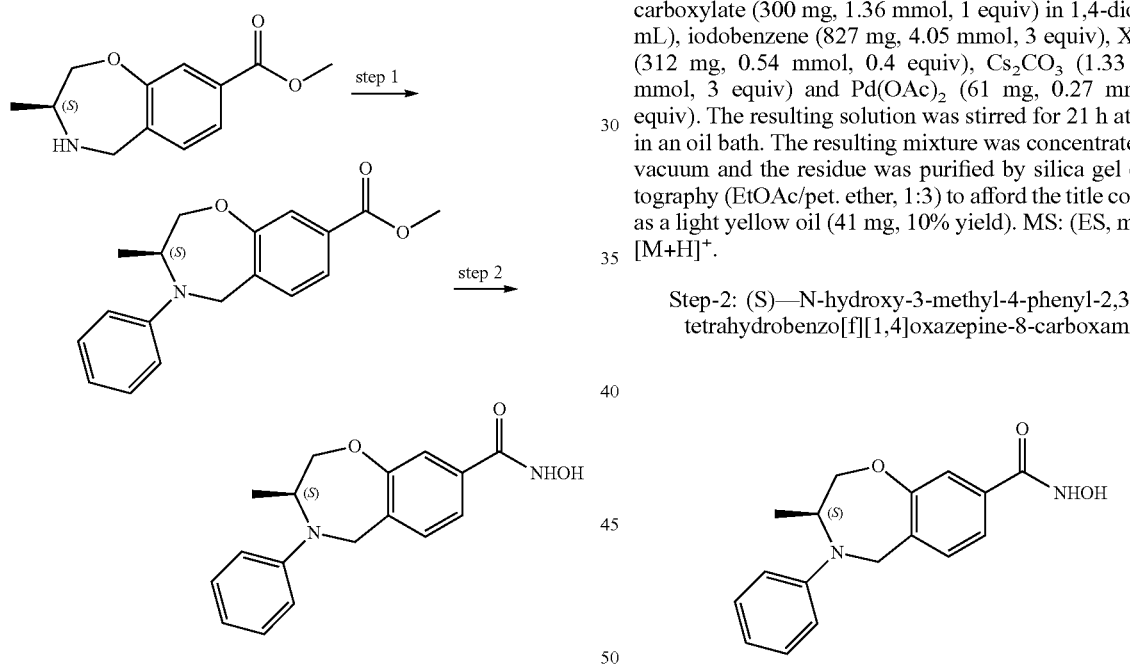

Step-1: Methyl (S)-3-methyl-4-phenyl-2,3,4,5-tetrahydrobenzo[f][1,4]oxazepine-8-carboxylate Into a 25-mL vial purged and maintained with an inert atmosphere of nitrogen, were placed a solution of methyl (S)-3-methyl-2,3,4,5-tetrahydrobenzo[f][1,4]oxazepine-8-carboxylate (300 mg, 1.36 mmol, 1 equiv) in 1,4-dioxane (8 mL), iodobenzene (827 mg, 4.05 mmol, 3 equiv), Xantphos (312 mg, 0.54 mmol, 0.4 equiv), Cs$_2$CO$_3$ (1.33 g, 4.05 mmol, 3 equiv) and Pd(OAc)$_2$ (61 mg, 0.27 mmol, 0.2 equiv). The resulting solution was stirred for 21 h at 110° C. in an oil bath. The resulting mixture was concentrated under vacuum and the residue was purified by silica gel chromatography (EtOAc/pet. ether, 1:3) to afford the title compound as a light yellow oil (41 mg, 10% yield). MS: (ES, m/z): 298 [M+H]$^+$.

Step-2: (S)—N-hydroxy-3-methyl-4-phenyl-2,3,4,5-tetrahydrobenzo[f][1,4]oxazepine-8-carboxamide Into a 8-mL vial, was placed methyl (S)-3-methyl-4-phenyl-2,3,4,5-tetrahydrobenzo[f][1,4]oxazepine-8-carboxylate (41 mg, 0.14 mmol, 1 equiv) in THF/MeOH (4:1, 2 mL). To this was added aq. 1N NaOH (0.28 mL, 2 equiv) and NH$_2$OH (50% in water, 0.28 mL, 30 equiv). The resulting solution was stirred for 3 h at room temperature. The crude product was purified by Prep-HPLC (Column: XBridge XP C18 OBD, 5 μm, 19×150 mm; Mobile Phase A: Water/0.05% TFA; Mobile Phase B: MeCN; Flow rate: 0.7 mL/min; Gradient: 5% B to 80% B in 7 min; Detector, UV 254, 220 nm) to afford the title compound as a light brown solid (13 mg, 33% yield). $^1$H-NMR (300 MHz, DMSO-d$_6$) δ(ppm): 11.10-11 (br s, 1H), 7.49-7.46 (m, 1H), 7.34-7.32 (m, 1H), 7.10-7.04 (m, 3H), 6.66-6.64 (m, 2H), 6.56-6.51 (m, 1H), 5.03-4.97 (d, J=17.4 Hz, 1H), 4.41-4.20 (m, 4H), 1.20-1.18 (d, J=5.7 Hz, 3H). MS: (ES, m/z): 299 [M+H]$^+$.

TABLE-17

The following compound was prepared according to the method of Example 38, using methyl (R)-3-methyl-2,3,4,5-tetrahydrobenzo[f][1,4]oxazepine-8-carboxylate.

| Structure | Found M + H | $^1$H-NMR (400 MHz, DMSO-d$_6$) δ(ppm) |
|---|---|---|
| (structure shown) | (ES, m/z): 299 [M + H]$^+$ | 11.09 (br s, 1H), 7.49-7.47 (m, 1H), 7.34-7.32 (m, 1H), 7.10-7.05 (m, 3H), 6.66-6.64 (m, 2H), 6.56-6.52 (m, 1H), 5.03-4.95 (d, J = 17.4 Hz, 1H), 4.49-4.20 (m, 4H), 1.23-1.18 (d, J = 5.7 Hz, 3H) |

Example 39—Preparation of (S)—N-hydroxy-3-methyl-2,3,4,5-tetrahydrobenzo[f][1,4]oxazepine-8-carboxamide

Example 40—Preparation of (S)—N-hydroxy-3,4-dimethyl-2,3,4,5-tetrahydrobenzo[f][1,4]oxazepine-8-carboxamide

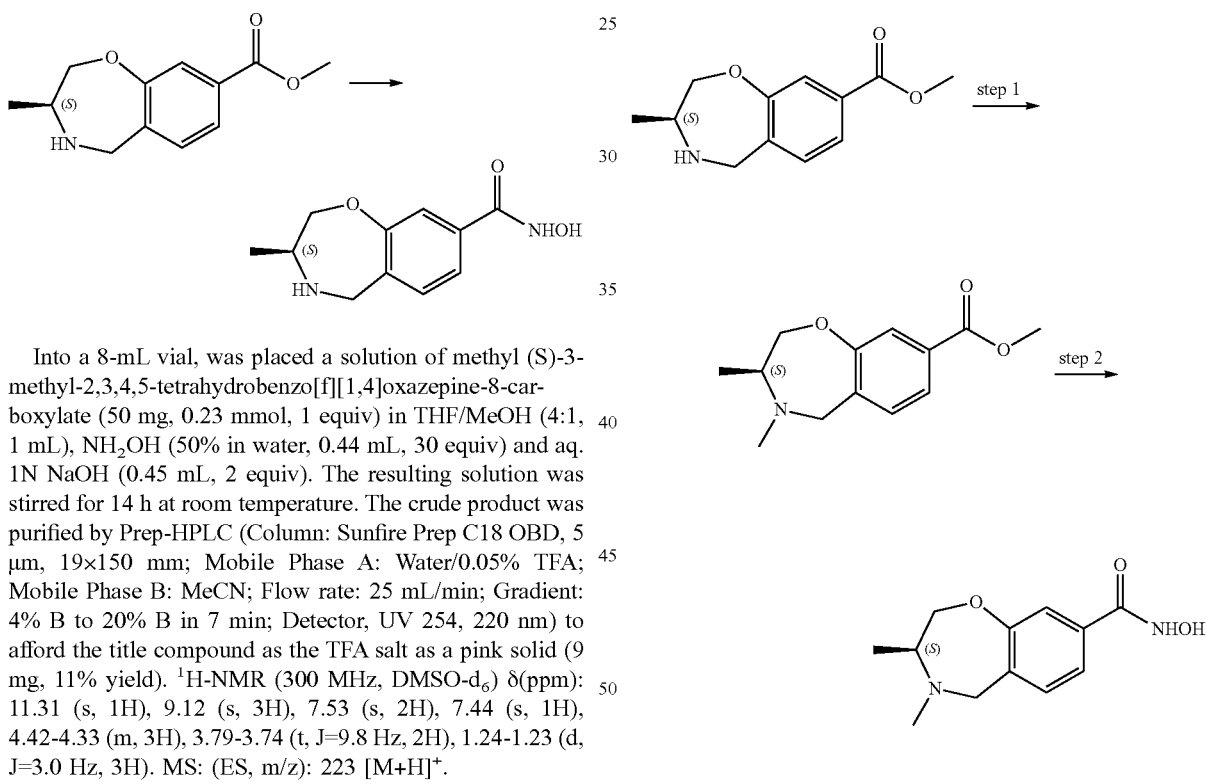

Into a 8-mL vial, was placed a solution of methyl (S)-3-methyl-2,3,4,5-tetrahydrobenzo[f][1,4]oxazepine-8-carboxylate (50 mg, 0.23 mmol, 1 equiv) in THF/MeOH (4:1, 1 mL), NH$_2$OH (50% in water, 0.44 mL, 30 equiv) and aq. 1N NaOH (0.45 mL, 2 equiv). The resulting solution was stirred for 14 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 4% B to 20% B in 7 min; Detector, UV 254, 220 nm) to afford the title compound as the TFA salt as a pink solid (9 mg, 11% yield). $^1$H-NMR (300 MHz, DMSO-d$_6$) δ(ppm): 11.31 (s, 1H), 9.12 (s, 3H), 7.53 (s, 2H), 7.44 (s, 1H), 4.42-4.33 (m, 3H), 3.79-3.74 (t, J=9.8 Hz, 2H), 1.24-1.23 (d, J=3.0 Hz, 3H). MS: (ES, m/z): 223 [M+H]$^+$.

TABLE-18

The following compound was prepared according to the method of Example 39, using methyl (R)-3-methyl-2,3,4,5-tetrahydrobenzo[f][1,4]oxazepine-8-carboxylate.

| Structure | Found M + H | $^1$H-NMR (400 MHz, DMSO-d$_6$) δ(ppm) |
|---|---|---|
| (structure shown) | (ES, m/z): 223 [M + H]$^+$ | 11.30 (s, 1H), 9.50-9.44 (s, 1H), 9.12-8.99 (s, 2H), 7.53-7.44 (d, J = 17.8 Hz, 3H), 4.42-4.33 (m, 3H), 3.79-3.75 (d, J = 20.4 Hz, 2H), 1.29-1.22 (s, 3H) |

Step-1: Methyl (S)-3,4-dimethyl-2,3,4,5-tetrahydrobenzo[f][1,4]oxazepine-8-carboxylate

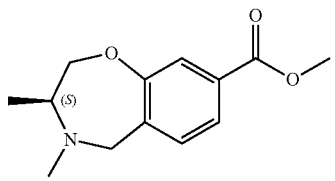

Into a 8-mL vial, was placed a solution of methyl (S)-3-methyl-2,3,4,5-tetrahydrobenzo[f][1,4]oxazepine-8-carboxylate (100 mg, 0.45 mmol, 1 equiv) in acetic acid (1.5 mL). This was followed by the addition of formaldehyde (41 mg, 1.37 mmol, 3 equiv). The mixture was stirred for 2 h at room temperature and NaBH(OAc)$_3$ (477 mg, 2.26 mmol, 5 equiv) was added in portions at 0° C. The resulting solution was stirred for 18 h at room temperature. EtOAc was added and the resulting mixture was washed with H$_2$O (2×20 mL). The organic layer was dried over anhydrous Na$_2$SO$_4$, filtered, and concentrated under vacuum to afford the title compound as a brown oil (70 mg, 66% yield). MS: (ES, m/z): 236 [M+H]$^+$.

Step-2: (S)—N-Hydroxy-3,4-dimethyl-2,3,4,5-tetrahydrobenzo[f][1,4]oxazepine-8-carboxamide

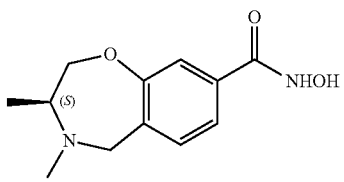

Into a 8-mL vial, was placed a solution of methyl (S)-3,4-dimethyl-2,3,4,5-tetrahydrobenzo[f][1,4]oxazepine-8-carboxylate (85 mg, 0.36 mmol, 1 equiv) in THF/MeOH (4:1, 1.5 mL), then aq. 1N NaOH (1.1 mL, 3 equiv) and NH$_2$OH (50% in water, 0.72 mL, 30 equiv) were added simultaneously. The resulting solution was stirred for 15 h at room temperature. The crude product was purified by Prep-HPLC (Column: Atlantis T3 C18, 5 μm, 19×150 mm; Mobile Phase A: Water/0.05% TFA; Mobile Phase B: MeCN; Flow rate: 25 mL/min; Gradient: 2% B to 2% B in 13 min; Detector, UV 254, 220 nm) to afford the title compound as a TFA salt as an orange oil (9 mg, 7% yield). $^1$H-NMR (300 MHz, DMSO-d$_6$) δ(ppm): 11.31 (s, 1H), 10.08-10.06 (s, 1H), 9.14 (s, 1H), 7.55-7.43 (m, 3H), 4.63-4.41 (m, 2H), 4.16-4.10 (m, 2H), 3.84-3.61 (s, 1H), 2.85 (s, 1H), 2.67-2.64 (s, 2H), 1.54-1.29 (m, 3H). MS: (ES, m/z): 237 [M+H]$^+$.

Example 41—Preparation of (S)—N-hydroxy-3-methyl-4-(o-tolyl)-2,3,4,5-tetrahydrobenzo[f][1,4]oxazepine-8-carboxamide

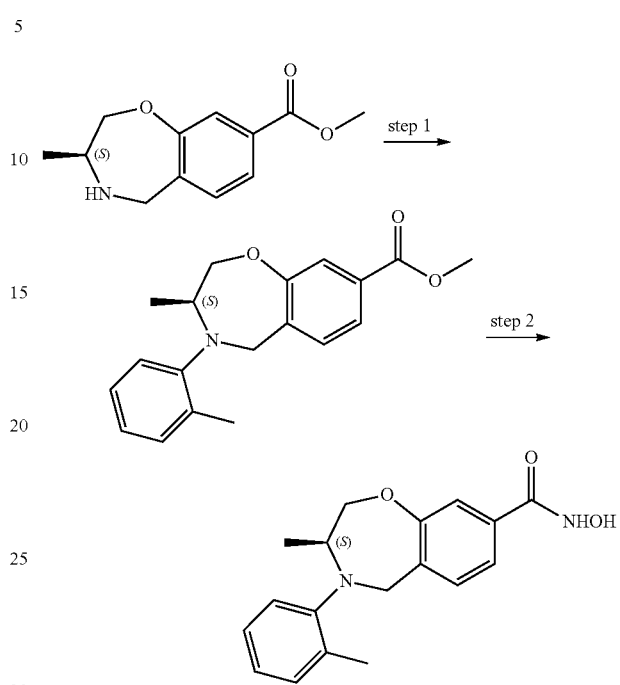

Step-1: Methyl (S)-3-methyl-4-(o-tolyl)-2,3,4,5-tetrahydrobenzo[f][1,4]oxazepine-8-carboxylate

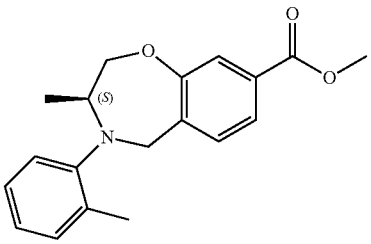

Into a 8-mL sealed tube purged and maintained with an inert atmosphere of nitrogen, was placed a solution of methyl (S)-3-methyl-2,3,4,5-tetrahydrobenzo[f][1,4]oxazepine-8-carboxylate (200 mg, 0.90 mmol, 1 equiv) in

TABLE-19

The following compound was prepared according to the method of Example 40, using methyl (R)-3-methyl-2,3,4,5-tetrahydrobenzo[f][1,4]oxazepine-8-carboxylate.

| Structure | Found M + H | $^1$H-NMR (400 MHz, DMSO-d$_6$) δ(ppm) |
|---|---|---|
| | (ES, m/z): 237 [M + H]$^+$ | 11.31 (s, 1H), 10.67-10.23 (br, 1H), 9.14 (br, 1H), 7.54-7.43 (m, 3H), 4.70-4.51 (m, 2H), 4.37-3.70 (m, 3H), 2.94-2.59 (m, 3H), 1.40-1.27 (d, J = 52.7, 3H) | toluene (3 mL), 1-bromo-2-methylbenzene (462 mg, 2.70 mmol, 3 equiv), Cs$_2$CO$_3$ (887 mg, 2.70 mmol, 3 equiv), BINAP (225 mg, 0.36 mmol, 0.4 equiv) and Pd(OAc)$_2$ (41 mg, 0.18 mmol, 0.2 equiv). The resulting solution was stirred for 20 h at 110° C. in an oil bath. The resulting mixture was concentrated under vacuum. The resulting solution was diluted with H$_2$O (10 mL) and extracted with EtOAc (3×10 mL). The combined organic layers were washed with H$_2$O (2×10 mL) and concentrated under vacuum. The residue was purified by silica gel chromatography (EtOAc/pet. ether, 1:5) to afford the title compound as a yellow oil (30 mg, 11% yield). MS: (ES, m/z): 312[M+H]$^+$.

Step-2: (S)—N-hydroxy-3-methyl-4-(o-tolyl)-2,3,4,5-tetrahydrobenzo[f][1,4]oxazepine-8-carboxamide

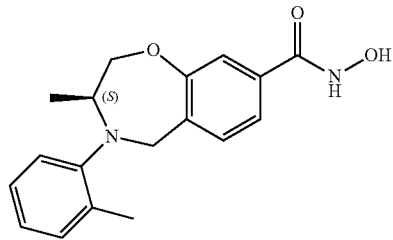

Into a 8-mL vial, was placed a solution of methyl (S)-3-methyl-4-(o-tolyl)-2,3,4,5-tetrahydrobenzo[f][1,4]oxazepine-8-carboxylate (30 mg, 0.10 mmol, 1 equiv) in THF/MeOH (4:1, 3 mL). This was followed by the addition of NH$_2$OH (50% in water, 0.19 mL, 30 equiv) and aq. 1N NaOH (0.19 mL, 2 equiv). The resulting solution was stirred for 2 h at room temperature. The crude product was purified by Prep-HPLC (Column: Xbridge Prep C18 OBD, 5 µm, 19×150 mm; Mobile Phase A: Water/0.05% formic acid; Mobile Phase B: MeCN; Flow rate: 0.7 mL/min; Gradient: 15% B to 60% B in 7 min; Detector: UV 254, 220 nm) to afford the title compound as a white solid (8.2 mg, 24% yield). $^1$H-NMR (400 MHz, DMSO-d$_6$) δ(ppm): 7.44-7.33 (m, 2H), 7.30 (m, 1H), 7.29-7.12 (m, 3H), 6.98-6.96 (m, 1H), 4.46-4.39 (m, 2H), 4.31-4.16 (m, 1H), 4.08-4.04 (m, 1H), 3.70 (s, 1H), 2.18 (s, 3H), 1.04-1.02 (d, J=8.0 Hz, 3H). MS: (ES, m/z): 313 [M+H]$^+$.

Example 42—Preparation of (S)—N-hydroxy-4-(2-methoxyphenyl)-3-methyl-2,3,4,5-tetrahydrobenzo[f][1,4]oxazepine-8-carboxamide

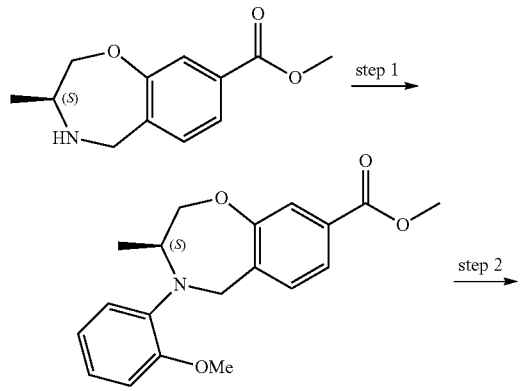

Step-1: Methyl (S)-4-(2-methoxyphenyl)-3-methyl-2,3,4,5-tetrahydrobenzo[f][1,4]oxazepine-8-carboxylate

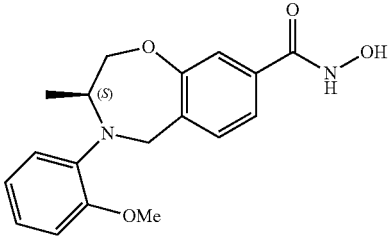

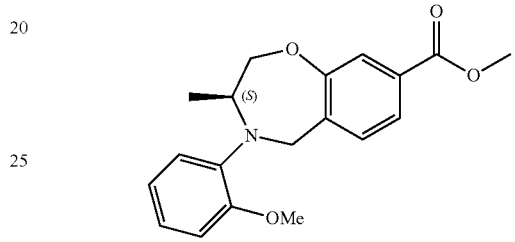

Into a 100-mL round-bottom flask, was placed a solution of methyl (S)-3-methyl-2,3,4,5-tetrahydrobenzo[f][1,4]oxazepine-8-carboxylate (220 mg, 0.99 mmol, 1 equiv) in CH$_2$Cl$_2$ (30 mL), (2-methoxyphenyl)boronic acid (452 mg, 2.97 mmol, 3 equiv), Et$_3$N (300 mg, 2.97 mmol, 3 equiv) and Cu(OAc)$_2$ (182 mg, 1.00 mmol, 1 equiv). To the above oxygen gas was introduced in. The resulting solution was stirred for 27 h at room temperature and then washed with H$_2$O (3×10 mL). The organic layers was concentrated under vacuum. The residue was purified by silica gel chromatography (EtOAc/pet. ether, 1:3) to afford the title compound as a solid (50 mg, 15% yield MS: (ES, m/z): 328 [M+H]$^+$.

Step-2: (S)—N-Hydroxy-4-(2-methoxyphenyl)-3-methyl-2,3,4,5-tetrahydrobenzo[f][1,4]oxazepine-8-carboxamide

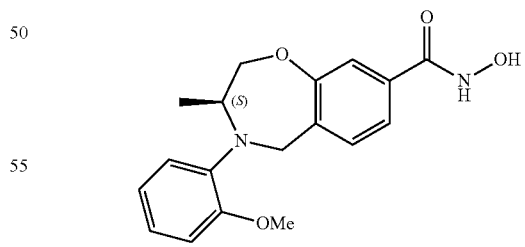

Into a 8-mL vial, was placed a solution of methyl (S)-4-(2-methoxyphenyl)-3-methyl-2,3,4,5-tetrahydrobenzo[f][1,4]oxazepine-8-carboxylate (50 mg, 0.15 mmol, 1 equiv) in THF/MeOH (4:1, 1.5 mL). This was followed by the addition of NH$_2$OH (50% in water, 0.30 mL, 30 equiv). To this was added aq. 1N NaOH (0.30 mL, 2 equiv). The resulting solution was stirred for 2 h at room temperature. The crude product was purified by Prep-HPLC (Column: Xbridge Prep C18 OBD, 5 μm, 119×150 mm; Mobile Phase A: Water/ 0.05% formic acid; Mobile Phase B: MeCN; Flow rate: 0.7 mL/min; Gradient: 5% B to 60% B in 8 min; Detector: UV 254, 220 nm) to afford the title compound as a yellow solid (3.9 mg, 7% yield). $^1$H-NMR (400 MHz, DMSO-$d_6$) δ(ppm): 11.24 (br s, 1H), 7.40-7.38 (m, 1H), 7.33-7.31 (m, 1H), 7.26-7.20 (m, 1H), 7.15-6.78 (m, 4H), 4.74-4.70 (d, J=16.0 Hz, 1H), 4.35-4.31 (m, 2H), 4.16-4.13 (m, 2H), 3.87 (s, 3H), 1.14-1.13 (d, J=4.0 Hz, 3H). MS: (ES, m/z): 329 [M+H]$^+$.

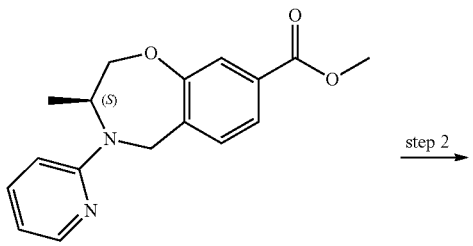

step 2

TABLE-20

The following compounds were prepared according to the method of Example 42.

| Structure | Found M + H | $^1$H-NMR (400 MHz, DMSO-$d_6$) δ(ppm) |
|---|---|---|
| | (ES, m/z): 317 [M + H]$^+$ | 11.09 (s, 1H), 8.98 (s, 1H), 7.46-7.44 (m, 1H), 7.33-7.31 (m, 1H), 7.09 (s, 1H), 6.92-6.87 (m, 2H), 6.63-6.60 (m, 2H), 5.00-4.96 (m, 1H), 4.36-4.26 (m, 2H), 4.21-4.15 (m, 2H), 1.22-1.17 (m, 3H) |
| | (ES, m/z): 317 [M + H]$^+$ | 11.08 (s, 1H), 8.98 (s, 1H), 7.50-7.48 (d, J = 8 Hz, 1H), 7.33-7.30 (m, 1H), 7.09-7.03 (m, 2H), 6.49-6.46 (m, 1H), 6.43-6.38 (d, J = 8 Hz, 1H), 6.33-6.28 (m, 1H), 5.03-4.99 (d, J = 8 Hz, 1H), 4.40-4.27 (m, 2H), 4.26-4.18 (m, 2H), 1.22-1.18 (m, 3H) |
| 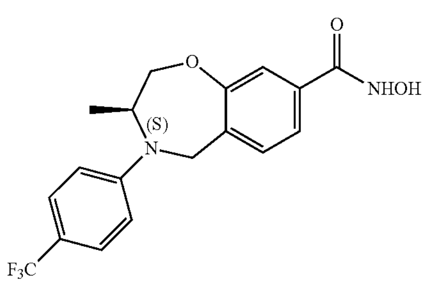 | (ES, m/z): 367 [M + H]$^+$ | 11.06 (s, 1H), 8.99 (s, 1H), 7.52-7.50 (d, J = 7.8 Hz, 1H), 7.40-7.33 (m, 3H), 7.12-7.11 (d, J = 1.5 Hz, 1H), 6.81-6.78 (d, J = 9 Hz, 2H), 5.12-5.06 (d, J = 17.4 Hz, 1H), 4.47-4.37 (m, 3H), 4.35-4.22 (m, 1H), 1.22-1.20 (d, J = 6 Hz, 3H) |

Example 43—Preparation of (S)—N-hydroxy-3-methyl-4-(pyridin-2-yl)-2,3,4,5-tetrahydrobenzo[f][1,4]oxazepine-8-carboxamide

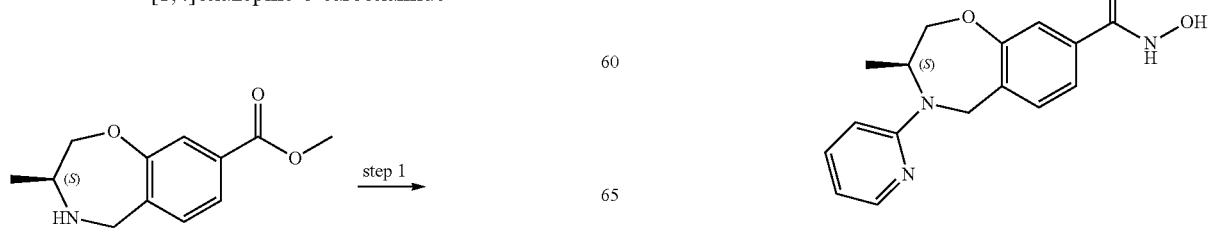

Step-1: Methyl (S)-3-methyl-4-(pyridin-2-yl)-2,3,4,5-tetrahydrobenzo[f][1,4]oxazepine-8-carboxylate

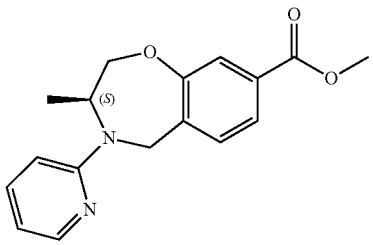

Into a 8-mL sealed tube purged and maintained with an inert atmosphere of nitrogen, were placed a solution of methyl (S)-3-methyl-2,3,4,5-tetrahydrobenzo[f][1,4]oxazepine-8-carboxylate (200 mg, 0.90 mmol, 1 equiv) in toluene (3 mL), 2-bromopyridine (529 mg, 3.35 mmol, 3 equiv), RuPhos (169 mg, 0.36 mmol, 0.4 equiv), t-BuONa (213 mg, 2.22 mmol, 3 equiv) and Pd$_2$(dba)$_3$·CHCl$_3$ (187 mg, 0.18 mmol, 0.2 equiv). The resulting mixture was stirred for 18 h at 120° C. in an oil bath. The solids were filtered out. The filtrate was concentrated under vacuum. The residue was dissolved in EtOAc (20 mL), washed with H$_2$O (2×20 mL), dried over anhydrous Na$_2$SO$_4$, filtered, and concentrated under vacuum. The residue was purified by silica gel chromatography (EtOAc/pet. ether, 1:3) to afford the title compound as a light brown oil (110 mg, 41% yield). MS: (ES, m/z): 299 [M+H]$^+$.

Step-2: (S)—N-Hydroxy-3-methyl-4-(pyridin-2-yl)-2,3,4,5-tetrahydrobenzo[f][1,4]oxazepine-8-carboxamide Into a 8-mL vial, was placed a solution of methyl (S)-3-methyl-4-(pyridin-2-yl)-2,3,4,5-tetrahydrobenzo[f][1,4]oxazepine-8-carboxylate (100 mg, 0.34 mmol, 1 equiv) in THF/MeOH (4:2, 1.5 mL). This was followed by the addition of aq. 1N NaOH (0.67 mL, 2 equiv) and NH$_2$OH (50% in water, 0.61 mL, 30 equiv) simultaneously. The resulting solution was stirred for 2 h at room temperature. The crude product was purified by Prep-HPLC (Column: Xbridge Prep C18 OBD, 5 μm, 19×100 mm; Mobile Phase A: Water/0.05% formic acid; Mobile Phase B: MeCN; Flow rate: 25 mL/min; Gradient: 5% B to 50% B in 6 min; Detector: UV 254, 220 nm) to afford the title compound as a light brown solid (13.3 mg, 13% yield). $^1$H-NMR (400 MHz, DMSO-d$_6$) δ(ppm): 11.15 (br s, 1H), 8.10-8.00 (m, 1H), 7.90-7.71 (m, 1H), 7.63-7.50 (m, 1H), 7.45-7.35 (m, 1H), 7.23-7.10 (m, 1H), 7.09-6.70 (m, 2H), 5.29-5.10 (m, 1H), 4.95-4.74 (m, 2H), 4.59-4.23 (m, 2H), 1.30-1.12 (m, 3H). MS: (ES, m/z): 300 [M+H]$^+$.

TABLE-21

The following compound was prepared according to the method of Example 43.

| Structure | Found M + H | $^1$H-NMR (400 MHz, DMSO-d$_6$) δ(ppm) |
|---|---|---|
| 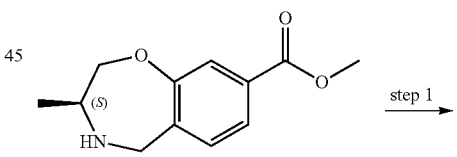 | 300 [M + H]$^+$ | (ES, m/z): 11.18 (m, 1H), 8.24-8.23 (d, J = 1.4 Hz, 1H), 8.05-8.04 (d, J = 2.6 Hz, 1H), 7.88-7.85 (m, 1H), 7.76-7.73 (m, 1H), 7.59-7.57 (d, J = 4.0 Hz, 1H), 7.45-7.33 (m, 1H), 7.16-7.15 (d, J = 0.8 Hz, 1H), 5.22-5.18 (d, J = 8.8 Hz, 1H), 4.65-4.61 (d, J = 9.0 Hz, 1H), 4.52-4.47 (m, 2H), 4.32-4.25 (m, 1H), 1.25-1.23 (d, J = 2.6 Hz, 3H) |

Example 44—Preparation of (S)—N-hydroxy-3-methyl-4-(pyridin-4-yl)-2,3,4,5-tetrahydrobenzo[f][1,4]oxazepine-8-carboxamide

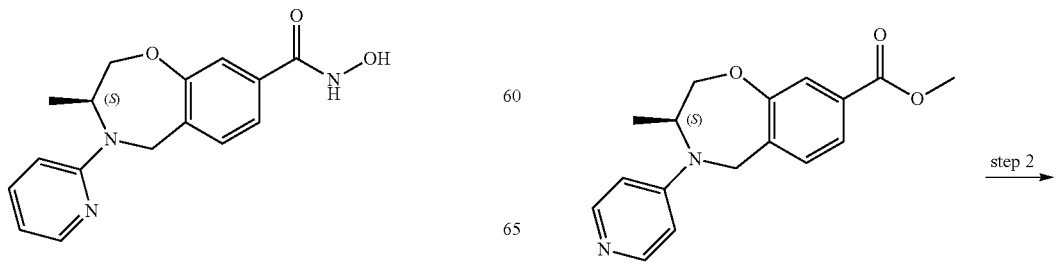

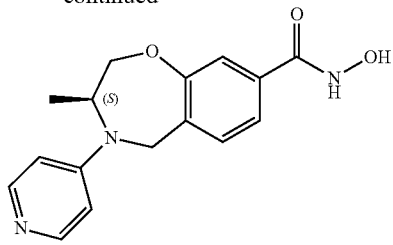

Step-1: Methyl (S)-3-methyl-4-(pyridin-4-yl)-2,3,4,5-tetrahydrobenzo[f][1,4]oxazepine-8-carboxylate

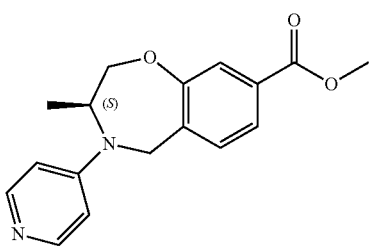

Into a 25-mL sealed tube, were placed methyl (S)-3-methyl-2,3,4,5-tetrahydrobenzo[f][1,4]oxazepine-8-carboxylate (150 mg, 0.45 mmol, 1 equiv) in toluene (5 mL), 4-bromopyridine hydrochloride (174 mg, 0.89 mmol, 2 equiv), RuPhos-Pd-G2 (35 mg, 0.05 mmol, 0.1 equiv), RuPhos (21 mg, 0.04 mmol, 0.1 equiv) and Cs$_2$CO$_3$ (438 mg, 1.34 mmol, 3 equiv). The resulting solution was stirred for 18 h at 100° C. in an oil bath. The resulting mixture was concentrated under vacuum. The residue was dissolved in EtOAc (50 mL), washed with H$_2$O (3×30 mL), dried over Na$_2$SO$_4$, filtered, and concentrated under vacuum. The residue was purified by silica gel chromatography (MeOH/CH$_2$Cl$_2$, 1:12) to afford the title compound as a yellow oil (74.6 mg, 56% yield). MS: (ES, m/z): 299 [M+H]$^+$.

Step-2: (S)—N-Hydroxy-3-methyl-4-(pyridin-4-yl)-2,3,4,5-tetrahydrobenzo[f][1,4]oxazepine-8-carboxamide

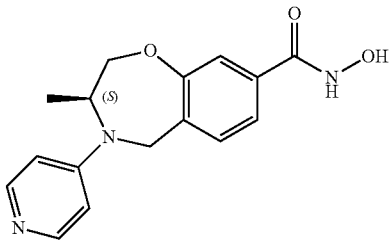

Into a 8-mL vial, was placed a solution of methyl (S)-3-methyl-4-(pyridin-4-yl)-2,3,4,5-tetrahydrobenzo[f][1,4]oxazepine-8-carboxylate) (78 mg, 0.26 mmol, 1 equiv) in THF/MeOH (4:1, 3 mL). This was followed NH$_2$OH (50% in water, 0.52 mL, 30 equiv) and aq. 1N NaOH (0.52 mL, 2 equiv) dropwise with stirring simultaneously. The resulting solution was stirred for 2 h at room temperature. The crude product was purified by Prep-HPLC (Column: Xbridge Prep C18 OBD, 5 μm, 119×150 mm; Mobile Phase A: Water/0.05% formic acid; Mobile Phase B: MeCN; Flow rate: 20 mL/min; Gradient: 3% B to 12% B in 8 min; Detector: UV 254, 220 nm) to afford the title compound as an off-white solid (35.7 mg, 46% yield). $^1$H-NMR (400 MHz, DMSO-d$_6$) δ(ppm): 11.13-11.09 (br s, 1H), 8.04-8.02 (d, J=2.8 Hz, 2H), 7.51-7.49 (d, J=4.0 Hz, 1H), 7.33-7.30 (m, 1H), 7.10-7.09 (d, J=0.8 Hz, 1H), 6.65-6.61 (m, 2H), 5.06-5.01 (m, 1H), 4.47-4.31 (m, 3H), 4.25-4.21 (m, 1H), 1.16-1.15 (d, J=2.0 Hz, 3H). MS: (ES, m/z): 300 [M+H]$^+$.

Example 45—Preparation of (S)—N-hydroxy-3-methyl-4-(oxetan-3-yl)-2,3,4,5-tetrahydrobenzo[f][1,4]oxazepine-8-carboxamide

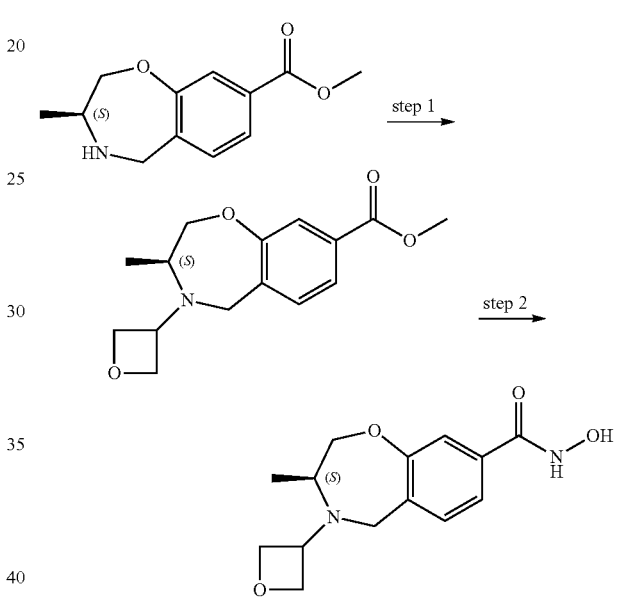

Step-1: Methyl (S)-3-methyl-4-(oxetan-3-yl)-2,3,4,5-tetrahydrobenzo[f][1,4]oxazepine-8-carboxylate

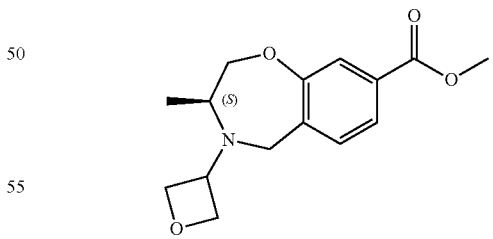

Into a 8 mL vial were added methyl (S)-3-methyl-2,3,4,5-tetrahydrobenzo[f][1,4]oxazepine-8-carboxylate hydrochloride (50 mg, 0.194 mmol, 1 equiv) and Et$_3$N (0.027 mL, 0.194 mmol, 1 equiv) and 1,2-dichloroethane (5 mL). This solution was stirred at room temperature for 15 minutes. Next, oxetan-3-one (16.8 mg, 0.233 mmol, 1.2 equiv), acetic acid (0.011 mL, 0.194 mmol, 1 equiv), and NaBH(OAc)$_3$ (103 mg, 0.485 mmol, 2.5 equiv) were added. The resulting solution was allowed to stir at 50° C. for 16 hours. The reaction was washed with H₂O (2×5 mL). The organic layer was separated, dried over Na₂SO₄, filtered and concentrated to afford the title compound as a white solid (65 mg) that was used without further purification. MS: (ES, m/z): 278 [M+H]⁺.

Step-2: (S)—N-Hydroxy-3-methyl-4-(oxetan-3-yl)-2,3,4,5-tetrahydrobenzo[f][1,4]oxazepine-8-carboxamide

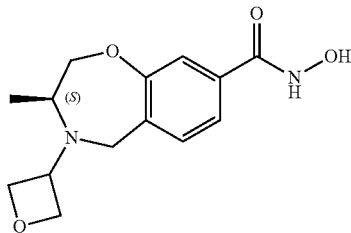

Into a 4-mL vial was added methyl (S)-3-methyl-4-(oxetan-3-yl)-2,3,4,5-tetrahydrobenzo[f][1,4]oxazepine-8-carboxylate (29.6 mg, 0.081 mmol, 1 equiv), NH₂OH (50% in water, 107 μL, 1.62 mmol, 20 equiv) and aq. 1N NaOH (324 μL, 0.162 mmol, 4 equiv) in a solution of THF/MeOH (4:1, 1.0 mL). The resulting solution was allowed to stir at room temperature for 16 hours. The reaction was concentrated to dryness and purified by Prep-HPLC (Column: Xbridge Prep C18 OBD, 5 μm, 19×50 mm; Mobile Phase A: Water/0.1% formic acid; Mobile Phase B: MeCN/0.1% formic acid; Flow rate: 23 mL/min; Gradient: 0% B to 35% B in 8 min; Detector: UV 254, 220 nm) to afford the title compound as a light brown oil (34.4 mg, 53% yield). ¹H-NMR (400 MHz, DMSO-d₆) δ(ppm): 11.16 (s, 1H), 9.45 (br s, 1H), 9.02 (s, 1H), 8.60 (d, J=1.2 Hz, 1H), 7.28-7.39 (m, 1H), 7.25 (d, J=1.8 Hz, 1H), 7.17 (br d, J=7.6 Hz, 1H), 4.77 (quin, J=6.3 Hz, 1H), 4.32-4.49 (m, 2H), 4.22 (br d, J=15.8 Hz, 1H), 3.76-4.11 (m, 2H), 3.34 (s, 6H), 2.94 (s, 2H), 2.78 (s, 2H), 2.37-2.58 (m, 3H), 1.86-1.96 (m, 2H), 1.12-1.20 (m, 1H), 1.01-1.25 (m, 3H), 1.01-1.07 (m, 1H). MS: (ES, m/z): 279 [M+H]⁺.

Example 46—Preparation of (S)—N-hydroxy-3-methyl-4-(oxetan-3-ylmethyl)-2,3,4,5-tetrahydrobenzo[f][1,4]oxazepine-8-carboxamide

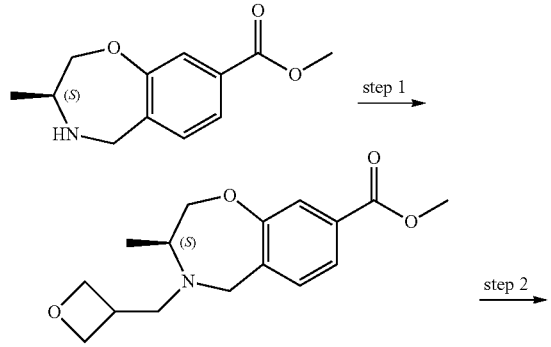

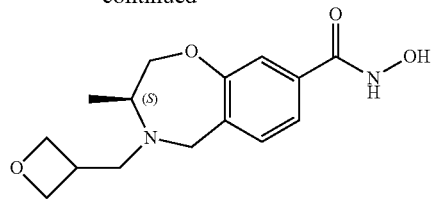

Step-1: Methyl (S)-3-methyl-4-(oxetan-3-ylmethyl)-2,3,4,5-tetrahydrobenzo[f][1,4]oxazepine-8-carboxylate

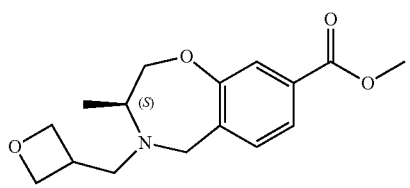

Into a 100-mL round-bottom flask, were placed methyl (S)-3-methyl-4-(oxetan-3-ylmethyl)-2,3,4,5-tetrahydrobenzo[f][1,4]oxazepine-8-carboxylate (150 mg, 0.68 mmol, 1 equiv) and acetic acid (5 mL). To this was added oxetane-3-carbaldehyde (117 mg, 1.36 mmol, 2 equiv). The resulting solution was stirred for 1.5 h at room temperature. This was followed by the addition of acetyl ethaneperoxoate sodioboranyl acetate (2.28 g, 10.76 mmol, 10 equiv) in several batches. The resulting solution was stirred for 16 h at room temperature, then concentrated under vacuum. The residue was dissolved in EtOAc (100 mL) and washed with H₂O (4×30 mL). The combined organic layers were dried over anhydrous Na₂SO₄, filtered, and concentrated under vacuum. The residue was purified by silica gel chromatography (MeOH/CH₂Cl₂, 1:20) to afford the title compound as a yellow solid (48 mg, 24% yield. MS: (ES, m/z): 292 [M+H]⁺.

Step-2: (S)—N-Hydroxy-3-methyl-4-(oxetan-3-ylmethyl)-2,3,4,5-tetrahydrobenzo[f][1,4]oxazepine-8-carboxamide

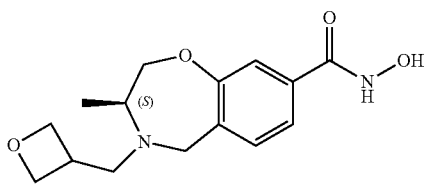

Into a 8-mL vial, were placed methyl (S)-3-methyl-4-(oxetan-3-ylmethyl)-2,3,4,5-tetrahydrobenzo[f][1,4]oxazepine-8-carboxylate (60 mg, 0.21 mmol, 1 equiv) and THF/MeOH (4:1, 1.5 mL). Then a solution of NH₂OH (50% in water, 0.42 mL, 30 equiv) and a solution of sodium hydroxide (1 mol/L, 0.42 mL, 2 equiv) were added at the same time. The resulting solution was stirred for 2 h at room temperature. The crude product was purified by Prep-HPLC (Column: Xbridge RP C18 OBD, 5 μm, 19×100 mm; Mobile Phase A: Water/0.05% TFA; Mobile Phase B: MeCN; Flow rate: 25 mL/min; Gradient: 4% B to 58% B in 7 min; Detector: UV 254, 220 nm) to afford the title compound as a yellow solid (9 mg, 11% yield). $^1$H-NMR (400 M Hz, DMSO-$d_6$) δ(ppm): 11.35 (br s, 1H), 10.30-10.01 (br s, 1H), 9.14 (br s, 1H), 7.52-7.24 (m, 3H), 4.65-4.64 (d, J=5.2 hz, 3H), 4.51-3.76 (m, 8H), 3.57-3.45 (m, 1H), 1.49-1.15 (m, 3H). MS: (ES, m/z): 293 [M+H]$^+$.

Example 47—Preparation of (S)—N-hydroxy-4-(4-methoxypiperidine-1-carbonyl)-3-methyl-2,3,4,5-tetrahydrobenzo[f][1,4]oxazepine-8-carboxamide

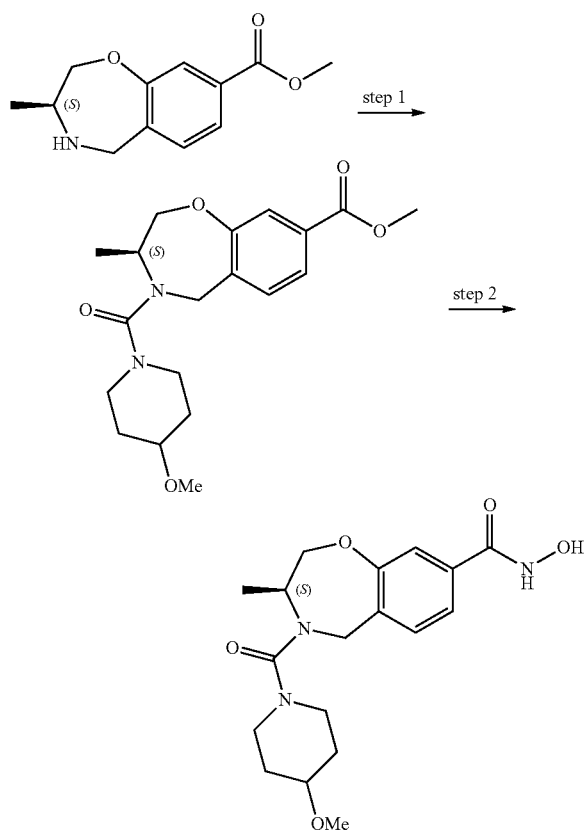

Step-1: Methyl (S)-4-(4-methoxypiperidine-1-carbonyl)-3-methyl-2,3,4,5-tetrahydrobenzo[f][1,4]oxazepine-8-carboxylate

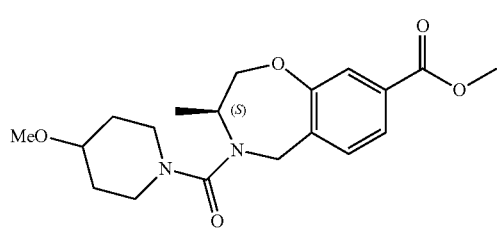

Into a 25-mL round-bottom flask, was placed a solution of methyl (S)-3-methyl-2,3,4,5-tetrahydrobenzo[f][1,4]oxazepine-8-carboxylate (100 mg, 0.45 mmol, 1 equiv) in CH$_2$Cl$_2$ (10 mL), triphosgene (44 mg, 0.16 mmol, 0.33 equiv), the resulting solution was stirred for 10 min at 25° C. Then Et$_3$N (91 mg, 0.90 mmol, 2 equiv) was added into the solution at 0° C. and was stirred for 20 min at 25° C. Then a solution of 4-methoxypiperidine (208 mg, 1.81 mmol, 4 equiv) in CH$_2$Cl$_2$ was added and the reaction was stirred for 30 min at 25° C. The resulting solution was diluted with H$_2$O (20 mL) and extracted with CH$_2$Cl$_2$ (3×15 mL). The combined organic layers were dried over anhydrous Na$_2$SO$_4$, filtered, and concentrated under vacuum to afford the title compound as yellow oil (150 mg) which was used without further purification. MS: (ES, m/z): 363 [M+H]$^+$.

Step-2: (S)—N-Hydroxy-4-(4-methoxypiperidine-1-carbonyl)-3-methyl-2,3,4,5-tetrahydrobenzo[f][1,4]oxazepine-8-carboxamide

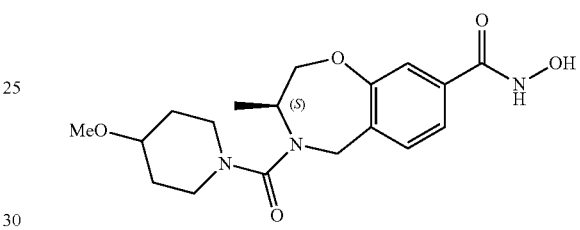

Into a 10-mL round-bottom flask, was placed methyl (S)-4-(4-methoxypiperidine-1-carbonyl)-3-methyl-2,3,4,5-tetrahydrobenzo[f][1,4]oxazepine-8-carboxylate (150 mg, 0.41 mmol, 1 equiv), NH$_2$OH (50% in water, 1.62 g, 49 mmol, 120 equiv), and aq. 1N NaOH (33 mg, 0.83 mmol, 2 equiv). The resulting solution was stirred for 2 h at 25° C. The crude product was purified by Prep-HPLC (Column: Sunfire Prep C18 OBD, 5 μm, 19×150 mm; Mobile Phase A: Water/0.05% formic acid; Mobile Phase B: MeCN; Flow rate: 23 mL/min; Gradient: 20% B to 30% B in 8 min; Detector: UV 254, 220 nm) to afford the title compound as a light pink solid (29.5 mg, 20% yield). $^1$H-NMR (300 MHz, DMSO-$d_6$) δ(ppm): 11.11 (s, 1H), 9.01 (s, 1H), 7.34-7.21 (m, 3H), 4.60-4.55 (d, J=17.1 Hz, 1H), 4.32-4.26 (d, J=16.8 Hz, 1H), 4.16-4.03 (m, 3H), 3.26-3.21 (m, 6H), 2.81-2.68 (m, 2H), 1.84-1.70 (m, 2H), 1.43-1.29 (m, 2H), 1.19 (s, 3H). MS: (ES, m/z): 364[M+H]$^+$.

Example 48—Preparation of (S)-4-(azetidine-1-carbonyl)-N-hydroxy-3-methyl-2,3,4,5-tetrahydrobenzo[f][1,4]oxazepine-8-carboxamide

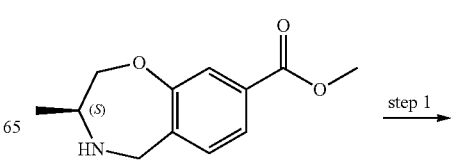

-continued

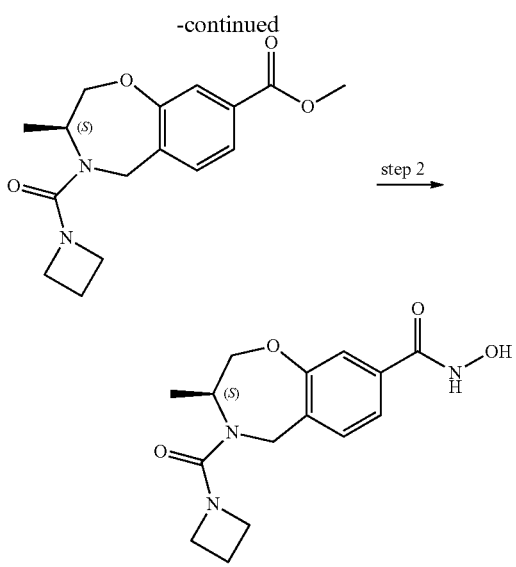

Step-1: Methyl (S)-4-(azetidine-1-carbonyl)-3-methyl-2,3,4,5-tetrahydrobenzo[f][1,4]oxazepine-8-carboxylate

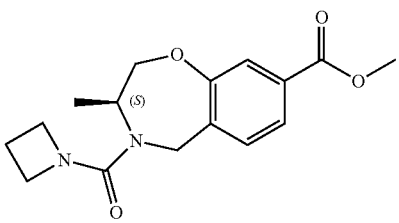

Into an 8 mL vial were added triphsogene (34.5 mg, 0.116 mmol, 0.4 equiv) in CH$_2$Cl$_2$ (2 mL). A solution of methyl (S)-3-methyl-2,3,4,5-tetrahydrobenzo[f][1,4]oxazepine-8-carboxylate hydrochloride (75 mg, 0.194 mmol, 1 equiv), Et$_3$N (0.162 mL, 1.164 mmol, 4 equiv) and azetidine hydrochloride (27.2 mg, 0.291 mmol, 1 equiv) in CH$_2$Cl$_2$ (2 mL) was added to the stirring solution. This solution was stirred at room temperature for 16 hours. The reaction was quenched with brine (2 mL) and concentrated to dryness. The crude product was purified by Prep-HPLC (Column: Xbridge Prep C18 OBD, 5 μm, 19×50 mm; Mobile Phase A: Water/0.1% formic acid; Mobile Phase B: MeCN/0.1% formic acid; Flow rate: 23 mL/min; Gradient: 15% B to 65% B in 8 min; Detector: UV 254, 220 nm) to afford the title compound as a white solid (16.3 mg, 18% yield). MS: (ES, m/z): 305 [M+H]$^+$.

Step-2: (S)-4-(Azetidine-1-carbonyl)-N-hydroxy-3-methyl-2,3,4,5-tetrahydrobenzo[f][1,4]oxazepine-8-carboxamide

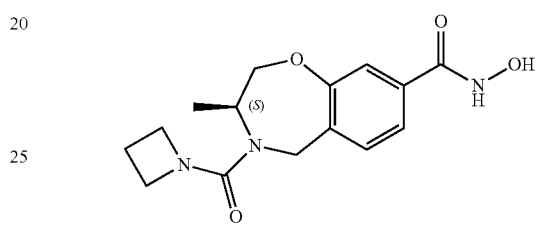

Into a 4-mL vial was added methyl (S)-4-(azetidine-1-carbonyl)-3-methyl-2,3,4,5-tetrahydrobenzo[f][1,4]oxazepine-8-carboxylate (16.3 mg, 0.054 mmol, 1 equiv), NH$_2$OH (50% in water, 53.1 μL, 1.60 mmol, 20 equiv) and aq. 1N NaOH (107 μL, 0.107 mmol, 4 equiv) in a solution of THF/MeOH (4:1, 1.0 mL). The resulting solution was allowed to stir at room temperature for 16 hours. The reaction was concentrated to dryness and was purified by Prep-HPLC (Column: Xbridge Prep C18 OBD, 5 μm, 19×50 mm; Mobile Phase A: Water/0.1% formic acid; Mobile Phase B: MeCN/0.1% formic acid; Flow rate: 23 mL/min; Gradient: 0% B to 35% B in 8 min; Detector: UV 254, 220 nm) to afford the title compound. MS: (ES, m/z): 306 [M+H]$^+$.

TABLE-22

The following compound was prepared according to the method of Example 48.

| Structure | Found M + H |
|---|---|
| ![structure] | (ES, m/z): 336 [M + H]$^+$ |
| ![structure] | (ES, m/z): 350 [M + H]$^+$ |

TABLE-22-continued

The following compound was prepared according to the method of Example 48.

| Structure | Found M + H |
|---|---|
| | (ES, m/z): 343 [M + H]⁺ |
| | (ES, m/z): 348 [M + H]⁺ |
| | (ES, m/z): 343 [M + H]⁺ |
| | (ES, m/z): 350 [M + H]⁺ |
| | (ES, m/z): 364 [M + H]⁺ |

TABLE-22-continued
The following compound was prepared according to the method of Example 48.
| Structure | Found M + H |
|---|---|
| | (ES, m/z): 343 [M + H]⁺ |
| | (ES, m/z): 362 [M + H]⁺ |
| | (ES, m/z): 362 [M + H]⁺ |
| | (ES, m/z): 384 [M + H]⁺ |
Example 49—Preparation of cyclopentyl (S)-8-(hydroxycarbamoyl)-3-methyl-2,3-dihydrobenzo[f][1,4]oxazepine-4(5H)-carboxylate
-continued
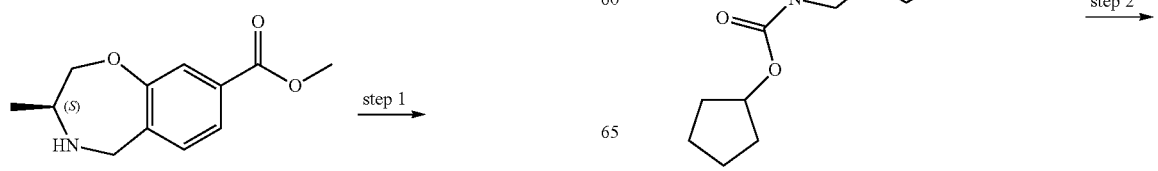
step 2

-continued

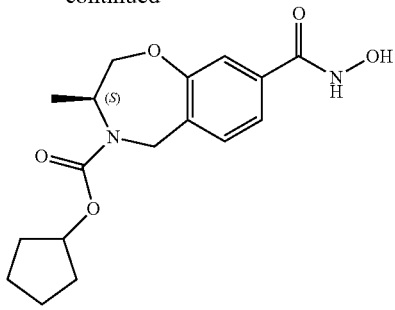

Step-1: 4-Cyclopentyl 8-methyl (S)-3-methyl-2,3-dihydrobenzo[f][1,4]oxazepine-4,8(5H)-dicarboxylate

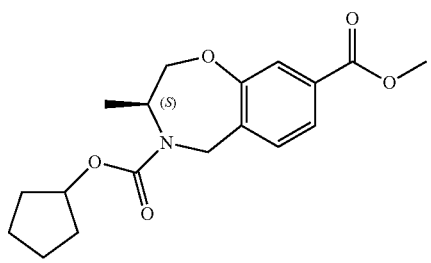

Into a 8-mL vial, was placed a solution of methyl (S)-3-methyl-2,3,4,5-tetrahydrobenzo[f][1,4]oxazepine-8-carboxylate 2,2,2-trifluoroacetate (80 mg, 0.24 mmol, 1 equiv) in CH$_2$Cl$_2$ (2.5 mL), Et$_3$N (96.9 mg, 0.96 mmol, 4 equiv), cyclopentyl chloroformate (53 mg, 0.36 mmol, 1.5 equiv). The resulting solution was stirred for 5 h at room temperature. The residue was concentrated under vacuum and purified by silica gel chromatography (EtOAc/pet. ether, 1:1) to afford the title compound as a white solid (40 mg, 50% yield). MS: (ES, m/z): 334 [M+H]$^+$.

Step-2: Cyclopentyl (S)-8-(hydroxycarbamoyl)-3-methyl-2,3-dihydrobenzo[f][1,4]oxazepine-4(5H)-carboxylate

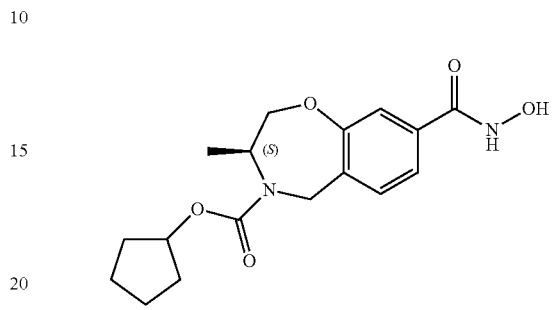

Into a 8-mL vial, was placed a solution of 4-cyclopentyl 8-methyl (S)-3-methyl-2,3-dihydrobenzo[f][1,4]oxazepine-4,8(5H)-dicarboxylate (40 mg, 0.12 mmol, 1 equiv) THF/MeOH (4:1, 2.5 mL). Then aq. 1N NaOH (0.30 mL, 2 equiv) and NH$_2$OH (50% in water, 0.30 mL, 30 equiv) were added simultaneously. The resulting solution was stirred for 1 h at room temperature. The crude product was purified by Prep-HPLC (Column: Xbridge Prep C18 OBD, 5 μm, 19×150 mm; Mobile Phase A: Water/0.1% formic acid; Mobile Phase B: MeCN; Flow rate: 20 mL/min; Gradient: 5% B to 65% B in 8 min; Detector: UV 254, 220 nm) to afford the title compound as a white solid (11.7 mg, 29% yield). $^1$H-NMR (400 MHz, DMSO-d$_6$) δ(ppm): 11.13 (s, 1H), 9.02 (s, 1H), 7.31-7.30 (m, 1H), 7.22-7.18 (m, 2H), 4.96-4.90 (m, 1H), 4.64-4.60 (m, 1H), 4.50-4.39 (m, 2H), 4.24-4.11 (m, 2H), 1.82-1.70 (m, 1H), 1.68-1.55 (m, 5H), 1.32-1.21 (m, 2H), 1.20-1.09 (m, 3H). MS: (ES, m/z): 335 [M+H]$^+$.

TABLE-23

The following compound was prepared according to the method of Example 49.

| Structure | Found M + H | $^1$H-NMR 400 MHz, DMSO-d$_6$ δ(ppm) |
|---|---|---|
| (structure shown) | 349 [M + H]$^+$ | (ES, m/z): 11.13 (br s, 1H), 9.01 (br s, 1H), 7.30 (m, 1H), 7.24-7.19 (m, 2H), 4.65 (m, 1H), 4.50-4.54 (m, 3H), 4.26-4.12 (m, 2H), 1.69-1.60 (m, 3H), 1.42-1.24 (m, 6H), 1.12-1.10 (m, 4H) |

TABLE-23-continued
The following compound was prepared according to the method of Example 49.
| Structure | Found M + H | ¹H-NMR 400 MHz, DMSO-$d_6$) δ(ppm) |
|---|---|---|
| | (ES, m/z): 295 [M + H]⁺ | 11.12 (s, 1H), 9.08-9.02 (s, 1H), 7.32-7.18 (m, 3H), 4.64-4.48 (m, 3H), 4.26-4.11 (m, 2H), 4.04-3.94 (m, 2H), 1.16-0.99 (m, 6H) |
| | (ES, m/z): 361 [M + H]⁺ | 11.14 (br s, 1H), 9.08-9.02 (brs, 1H), 7.34-7.13 (m, 6H), 6.99-6.95 (m, 1H), 4.89-4.65 (m, 3H), 4.36-4.20 (m, 2H), 1.27-1.18 (m, 3H) |
| | (ES, m/z): 309 [M + H]⁺ | 11.13 (s, 1H), 8.99 (s, 1H), 7.31-7.18 (m, 3H), 4.70-4.47 (m, 4H), 4.25-4.15 (m, 2H), 1.16-0.92 (m, 9H) |
Example 50—Preparation of cyclobutyl (S)-8-(hydroxycarbamoyl)-3-methyl-2,3-dihydrobenzo[f][1,4]oxazepine-4(5H)-carboxylate
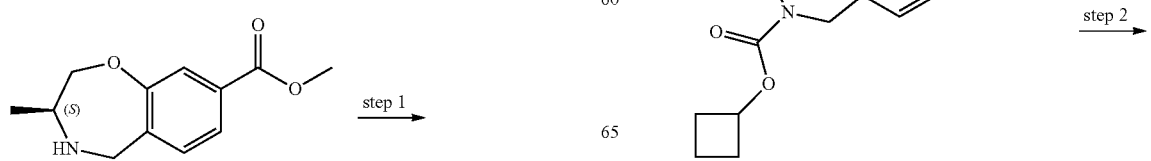

-continued

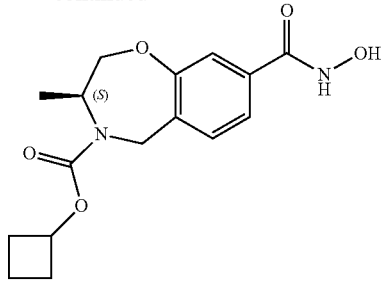

Step-1: 4-Cyclobutyl 8-methyl (S)-3-methyl-2,3-dihydrobenzo[f][1,4]oxazepine-4,8(5H)-dicarboxylate

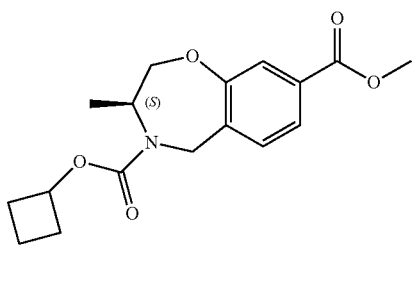

Into a 25-mL round-bottom flask, was placed cyclobutanol (65 mg, 0.90 mmol, 1 equiv), THF (8 mL), triphosgene (90 mg, 0.33 equiv), and Et₃N (48 mg, 0.47 mmol, 2 equiv). The resulting solution was stirred for 30 min at room temperature. Then, methyl (S)-3-methyl-2,3,4,5-tetrahydrobenzo[f][1,4]oxazepine-8-carboxylate (48 mg, 0.22 mmol, 0.24 equiv) was added and the reaction was stirred for 30 min at room temperature. The reaction was then quenched by the addition of water (10 mL), extracted with CH₂Cl₂ (3×30 mL), dried over anhydrous Na₂SO₄, filtered, and concentrated under vacuum to afford the title compound as brown oil (130 mg, 45% yield). MS: (ES, m/z): 320 [M+H]⁺.

Step-2: Cyclobutyl (S)-8-(hydroxycarbamoyl)-3-methyl-2,3-dihydrobenzo[f][1,4]oxazepine-4(5H)-carboxylate

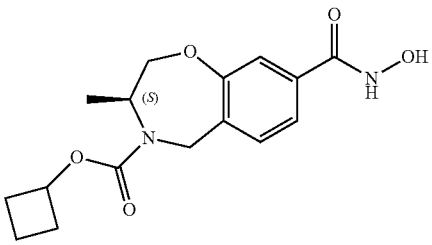

Into a 25-mL round-bottom flask, was placed 4-cyclobutyl 8-methyl (S)-3-methyl-2,3-dihydrobenzo[f][1,4]oxazepine-4,8(5H)-dicarboxylate (130 mg, 0.41 mmol, 1 equiv), THF/MeOH (4:1, 3 mL), NH₂OH (50% in water, 3228 mg, 120 equiv), aq. 1N NaOH (0.82 mL, 2 equiv). The resulting solution was stirred for 2 h at room temperature. The solids were filtered out. The crude product was purified by Prep-HPLC (Column: Xbridge Prep C18 OBD, 5 μm, 19×150 mm; Mobile Phase A: Water/10 mmol NH₄HCO₃; Mobile Phase B: MeCN; Flow rate: 23 mL/min; Gradient: 25% B to 50% B in 7 min; Detector: UV 254, 220 nm) to afford the title compound as a white solid (37.1 mg, 28% yield). $^1$H-NMR (300 MHz, DMSO-d₆) δ(ppm): 7.30-7.18 (m, 3H), 4.80-4.57 (m, 3H), 4.44 (s, 1H), 4.25-4.15 (m, 2H), 2.20-2.01 (m, 2H), 1.98-1.92 (m, 1H), 1.67-1.57 (m, 3H), 1.12-1.10 (d, J=6.0 Hz, 3H). MS: (ES, m/z): 321 [M+H]⁺.

TABLE-24

The following compound was prepared according to the method of Example 50.

| Structure | Found M + H | $^1$H-NMR 400 MHz, DMSO-d₆ δ(ppm) |
|---|---|---|
| (structure shown) | (ES, m/z): 351 [M + H]⁺ | 11.07 (br s, 1H), 9.07 (br s, 1H), 7.31-7.19 (m, 3H), 4.70-4.53 (m, 4H), 4.28-4.17 (m, 2H), 3.74-3.32 (m, 4H), 1.82 (s, 2H), 1.53 (s, 2H), 1.21-1.11 (m, 3H) |

Example 51—Preparation of N-hydroxy-4-methyl-4,5-dihydro-2H-spiro[benzo[f][1,4]oxazepine-3,1'-cyclopropane]-8-carboxamide

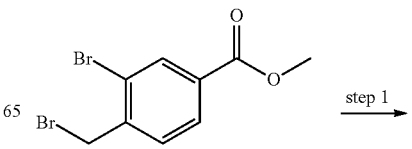

Step-1: Methyl 3-bromo-4-(((1-(hydroxymethyl)cyclopropyl)amino)methyl)benzoate

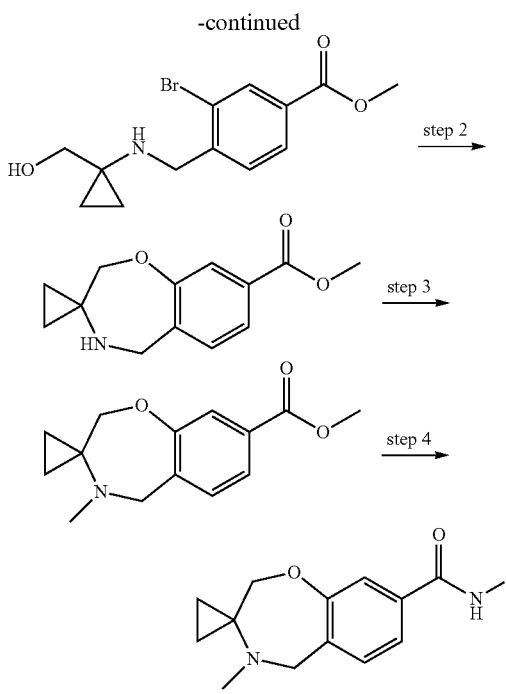

Into a 500-mL round-bottom flask, was placed (1-aminocyclopropyl)methanol hydrochloride (6 g, 48.55 mmol, 2 equiv), $K_2CO_3$ (11 g, 79.59 mmol, 3.5 equiv) in MeCN (120 mL), The mixture was stirred at room temperature for 10 min. This was followed by the addition of a solution of methyl 3-bromo-4-(bromomethyl)benzoate (15 g, 48.71 mmol, 1 equiv) in MeCN (150 mL) dropwise with stirring at 0° C. over 2h. The resulting solution was stirred overnight at room temperature. The resulting mixture was concentrated under vacuum. The residue was purified by silica gel chromatography (EtOAc/pet. ether, 1:3) to afford the title compound as a yellow oil (7 g, 46% yield). MS: (ES, m/z): 314,316 [M+H]$^+$.

Step-2: Methyl 4,5-dihydro-2H-spiro[benzo[f][1,4]oxazepine-3,1'-cyclopropane]-8-carboxylate

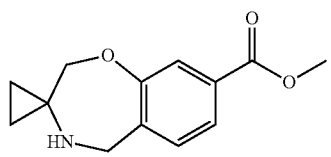 [SMILES: COC(=O)c1ccc2c(c1)OCC1(CC1)NC2]

Into a 40-mL sealed tube purged and maintained with an inert atmosphere of nitrogen, was placed a solution of methyl 3-bromo-4-(((1-(hydroxymethyl)cyclopropyl)amino)methyl)benzoate (1.5 g, 4.77 mmol, 1 equiv), CuI (273 mg, 1.43 mmol, 0.3 equiv), $K_2CO_3$ (992 mg, 7.18 mmol, 1.5 equiv) in isopropanol (28 mL). The resulting solution was stirred overnight at 110° C. in an oil bath. The resulting mixture was concentrated under vacuum and the residue was diluted with $CH_2Cl_2$ (150 mL). The solids were filtered out and the filtrate was concentrated under vacuum. The residue was purified by C18 chromatography (MeCN/$H_2O$+0.05% TFA, 1:4) to afford the title compound as a yellow solid (0.8 g, 72% yield). MS: (ES, m/z): 234 [M+H]$^+$.

Step-3: Methyl 4-methyl-4,5-dihydro-2H-spiro[benzo[f][1,4]oxazepine-3,1'-cyclopropane]-8-carboxylate

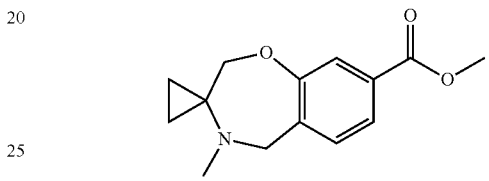

Into a 25-mL round-bottom flask, was placed methyl 4,5-dihydro-2H-spiro[benzo[f][1,4]oxazepine-3,1'-cyclopropane]-8-carboxylate (130 mg, 0.56 mmol, 1 equiv), acetic acid (3 mL), acetal (147 g, 3.35 mmol, 6 equiv). The resulting solution was stirred for 2 h at room temperature. Then NaBH(OAc)$_3$ (1.18 g, 5.58 mmol, 10 equiv) was added. The resulting solution was stirred overnight at room temperature. The resulting mixture was concentrated under vacuum. The residue was purified by silica gel chromatography (EtOAc/pet. ether, 1:5) to afford the title compound as a white solid (18.3 mg, 13% yield). MS: (ES, m/z): 248 [M+H]$^+$.

Step-4: N-Hydroxy-4-methyl-4,5-dihydro-2H-spiro[benzo[f][1,4]oxazepine-3,1'-cyclopropane]-8-carboxamide

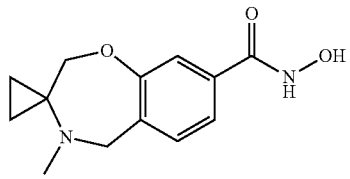 [SMILES: CN1Cc2ccc(C(=O)NO)cc2OCC12CC2]

Into a 25-mL round-bottom flask, was placed methyl 4-methyl-4,5-dihydro-2H-spiro[benzo[f][1,4]oxazepine-3,1'-cyclopropane]-8-carboxylate (18.3 mg, 0.07 mmol, 1 equiv), THF/MeOH (4:1, 1.5 mL), NH$_2$OH (50% in water 489 mg, 7.41 mmol, 105 equiv), aq. 1N NaOH (0.15 mL, 2.14 equiv). The resulting solution was stirred for 2.5 h at room temperature. The crude product was purified by Prep-HPLC (Column: Xbridge Prep C18 OBD, 5 m; Mobile Phase A: Water/0.05% formic acid; Mobile Phase B: MeCN; Detector: UV 254, 220 nm) to afford the title compound as a pink solid (8.9 mg, 42% yield). $^1$H-NMR (400 MHz, DMSO-d$_6$) δ(ppm): 11.34 (br s, 1H), 9.38-8.98 (br s, 1H), 7.69-7.47 (m, 3H), 4.73-4.59 (m, 2H), 4.39-4.22 (m, 1H), 3.73-3.69 (m, 1H), 2.63 (s, 3H), 1.69-1.62 (m, 1H), 1.43-1.32 (m, 1H), 1.29-1.17 (m, 1H), 1.04-0.94 (m, 1H). MS: (ES, m/z): 249 [M+H]$^+$.

TABLE-25

The following compound was prepared according to the method of Example 51.

| Structure | Found M + H | $^1$H-NMR (400 MHz, DMSO-$d_6$) δ(ppm) |
|---|---|---|
| 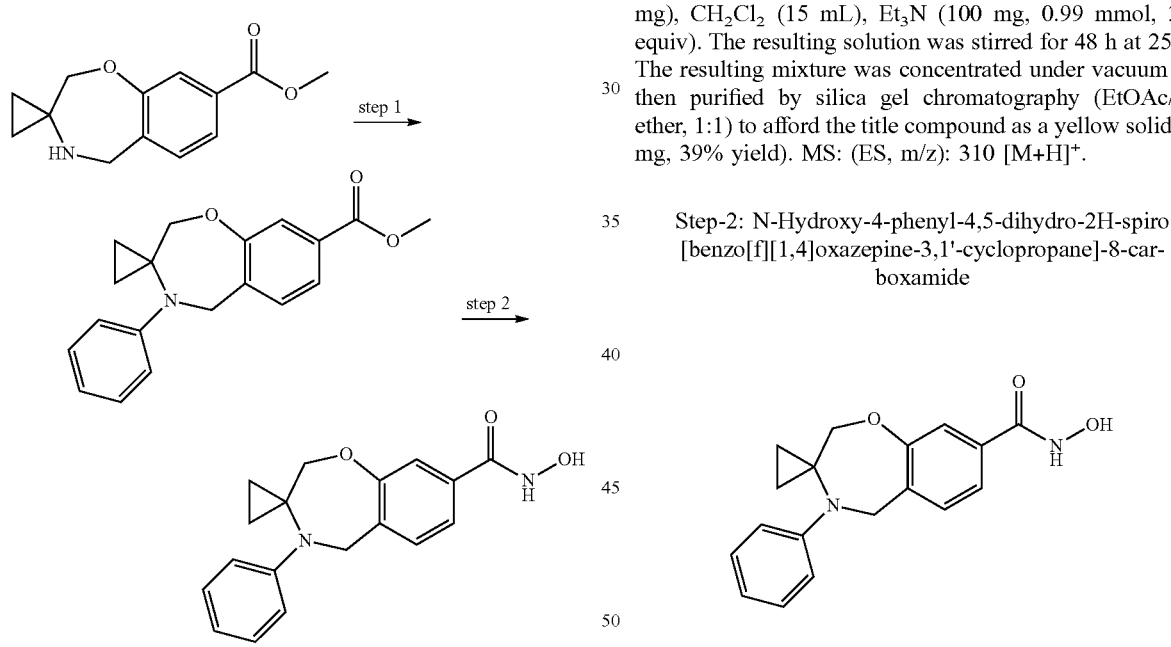 | (ES, m/z): 355 [M + H]$^+$ | 11.31 (br s, 2H), 7.51-7.33 (m, 5H), 6.92 (d, J = 8.4 Hz, 2H), 4.90-4.17 (m, 4H), 3.77 (m, 5H), 0.82 (s, 4H) |

Example 52—Preparation of N-hydroxy-4-phenyl-4,5-dihydro-2H-spiro[benzo[f][1,4]oxazepine-3,1'-cyclopropane]-8-carboxamide

Step-1: Methyl 4-phenyl-4,5-dihydro-2H-spiro[benzo[f][1,4]oxazepine-3,1'-cyclopropane]-8-carboxylate

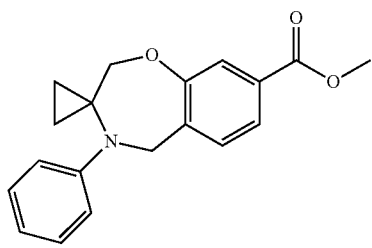 [SMILES: COC(=O)c1ccc2c(c1)OCC1(CC1)N(c1ccccc1)C2]

Into a 50-mL round-bottom flask, was placed Cu(OAc)$_2$ (100 mg, 0.55 mmol, 2.14 equiv), methyl 4,5-dihydro-2H-spiro[benzo[f][1,4]oxazepine-3,1'-cyclopropane]-8-carboxylate (60 mg, 0.26 mmol, 1 equiv). phenyl boronic acid (65 mg, 0.53 mmol, 2.05 equiv), 4 Å molecular sieves (50 mg), CH$_2$Cl$_2$ (15 mL), Et$_3$N (100 mg, 0.99 mmol, 3.84 equiv). The resulting solution was stirred for 48 h at 25° C. The resulting mixture was concentrated under vacuum and then purified by silica gel chromatography (EtOAc/pet. ether, 1:1) to afford the title compound as a yellow solid (31 mg, 39% yield). MS: (ES, m/z): 310 [M+H]$^+$.

Step-2: N-Hydroxy-4-phenyl-4,5-dihydro-2H-spiro[benzo[f][1,4]oxazepine-3,1'-cyclopropane]-8-carboxamide Into a 25-mL round-bottom flask, was placed methyl 4-phenyl-4,5-dihydro-2H-spiro[benzo[f][1,4]oxazepine-3,1'-cyclopropane]-8-carboxylate (25 mg, 0.08 mmol, 1 equiv), NH$_2$OH (50% in water, 0.32 g, 4.8 mmol, 60 equiv), aq. 1N NaOH (0.16 mL, 2 equiv), THF/MeOH (4:1, 2 mL). The resulting solution was stirred for 5 h at 25° C. The crude product was purified by Prep-HPLC. (Column: Xbridge Prep C18 OBD, 5 μm, 19×150 mm; Mobile Phase A: Water/0.05% TFA; Mobile Phase B: MeCN; Flow rate: 20 mL/min; Gradient: 30% B to 70% B in 10 min; Detector: UV 254, 220 nm) to afford the title compound as a brown oil (3.1 mg, 12% yield). $^1$H-NMR (400 MHz, DMSO-$d_6$) δ(ppm): 11.13 (br s, 1H), 7.61 (d, J=2 hz, 2H), 7.51-7.26 (m, 2H), 7.14-7.03 (m, 4H), 6.64-6.61 (m, 1H), 5.07 (s, 2H), 4.42 (s, 2H), 1.23-1.16 (m, 2H), 0.99-0.85 (m, 2H). MS: (ES, m/z): 311 [M+H]$^+$.

Example 53—Preparation of (S)-3-ethyl-N-hydroxy-4-methyl-2,3,4,5-tetrahydrobenzo[f][1,4]oxazepine-8-carboxamide

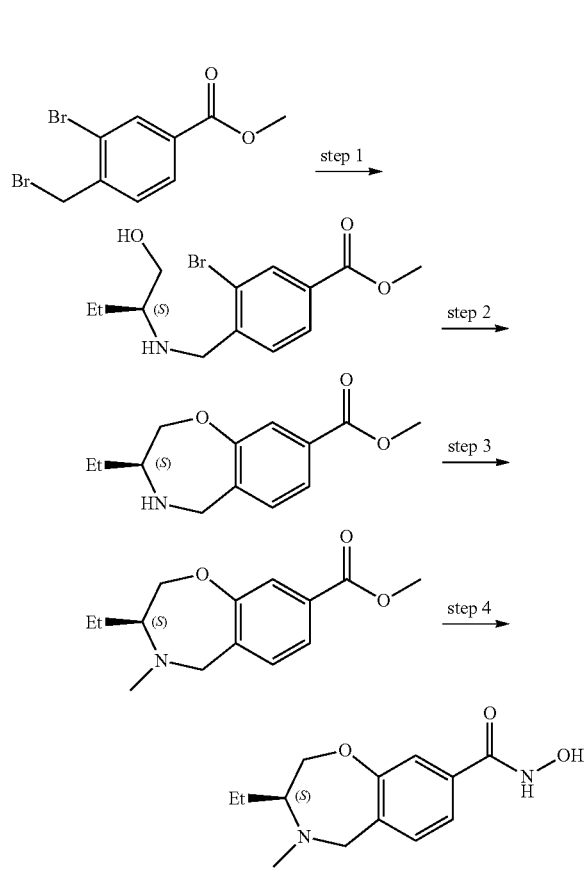

Step-1: Methyl (S)-3-bromo-4-(((1-hydroxybutan-2-yl)amino)methyl)benzoate

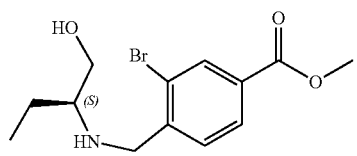

Into a 500-mL round-bottom flask, was placed a solution of (2S)-2-aminobutan-1-ol (7 g, 78.53 mmol, 1.8 equiv) in MeCN (150 mL), K₂CO₃ (9 g, 65.22 mmol, 1.5 equiv) and a solution of methyl 3-bromo-4-(bromomethyl)benzoate (13.5 g, 43.84 mmol, 1 equiv) in MeCN (100 mL). The resulting mixture was stirred for 14 h at room temperature and then concentrated under vacuum. The residue was diluted with H₂O (200 mL) and extracted with EtOAc (2×200 mL). The combined organic layers were washed with H₂O (2×200 mL) and concentrated under vacuum. The residue was purified by silica gel chromatography (EtOAc/pet. ether, 1:9) to afford the title compound as an off-white solid (6.9 g, 50% yield). MS: (ES, m/z): 316 [M+H]⁺.

Step-2: Methyl (S)-3-ethyl-2,3,4,5-tetrahydrobenzo[f][1,4]oxazepine-8-carboxylate

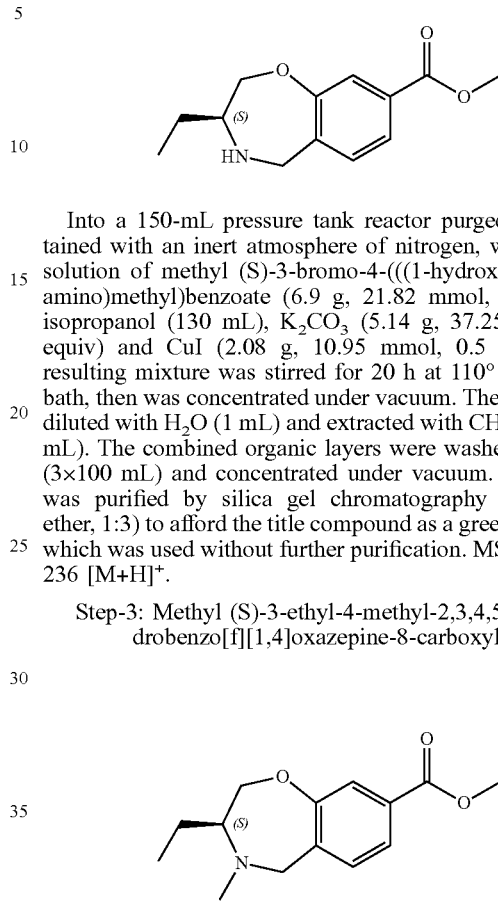

Into a 150-mL pressure tank reactor purged and maintained with an inert atmosphere of nitrogen, was placed a solution of methyl (S)-3-bromo-4-(((1-hydroxybutan-2-yl)amino)methyl)benzoate (6.9 g, 21.82 mmol, 1 equiv) in isopropanol (130 mL), K₂CO₃ (5.14 g, 37.25 mmol, 1.7 equiv) and CuI (2.08 g, 10.95 mmol, 0.5 equiv). The resulting mixture was stirred for 20 h at 110° C. in an oil bath, then was concentrated under vacuum. The residue was diluted with H₂O (1 mL) and extracted with CH₂Cl₂ (3×100 mL). The combined organic layers were washed with H₂O (3×100 mL) and concentrated under vacuum. The residue was purified by silica gel chromatography (EtOAc/pet. ether, 1:3) to afford the title compound as a green oil (2.1 g), which was used without further purification. MS: (ES, m/z): 236 [M+H]⁺.

Step-3: Methyl (S)-3-ethyl-4-methyl-2,3,4,5-tetrahydrobenzo[f][1,4]oxazepine-8-carboxylate Into a 8-mL vial, was placed a solution of methyl (S)-3-ethyl-2,3,4,5-tetrahydrobenzo[f][1,4]oxazepine-8-carboxylate (130 mg, 0.55 mmol, 1 equiv) in acetic acid (3 mL). This was followed by the addition of formaldehyde (100 mg, 3.33 mmol, 6 equiv) and the reaction was stirred for 2 h. To this was added NaBH(OAc)₃ (1.16 g, 5.50 mmol, 10 equiv). The resulting solution was stirred for 26 h at room temperature and concentrated under vacuum. The residue was diluted with H₂O (10 mL), extracted with EtOAc (3×10 mL). The organic combined layers were concentrated under vacuum. The residue was purified by silica gel chromatography (EtOAc/pet. ether, 1:3) to afford the title compound as a colorless oil (79 mg, 57% yield). MS: (ES, m/z): 250 [M+H]⁺.

Step-4: (S)-3-Ethyl-N-hydroxy-4-methyl-2,3,4,5-tetrahydrobenzo[f][1,4]oxazepine-8-carboxamide

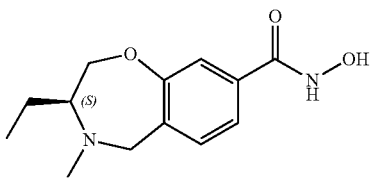

Into a 8-mL vial, was placed a solution of methyl (S)-3-ethyl-4-methyl-2,3,4,5-tetrahydrobenzo[f][1,4]oxazepine-8-carboxylate (79 mg, 0.32 mmol, 1 equiv) in THF:MeOH (4:1, 2 mL). This were followed by the addition of NH$_2$OH (50% in H$_2$O, 0.63 mL, 30 equiv) and aq. 1N NaOH (0.64 mL, 2 equiv). The resulting solution was stirred for 2 h at room temperature. The crude product was purified by Prep-HPLC (Column: Xbridge Prep C18 OBD, 5 μm, 19×250 mm; Mobile Phase A: Water/0.05% formic acid; Mobile Phase B: MeCN; Flow rate: 30 mL/min; Gradient: 15% B to 40% B in 7 min; Detector: UV 254, 220 nm). Aq. 1N HCl (0.32 mL) was added to the product fractions and lyophilized to afford the title compound as the HCl salt as a light brown solid (13.9 mg, 15% yield). $^1$H-NMR (400 MHz, DMSO-d$_6$) δ(ppm): 11.60 (s, 1H), 11.59-11.21 (m, 1H), 7.58-7.42 (m, 3H), 4.78-4.77 (d, J=4.0 Hz, 0.6H), 4.71-4.67 (d, J=16.0 Hz, 0.6H), 4.39-4.32 (m, 2.7H), 4.10-4.06 (m, 0.5H), 3.77 (m, 0.5H), 3.47-3.46 (m, 0.5H), 2.76-2.75 (m, 1.5H), 2.67-2.51 (m, 1.5H), 2.08-2.00 (m, 1H), 1.83-1.80 (m, 0.5H), 1.58-1.56 (m, 0.5H), 1.05-1.01 (m, 3H). MS: (ES, m/z): 251 [M+H]$^+$.

Example 54—Preparation of (S)-3-ethyl-N-hydroxy-4-(4-methoxybenzyl)-2,3,4,5-tetrahydrobenzo[f][1,4]oxazepine-8-carboxamide

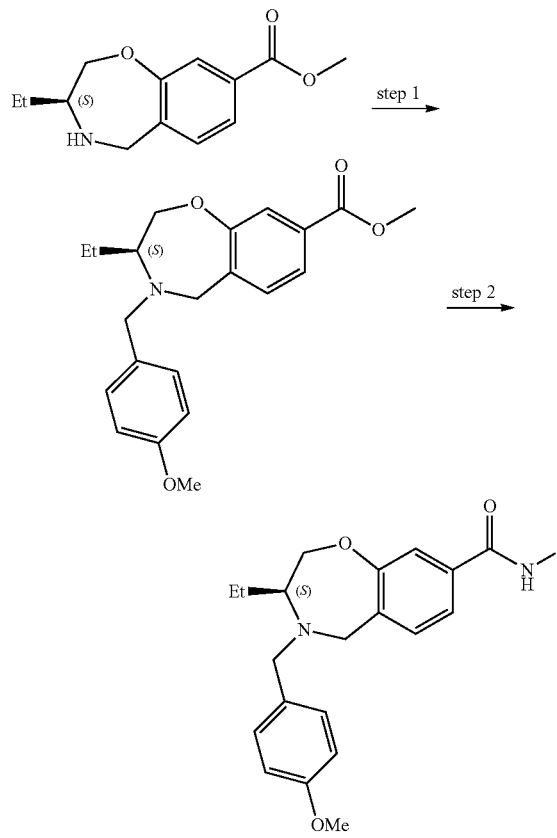

Step-1: Methyl (S)-3-ethyl-4-(4-methoxybenzyl)-2,3,4,5-tetrahydrobenzo[f][1,4]oxazepine-8-carboxylate

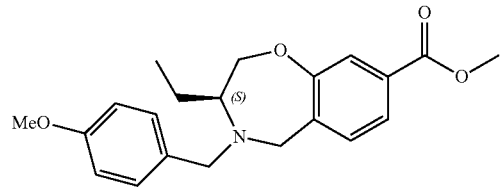

Into a 8-mL vial, was placed a solution of methyl (S)-3-ethyl-2,3,4,5-tetrahydrobenzo[f][1,4]oxazepine-8-carboxylate (130 mg, 0.55 mmol, 1 equiv) in THF (2 mL). This was followed by the addition of sodium hydride (60% dispersion in oil, 68 mg, 3 equiv) at 0° C. in 30 min. To this was added 1-(bromomethyl)-4-methoxybenzene (111 mg, 0.55 mmol, 1 equiv). The resulting solution was stirred for 20 h at room temperature. The reaction was then quenched by the addition of aq. NH$_4$Cl solution (3 mL), then concentrated under vacuum. The residue was diluted with H$_2$O (10 mL), extracted with EtOAc (3×10 mL), and the combined organic layers were concentrated under vacuum. The residue was purified by silica gel chromatography (EtOAc/pet. ether, 1:4) to afford the title compound as a yellow oil (140 mg). MS: (ES, m/z): 356 [M+H]$^+$.

Step-2: (S)-3-Ethyl-N-hydroxy-4-(4-methoxybenzyl)-2,3,4,5-tetrahydrobenzo[f][1,4]oxazepine-8-carboxamide

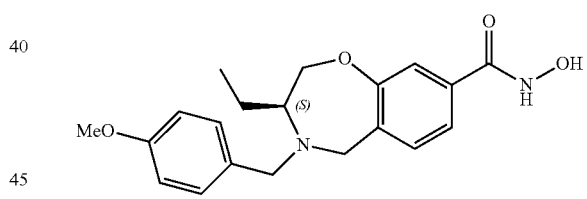

Into a 8-mL vial, was placed a solution of methyl (S)-3-ethyl-4-(4-methoxybenzyl)-2,3,4,5-tetrahydrobenzo[f][1,4]oxazepine-8-carboxylate (140 mg, 0.39 mmol, 1 equiv) in THF:MeOH (4:1, 2 mL). This were followed by the addition of NH$_2$OH (50% in H$_2$O, 0.79 mL, 30 equiv) and aq. 1N NaOH (0.79 mL, 2 equiv). The resulting solution was stirred for 2 h at room temperature. The crude product was purified by Prep-HPLC (Column: Xbridge Prep C18 OBD, 5 μm, 19×250 mm; Mobile Phase A: Water/0.05% formic acid; Mobile Phase B: MeCN; Flow rate: 30 mL/min; Gradient: 30% B to 70% B in 10 min; Detector: UV 254, 220 nm). Aq. 1N HCl (0.4 mL) was added to the product fractions and lyophilized to afford the title compound as the HCl salt as a pink solid (68.7 mg, 44% yield). $^1$H-NMR (400 MHz, DMSO-d$_6$) δ(ppm): 11.34 (s, 1H), 11.02-10.74 (m, 1H), 9.19-9.14 (br, 1H), 7.56-7.20 (m, 5H), 7.10-7.02 (m, 2H), 4.80-4.72 (d, J=32 Hz, 0.71H), 4.60-4.52 (m, J=32 Hz, 0.76H), 4.51-4.19 (m, 5H), 3.88 (m, 3H), 3.50-3.31 (m, 1H), 2.08-1.91 (m, 2H), 1.01-0.92 (m, 3H). MS: (ES, m/z): 357 [M+H]$^+$.

Example 55—Preparation of (S)-3-ethyl-N-hydroxy-4-phenyl-2,3,4,5-tetrahydrobenzo[f][1,4]oxazepine-8-carboxamide

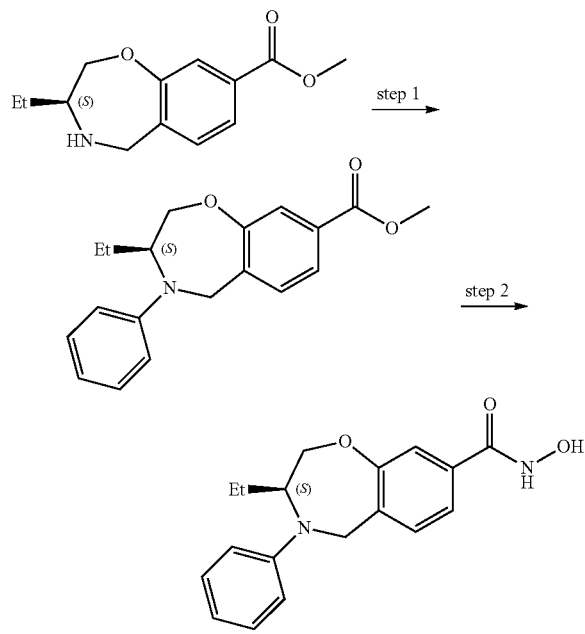

Step-1: Methyl (S)-3-ethyl-4-phenyl-2,3,4,5-tetrahydrobenzo[f][1,4]oxazepine-8-carboxylate

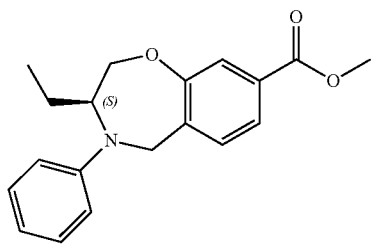

Into a 8-mL sealed tube purged and maintained with an inert atmosphere of nitrogen, was placed a solution of methyl (S)-3-ethyl-2,3,4,5-tetrahydrobenzo[f][1,4]oxazepine-8-carboxylate (200 mg, 0.85 mmol, 1 equiv) in toluene (2.5 mL), iodobenzene (519 mg, 2.54 mmol, 3 equiv), Cs$_2$CO$_3$ (834 mg, 2.56 mmol, 3 equiv), BINAP (211 mg, 0.34 mmol, 0.4 equiv) and Pd(OAc)$_2$ (38 mg, 0.17 mmol, 0.2 equiv). The resulting mixture was stirred for 20 h at 110° C. in an oil bath. The resulting mixture was concentrated under vacuum. The residue was diluted with H$_2$O (10 mL), extracted with EtOAc (3×10 mL), and the combined organic layers were concentrated under vacuum. The residue was purified by silica gel chromatography (EtOAc/pet. ether, 1:5) to afford the title compound as a yellow oil (40 mg, 15% yield). MS: (ES, m/z): 312 [M+H]$^+$.

Step-2: (S)-3-Ethyl-N-hydroxy-4-phenyl-2,3,4,5-tetrahydrobenzo[f][1,4]oxazepine-8-carboxamide

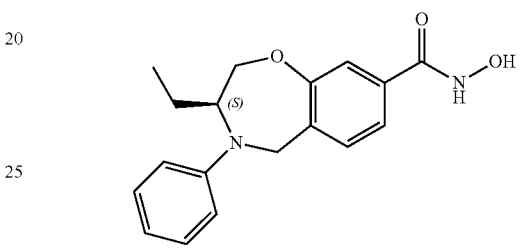

Into a 8-mL vial, was placed a solution of methyl (S)-3-ethyl-4-phenyl-2,3,4,5-tetrahydrobenzo[f][1,4]oxazepine-8-carboxylate (40 mg, 0.13 mmol, 1 equiv) in THF/MeOH (4:1, 1.5 mL). This were followed by the addition of NH$_2$OH (50% in H$_2$O, 0.26 mL, 30 equiv.) and aq. 1N NaOH (0.26 mL, 2 equiv,). The resulting solution was stirred for 2 h at room temperature. The crude product was purified by Prep-HPLC (Column: Xbridge Prep C18 OBD, 5 μm, 19×150 mm; Mobile Phase A: Water/0.05% formic acid; Mobile Phase B: MeCN; Flow rate: 30 mL/min; Gradient: 15% B to 60% B in 7 min; Detector: UV 254, 220 nm). Aq. 1N HCl (0.13 mL) was added to the product fractions and lyophilized to afford the title compound as the HCl salt as an off-white solid (12.2 mg, 27% yield). $^1$H-NMR (400 MHz, DMSO-d$_6$) δ(ppm): 11.01 (s, 1H), 7.49-7.47 (d, J=8.0 Hz, 1H), 7.36-7.34 (d, J=8.0 Hz, 1H), 7.09-7.03 (m, 3H), 6.71-6.69 (d, J=8.0 Hz, 2H), 6.55-6.53 (d, J=8.0 Hz, 1H), 4.95-4.91 (m, 1H), 4.41-4.36 (m, 1H), 4.35-4.29 (m, 2H), 4.13 (m, 1H), 1.67-1.56 (m, 2H), 1.01-0.98 (m, 3H). MS: (ES, m/z): 313 [M+H]$^+$.

TABLE-26

The following compound was prepared according to the method of Example 55, using 1-bromo-2-methylbenzene in Step 1.

| Structure | Found M + H | $^1$H-NMR (400 MHz, DMSO-d$_6$) δ(ppm) |
|---|---|---|
| (structure: (S)-3-ethyl-N-hydroxy-4-(2-methylphenyl)-2,3,4,5-tetrahydrobenzo[f][1,4]oxazepine-8-carboxamide) | (ES, m/z): 327 [M + H]$^+$ | 11.10 (br, 1H), 7.26-7.23 (m, 2H), 7.19-7.17 (m, 1H), 7.09-7.06 (m, 2H), 7.04-7.02 (m, 1H), 6.91-6.89 (m, 1H), 4.55-4.51 (d, J = 16.0 Hz, 1H), 4.38-4.26 (m, 2H), 4.14-4.10 (d, J = 16.0 Hz, 1H), 3.54-3.52 (m, 1H), 2.24 (s, 3H), 1.56-1.41 (m, 2H), 0.88-0.84 (m, 3H) |

Example 56—Preparation of (S)—N-hydroxy-3-(methoxymethyl)-4-methyl-2,3,4,5-tetrahydrobenzo[f][1,4]oxazepine-8-carboxamide

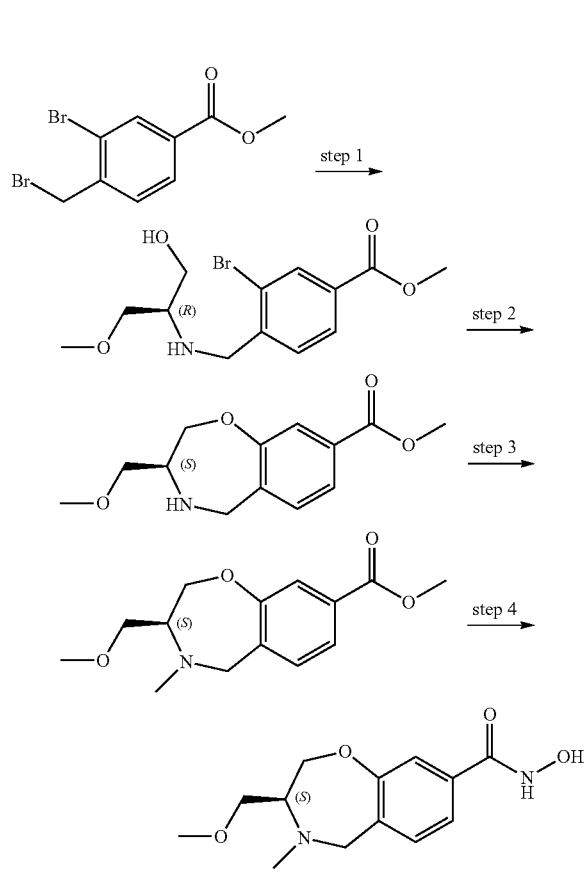

Step-1: Methyl (R)-3-bromo-4-(((1-hydroxy-3-methoxypropan-2-yl)amino)methyl)benzoate

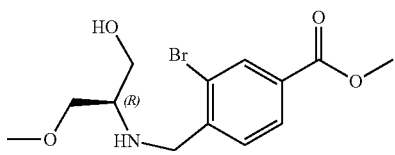

Into a 500-mL round-bottom flask, was placed (2R)-2-amino-3-methoxypropan-1-ol hydrochloride (6 g, 42.37 mmol, 1.2 equiv), a solution of K$_2$CO$_3$ (14 g, 101.3 mmol, 2.8 equiv) in MeCN (100 mL). This was followed by the addition of a solution of methyl 3-bromo-4-(bromomethyl)benzoate (11 g, 35.72 mmol, 1 equiv) in MeCN (100 mL) dropwise with stirring at 0° C. The resulting solution was stirred overnight at room temperature, then concentrated under vacuum. The residue was purified by silica gel chromatography (EtOAc/pet. ether, 1:1) to afford the title compound as a yellow solid (4.5 g, 38% yield). MS: (ES, m/z): 332, 334 [M+H]$^+$.

Step-2: Methyl (S)-3-(methoxymethyl)-2,3,4,5-tetrahydrobenzo[f][1,4]oxazepine-8-carboxylate

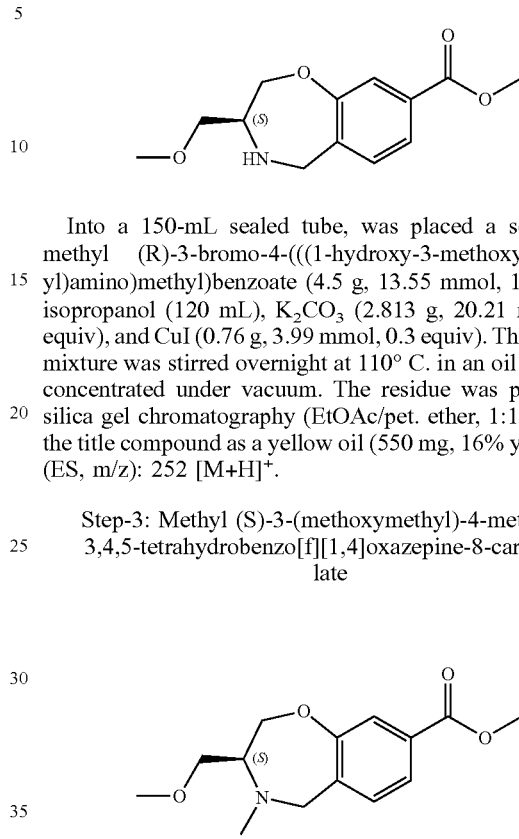

Into a 150-mL sealed tube, was placed a solution of methyl (R)-3-bromo-4-(((1-hydroxy-3-methoxypropan-2-yl)amino)methyl)benzoate (4.5 g, 13.55 mmol, 1 equiv) in isopropanol (120 mL), K$_2$CO$_3$ (2.813 g, 20.21 mmol, 1.5 equiv), and CuI (0.76 g, 3.99 mmol, 0.3 equiv). The resulting mixture was stirred overnight at 110° C. in an oil bath, then concentrated under vacuum. The residue was purified by silica gel chromatography (EtOAc/pet. ether, 1:1) to afford the title compound as a yellow oil (550 mg, 16% yield). MS: (ES, m/z): 252 [M+H]$^+$.

Step-3: Methyl (S)-3-(methoxymethyl)-4-methyl-2,3,4,5-tetrahydrobenzo[f][1,4]oxazepine-8-carboxylate

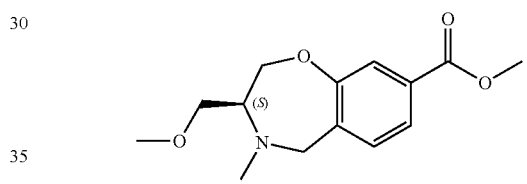

Into a 25-mL round-bottom flask, was placed methyl (S)-3-(methoxymethyl)-2,3,4,5-tetrahydrobenzo[f][1,4]oxazepine-8-carboxylate (200 mg, 0.80 mmol, 1 equiv), acetic acid (5 mL), acetal (175.2 mg, 4 mmol, 5 equiv). The resulting solution was stirred for 2 h at room temperature. This was followed by the addition of NaBH(OAc)$_3$ (1182.5 mg, 5.58 mmol, 7 equiv). The resulting mixture was stirred overnight at room temperature. Then the solids were filtered out and the filtrate was concentrated under vacuum. The residue was purified by silica gel chromatography (EtOAc/pet. ether, 1:1) to afford the title compound as a colorless oil (60.2 mg, 29% yield). MS: (ES, m/z): 266 [M+H]$^+$.

Step-4: (S)—N-Hydroxy-3-(methoxymethyl)-4-methyl-2,3,4,5-tetrahydrobenzo[f][1,4]oxazepine-8-carboxamide

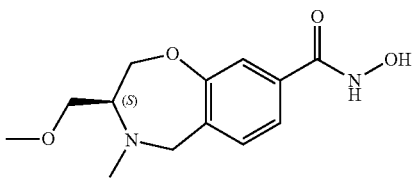

Into a 25-mL round-bottom flask, was placed methyl (S)-3-(methoxymethyl)-4-methyl-2,3,4,5-tetrahydrobenzo[f][1,4]oxazepine-8-carboxylate (60.2 mg, 0.23 mmol, 1 equiv), THF/MeOH (4:1, 1.2 mL), NH$_2$OH (50% in water, 1499 mg, 22.72 mmol, 100 equiv), aq. 1N NaOH (0.45 mL, 2 equiv). The resulting solution was stirred for 1 h at room temperature. The crude product was purified by Prep-HPLC (Column: Xbridge Prep C18 OBD, 5 μm, 19×150 mm; Mobile Phase A: Water/0.05% TFA; Mobile Phase B: MeCN; Detector: UV 254, 220 nm) to afford the title compound as a yellow solid (22 mg, 32% yield). $^1$H-NMR (400 MHz, DMSO-d$_6$) δ(ppm): 11.55-10.78 (m, 2H), 7.62-7.41 (m, 3H), 4.74-4.70 (d, J=16 Hz, 1H), 4.58-4.27 (m, 3H), 4.14-4.11 (m, 1H), 3.99-3.91 (m, 1H), 3.90-3.81 (m, 1H), 3.78-3.63 (m, 1H), 3.37-3.33 (d, J=16 Hz, 3H), 2.84 (s, 2H), 2.58 (s, 1H). MS: (ES, m/z): 267 [M+H]$^+$.

Example 57—Preparation of (S)—N-hydroxy-3-(methoxymethyl)-4-phenyl-2,3,4,5-tetrahydrobenzo[f][1,4]oxazepine-8-carboxamide

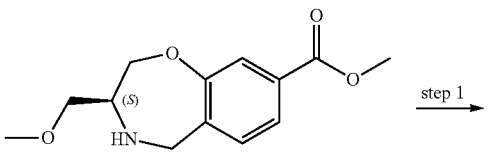

step 1

TABLE-27

The following compounds were prepared according to the method of Example 56, using (2S)-2-amino-3-methoxypropan-1-ol hydrochloride in Step 1 where appropriate.

| Structure | Found M + H | $^1$H-NMR (400 MHz, DMSO-d$_6$) δ(ppm) |
|---|---|---|
| 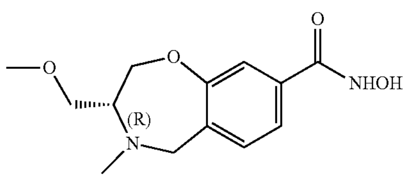 | (ES, m/z): 267 [M + H]$^+$ | 11.49-10.83 (m, 2H), 9.20 (br s, 1H), 7.6-7.34 (m, 3H), 4.73-3.43 (m, 10H), 2.96-2.84 (m, 3H) |
| | (ES, m/z): 373 [M + H]$^+$ | 11.82-11.16 (m, 2H), 7.56-7.44 (m, 5H), 6.99-6.97 (d, J = 6 Hz, 2H), 4.81-4.77 (m, 1H), 4.57-4.53 (m, 1H), 4.70-4.36 (m, 3H), 4.24 (m, 2H), 4.01 (m, 1H), 3.88-3.83 (m, 1H), 3.77 (s, 3H), 3.56 (s, 1H), 3.32-3.28 (m, 2H) |
| | (ES, m/z): 373 [M + H]$^+$ | 11.45-11.08 (m, 1H), 10.71-10.53 (m, 1H), 9.58-8.69 (br s, 1H), 7.61-7.12 (m, 5H), 7.04-3.93 (m, 2H), 4.91-3.98 (m, 7H), 3.97-3.68 (m, 5H), 3.33-3.24 (s, 3H) |

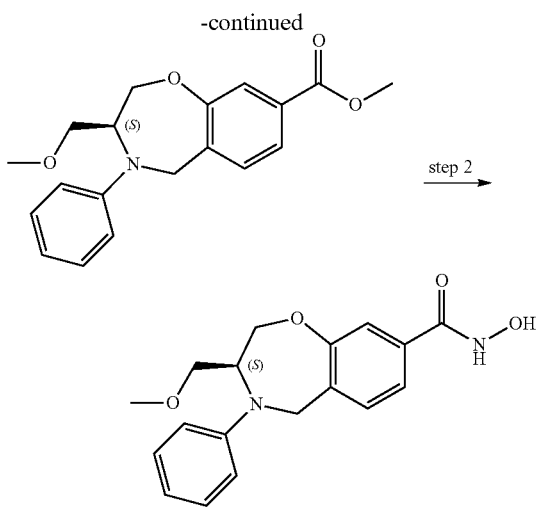

Step-1: Methyl (S)-3-(methoxymethyl)-4-phenyl-2,3,4,5-tetrahydrobenzo[f][1,4]oxazepine-8-carboxylate Into a 50-mL round-bottom flask, was placed methyl (S)-3-(methoxymethyl)-2,3,4,5-tetrahydrobenzo[f][1,4]oxazepine-8-carboxylate (200 mg, 0.80 mmol, 1 equiv), a solution of phenylboronic acid (291 mg, 2.39 mmol, 3 equiv) in $CH_2Cl_2$ (5 mL), 4 Å molecular sieve (60 mg), $Et_3N$ (241 mg, 2.38 mmol, 3 equiv) and $Cu(OAc)_2$ (144 mg, 0.79 mmol, 1 equiv). The resulting solution was stirred overnight at room temperature. The reaction was then quenched by the addition of $H_2O$ (10 mL) and extracted with $CH_2Cl_2$ (3×50 mL). The combined organic layers were concentrated under vacuum. The residue was purified by silica gel chromatography (EtOAc/pet. ether, 1:10) to afford the title compound as a yellow solid (33 mg, 12% yield). MS: (ES, m/z): 328 [M+H]$^+$.

Step-2: (S)—N-Hydroxy-3-(methoxymethyl)-4-phenyl-2,3,4,5-tetrahydrobenzo[f][1,4]oxazepine-8-carboxamide

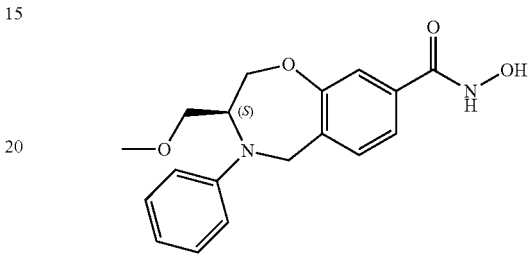

Into a 50-mL round-bottom flask, was placed a solution of methyl (S)-3-(methoxymethyl)-4-phenyl-2,3,4,5-tetrahydrobenzo[f][1,4]oxazepine-8-carboxylate (33 mg, 0.10 mmol, 1 equiv) in THF/MeOH (4:1, 2.5 mL), $NH_2OH$ (50% in water, 0.42 mL, 60 equiv), aq. 1N NaOH (0.2 mL, 2 equiv). The resulting solution was stirred for 3 h at room temperature. The crude product was purified by Prep-HPLC (Column: Xbridge Prep C18 OBD, 5 rpm, 19×150 mm; Mobile Phase A: Water/0.05% formic acid; Mobile Phase B: MeCN; Flow rate: 25 mL/min; Gradient: 30% B to 70% B in 10 min; Detector: UV 254, 220 nm). Aq. 1N HCl (0.1 mL) was added to the product fractions and lyophilized to afford the title compound as the HCl salt as a yellow solid (8.5 mg, 23% yield). $^1$H-NMR (300 MHz, DMSO-d$_6$) δ(ppm): 11.20 (br s, 1H), 7.48-7.46 (d, J=6 Hz, 1H), 7.35-7.32 (d, J=9 Hz, 1H), 7.10-7.03 (m, 3H), 6.70-6.67 (d, J=9 Hz, 2H), 6.58-6.54 (m, 1H), 5.09-5.03 (d, J=18 Hz, 1H), 4.51-4.27 (m, 4H), 3.59-3.57 (d, J=6 Hz, 2H), 3.33 (s, 3H). MS: (ES, m/z): 329 [M+H]$^+$.

TABLE-28

The following compounds were prepared according to the method of Example 57, using (2S)-2-amino-3-methoxypropan-1-ol hydrochloride in Step 1 where appropriate.

| Structure | Found M + H | $^1$H-NMR 400 MHz, DMSO-d$_6$ δ(ppm) |
|---|---|---|
| (structure shown) | (ES, m/z): 329 [M + H]$^+$ | 11.18-11.05 (br s, 1H), 7.49-7.47 (d, J = 8 Hz, 1H), 7.35-7.33 (d, J = 8 Hz, 1H), 7.11-7.04 (m, 3H), 6.70-6.68 (d, J = 8 Hz, 2H), 6.59-6.52 (m, 1H), 5.09-5.05 (d, J = 16 Hz, 1H), 4.55-4.46 (m, 1H), 4.41-4.22 (m, 3H), 3.59-3.58 (d, J = 4 Hz, 2H), 3.33 (s, 3H) |

TABLE-28-continued

The following compounds were prepared according to the method of Example 57,
using (2S)-2-amino-3-methoxypropan-1-ol hydrochloride in Step 1 where appropriate.

| Structure | Found M + H | $^1$H-NMR 400 MHz, DMSO-d$_6$ δ(ppm) |
|---|---|---|
| | (ES, m/z): 343 [M + H]$^+$ | 11.13 (br s, 1H), 9.60 (br s, 1H), 7.27-7.20 (m, 3H), 7.17-7.07 (m, 3H), 6.97-6.93 (m, 1H), 4.46-4.41 (m, 3H), 4.26-4.22 (d, J = 16Hz, 1H), 3.80-3.77 (m, 1H), 3.51-3.41 (m, 1H), 3.31-3.27 (m, 1H), 3.22 (s, 3H), 2.17 (s, 3H). |
| | (ES, m/z): 343 [M + H]$^+$ | 11.23 (br s, 1H), 7.20-7.27 (m, 3H), 7.07-7.17 (m, 3H), 6.93-6.97 (t, J = 7.2 hz, 1H), 4.41-4.46 (m, 3H), 4.22-4.26 (d, J = 16.4 Hz, 1H), 3.77-3.80 (m, 1H), 3.47-3.51 (t, J = 8.8 Hz, 1H), 3.27-3.31 (m, 1H), 3.22 (s, 3H), 2.17 (s, 3H) |

Example 58—Preparation of (S)-3-benzyl-N-hydroxy-4-(morpholine-4-carbonyl)-2,3,4,5-tetrahydrobenzo[f][1,4]oxazepine-8-carboxamide

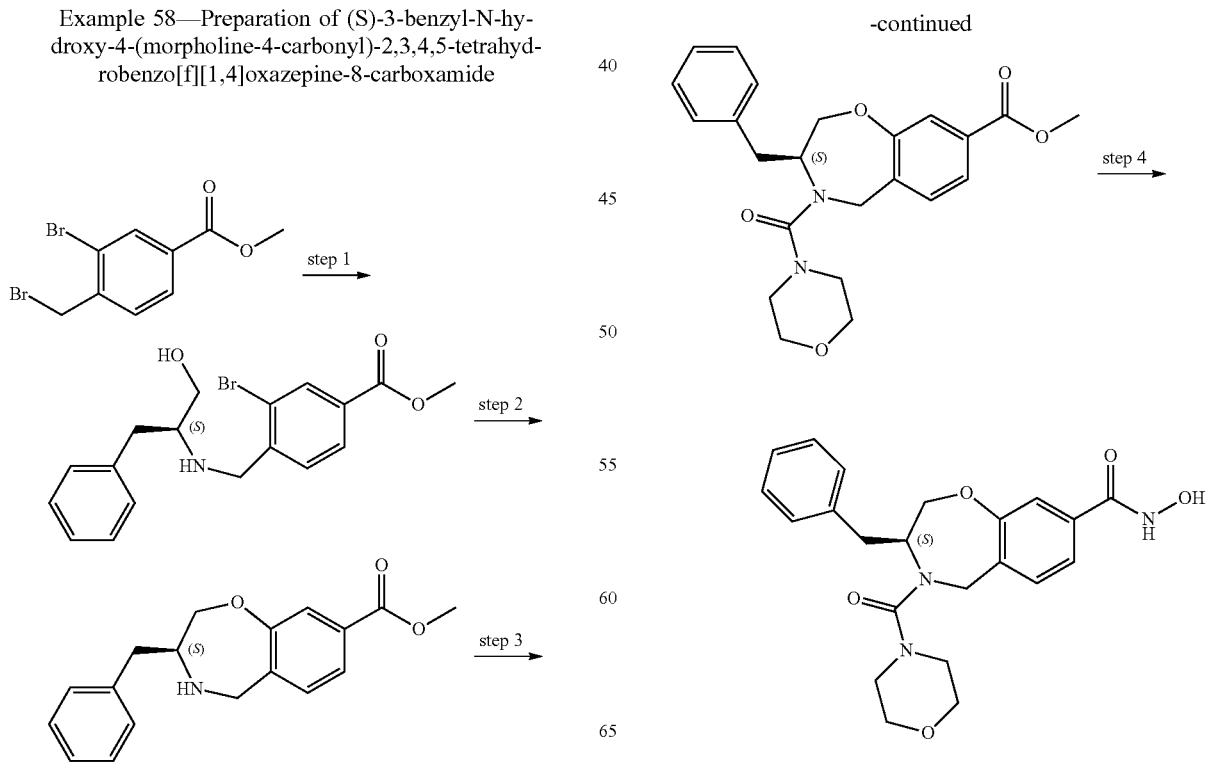

Step-1: Methyl (S)-3-bromo-4-(((1-hydroxy-3-phenylpropan-2-yl)amino)methyl)benzoate

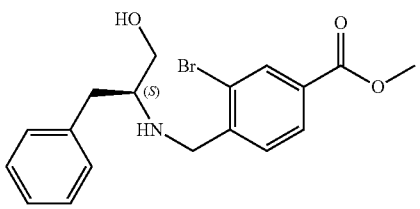

Into a 40-mL scintillation vial was placed (S)-2-amino-3-phenylpropan-1-ol (271 mg, 1.79 mmol, 1.30 equiv), K₂CO₃ (572 mg, 4.14 mmol, 3.00 equiv) and MeCN (15 ml). The resulting slurry was cooled to 0° C. in an ice-water bath. Next, a solution of methyl 3-bromo-4-(bromomethyl)benzoate (425 mg, 1.380 mmol, 1.00 equiv) in MeCN (3 mL) was added dropwise over 10 min while maintaining the internal temperature at 0° C. The ice bath was removed and the resulting slurry was allowed to slowly warm to room temperature. Stirring continued at room temperature for 16 h. The reaction was concentrated under reduced pressure to remove most of the MeCN. The concentrated mixture was partitioned between EtOAc (10 mL) and H₂O (5 ml). The organic phase was washed with brine (5 mL), dried over Na₂SO₄, filtered and concentrated to afford the title compound as a yellow oil (628 mg), which was used without further purification. MS: (ES, m/z): 379 [M+H]⁺.

Step-2: Methyl (S)-3-benzyl-2,3,4,5-tetrahydrobenzo[f][1,4]oxazepine-8-carboxylate

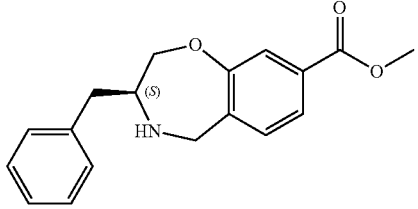

Into a 40-mL scintillation vial was placed methyl (S)-3-bromo-4-(((1-hydroxy-3-phenylpropan-2-yl)amino)methyl) benzoate hydrochloride (522 mg, 1.39 mmol, 1 equiv) in isopropanol (5 mL). K₂CO₃ (381 mg, 2.76 mmol, 2 equiv) was added followed by CuI (52.6 mg, 0.276 mmol, 0.2 equiv). The resulting solution was heated to reflux for 18 h. The resulting mixture was filtered through a celite pad and washed with isopropanol (10 mL). The filtrate was reduced in volume to ~5 mL and 10N HCl (1.1 equiv) was added dropwise, with stirring, to the filtrate. The resulting slurry was cooled in an ice bath for 30 min before being filtered to afford the title compound as the HCl salt as a yellow solid (252 mg, 49.3% yield). ¹H-NMR (400 MHz, DMSO-d₆) δ(ppm): 7.68-7.77 (m, 1H), 7.58-7.66 (m, 1H), 7.54 (d, J=1.8 Hz, 1H), 7.23-7.45 (m, 4H), 4.36-4.58 (m, 2H), 4.26 (br d, J=11.4 Hz, 1H), 3.74-4.05 (m, 4H), 3.42 (s, 1H), 3.07-3.27 (m, 2H), 2.90 (br dd, J=13.6, 9.2 Hz, 1H), 1.03 (d, J=6.2 Hz, 1H). MS: (ES, m/z): 298 [M+H]⁺.

Step-3: Methyl (S)-3-benzyl-4-(morpholine-4-carbonyl)-2,3,4,5-tetrahydrobenzo[f][1,4]oxazepine-8-carboxylate

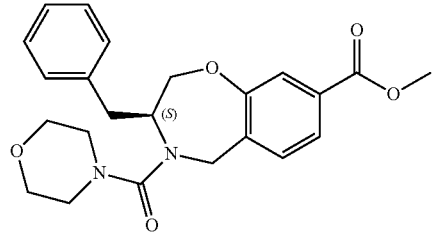

Into a 4-mL vial equipped with a stir bar was placed a solution of triphosgene (17.8 mg, 0.060 mmol, 0.4 equiv) in CH₂Cl₂ (2 mL). Next, a solution of methyl (S)-3-benzyl-2,3,4,5-tetrahydrobenzo[f][1,4]oxazepine-8-carboxylate hydrochloride (50 mg, 0.150 mmol, 1 equiv), Et₃N (0.063 mL, 0.449 mmol, 3 equiv), and morpholine (13.5 mg, 0.150 mmol, 1 equiv) and CH₂Cl₂ (2 mL) was added. The resulting solution was stirred at room temperature for 16 h. The reaction was concentrated to dryness to afford the title compound (61.4 mg) which was used without further purification. MS: (ES, m/z): 410 [M+H]⁺.

Step-3: (S)-3-Benzyl-N-hydroxy-4-(morpholine-4-carbonyl)-2,3,4,5-tetrahydrobenzo[f][1,4]oxazepine-8-carboxamide

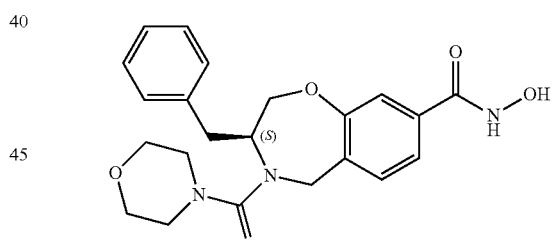

Into a 4-mL vial was placed methyl (S)-3-benzyl-4-(morpholine-4-carbonyl)-2,3,4,5-tetrahydrobenzo[f][1,4]oxazepine-8-carboxylate (61.6 mg, 0.150 mmol, 1 equiv), NH₂OH (50% in water, 0.1 mL, 1.5 mmol, 10 equiv), and aq. 1N NaOH (0.3 mL, 0.3 mmol, 2 equiv) in a solution of THF/MeOH (4:1, 2.0 mL). The resulting solution was stirred at room temperature for 2 h, then concentrated. The residue was purified by Prep-HPLC (Column: Xbridge Prep C18 OBD, 5 μm, 19×50 mm; Mobile Phase A: Water/0.1% formic acid; Mobile Phase B: MeCN/0.1% formic acid; Flow rate: 23 mL/min; Gradient: 15% B to 65% B in 8 min; Detector: UV 254, 220 nm) to afford the title compound as a white solid (4.5 mg, 11% yield). MS: (ES, m/z): 412 [M+H]⁺.

Example 59—Preparation of (R)—N-hydroxy-4-(4-methoxybenzyl)-5-methyl-2,3,4,5-tetrahydrobenzo[f][1,4]oxazepine-8-carboxamide

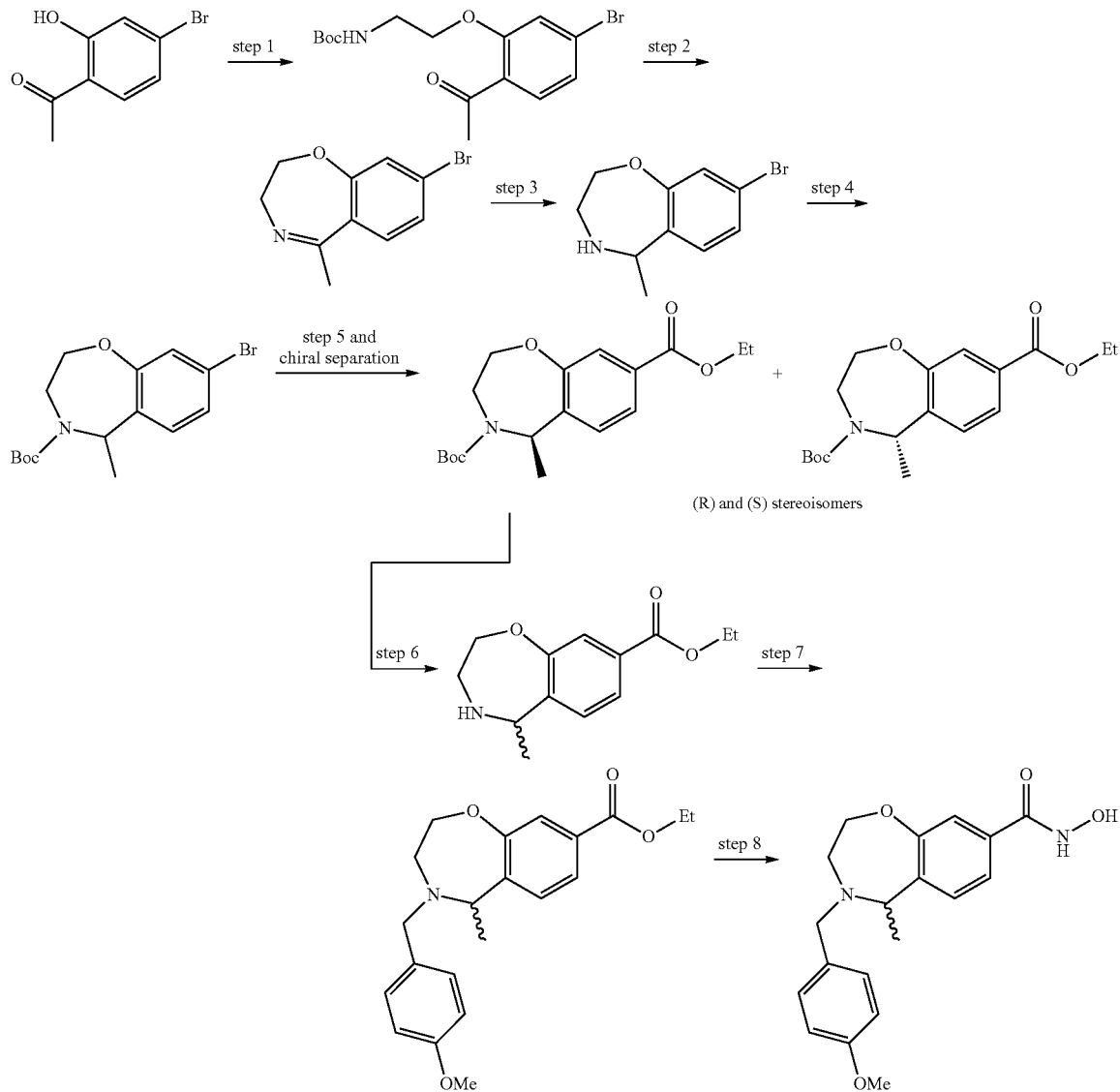

(R) and (S) stereoisomers

Step-1: tert-Butyl (2-(2-acetyl-5-bromophenoxy)ethyl)carbamate

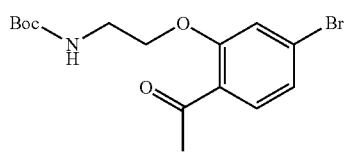 [SMILES: CC(=O)c1ccc(Br)cc1OCCNC(=O)OC(C)(C)C]

Into a 500-mL 3-necked round-bottom flask, was placed 1-(4-bromo-2-hydroxyphenyl)ethan-1-one (30 g, 139 mmol, 1 equiv) in DMF (150 mL), $K_2CO_3$ (29 g, 209 mmol, 1.5 equiv), potassium iodide (23.2 g, 1 equiv) and tert-butyl N-(2-bromoethyl)carbamate (47 g, 209 mmol, 1.5 equiv). The resulting mixture was stirred overnight at 50° C. The solids were filtered out. The filtrate was quenched with of $H_2O$ (50 mL) and extracted with EtOAc (5×100 mL). The combined organic layers were washed with brine (3×50 mL), dried over anhydrous $Na_2SO_4$, filtered, and concentrated under vacuum. The residue was triturated with a solution of EtOAc/pet. ether (1:10, 100 mL) to afford the title compound as an off-white solid (42 g, 84% yield). MS: (ES, m/z): 358 [M+H]+.

Step-2: 8-Bromo-5-methyl-2,3-dihydrobenzo[f][1,4]oxazepine

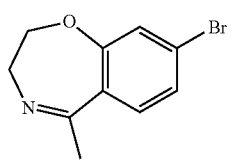

Into a 500-mL round-bottom flask, was placed tert-butyl 2-(2-acetyl-5-bromophenoxy)ethylcarbamate (23 g, 64.20 mmol, 1 equiv) in CH$_2$Cl$_2$ (100 mL) and TFA (25 mL). The resulting solution was stirred overnight at room temperature, then concentrated under vacuum to afford the title compound as a yellow solid (15.4 g), which was used without further purification. MS: (ES, m/z): 240 [M+H]$^+$.

Step-3: 8-Bromo-5-methyl-2,3,4,5-tetrahydrobenzo[f][1,4]oxazepine

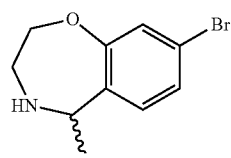

Into a 500-mL round-bottom flask, was placed a solution of 8-bromo-5-methyl-2,3-dihydrobenzo[f][1,4]oxazepine (15.4 g, 64.14 mmol, 1 equiv) in MeOH (200 mL). The pH value of the solution was adjusted to 7 with anhydrous NaOAc at 0° C. Then Na(CN)BH$_3$ (18.1 g, 288 mmol, 4.5 equiv) was added at 0° C. The resulting mixture was stirred for 4 h at room temperature and concentrated under vacuum. H$_2$O (50 mL) was added to the residue and the solids were collected by filtration to afford the title compound as a white solid (15 g). MS: (ES, m/z): 242 [M+H]$^+$.

Step-4: tert-Butyl 8-bromo-5-methyl-2,3-dihydrobenzo[f][1,4]oxazepine-4(5H)-carboxylate

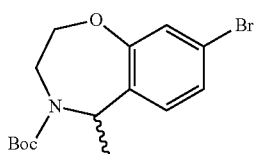 [SMILES: CC1c2ccc(Br)cc2OCCN1C(=O)OC(C)(C)C]

Into a 500-mL round-bottom flask, was placed tert-butyl 8-bromo-5-methyl-2,3-dihydrobenzo[f][1,4]oxazepine-4(5H)-carboxylate (9 g, 37.17 mmol, 1 equiv) in CH$_2$Cl$_2$ (80 mL), Et$_3$N (11.25 g, 111 mmol, 3 equiv) and di-tert-butyl dicarbonate (12.1 g, 55.44 mmol, 1.5 equiv). The resulting solution was stirred overnight at room temperature, then concentrated under vacuum. The crude product was purified by Flash-Prep-HPLC (Column: silica gel; Mobile Phase A: pet. ether, Mobile Phase B: EtOAc; Gradient: 0% B to 10% B in 50 min; Detector: 254 nm) to afford the title compound as white solid (11 g, 86% yield). MS: (ES, m/z): 342 [M+H]$^+$.

Step-5: 4-(tert-Butyl) 8-ethyl (R)-5-methyl-2,3-dihydrobenzo[f][1,4]oxazepine-4,8(5H)-dicarboxylate and 4-(tert-butyl) 8-ethyl (S)-5-methyl-2,3-dihydrobenzo[f][1,4]oxazepine-4,8(5H)-dicarboxylate

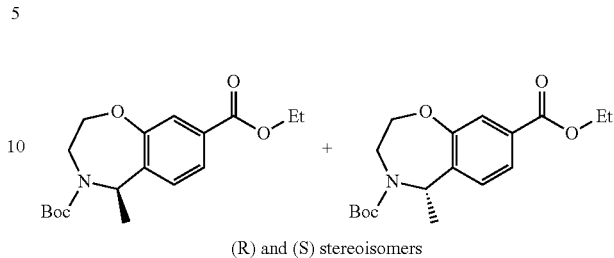

(R) and (S) stereoisomers

Into a 50-mL sealed tube, was placed tert-butyl 8-bromo-5-methyl-2,3-dihydrobenzo[f][1,4]oxazepine-4(5H)-carboxylate ((2.5 g, 7.33 mmol, 1 equiv) in EtOH (25 mL), Et$_3$N (2.22 g, 22 mmol, 3 equiv) and Pd(dppf)Cl$_2$ (0.534 g, 0.73 mmol, 0.1 equiv). To the above reaction mixture CO (g) (60 atm) was introduced. The resulting mixture was stirred overnight at 120° C., then concentrated under vacuum. The crude product was purified by Flash-Prep-HPLC (Column: silica gel; Mobile Phase A: pet. ether, Mobile Phase B: EtOAc; Gradient: 0% B to 10% B in 30 min; Detector: 254 nm) to afford the title compounds as a racemic mixture. The racemate was then purified by Prep-SFC (Column: (R,R) WHELK-01 Kromasil, 10 m, 21.1×250 mm; Mobile Phase A: 75% CO$_2$, 25% isopropanol (0.2% N,N-diethylaniline); Flow rate: 45 mL/min; Detector: UV 254 nm) to afford the single isomers as a light yellow oil (first eluting isomer: 540 mg, 21.9% yield; second eluting isomer: 680 mg, 27.7% yield). MS: (ES, m/z): 336 [M+H]$^+$.

Step-6: Ethyl (R)-5-methyl-2,3,4,5-tetrahydrobenzo[f][1,4]oxazepine-8-carboxylate

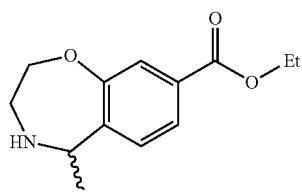 [SMILES: CCOC(=O)c1ccc2c(c1)OCCNC2C]

Into a 25-mL round-bottom flask, was placed the first eluting isomer from Step 5 (4-(tert-butyl) 8-ethyl (R)-5-methyl-2,3-dihydrobenzo[f][1,4]oxazepine-4,8(5H)-dicarboxylate) (540 mg, 1.61 mmol, 1 equiv), CH$_2$Cl$_2$ (5 mL), and TFA (2 mL). The resulting solution was stirred overnight at room temperature, then concentrated under vacuum. The crude product was purified by Flash-Prep-HPLC (Column: C18 silica gel; Mobile Phase A: H$_2$O/0.05% TFA, Mobile Phase B: MeCN; Gradient: 5% B to 50% B in 30 min; Detector: 254 nm) to afford the title compound as a white solid (450 mg), which was used without further purification. MS: (ES, m/z): 236 [M+H]$^+$.

Step-7: Ethyl (R)-4-(4-methoxybenzyl)-5-methyl-2,3,4,5-tetrahydrobenzo[f][1,4]oxazepine-8-carboxylate

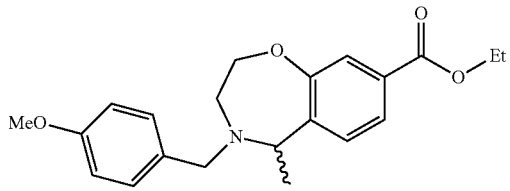 [SMILES: CCOC(=O)c1ccc2c(c1)OCCN(Cc1ccc(OC)cc1)C2C]

Into a 25-mL round-bottom flask, was placed ethyl (R)-5-methyl-2,3,4,5-tetrahydrobenzo[f][1,4]oxazepine-8-carboxylate (100 mg, 0.43 mmol, 1 equiv) and 4-methoxybenzaldehyde (57 mg, 0.42 mmol, 1 equiv) in MeOH (2 mL). After stirring for 30 min, Na(CN)BH$_3$ (80 mg, 1.27 mmol, 3 equiv) was added at 0° C. The resulting solution was stirred overnight at room temperature. The reaction was then quenched by the addition of H$_2$O (2 mL) and extracted with CH$_2$Cl$_2$ (5×10 mL). The combined organic layers were dried over anhydrous Na$_2$SO$_4$, filtered, and concentrated under vacuum. The residue was purified by silica gel chromatography (EtOAc/pet. ether, 1:3) to afford the title compound as a yellow oil (50 mg, 34% yield). MS: (ES, m/z): 356 [M+H]$^+$.

Step-8: (R)—N-Hydroxy-4-(4-methoxybenzyl)-5-methyl-2,3,4,5-tetrahydrobenzo[f][1,4]oxazepine-8-carboxamide

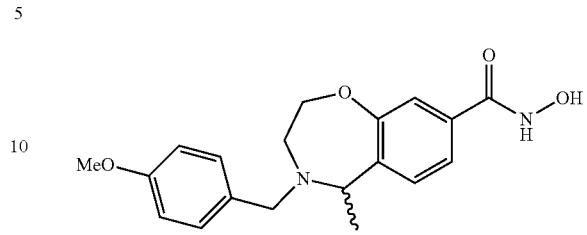

Into a 25-mL round-bottom flask, was placed ethyl (R)-4-(4-methoxybenzyl)-5-methyl-2,3,4,5-tetrahydrobenzo[f][1,4]oxazepine-8-carboxylate (50 mg, 0.14 mmol, 1 equiv), THF/MeOH (4/1, 2 mL), NH$_2$OH (50% in water, 579 mg, 60 equiv), aq. 1N NaOH (0.28 mL, 2 equiv). The resulting solution was stirred for 8 h at room temperature. The mixture was purified by Prep-HPLC (Column: Sunfire C18 OBD, 5 μm, 19×150 mm; Mobile Phase A: Water/0.05% formic acid; Mobile Phase B: MeCN; Flow rate: 0.7 mL/min; Gradient: 5% B to 20% B in 7 min; Detector: UV 254 nm) to afford the title compound as a brown solid (36 mg, 75% yield). $^1$H-NMR (DMSO, 400 MHz) δ (ppm): 11.41-10.87 (m, 2H), 9.17 (br s, 1H,), 7.59-7.33 (m, 5H), 7.04-6.98 (m, 2H), 4.73 (s, 1H), 4.49-4.34 (m, 3H), 4.13-4.11 (m, 1H), 3.86-3.78 (m, 4H), 3.36-3.09 (m, 1H), 1.70-1.67 (m, 3H). MS: (ES, m/z): 343 [M+H]$^+$.

TABLE-29

The following compound was prepared according to the method of Example 59, using the second eluting isomer of the Step 5 product.

| Structure | Found M + H | $^1$H-NMR 400 MHz, DMSO-d$_6$ δ(ppm) |
|---|---|---|
| 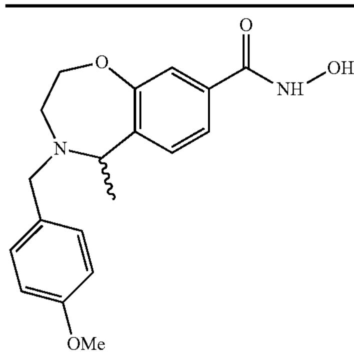 | (ES, m/z): 343 [M + H]$^+$ | 11.33-10.60 (m, 2H), 9.17-9.14 (m, 1H), 7.54-6.88 (m, 7H), 4.74-4.34 (m, 3H), 4.11-3.44 (m, 6H), 3.13-2.76 (m, 1H), 1.69-1.42 (m, 3H) |

Example 60—Preparation of (R)—N-hydroxy-4-(4-methoxybenzyl)-5-methyl-2,3,4,5-tetrahydrobenzo[f][1,4]oxazepine-7-carboxamide

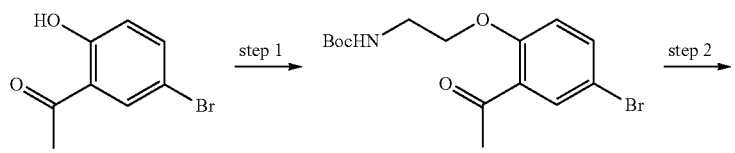

173 174

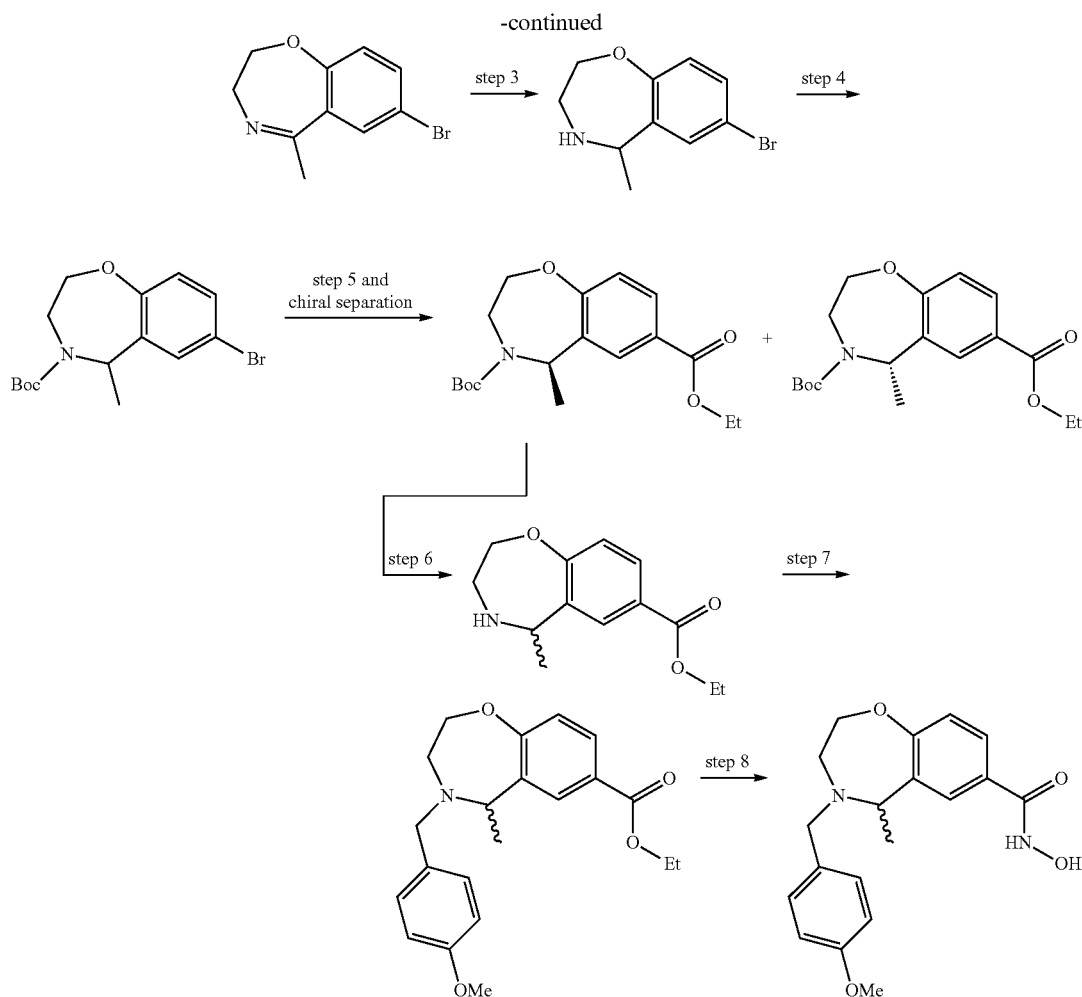

-continued

Step-1: tert-Butyl (2-(2-acetyl-4-bromophenoxy)ethyl)carbamate

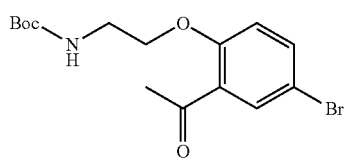 [SMILES: CC(=O)c1cc(Br)ccc1OCCNC(=O)OC(C)(C)C]

Into a 500-mL 3-necked round-bottom flask, was placed a solution of 1-(5-bromo-2-hydroxyphenyl)ethan-1-one (30 g, 139.51 mmol, 1 equiv), $K_2CO_3$ (29 g, 209.83 mmol, 3 equiv), potassium iodide (23.2 g, 1 equiv) and tert-butyl N-(2-bromoethyl)carbamate (37.5 g, 167.34 mmol, 1.2 equiv) in DMF (150 mL). The resulting solution was stirred overnight at 50° C. in an oil bath. The reaction mixture was cooled to 0° C. and quenched with $H_2O$ (50 mL). The resulting solution was extracted with $CH_2Cl_2$ (2×100 mL), washed with brine (5×100 mL) and dried over anhydrous $Na_2SO_4$. The solids were filtered out and the filtrate was concentrated under vacuum. The crude product was purified by silica gel chromatography (Gradient 0-50% EtOAc/pet. ether over 50 min) to afford the title compound as a light yellow solid (39 g, 78% yield). MS: (ES, m/z): 358 [M+H]+.

Step-2: 7-Bromo-5-methyl-2,3-dihydrobenzo[f][1,4]oxazepine

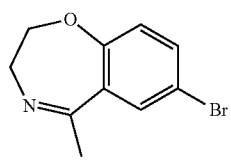

Into a 500-mL round-bottom flask, was placed tert-butyl N-[2-(2-acetyl-4-bromophenoxy)ethyl]carbamate (20 g, 55.83 mmol, 1 equiv), $CH_2Cl_2$ (100 mL) and TFA (20 mL). The resulting solution was stirred overnight at room temperature. The resulting mixture was concentrated under vacuum to afford the title compound as a red solid (20 g) which was used without further purification. MS: (ES, m/z): 240 [M+H]+.

Step-3: 7-Bromo-5-methyl-2,3,4,5-tetrahydro-1,4-benzoxazepine

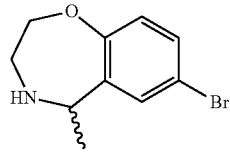

Into a 500-mL round-bottom flask, was placed a solution of 7-bromo-5-methyl-2,3-dihydrobenzo[f][1,4]oxazepine (10 g, 38.74 mmol, 1 equiv) in MeOH (100 mL), the pH value of the solution was adjusted to 7 with anhydrous sodium acetate at 0° C. Then Na(CN)BH$_3$ (7.9 g, 113.52 mmol, 3 equiv) was added at 0° C. The resulting solution was stirred for 2 h at room temperature. The resulting mixture was concentrated under vacuum and 20 mL of water was added. The solids were collected by filtration to afford the title compound as a white solid (7 g, 75% yield) which was used without further purification. MS: (ES, m/z): 242 [M+H]$^+$.

Step-4: tert-Butyl 7-bromo-5-methyl-2,3,4,5-tetrahydro-1,4-benzoxazepine-4-carboxylate

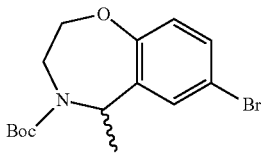 [SMILES: CC1c2cc(Br)ccc2OCCN1C(=O)OC(C)(C)C]

Into a 50-mL round-bottom flask, was placed 7-bromo-5-methyl-2,3,4,5-tetrahydro-1,4-benzoxazepine (2 g, 8.26 mmol, 1 equiv), CH$_2$Cl$_2$ (20 mL), Et$_3$N (2.51 g, 24.80 mmol, 3 equiv), di-tert-butyl dicarbonate (2.71 g, 12.42 mmol, 1.5 equiv). The resulting solution was stirred overnight at room temperature. The resulting mixture was concentrated under vacuum. The crude product was purified by silica gel chromatography (Gradient 0-30% EtOAc/pet. ether over 20 min) to afford the title compound as a light yellow oil (2.4 g, 85% yield). MS: (ES, m/z): 342 [M+H]$^+$.

Step-5: 4-(tert-Butyl) 7-ethyl (R)-5-methyl-2,3-dihydrobenzo[f][1,4]oxazepine-4,7(5H)-dicarboxylate

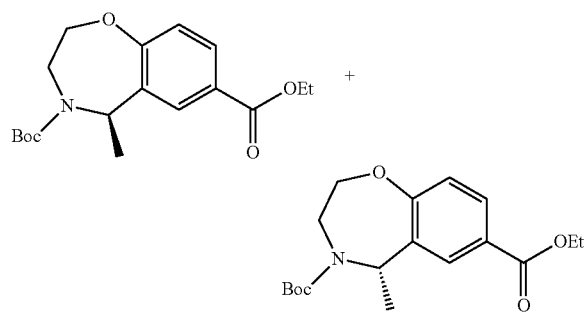

Into a 50-mL pressure tank reactor, was placed tert-butyl 7-bromo-5-methyl-2,3,4,5-tetrahydro-1,4-benzoxazepine-4-carboxylate (2.4 g, 7.01 mmol, 1 equiv), ethanol (40 mL), Et$_3$N (2.1 g, 20.75 mmol, 3 equiv), and Pd(dppf)Cl$_2$ (515.1 mg, 0.70 mmol, 0.1 equiv). CO (g) (60 atm) was introduced and the resulting solution was stirred overnight at 120° C. The solids were filtered out and the filtrate was concentrated under vacuum and purified by silica gel chromatography (Gradient 0-10% EtOAc/pet. ether over 30 min) to afford the racemic mixture of the title compounds, which were separated by Prep-SFC (Column Chiralpak IC OBD, 5 μm, 5×250 mm; Mobile Phase: 75% CO$_2$, 25% Isopropanol; Flow rate: 170 mL/min; Detector, UV 254, 220 nm) to afford the single isomers of the title compounds as light yellow oils (first eluting isomer: 440 mg, 19% yield; second eluting isomer: 500 mg, 21% yield). MS: (ES, m/z): 336 [M+H]$^+$.

Step-6: Ethyl (R)-5-methyl-2,3,4,5-tetrahydrobenzo[f][1,4]oxazepine-7-carboxylate

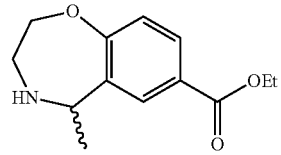 [SMILES: CCOC(=O)c1ccc2c(c1)C(C)NCCO2]

Into a 50-mL round-bottom flask, was placed the first eluting isomer from Step 5 (4-(tert-butyl) 7-ethyl (R)-5-methyl-2,3-dihydrobenzo[f][1,4]oxazepine-4,7(5H)-dicarboxylate) (440 mg, 1.31 mmol, 1 equiv), CH$_2$Cl$_2$ (5 mL), and TFA (2 mL). The resulting solution was stirred overnight at room temperature and concentrated under vacuum. The crude product was purified by silica gel chromatography (Gradient 10-50% EtOAc/pet. ether over 30 min) to afford the title compound as a light yellow oil (300 mg, 97% yield). MS: (ES, m/z): 236 [M+H]$^+$.

Step-7: Ethyl (R)-4-(4-methoxybenzyl)-5-methyl-2,3,4,5-tetrahydrobenzo[f][1,4]oxazepine-7-carboxylate

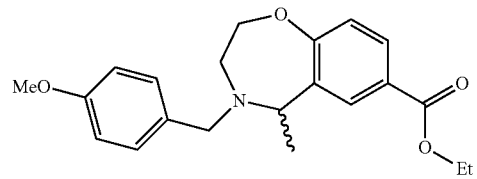 [SMILES: CCOC(=O)c1ccc2c(c1)C(C)N(Cc1ccc(OC)cc1)CCO2]

Into a 50-mL round-bottom flask, was placed 4-methoxybenzaldehyde (57.8 mg, 0.42 mmol, 1 equiv), MeOH (2 mL), and ethyl (R)-5-methyl-2,3,4,5-tetrahydrobenzo[f][1,4]oxazepine-7-carboxylate (100 mg, 0.43 mmol, 1 equiv). The mixture was stirred for 30 min at room temperature, and then Na(CN)BH$_3$ (80.4 mg, 1.28 mmol, 3 equiv) was added at 0° C. The resulting solution was stirred overnight at room temperature. The reaction was then quenched with H$_2$O (2 mL) and extracted with CH$_2$Cl$_2$ (5×10 mL). The combined organic layers were and dried over anhydrous Na$_2$SO$_4$, filtered, and concentrated under vacuum. The residue was purified by silica gel chromatography (EtOAc/pet. ether, 1:3) to afford the title compounds as a light yellow oil (80 mg, 53% yield). MS: (ES, m/z): 356 [M+H]$^+$.

Step-8: (R)—N-Hydroxy-4-(4-methoxybenzyl)-5-methyl-2,3,4,5-tetrahydrobenzo[f][1,4]oxazepine-7-carboxamide

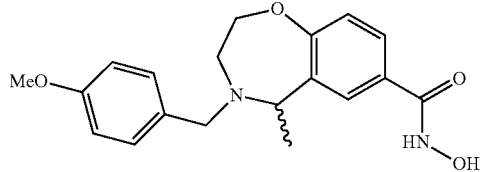 [SMILES: COc1ccc(CN2CCOc3ccc(C(=O)NO)cc3C2C)cc1]

Into a 25-mL round-bottom flask, was placed ethyl (R)-4-(4-methoxybenzyl)-5-methyl-2,3,4,5-tetrahydrobenzo[f][1,4]oxazepine-7-carboxylate (80 mg, 0.23 mmol, 1 equiv), THF/MeOH (1.5 mL, 4:1). This was followed by the addition of NH$_2$OH (50% in water, 913 mg, 60 equiv) and aq. 1N NaOH (0.46 mL, 2 equiv). The resulting solution was stirred for 2 days at room temperature. The crude product was purified by Prep-HPLC (Column: Atlantis T3 C18 OBD, 5 μm, 19×150 mm; Mobile Phase A: Water/0.05% TFA; Mobile Phase B: MeCN; Flow rate: 25 mL/min; Gradient: 10% B to 40% B in 10 min; Detector, UV 254, 220 nm) to afford the title compound as an off-white solid (12 mg, 11% yield). $^1$H-NMR (400 MHz, DMSO-d$_6$) δ(ppm): 11.24 (s, 1H), 10.20-10.13 (br s, 1H), 9.13-9.09 (br s, 1H), 7.83-7.76 (br s, 2H), 7.49-7.41 (m, 2H), 7.24-7 (m, 3H), 4.84-4.69 (m, 1H), 4.60-3.79 (m, 5H), 3.79 (s, 3H), 3.40-3 (m, 1H), 1.69-1.55 (m, 3H). MS: (ES, m/z): 343 [M+H]$^+$.

Example 61—Preparation of N8-hydroxy-N4-(4-methoxyphenyl)-2,3-dihydropyrido[2,3-f][1,4]oxazepine-4,8(5H)-dicarboxamide

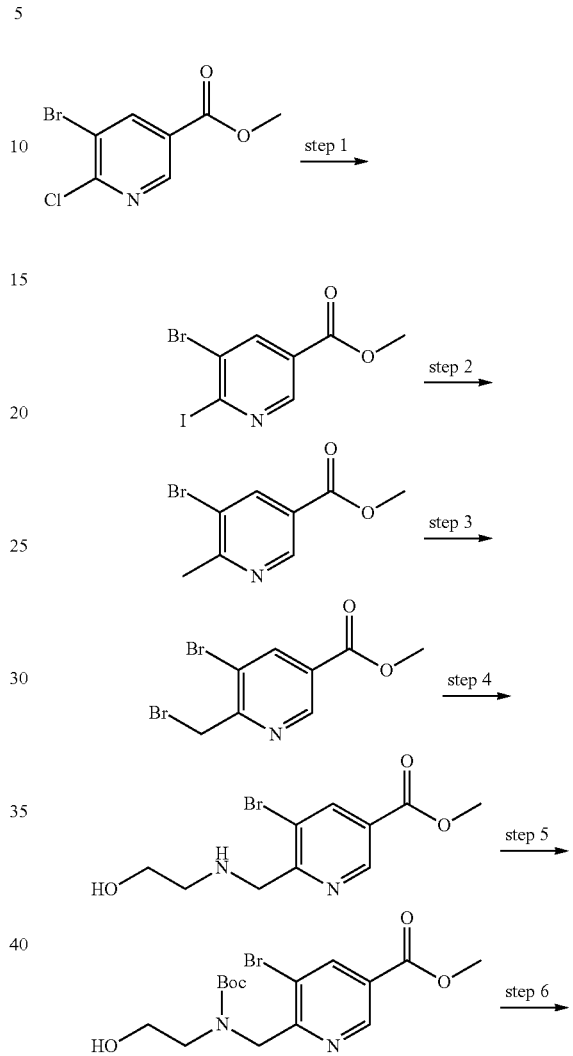

TABLE 30

The following compounds were prepared according to the method of Example 60, using the second eluting isomer of the Step 5 product.

| Structure | Found M + H | $^1$H-NMR (400 MHz, DMSO-d$_6$) δ (ppm) |
|---|---|---|
| (R)/(S) isomer | (ES, m/z): 343 [M + H]$^+$ | 11.24 (s, 1H), 10.23-10.12 (br s, 1H), 9.13-9.04 (br s, 1H), 7.76 (s, 2H), 7.50-7.42 (m, 2H), 7.17-7.04 (m, 3H), 4.83 (br, 1H), 4.48-4 (m, 5H), 3.78 (s, 3H), 3.34-3.05 (m, 1H), 1.68-1.53 (m, 3H) |

-continued

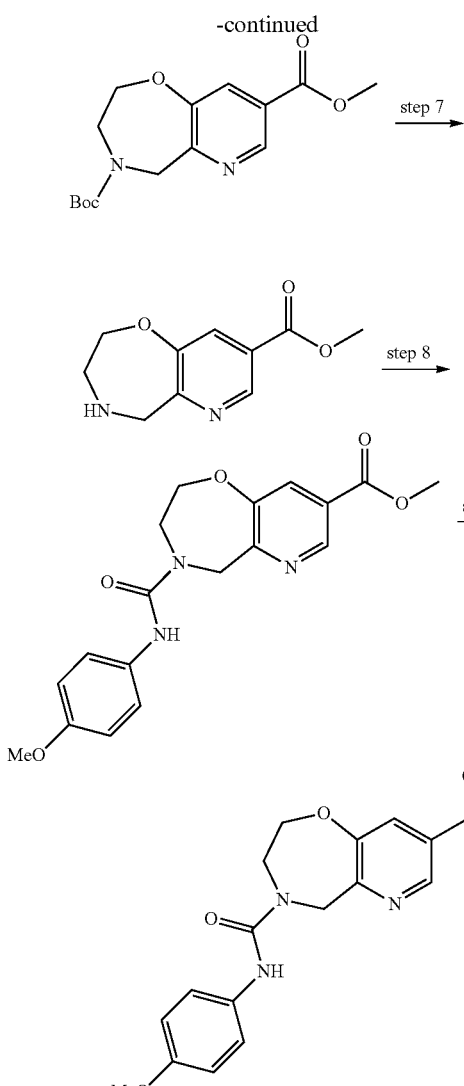

Step-1: Methyl
5-bromo-6-iodopyridine-3-carboxylate

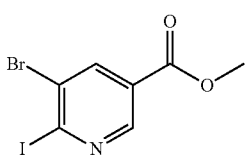

Into a 1000-mL round-bottom flask, was placed methyl 5-bromo-6-chloropyridine-3-carboxylate (11 g, 43.92 mmol, 1 equiv), MeCN (330 mL), trimethylsilyl iodide (8.767 g, 1 equiv) and sodium iodide (19.7 g, 3 equiv). The resulting mixture was stirred for 4 h at 25° C. and then concentrated. The residue was diluted with H₂O (300 mL). The pH value of the solution was adjusted to 7 with 2N NaOH. The solids were collected by filtration to afford the title compound as a yellow solid (16 g) which was used without further purification. MS: (ES, m/z): 250 [M+H]⁺.

Step-2: Methyl
5-bromo-6-methylpyridine-3-carboxylate

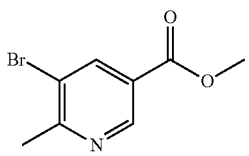

Into a 250-mL 3-necked round-bottom flask purged and maintained with an inert atmosphere of nitrogen, was placed methyl 5-bromo-6-iodopyridine-3-carboxylate (6 g, 17.55 mmol, 1 equiv), 1,4-dioxane (60 mL), trimethyl-1,3,5,2,4,6-trioxatriborinane (15 mL, 50% in THF, 3 equiv), Pd(dppf)Cl₂·CH₂Cl₂ (1.44 g, 0.1 equiv) and potassium carbonate (7.34 g, 53.10 mmol, 3 equiv). The resulting solution was stirred for 72 h at 75° C. in an oil bath. The reaction mixture was cooled to room temperature. The solids were filtered out. The filtrate was diluted with EtOAc (100 mL), washed with brine (3×30 mL), dried over anhydrous Na₂SO₄, filtered, and concentrated. The residue was purified by silica gel chromatography (EtOAc/pet. ether, 1:10) to afford the title compound as an off-white solid (3 g, 74% yield). MS: (ES, m/z): 230 [M+H]⁺.

Step-3: Methyl
5-bromo-6-(bromomethyl)pyridine-3-carboxylate

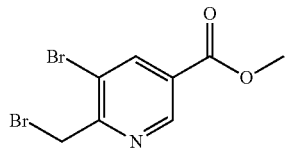

Into a 250-mL 3-necked round-bottom flask purged and maintained with an inert atmosphere of nitrogen, was placed methyl 5-bromo-6-methylpyridine-3-carboxylate (3 g, 13.04 mmol, 1 equiv), CCl₄ (60 mL), NBS (2.435 g, 13.68 mmol, 1.05 equiv) and benzoyl peroxide (158 mg, 0.62 mmol, 0.05 equiv). The resulting mixture was stirred for 16 h at 80° C. in an oil bath. The reaction mixture was cooled to room temperature. The solids were filtered out. The filtrate was concentrated and diluted with EtOAc (150 mL), washed with brine (3×50 mL). The organic phase was dried over anhydrous Na₂SO₄, filtered, and concentrated to afford the title compound as a brown oil (2.5 g) which was used without further purification. MS: (ES, m/z): 310 [M+H]⁺.

Step-4: Methyl 5-bromo-6-[[(2-hydroxyethyl)amino]methyl]pyridine-3-carboxylate

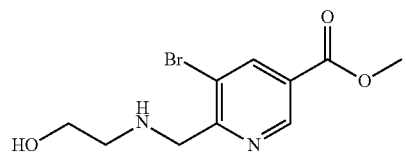 [SMILES: COC(=O)c1cnc(CNCCO)c(Br)c1]

Into a 250-mL round-bottom flask, was placed MeCN (50 mL), 2-aminoethan-1-ol (990 mg, 16.21 mmol, 2 equiv) and potassium carbonate (2.26 g, 16.32 mmol, 2 equiv). This was followed by the addition of a solution of methyl 5-bromo-6-(bromomethyl)pyridine-3-carboxylate (2.5 g, 4.86 mmol, 1 equiv) in MeCN (20 mL) dropwise with stirring at 0° C. The resulting solution was stirred for additional 2 h at 0° C. The solids were filtered out. The filtrate was concentrated. The residue was purified by silica gel chromatography (CH$_2$Cl$_2$/MeOH, 20:1) to afford the title compound as a yellow solid (0.7 g, 50% yield). MS: (ES, m/z): 289 [M+H]$^+$.

Step-5: Methyl 5-bromo-6-(((tert-butoxycarbonyl) (2-hydroxyethyl)amino)methyl)nicotinate

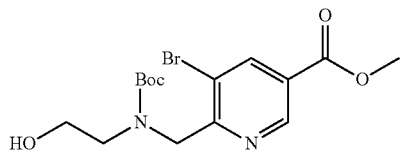 [SMILES: COC(=O)c1cnc(CN(CCO)C(=O)OC(C)(C)C)c(Br)c1]

Into a 25-mL round-bottom flask, was placed methyl 5-bromo-6-[[(2-hydroxyethyl)amino]methyl]pyridine-3-carboxylate (500 mg, 1.73 mmol, 1 equiv), THF (10 mL), di-tert-butyl dicarbonate (416 mg, 1.91 mmol, 1.10 equiv), and Et$_3$N (350 mg, 3.47 mmol, 2 equiv). The resulting mixture was stirred for 1 h at 25° C. and then concentrated. The residue was purified by silica gel chromatography (EtOAc/pet. ether, 1:3) to afford the title compound as a yellow-green oil (0.55 g, 82% yield). MS: (ES, m/z): 389 [M+H]$^+$.

Step-6: 4-(tert-Butyl) 8-methyl 2,3-dihydropyrido[2,3-f][1,4]oxazepine-4,8(5H)-dicarboxylate

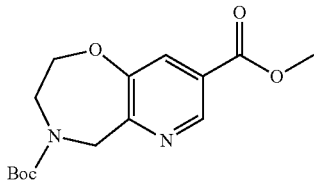 [SMILES: COC(=O)c1cnc2c(c1)OCCN(C(=O)OC(C)(C)C)C2]

Into a 100-mL 3-necked round-bottom flask purged and maintained with an inert atmosphere of nitrogen, was placed Pd(OAc)$_2$ (87 mg, 0.39 mmol, 0.05 equiv), Johnphos (0.184 g, 0.08 equiv), Cs$_2$CO$_3$ (3.784 g, 11.61 mmol, 1.5 equiv) and 1,4-dioxane (30 mL). This was followed by the addition of a solution of methyl 5-bromo-6-(((tert-butoxycarbonyl)(2-hydroxyethyl)amino)methyl)nicotinate (3 g, 7.71 mmol, 1 equiv) in 1,4-dioxane (20 mL). The resulting mixture was stirred for 16 h at 95° C. in an oil bath. The reaction mixture was cooled to room temperature and diluted with EtOAc (50 mL) and H$_2$O (50 mL). The resulting solution was washed with brine (3×50 mL). The organic phase was dried over anhydrous Na$_2$SO$_4$, filtered, and concentrated. The residue was purified by silica gel chromatography (CH$_2$Cl$_2$/MeOH, 20:1) to afford the title compound as an orange solid (1.2 g, 50% yield). MS: (ES, m/z): 309 [M+H]$^+$.

Step-7: Methyl 2,3,4,5-tetrahydropyrido[2,3-f][1,4]oxazepine-8-carboxylate

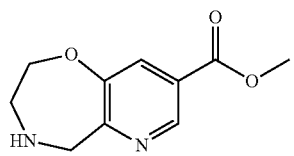

Into a 100-mL round-bottom flask, was placed 4-(tert-butyl) 8-methyl 2,3-dihydropyrido[2,3-f][1,4]oxazepine-4,8(5H)-dicarboxylate (1.2 g, 3.89 mmol, 1 equiv), CH$_2$Cl$_2$ (40 mL) and TFA (5 mL). The resulting solution was stirred for 2 h at 25° C. The pH value of the solution was adjusted to 7-8 with NaHCO$_3$. The solution was dried over anhydrous Na$_2$SO$_4$, filtered, and concentrated. The residue was purified by silica gel chromatography (CH$_2$Cl$_2$/MeOH, 10:1) to afford the title compound as an orange solid (0.6 g, 74% yield). $^1$H-NMR (400 MHz, DMSO-d$_6$) δ(ppm): 8.88 (s, 1H), 7.90 (s, 1H), 4.23 (s, 2H), 4.12-4.08 (t, 2H), 3.94 (s, 3H), 3.30-3.17 (t, 2H). MS: (ES, m/z): 209 [M+H]$^+$.

Step-8: Methyl 4-((4-methoxyphenyl)carbamoyl)-2,3,4,5-tetrahydropyrido[2,3-f][1,4]oxazepine-8-carboxylate

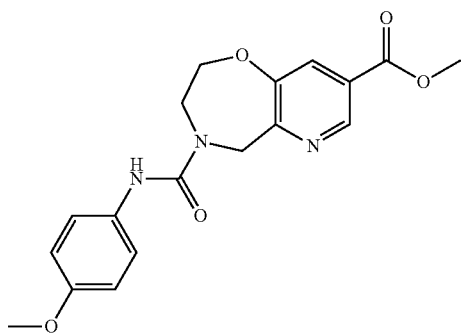

Into a 10-mL round-bottom flask, was placed methyl 2,3,4,5-tetrahydropyrido[2,3-f][1,4]oxazepine-8-carboxylate (50 mg, 0.24 mmol, 1 equiv), 1-isocyanato-4-methoxybenzene (43 mg, 0.29 mmol, 1.2 equiv), Et$_3$N (73 mg, 0.72 mmol, 3 equiv) and CH$_2$Cl$_2$ (3 mL). The resulting mixture was stirred for 3 h at 25° C. and concentrated under vacuum. The residue was purified by silica gel chromatography (CH$_2$Cl$_2$/MeOH, 20:1) to afford the title compound as a yellow oil (60 mg, 70% yield). MS: (ES, m/z): 358 [M+H]$^+$.

Step-9: 8-N-Hydroxy-4-N-(4-methoxyphenyl)-2,3,4,5-tetrahydro-1,4-benzoxazepine-4,8-dicarboxamide

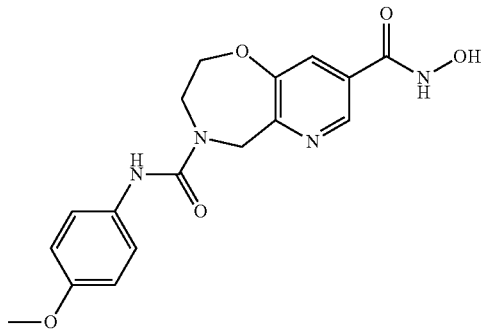 [SMILES: COc1ccc(NC(=O)N2CCOc3cc(C(=O)NO)cnc3C2)cc1]

Into a 25-mL round-bottom flask, was placed methyl 4-((4-methoxyphenyl)carbamoyl)-2,3,4,5-tetrahydropyrido[2,3-f][1,4]oxazepine-8-carboxylate (60 mg, 0.17 mmol, 1 equiv), aq. 1N NaOH (0.34 mL, 2 equiv), NH$_2$OH (50% in water, 0.33 g, 30 equiv), THF/MeOH (4:1, 2 mL). The resulting solution was stirred for 1 h at 25° C. The pH value of the solution was adjusted to 6 with 1N HCl. The crude product was purified by Prep-HPLC (Column HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 23% B in 6 min, hold 1 min; Detector, UV 254, 220 nm) to afford the title compound as an off-white solid (31 mg, 52% yield). $^1$H-NMR (400 MHz, DMSO-d$_6$) δ(ppm): 11.35 (s, 1H), 8.45-8.51 (t, 2H), 7.61-7.62 (d, 1H), 7.25-7.28 (m, 2H), 6.78-6.82 (m, 2H), 4.88-4.94 (d, 2H), 4.31-4.32 (d, 2H), 3.88-3.92 (d, 2H), 3.68-3.74 (d, 3H). MS: (ES, m/z): 359 [M+H]$^+$.

Example 62—Preparation of N-hydroxy-4-((4-methoxyphenyl)sulfonyl)-2,3,4,5-tetrahydropyrido[2,3-f][1,4]oxazepine-8-carboxamide

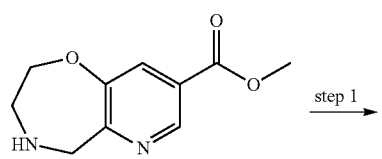
step 1

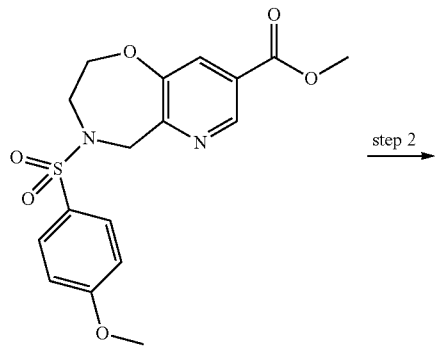
step 2

Step-1: Methyl 4-((4-methoxyphenyl)sulfonyl)-2,3,4,5-tetrahydropyrido[2,3-f][1,4]oxazepine-8-carboxylate

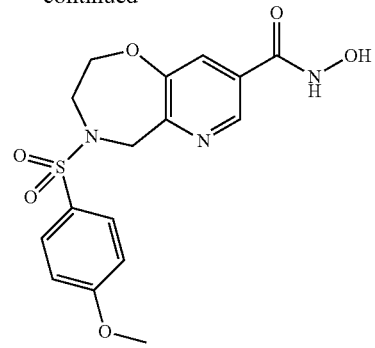

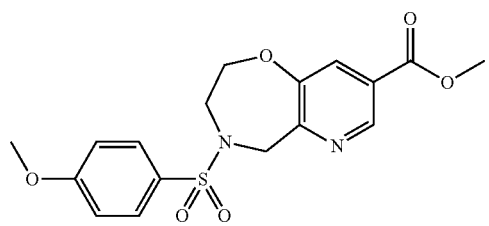

Into a 10-mL round-bottom flask, was placed methyl 2,3,4,5-tetrahydropyrido[2,3-f][1,4]oxazepine-8-carboxylate (100 mg, 0.48 mmol, 1 equiv), 4-methoxybenzene-1-sulfonyl chloride (249 mg, 1.20 mmol, 2.5 equiv), 4-dimethylaminopyridine (29 mg, 0.24 mmol, 0.5 equiv), Et$_3$N (146 mg, 1.44 mmol, 3 equiv) and CH$_2$Cl$_2$ (3 mL). The resulting mixture was stirred for 3 h at 25° C. The reaction was then quenched by the addition of NH$_4$Cl. The resulting solution was extracted with CH$_2$Cl$_2$ (3×10 mL). The combined organic layers were dried over anhydrous Na$_2$SO$_4$, filtered, and concentrated under vacuum. The residue was purified by silica gel chromatography (CH$_2$Cl$_2$/MeOH, 20:1) to afford the title compound as a yellow solid (100 mg, 55% yield). MS: (ES, m/z): 379 [M+H]$^+$.

Step-2: N-Hydroxy-4-((4-methoxyphenyl)sulfonyl)-2,3,4,5-tetrahydropyrido[2,3-f][1,4]oxazepine-8-carboxamide

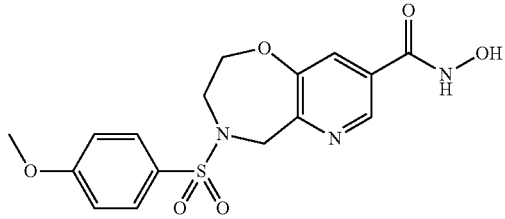 [SMILES: COc1ccc(S(=O)(=O)N2CCOc3cc(C(=O)NO)cnc3C2)cc1]

Into a 25-mL round-bottom flask, was placed methyl 4-((4-methoxyphenyl)sulfonyl)-2,3,4,5-tetrahydropyrido[2,3-f][1,4]oxazepine-8-carboxylate (110 mg, 0.29 mmol, 1 equiv), aq. 1N NaOH (0.58 mL, 2 equiv), and NH$_2$OH (50% in water, 0.57 g, 30 equiv), THF/MeOH (4:2, 2 mL). The resulting solution was stirred for 1 h at 25° C. The pH value of the solution was adjusted to 6 with 1N HCl. The crude product was purified by Prep-HPLC (Column: HSS C18 OBD, 1.8 µm, 2.1×50 mm; Mobile Phase A: Water/0.05% TFA; Mobile Phase B: MeCN/0.05% TFA; Flow rate: 0.7 mL/min; Gradient: 5% B to 23% B in 6 min, hold 1 min; Detector, UV 254, 220 nm) to afford the title compound as an off-white solid (36 mg, 33% yield). $^1$H-NMR (400 MHz, DMSO-d$_6$) δ(ppm): 11.35 (s, 1H), 8.50 (d, 1H), 7.52-7.57 (m, 2H), 7.39-7.40 (d, 1H), 6.94-6.98 (m, 2H), 4.69 (s, 2H), 4.19-4.22 (t, 2H), 3.78 (s, 3H), 3.64-3.68 (t, 2H). MS: (ES, m/z): 380 [M+H]$^+$.

Example 63—Preparation of N-hydroxy-4-(4-methoxybenzyl)-2,3,4,5-tetrahydropyrido[2,3-f][1,4]oxazepine-8-carboxamide

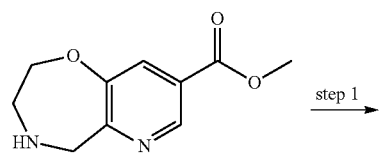

step 1

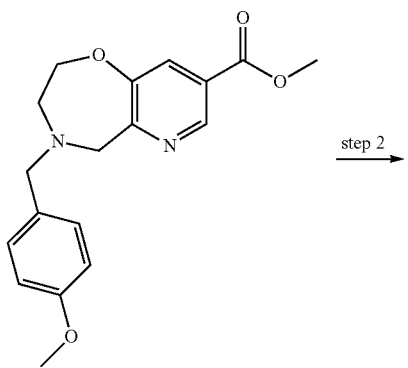

step 2

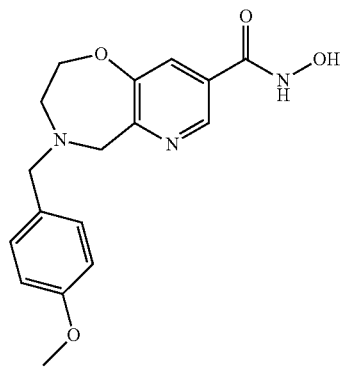

Step-1: Methyl 4-(4-methoxybenzyl)-2,3,4,5-tetrahydropyrido[2,3-f][1,4]oxazepine-8-carboxylate

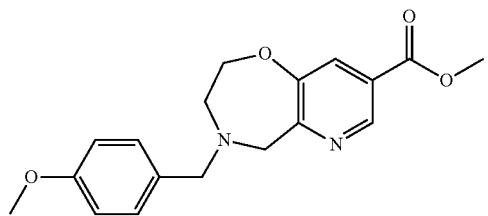

Into a 10-mL 2-necked round-bottom flask, was placed methyl 4-(4-methoxybenzyl)-2,3,4,5-tetrahydropyrido[2,3-f][1,4]oxazepine-8-carboxylate (100 mg, 0.48 mmol, 1 equiv) and THF (4 mL) and then sodium hydride (23 mg, 0.96 mmol, 1.2 equiv) was added at 0° C. The resulting mixture was stirred for 0.5 h at 0° C. And then 1-(bromomethyl)-4-methoxybenzene (87 mg, 0.43 mmol, 0.9 equiv) was added. The resulting mixture was stirred for an additional 3 h at 25° C. The reaction was then quenched by the addition of NH$_4$Cl. The resulting solution was extracted with EtOAc (3×10 mL). The combined organic layers were dried over anhydrous Na$_2$SO$_4$, filtered, and concentrated under vacuum. The residue was purified by silica gel chromatography (CH$_2$Cl$_2$/MeOH, 20:1) to afford the title compound as a yellow oil (100 mg, 63% yield). MS: (ES, m/z): 329 [M+H]$^+$.

Step-2: N-Hydroxy-4-(4-methoxybenzyl)-2,3,4,5-tetrahydropyrido[2,3-f][1,4]oxazepine-8-carboxamide

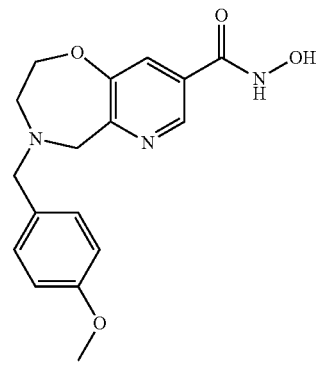 [SMILES: COc1ccc(CN2CCOc3cc(C(=O)NO)cnc3C2)cc1]

Into a 25-mL round-bottom flask, was placed methyl 4-[(4-methoxyphenyl)methyl]-2,3,4,5-tetrahydro-1,4-benzoxazepine-8-carboxylate (100 mg, 0.31 mmol, 1 equiv), aq. 1N NaOH (0.61 mL, 2 equiv), NH$_2$OH (0.6 g, 30 equiv, 50% in water) and MeOH/THF (4:1, 2 mL). The resulting solution was stirred for 1 h at 25° C. The pH value of the solution was adjusted to 6 with 3N HCl. The crude product was purified by Prep-HPLC (Column HSS C18 OBD, 1.8 µm, 2.1×50 mm; Mobile Phase A: Water/0.05% TFA; Mobile Phase B: MeCN/0.05% TFA; Flow rate: 0.7 mL/min; Gradient: 5% B to 23% B in 6 min, hold 1 min; Detector, UV 254, 220 nm) to afford the title compound as an orange solid (11 mg, 8% yield). $^1$H-NMR (400 MHz, DMSO-d$_6$) δ(ppm): 11.49 (s, 1H), 9.35-10.56 (d, 1H), 8.63 (s, 1H), 7.77 (s, 1H), 7.43-7.45 (d, 2H), 7.02-7.12 (t, 2H), 3.87-4.52 (m, 8H), 3.76-3.79 (d, 3H). MS: (ES, m/z): 330 [M+H]⁺.

Example 64—Preparation of N8-hydroxy-N4-(4-methoxyphenyl)-2,3-dihydropyrido[3,2-f][1,4]oxazepine-4,8(5H)-dicarboxamide

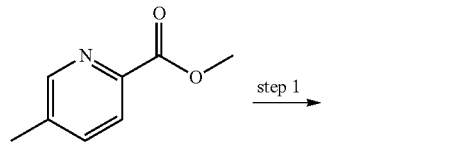 step 1

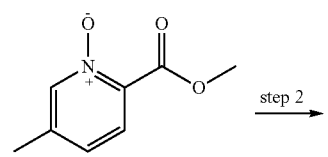 step 2

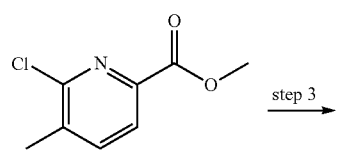 step 3

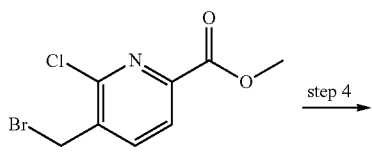 step 4

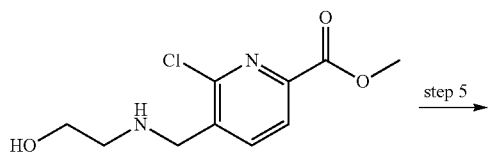 step 5

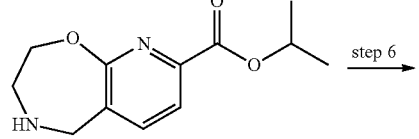 step 6

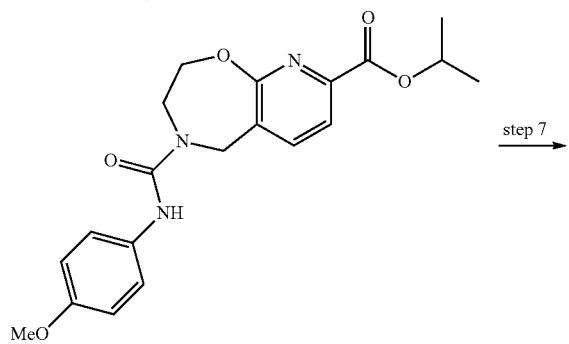 step 7

-continued

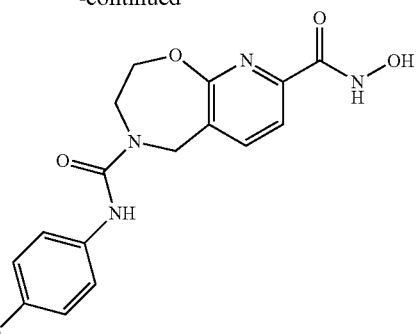

Step-1: 2-(Methoxycarbonyl)-5-methylpyridine 1-oxide

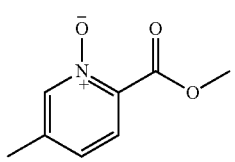

Into a 3 L 3-necked round-bottom flask, was placed methyl 5-methylpicolinate (43.7 g, 289 mmol, 1 equiv) and CH$_2$Cl$_2$ (1 L). This was followed by the addition of 3-chlorobenzene-1-carboperoxoic acid (106 g, 614 mmol, 2 equiv) in several batches at 0° C. The resulting mixture was stirred overnight at room temperature. The reaction was then quenched with sat. aq. Na$_2$SO$_3$ (500 mL) and extracted with CH$_2$Cl$_2$ (3×100 mL) The combined organic layers were washed with sat. aq. NaHCO$_3$ solution (400 mL), dried over anhydrous Na$_2$SO$_4$, filtered, and concentrated under vacuum. The crude product was re-crystallized from pet. ether:CH$_2$Cl$_2$ (20:1) to afford the title compound as a yellow solid (40 g, 83% yield). MS: (ES, m/z): 168 [M+H]⁺.

Step-2: Methyl 6-chloro-5-methylpyridine-2-carboxylate

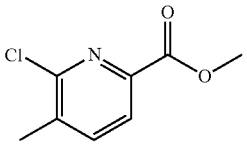

Into a 100-mL round-bottom flask, was placed 2-(methoxycarbonyl)-5-methylpyridine 1-oxide (10 g, 59.82 mmol, 1 equiv) and chloroform (50 mL), followed by the addition of phosphoroyl trichloride (42.2 mL, 9 equiv) dropwise with stirring. The resulting solution was stirred overnight at 80° C. in an oil bath. The resulting mixture was concentrated under vacuum and then quenched with water (20 mL). The pH value of the solution was adjusted to 7 with K$_2$CO$_3$ (10% in water) and extracted with EtOAc (3×20 mL). The combined organic layers were washed with H$_2$O (3×20 mL), dried over anhydrous Na$_2$SO$_4$, filtered, and concentrated under vacuum. The residue was purified by silica gel chromatography (Gradient 0-10% MeOH/CH$_2$Cl$_2$) to afford the title compound as a yellow solid (7 g, 57% yield). $^1$H-NMR (400 MHz, DMSO-d$_6$) δ(ppm): 7.96-8.02 (m, 2H), 3.88 (s, 1H), 2.41-2.51 (m, 3H). MS: (ES, m/z): 186 [M+H]$^+$.

Step-3: Methyl 5-(bromomethyl)-6-chloropyridine-2-carboxylate

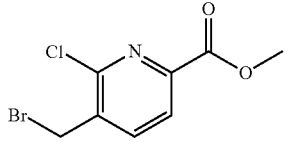

Into a 100-mL round-bottom flask purged and maintained with an inert atmosphere of nitrogen, was placed methyl 6-chloro-5-methylpyridine-2-carboxylate (4.2 g, 22.63 mmol, 1 equiv), benzoyl peroxide (549.9 mg, 2.27 mmol, 0.1 equiv), NBS (4.04 g, 22.70 mmol, 1 equiv) and CCl$_4$ (35 mL). The resulting mixture was stirred overnight at 80° C. in an oil bath. The reaction was concentrated under vacuum and quenched with water (20 mL), then extracted with EtOAc (3×30 mL). The combined organic layers were washed with H$_2$O (3×20 mL), and dried over anhydrous Na$_2$SO$_4$, filtered, and concentrated under vacuum. The residue was purified by silica gel chromatography (Gradient 0-10% MeOH/CH$_2$Cl$_2$) to afford the title compound as a yellow solid (2.5 g, 38% yield). MS: (ES, m/z): 265 [M+H]$^+$.

Step-4: Methyl 6-chloro-5-(((2-hydroxyethyl)amino)methyl)picolinate

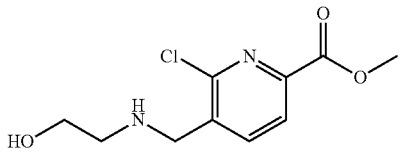

Into a 50-mL round-bottom flask, was placed a solution of 2-aminoethan-1-ol (1.4 g, 22.89 mmol, 2 equiv) in MeCN (20 mL) and K$_2$CO$_3$ (4.74 g, 34.03 mmol, 3 equiv). This was followed by the addition of a solution of methyl 5-(bromomethyl)-6-chloropyridine-2-carboxylate (3 g, 11.34 mmol, 1 equiv) in MeCN (10 mL) dropwise with stirring. The resulting mixture was stirred for 1 h at room temperature. The solids were filtered out. The filtrate was concentrated under vacuum. The residue was purified by silica gel chromatography (Gradient 0-10% MeOH/CH$_2$Cl$_2$) to afford the title compound as a yellow solid (1.5 g, 49% yield). MS: (ES, m/z): 245 [M+H]$^+$.

Step-5: Isopropyl 2,3,4,5-tetrahydropyrido[3,2-f][1,4]oxazepine-8-carboxylate

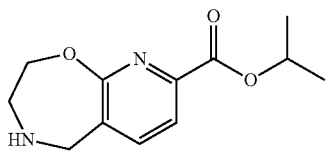 [SMILES: CC(C)OC(=O)c1ccc2c(n1)OCCNC2]

Into 20-mL sealed tube, was placed methyl 6-chloro-5-(((2-hydroxyethyl)amino)methyl)picolinate (1 g, 4.09 mmol, 1 equiv), K$_2$CO$_3$ (1.103 g, 7.98 mmol, 2 equiv), isopropanol (10 mL) and CuI (156 mg, 0.82 mmol, 0.2 equiv). The resulting solution was stirred overnight at 110° C. in an oil bath. The reaction was then quenched with water (10 mL) and extracted with EtOAc (3×10 mL). The combined organic layers were washed with H$_2$O (3×10 mL), dried over anhydrous Na$_2$SO$_4$, filtered, and concentrated under vacuum. The residue purified by silica gel chromatography (Gradient 0-10% MeOH/CH$_2$Cl$_2$) to afford the title compound as a green solid (148 mg, 14% yield). MS: (ES, m/z): 237 [M+H]$^+$.

Step-6: Isopropyl 4-((4-methoxyphenyl)carbamoyl)-2,3,4,5-tetrahydropyrido[3,2-f][1,4]oxazepine-8-carboxylate

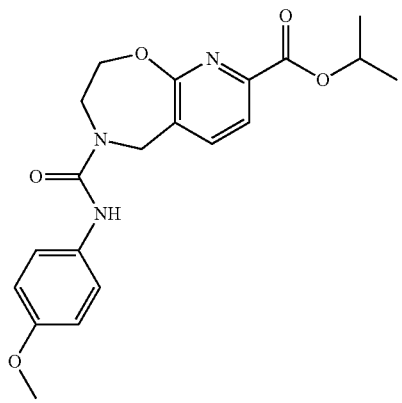 [SMILES: COc1ccc(NC(=O)N2CCOc3nc(C(=O)OC(C)C)ccc3C2)cc1]

Into a 8-mL vial, was placed a solution of isopropyl 2,3,4,5-tetrahydropyrido[3,2-f][1,4]oxazepine-8-carboxylate (30 mg, 0.13 mmol, 1 equiv) in CH$_2$Cl$_2$ (1.5 mL) and Et$_3$N (14 mg, 0.14 mmol, 1.1 equiv). The resulting mixture was stirred for 30 min at 0° C. This was followed by the addition of a solution of 1-isocyanato-4-methoxybenzene (21 mg, 0.14 mmol, 1.1 equiv) in CH$_2$Cl$_2$ (1 mL) dropwise with stirring at 0° C. The mixture was stirred for 4 h at room temperature and then concentrated. The residue purified by silica gel chromatography (Gradient 0-40% EtOAc/pet. ether) to afford the title compound as a yellow oil (42 mg, 86% yield). MS: (ES, m/z): 386 [M+H]$^+$.

Step-7: N8-Hydroxy-N4-(4-methoxyphenyl)-2,3-dihydropyrido[3,2-f][1,4]oxazepine-4,8(5H)-dicarboxamide

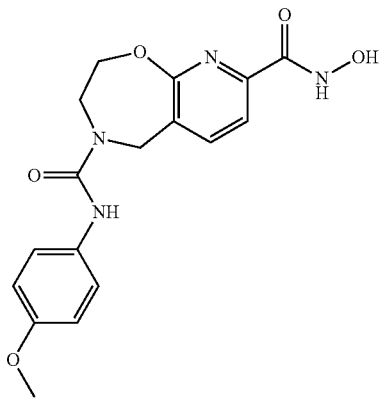 [SMILES: COc1ccc(NC(=O)N2CCOc3nc(C(=O)NO)ccc3C2)cc1]

Into a 8-mL vial, was placed isopropyl 4-((4-methoxyphenyl)carbamoyl)-2,3,4,5-tetrahydropyrido[3,2-f][1,4]oxazepine-8-carboxylate (42 mg, 0.11 mmol, 1 equiv), NH₂OH (0.864 g, 120 equiv, 50% in water), aq. 1N NaOH (0.218 mL, 2 equiv), THF/MeOH (2 mL, 4:1). The resulting mixture was stirred for 1 h at room temperature, then cooled to 0° C. and the pH value of the solution was adjusted to 6 with 6N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector, UV 254, 220 nm) to afford the title compound as a pink solid (17 mg, 32% yield). ¹H-NMR (400 MHz, DMSO-d₆) δ(ppm): 11.23 (s, 1H), 9.01 (s, 1H), 8.42 (s, 1H), 7.92-7.94 (d, J=8 Hz, 1H), 7.64-7.66 (d, J=8 Hz, 1H), 7.26-7.28 (d, J=8 Hz, 1H), 6.78-6.80 (d, J=8 Hz, 1H), 4.71 (s, 1H), 4.33-4.35 (t, J=4 Hz, 2H), 3.89-3.90 (t, J=4 Hz, 2H), 3.34 (s, 3H). MS: (ES, m/z): 359 [M+H]⁺.

Example 65—Preparation of N-hydroxy-4-((4-methoxyphenyl)sulfonyl)-2,3,4,5-tetrahydropyrido[3,2-f][1,4]oxazepine-8-carboxamide

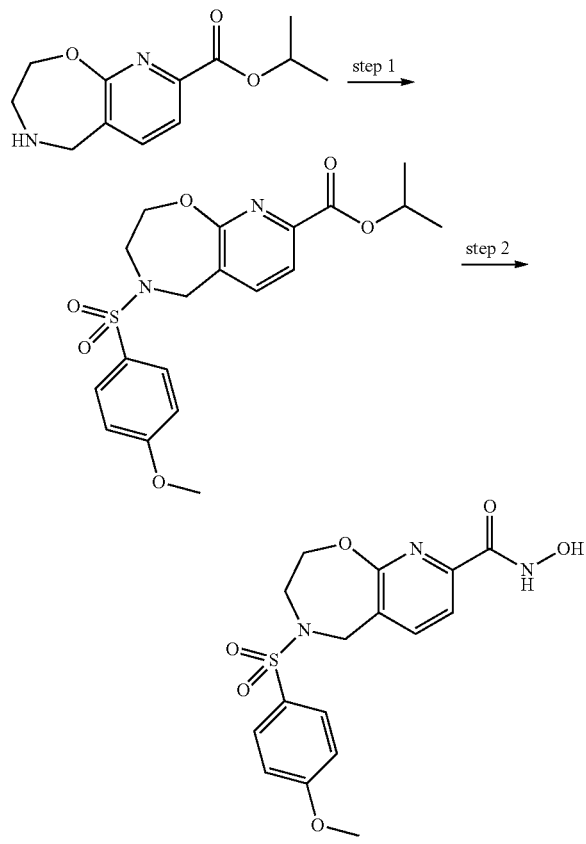

Step-1: Isopropyl 4-((4-methoxyphenyl)sulfonyl)-2,3,4,5-tetrahydropyrido[3,2-f][1,4]oxazepine-8-carboxylate

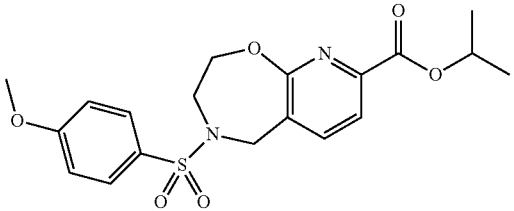 [SMILES: COc1ccc(S(=O)(=O)N2CCOc3nc(C(=O)OC(C)C)ccc3C2)cc1]

Into a 8-mL vial, was placed isopropyl 2,3,4,5-tetrahydropyrido[3,2-f][1,4]oxazepine-8-carboxylate (30 mg, 0.13 mmol, 1 equiv), CH₂Cl₂ (2.5 mL) and Et₃N (14 mg, 0.14 mmol, 1.10 equiv). The resulting mixture was stirred for 30 min at 0° C. This was followed by the addition of 4-methoxybenzene-1-sulfonyl chloride (26.18 g, 112 mmol, 1 equiv) dropwise with stirring at 0° C. The mixture was allowed to react, with stirring, for additional 2 h at room temperature and concentrated. The residue purified by silica gel chromatography (Gradient 0-5% MeOH/CH₂Cl₂) to afford the title compound as a brown solid (57 mg) which was used without further purification. MS: (ES, m/z): 407 [M+H]⁺.

Step-2: N-Hydroxy-4-((4-methoxyphenyl)sulfonyl)-2,3,4,5-tetrahydropyrido[3,2-f][1,4]oxazepine-8-carboxamide

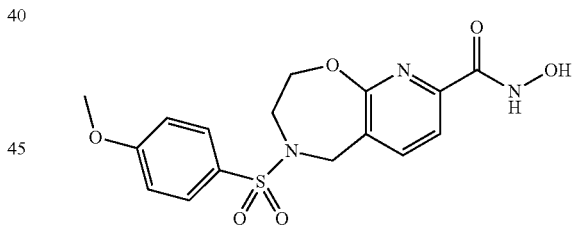

Into a 8-mL vial, was placed a solution of isopropyl 4-((4-methoxyphenyl)sulfonyl)-2,3,4,5-tetrahydropyrido[3,2-f][1,4]oxazepine-8-carboxylate (57 mg, 0.14 mmol, 1 equiv) in THF/MeOH (2 mL, 4:1), NH₂OH (1.11 g, 16.82 mmol, 120 equiv, 50% in water), and aq. 1N NaOH (0.28 mL, 2 equiv). The mixture was stirred for 1 h at room temperature. The pH value of the solution was adjusted to 6 with 6N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector, UV 254, 220 nm) to afford the title compound as a pink solid (13 mg, 19% yield). ¹H-NMR (400 MHz, DMSO-d₆) δ(ppm): 11.19 (s, 1H), 9.01 (s, 1H), 7.87-7.89 (d, J=8 Hz, 1H), 7.60-7.64 (m, 3H), 6.99-7.01 (d, J=8 Hz, 2H), 4.54 (s, 2H), 4.26-4.28 (t, J=4 Hz, 2H), 3.76 (s, 3H), 3.62-3.63 (t, J=8 Hz, 2H). MS: (ES, m/z): 380 [M+H]⁺.

Example 66—Preparation of N-hydroxy-4-(4-methoxybenzyl)-2,3,4,5-tetrahydropyrido[3,2-f][1,4]oxazepine-8-carboxamide

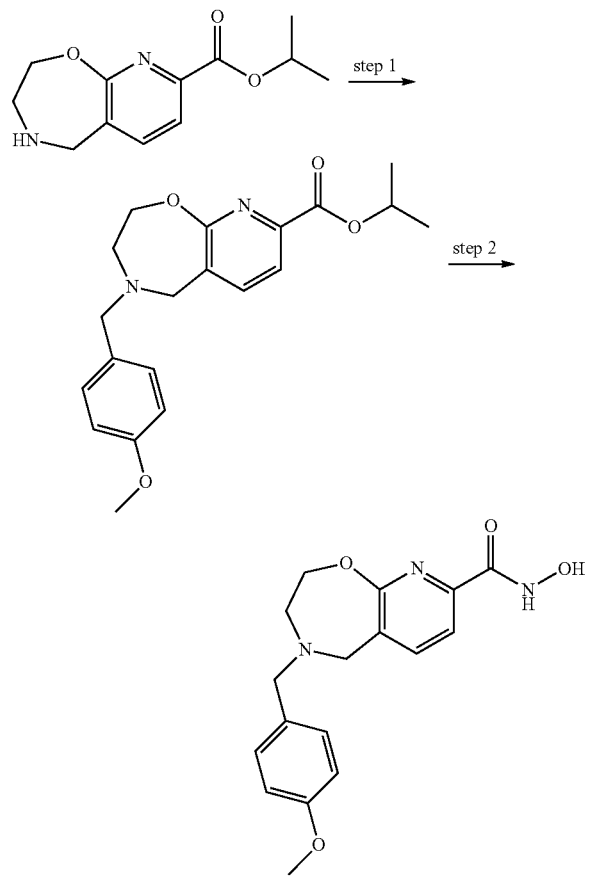

Step-1: Isopropyl 4-(4-methoxybenzyl)-2,3,4,5-tetrahydropyrido[3,2-f][1,4]oxazepine-8-carboxylate

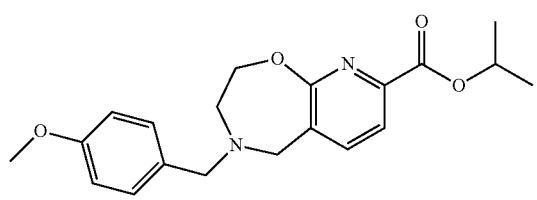 [SMILES: COc1ccc(CN2CCOc3nc(C(=O)OC(C)C)ccc3C2)cc1]

Into a 8-mL vial, was placed isopropyl 2,3,4,5-tetrahydropyrido[3,2-f][1,4]oxazepine-8-carboxylate (50 mg, 0.21 mmol, 1 equiv), 4-methoxybenzaldehyde (30.25 mg, 0.22 mmol, 1.05 equiv) and CH$_2$Cl$_2$ (1.5 mL). The resulting mixture was stirred for 30 min at room temperature. Then NaBH(OAc)$_3$ (449 mg, 2.12 mmol, 10 equiv) was added. The mixture was stirred overnight at room temperature and concentrated. The residue purified by silica gel chromatography (Gradient 0-40% EtOAc.pet. ether) to afford the title compound as a yellow oil (59 mg, 78% yield). MS: (ES, m/z): 357 [M+H]$^+$.

Step-2: N-Hydroxy-4-(4-methoxybenzyl)-2,3,4,5-tetrahydropyrido[3,2-f][1,4]oxazepine-8-carboxamide

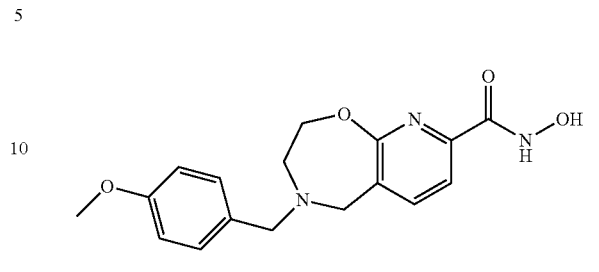

Into a 8-mL vial, was placed isopropyl 4-(4-methoxybenzyl)-2,3,4,5-tetrahydropyrido[3,2-f][1,4]oxazepine-8-carboxylate (63 mg, 0.18 mmol, 1 equiv), NH$_2$OH (1.4 g, 120 equiv, 50% in water), aq. 1N NaOH (0.35 mL, 2 equiv) and THF/MeOH (2 mL, 4:1). The resulting mixture was stirred for 1 h at room temperature. The pH value of the solution was adjusted to 6 with 6N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector, UV 254, 220 nm) to afford the title compound as a pink solid (33 mg, 42% yield). $^1$H-NMR (400 MHz, DMSO-d$_6$) δ(ppm): 11.39 (s, 1H), 10.60 (br s, 1H), 9.11 (br s, 1H), 7.94 (s, 1H), 7.76-7.78 (d, J=8 Hz, 1H), 7.42 (s, 2H), 7.01-7.03 (d, J=8 Hz, 2H), 4.28-4.69 (m, 7H), 3.71-3.86 (m, 4H). MS: (ES, m/z): 330 [M+H]$^+$.

Example 67—Preparation of N-Hydroxy-4-(4-methoxybenzyl)-5-oxo-2,3,4,5-tetrahydrobenzo[f][1,4]oxazepine-8-carboxamide

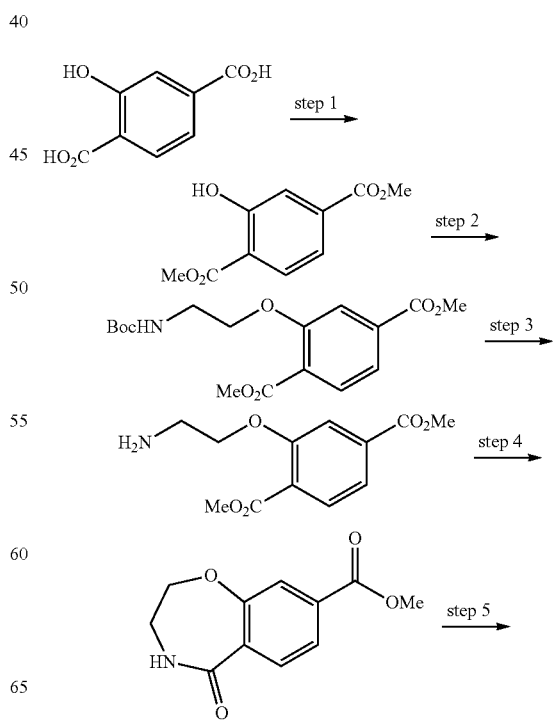

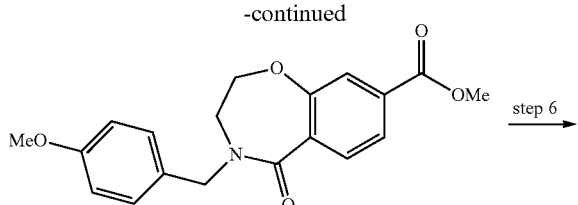

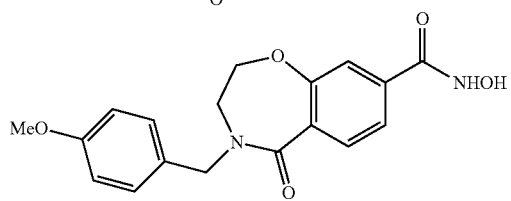

Step-1: Dimethyl 2-hydroxyterephalate

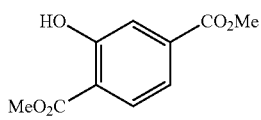

2-Hydroxyterephthalic acid (5 g, 27.5 mmol) was refluxed in MeOH (120 mL), containing 0.15 mL of conc. $H_2SO_4$. After 22 h the reaction mixture was concentrated under reduced pressure and the residue was redissolved in $CH_2Cl_2$ and washed sequentially with water, saturated aqueous solution of $NaHCO_3$, brine and dried over $Na_2SO_4$. The solution was filtered and concentrated. The crude material was purified by silica gel chromatography (Gradient: EtOAc/hexanes) to afford the title compound (1.7 g, 31% yield).

Step-2: Dimethyl 2-(2-((tert-butoxycarbonyl)amino)ethoxy)terephthalate

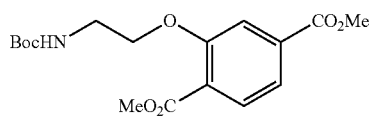 [SMILES: COC(=O)c1ccc(C(=O)OC)c(OCCNC(=O)OC(C)(C)C)c1]

To a suspension of dimethyl 2-hydroxyterephthalate (0.7 g, 3.3 mmol, 1 equiv) in THF (8 mL), tert-butyl (2-hydroxyethyl)carbamate (0.62 mL, 4.0 mmol, 1.2 equiv) and triphenylphosphine (1.4 g, 5.3 mmol, 1.6 equiv) were added at room temperature. The mixture was cooled to 0° C. and DEAD (0.84 mL, 5.3 mmol, 1.6 equiv) was added and the resulting mixture was slowly warmed up to room temperature and stirred 72 h. The mixture was concentrated and purified by silica gel chromatography (Gradient: EtOAc/hexanes) to afford the title compound (1.15 g, quantitative yield).

Step-3: Dimethyl 2-(2-aminoethoxy)terephthalate

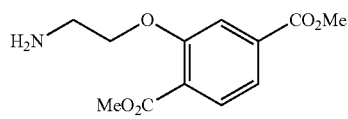 [SMILES: COC(=O)c1ccc(C(=O)OC)c(OCCN)c1]

Dimethyl 2-(2-((tert-butoxycarbonyl)amino)ethoxy)terephthalate (1.18 g, 3.34 mmol) was mixed with $CH_2Cl_2$ (3 mL) and then TFA (1.5 mL) was added at room temperature. The reaction mixture was stirred overnight at room temperature, then concentrated and co-evaporated several times with toluene. After trituration in MeOH/$Et_2O$ the title compound was obtained as its TFA salt (1.15 g, quantitative yield).

Step-4: Methyl 5-oxo-2,3,4,5-tetrahydrobenzo[f][1,4]oxazepine-8-carboxylate

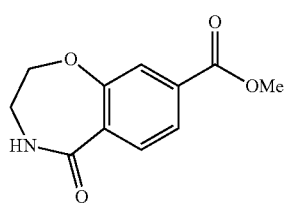 [SMILES: COC(=O)c1ccc2c(c1)OCCNC2=O]

Dimethyl 2-(2-aminoethoxy)terephthalate (1.15 g, 3.3 mmol) was mixed with toluene (7 mL) and $Et_3N$ (1.9 mL, 13.3 mmol) and stirred at 105° C. After 20 h, the reaction mixture was cooled to room temperature, concentrated and purified by silica gel chromatography (Gradient EtOAc/hexanes) to afford the title compound (380 mg, 52% yield). m. p.=149-150° C. $^1$H-NMR (300 MHz, CDCl$_3$) δ(ppm): 8.0.2 (d, J=8.25 Hz, 1H), 7.87, (d, J=8.25 Hz, 1H), 7.76 (dd, J=8.25, 1.65 Hz, 1H), 7.25 (d, J=8.25 Hz, 1H), 6.73 (br. s, 1H), 4.44-4 (m, 2H), 3.93 (s, 3H), 3.54-3.50 (m, 2H). MS: (APCI, m/z): 222 [M+H]$^+$.

Step-5: Methyl 4-(4-methoxybenzyl)-5-oxo-2,3,4,5-tetrahydrobenzo[f][1,4]oxazepine-8-carboxylate

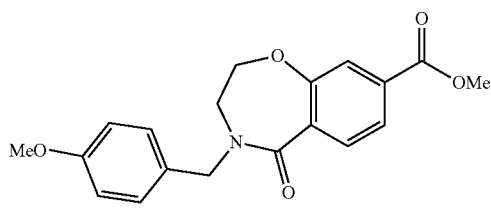 [SMILES: COC(=O)c1ccc2c(c1)OCCN(Cc1ccc(OC)cc1)C2=O]

Sodium hydride (60% dispersion in mineral oil, 8.14 mg, 0.203 mmol, 1.5 equiv) was added to a solution of methyl 5-oxo-2,3,4,5-tetrahydrobenzo[f][1,4]oxazepine-8-carboxylate (30 mg, 0.136 mmol, 1 equiv) in DMF (1.4 mL) and the solution was stirred at room temperature for 30 minutes. 1-(Bromomethyl)-4-methoxybenzene (57 μL, 0.407 mmol, 3 equiv) was added and the reaction was stirred at 50° C. overnight. The reaction mixture was partitioned between EtOAc and saturated aqueous solution of NaHCO$_3$. The layers were separated and the organic layer was washed with brine, dried over Na$_2$SO$_4$, filtered and concentrated. The residue was purified by silica gel chromatography (Gradient 20-80% EtOAc/hexanes) to afford the title compound as a colorless oil.

Step-6: N-Hydroxy-4-(4-methoxybenzyl)-5-oxo-2,3,4,5-tetrahydrobenzo[f][1,4]oxazepine-8-carboxamide

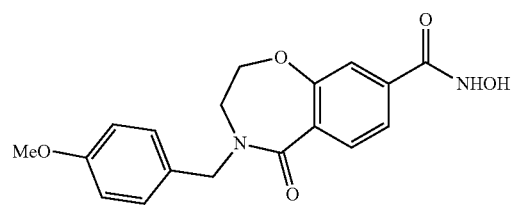

To a solution of methyl 4-(4-methoxybenzyl)-5-oxo-2,3,4,5-tetrahydrobenzo[f][1,4]oxazepine-8-carboxylate (46 mg, 0.136 mmol, 1 equiv) in MeOH (272 μL) and THF (1 mL) was added an aqueous 50% wt hydroxylamine solution (167 μL, 2.72 mmol, 20 equiv) and aqueous 2N NaOH solution (136 μL, 0.272 mmol, 2 equiv). The reaction was stirred at room temperature for 2 h. The reaction was acidified with 2N HCl and extracted with EtOAC. The organic layer was washed with water and brine, dried over Na$_2$SO$_4$, filtered and concentrated. The residue was purified by Prep-HPLC (Column: XBridge RP C18 OBD, 5 μM, 19×50 mm; Mobile Phase A: Water/0.1% Formic Acid; Mobile Phase B: MeCN/0.1% Formic Acid; Flow rate: 23 mL/min; Gradient: 10% B to 70% B in 7 min) to afford the title compound (22 mg, 47% over 2 steps). $^1$H-NMR (300 MHz, DMSO-d$_6$) δ(ppm): 11.28 (br s, 1H), 9.15 (br s, 1H), 7.73 (d, J=7.9 Hz, 1H), 7.51 (dd, J=8.1, 1.6 Hz, 1H), 7.15-7.40 (m, 3H), 6.73-7.06 (m, 2H), 4.65 (s, 2H), 4.18 (t, J=5.0 Hz, 2H), 3.68-3.76 (m, 3H), 3.46 (t, J=5.1 Hz, 2H). MS: (ES, m/z): 343 [M+H]$^+$.

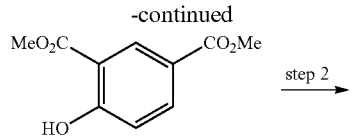
step 2

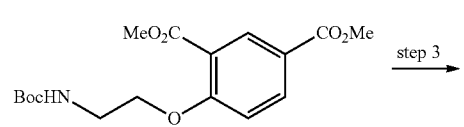
step 3

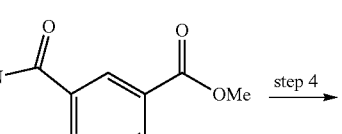
step 4

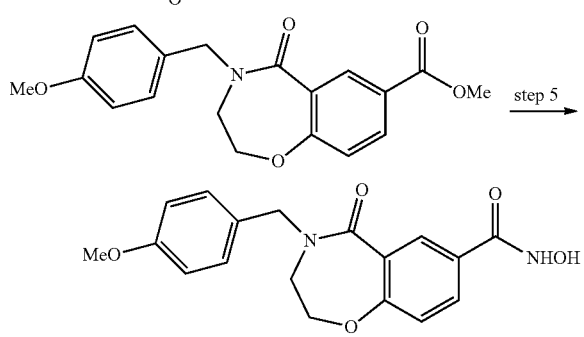
step 5

TABLE 31

The following compound was prepared according to the method of Example 67.

| Structure | Found M + H | $^1$H-NMR (300 DMSO-d$_6$) δ(ppm) |
|---|---|---|
| 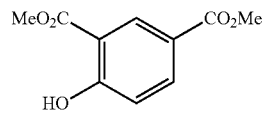 | 357 [M + H]$^+$ | (ES, m/z): 11.30 (s, 1 H), 9.13 (s, 1 H), 7.66 (d, J = 7.9 Hz, 1 H), 7.48 (dd, J = 8.1, 1.6 Hz, 1 H), 7.32 (d, J = 1.5 Hz, 1 H), 7.16 (m, J = 8.8 Hz, 2 H), 6.79-6.89 (m, 2 H), 4.24 (t, J = 5.0 Hz, 2 H), 3.64-3.72 (m, 5 H), 3.46 (br t, J = 5.0 Hz, 2 H), 2.73-2.84 (m, 2 H) |

Example 68—Preparation of N-Hydroxy-4-(4-methoxybenzyl)-5-oxo-2,3,4,5-tetrahydrobenzo[f][1,4]oxazepine-7-carboxamide

Step-1: Dimethyl 4-hydroxyisophthalate

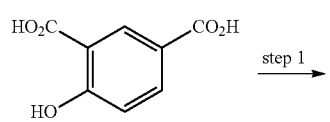
step 1

Under a nitrogen purge, 4-hydroxyisophthalic acid (10.9 g, 0.06 mol) was dissolved in MeOH (85 mL) in a 250 mL 3-neck round-bottomed flask. Sulfuric acid (98%, 8.5 mL) was placed in an addition funnel and added dropwise over 25 min, resulting in an exotherm to 35° C. After the addition was completed, the reaction was heated to a gentle reflux, and maintained for 28 h. Upon removal of heat source, a white precipitate began to form. The flask was further cooled in an ice bath, and the solids were then isolated by filtration. The solid was washed with cold isopropanol and then with hexanes, and then allowed to dry on the filter, providing the title compound as a white solid (10.4 g, 82% yield).

Step-2: Dimethyl 4-(2-((tert-butoxycarbonyl)amino) ethoxy)isophthalate

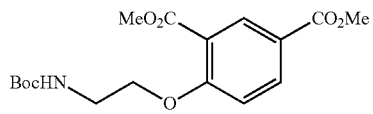 [SMILES: COC(=O)c1ccc(OCCNC(=O)OC(C)(C)C)c(C(=O)OC)c1]

Under a nitrogen purge, dimethyl 4-hydroxyisophthalate (2.10 g 0.01 mol) was dissolved in MeCN (70 mL) in a 250 mL 3-neck round-bottomed flask. 18-Crown-6 (0.13 g, 5 mol %) and potassium carbonate (1.5 g, 0.011 mol) were added sequentially, in single portions, washing in with MeCN (10 mL). Tert-butyl(2-bromoethyl)carbamate (2.24 g, 0.01 mol) was added in a single portion, and washed in with MeCN (5 mL). The resulting suspension was heated at reflux for 16 h. Heat was removed, and the reaction mixture was cooled in an ice/acetone bath. Solids were removed by filtration, and the filter cake was washed with more MeCN. The filtrate was pre-absorbed directly onto silica gel, and purified by silica gel chromatography (Gradient 15-50% EtOAc/hexanes) to afford the title compound as an amber oil which slowly solidified (1.1 g, 31% yield).

Step-3: Methyl 5-oxo-2,3,4,5-tetrahydrobenzo[f][1,4]oxazepine-7-carboxylate

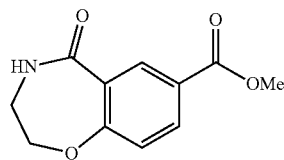 [SMILES: COC(=O)c1ccc2c(c1)C(=O)NCCO2]

Dimethyl 4-(2-((tert-butoxycarbonyl)amino)ethoxy) isophthalate (2.2 g, 6.2 mmol) was dissolved in CH₂Cl₂ (12 mL) in a 50 mL round-bottomed flask. TFA (4 mL) was added in a single portion, and the resulting solution was stirred for 16 h. Solvent was removed under reduced pressure to provide an oil. Five times, toluene was added and removed under reduced pressure. The resulting solid was suspended in toluene (40 mL), and Et₃N (3.5 mL, 0.025 mol) was added in a single portion. Upon heating to reflux, all solids slowly dissolved to provide a clear solution. The reaction was heated for another 16 h, then partitioned between EtOAc and water. The organic layer was washed with water and brine, dried over MgSO₄, filtered and concentrated. Purification by recrystallization from 2-propanol afforded the title compound as a pale beige solid (0.65 g, 47% yield). ¹H-NMR (300 MHz, CDCl₃) δ(ppm): 3.54-3.61 (m, 2H) 3.90 (s, 3H) 4.45-4.51 (m, 2H) 7.04 (d, J=8.53 Hz, 1H) 7.42 (br. s., 1H) 8.07 (dd, J=8.53, 2.20 Hz, 1H) 8.76 (d, J=2.20 Hz, 1H).

Step-4: Methyl 4-(4-methoxybenzyl)-5-oxo-2,3,4,5-tetrahydrobenzo[f][1,4]oxazepine-7-carboxylate

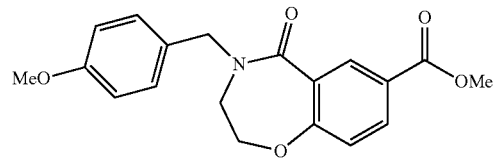 [SMILES: COC(=O)c1ccc2c(c1)C(=O)N(Cc1ccc(OC)cc1)CCO2]

Sodium hydride (60% dispersion in mineral oil, 13 mg, 0.325 mmol, 1.5 equiv) was added to a solution of methyl 5-oxo-2,3,4,5-tetrahydrobenzo[f][1,4]oxazepine-7-carboxylate (48 mg, 0.217 mmol, 1 equiv) in DMF (2.2 mL) and the solution was stirred at room temperature for 30 minutes. 1-(Bromomethyl)-4-methoxybenzene (33.5 μL, 0.239 mmol, 1.1 equiv) was added and the reaction was stirred at 50° C. overnight. The reaction mixture was partitioned between EtOAc and saturated aqueous solution of NaHCO₃. The layers were separated and the organic layer was washed with brine, dried over Na₂SO₄, filtered and concentrated. The residue was purified by silica gel chromatography (Gradient 20-80% EtOAc/hexanes) to afford the title compound as a white solid (33 mg, 45% yield). MS: (ES, m/z): 342 [M+H]⁺.

Step-5: N-Hydroxy-4-(4-methoxybenzyl)-5-oxo-2,3,4,5-tetrahydrobenzo[f][1,4]oxazepine-7-carboxamide

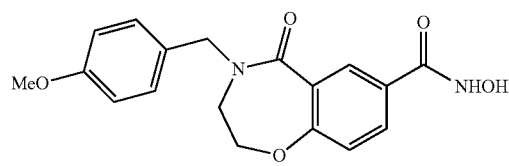

To a solution of methyl 4-(4-methoxybenzyl)-5-oxo-2,3,4,5-tetrahydrobenzo[f][1,4]oxazepine-7-carboxylate (33 mg, 0.097 mmol, 1 equiv) in MeOH (152 μL) and THF (608 μL) was added NH₂OH (50% in water, 118 μL, 1.94 mmol, 20 equiv) and aq. 2N NaOH (97 μL, 0.194 mmol, 2 equiv). The reaction was stirred at room temperature for 3 days. The reaction was directly purified by Prep-HPLC (Column: XBridge RP C18 OBD, 5 μM, 19×50 mm; Mobile Phase A: Water/0.1% Formic Acid; Mobile Phase B: MeCN/0.1% Formic Acid; Flow rate: 23 mL/min; Gradient: 10% B to 70% B in 7 min) to afford the title compound as an oil (3.5 mg, 13% yield). ¹H-NMR (300 MHz, DMSO-d₆) δ(ppm): 10.3 (s, 1H), 8.33 (s, 1H), 8.15 (s, 1H), 7.83-7.76 (m, 1H), 7.25 (br d, J=7.3 Hz, 2H), 7.03 (br d, J=8.5 Hz, 1H), 6.89 (br d, J=8.5 Hz, 2H), 4.65 (s, 2H), 4.22 (br s, 2H), 3.71 (s, 3H), 3.48 (br s, 2H). MS: (ES, m/z): 343 [M+H]⁺.

TABLE 32

The following compound was prepared according to the method of Example 68.

| Structure | Found M + H | ¹H-NMR (400 MHz, DMSO-d$_6$) δ(ppm) |
|---|---|---|
| 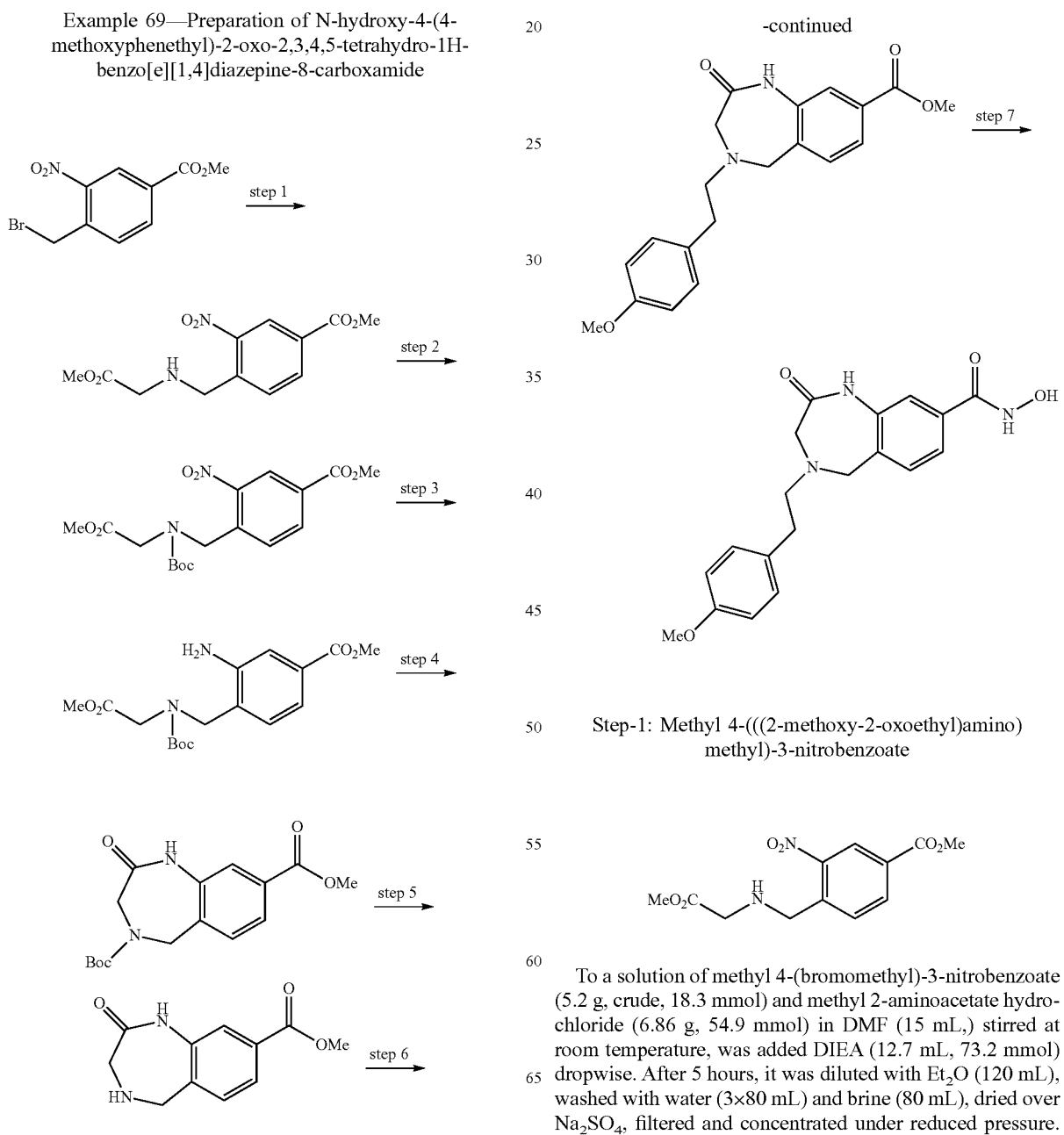 | (ES, m/z): 357 [M + H]⁺ | |

Example 69—Preparation of N-hydroxy-4-(4-methoxyphenethyl)-2-oxo-2,3,4,5-tetrahydro-1H-benzo[e][1,4]diazepine-8-carboxamide Step-1: Methyl 4-(((2-methoxy-2-oxoethyl)amino)methyl)-3-nitrobenzoate To a solution of methyl 4-(bromomethyl)-3-nitrobenzoate (5.2 g, crude, 18.3 mmol) and methyl 2-aminoacetate hydrochloride (6.86 g, 54.9 mmol) in DMF (15 mL,) stirred at room temperature, was added DIEA (12.7 mL, 73.2 mmol) dropwise. After 5 hours, it was diluted with Et$_2$O (120 mL), washed with water (3×80 mL) and brine (80 mL), dried over Na$_2$SO$_4$, filtered and concentrated under reduced pressure.

The brown solid residue was purified by silica gel chromatography (Gradient 0-100% EtOAc/hexanes) to give the title compound (4.2 g)

Step-2: Methyl 4-(((tert-butoxycarbonyl)(2-methoxy-2-oxoethyl)amino)methyl)-3-nitrobenzoate

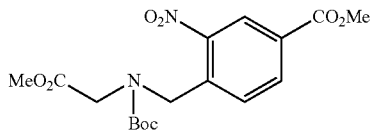 [SMILES: COC(=O)CN(Cc1ccc(C(=O)OC)cc1[N+](=O)[O-])C(=O)OC(C)(C)C]

To a solution of methyl 4-(((2-methoxy-2-oxoethyl)amino)methyl)-3-nitrobenzoate (4.2 g, 15 mmol) in EtOAc/hexanes (200 mL, 1:1) stirred at room temperature, was added di-tert-butyl dicarbonate (3.4 g, 15.6 mmol) followed by 4-dimethylaminopyridine (50 mg). The reaction was stirred at room temperature overnight. TLC indicated there was still a lot of starting material. More di-tert-butyl dicarbonate (2.0 g, 9.2 mmol) was added and the mixture was stirred for another 3 hours. It was concentrated under reduced pressure. The residue was purified by silica gel chromatography (Gradient 0-100% EtOAc/hexanes) to give the title compound as a yellow oil (4.9 g, 70% yield over 3 steps).

Step-3: Methyl 3-amino-4-(((tert-butoxycarbonyl)(2-methoxy-2-oxoethyl)amino)methyl)benzoate

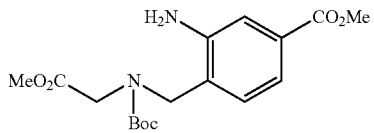 [SMILES: COC(=O)CN(Cc1ccc(C(=O)OC)cc1N)C(=O)OC(C)(C)C]

To a solution of methyl 4-(((tert-butoxycarbonyl)(2-methoxy-2-oxoethyl)amino)methyl)-3-nitrobenzoate (4.9 g, 12.8 mmol) in MeOH (100 mL) was added 10% Pd/C (2.5 g). The mixture was purged with $N_2$ for 10 min and then stirred under a hydrogen balloon for 16 h. The mixture was filtered through Celite and the filtrate was evaporated under reduced pressure to give the title compound as a greenish gum (4.0 g, 89% yield).

Step-4: 4-(tert-Butyl) 8-methyl 2-oxo-1,2,3,5-tetrahydro-4H-benzo[e][1,4]diazepine-4,8-dicarboxylate

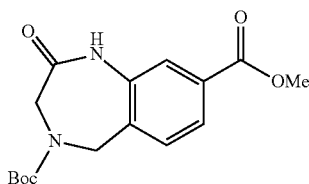 [SMILES: COC(=O)c1ccc2c(c1)NC(=O)CN(C(=O)OC(C)(C)C)C2]

A solution of methyl 3-amino-4-(((tert-butoxycarbonyl)(2-methoxy-2-oxoethyl)amino)methyl)-benzoate (4.0 g, 13 mmol) in anhydrous toluene (100 mL) was stirred under reflux overnight. After removal of solvent under reduced pressure, the residue was purified by silica gel chromatography (Gradient 10-100% EtOAc/hexanes) to give the title compound as an off-white solid (0.96 g, 27% yield).

Step-5: Methyl 2-oxo-2,3,4,5-tetrahydro-1H-benzo[e][1,4]diazepine-8-carboxylate

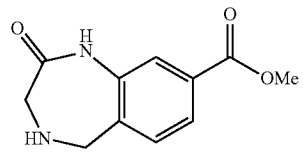 [SMILES: COC(=O)c1ccc2c(c1)NC(=O)CNC2]

To a solution of HCl in dioxane (4M, 30 mL) was added 4-(tert-butyl) 8-methyl 2-oxo-1,2,3,5-tetrahydro-4H-benzo[e][1,4]diazepine-4,8-dicarboxylate (956 mg, 2.98 mmol). The mixture was stirred at room temperature for 5 hours. The solid precipitates were collected by filtration and dried at 50° C. under vacuum overnight to give the title compound as its HCl salt as an off-white solid (745 mg, 97% yield). $^1$H-NMR (300 MHz, DMSO-$d_6$) δ(ppm): 10 69 (s, 1H), 10.17 (s, 1H), 7.79 (dd, J=7.7, 1.5 Hz, 1H), 7.70 (d, J=1.6 Hz, 1H), 7.60 (d, J=7.7 Hz, 1H), 4.28 (s, 2H), 3.88 (s, 3H), 3.65 (s, 2H). MS: (APCI, m/z): 221 [M−Cl]$^+$.

Step-6: Methyl 4-(4-methoxyphenethyl)-2-oxo-2,3,4,5-tetrahydro-1H-benzo[e][1,4]diazepine-8-carboxylate

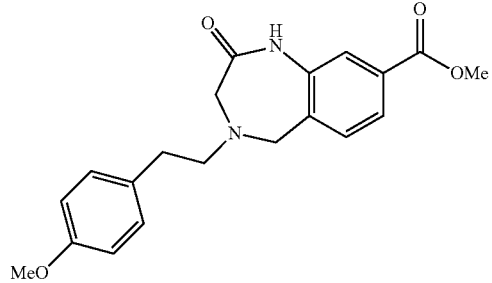 [SMILES: COC(=O)c1ccc2c(c1)NC(=O)CN(CCc1ccc(OC)cc1)C2]

To a suspension of methyl 2-oxo-2,3,4,5-tetrahydro-1H-benzo[e][1,4]diazepine-8-carboxylate hydrochloride (40 mg, 0.16 mmol, 1 equiv) and $K_2CO_3$ (43 mg, 0.31 mmol, 2 equiv) in MeOH was added 1-(2-bromoethyl)-4-methoxybenzene (76 μL, 0.49 mmol, 3 equiv). The resulting mixture was heated at 55° C. for 2 days. The reaction mixture was partitioned between EtOAc and a saturated aqueous solution of $NaHCO_3$. The layers were separated. The organic layer was washed with water, then with brine, and dried over anhydrous $Na_2SO_4$. The solution was filtered, and concentrated. This crude material was purified by silica gel chromatography (Gradient 0-10% MeOH/$CH_2Cl_2$ with 0.1% formic acid) to afford the title compound as a colorless oil (14.4 mg, 26% yield). MS: (ES, m/z): 355 [M+H]$^+$.

Step-7: N-Hydroxy-4-(4-methoxyphenethyl)-2-oxo-2,3,4,5-tetrahydro-1H-benzo[e][1,4]diazepine-8-carboxamide

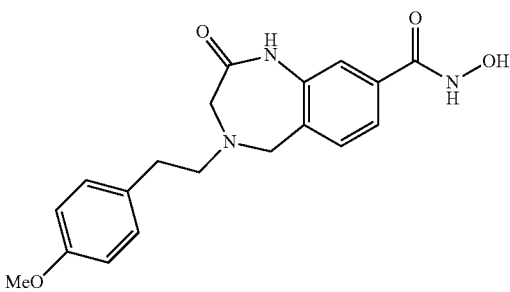 [SMILES: COc1ccc(CCN2CC(=O)Nc3cc(C(=O)NO)ccc3C2)cc1]

To a solution of methyl 4-(4-methoxyphenethyl)-2-oxo-2,3,4,5-tetrahydro-1H-benzo[e][1,4]diazepine-8-carboxylate (14 mg, 0.041 mmol, 1 equiv) in a MeOH/THF (1 mL, ¼) was added an NH$_2$OH (50% in water, 212 µL, 3.5 mmol, 85 equiv) and aq. 2N NaOH solution (40.6 µL, 0.081 mmol, 2 equiv). The reaction was stirred at room temperature for 2 h, then was acidified with 2N HCl. The mixture was extracted with EtOAc and the separated organic layer was washed with brine, then dried over anhydrous Na$_2$SO$_4$. The solution was filtered, and concentrated. This crude material was purified by Prep-HPLC (Column: XBridge RP C18 OBD, 5 µM, 19×50 mm; Mobile Phase A: Water/0.1% Formic Acid; Mobile Phase B: MeCN/0.1% Formic Acid; Flow rate: 23 mL/min; Gradient: 2% B to 50% B in 7 min) to afford the title compound (7.1 mg, 49% yield). $^1$H-NMR (300 MHz, DMSO-d$_6$) δ(ppm): 11.19 (br s, 1H), 10.06 (s, 1H), 8.17 (s, 1H), 7.42 (s, 1H). 7.29-7.40 (m, 2H), 7.09 (d, J=8.5 Hz, 2H), 6.80 (d, J=8.5 Hz, 2H), 3.77-3.97 (m, 2H), 3.68 (s, 3H), 3.27-3.33 (m, 2H), 2.65 (s, 4H). MS: (ES, m/z): 356 [M+H]$^+$.

TABLE 33

The following compound was prepared according to the method of Example 69.

| Structure | Found M + H |
|---|---|
| 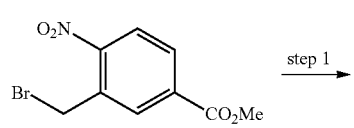 | (ES, m/z): 356 [M + H]$^+$ |

Example 70—Preparation of 4-((1H-benzo[d]imidazol-2-yl)methyl)-N-hydroxy-2-oxo-2,3,4,5-tetrahydro-1H-benzo[e][1,4]diazepine-7-carboxamide

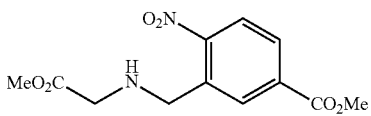 [SMILES: COC(=O)CNCc1cc(C(=O)OC)ccc1[N+](=O)[O-]]

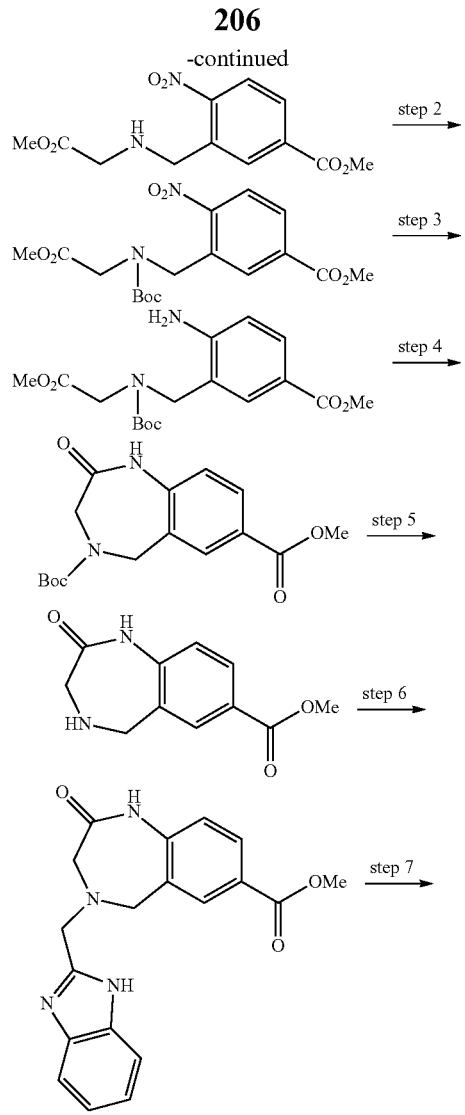

Step-1: Methyl 3-(((2-methoxy-2-oxoethyl)amino)methyl)-4-nitrobenzoate

Into a 250-mL round-bottom flask that has been purged and maintained with an inert atmosphere of nitrogen, were placed methyl 2-aminoacetate (12 g, 135 mmol, 1.5 equiv), methyl 3-(bromomethyl)-4-nitrobenzoate (12 g, 26 mmol, 1 equiv), DIEA (32 mL, 3 equiv) and DMF (120 mL). The resulting solution was stirred for 12 h at room temperature. The reaction was then quenched by the addition of water. The resulting solution was extracted with EtOAc (3×100 mL) and the combined organic layer was washed with brine (100 mL). The organic mixture was dried over anhydrous $Na_2SO_4$, filtered, and concentrated under vacuum. The residue was purified by silica gel chromatography (Gradient 1:10 to 1:1 EtOAc/hexanes) to afford the title compound as a yellow solid (4.9 g, 66% yield). MS: (ES, m/z): 283 $[M+H]^+$.

Step-2: Methyl 3-(((tert-butoxycarbonyl)(2-methoxy-2-oxoethyl)amino)methyl)-4-nitrobenzoate

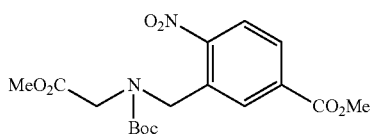 [SMILES: COC(=O)CN(Cc1cc(C(=O)OC)ccc1[N+](=O)[O-])C(=O)OC(C)(C)C]

Into a 100-mL round-bottom flask, were placed methyl 3-(((2-methoxy-2-oxoethyl)amino)methyl)-4-nitrobenzoate (4.7 g, 16.8 mmol, 1 equiv), $CH_2Cl_2$ (100 mL), di-tert-butyl dicarbonate (4.4 g, 20.2 mmol, 1.2 equiv) and 4-dimethylaminopyridine (82 mg, 0.67 mmol, 0.04 equiv). The resulting solution was stirred for 4 h at room temperature. The resulting mixture was concentrated under vacuum. The residue was purified by silica gel chromatography (Gradient 1:10 to 1:1 EtOAc/petroleum ether) to afford the title compound as a yellow oil (2.8 g, 44% yield). MS: (ES, m/z): 283 $[M-Boc+H]^+$.

Step-3: Methyl 4-amino-3-(((tert-butoxycarbonyl)(2-methoxy-2-oxoethyl)amino)methyl)benzoate

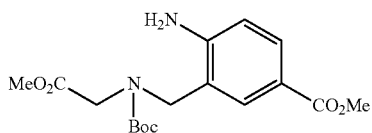

Into a 100-mL round-bottom flask, were placed methyl 3-(((tert-butoxycarbonyl)(2-methoxy-2-oxoethyl)amino)methyl)-4-nitrobenzoate (2.8 g, 7.3 mmol, 1 equiv), MeOH (30 mL) and palladium on carbon (280 mg). The resulting solution was stirred for 18 h at room temperature under a $H_2$ balloon. The solids were filtered out and the filtrate was concentrated under reduced pressure to afford the title compound as a brown oil (1.9 g, 74% yield). MS: (ES, m/z): 253 $[M-Boc+H]^+$.

Step-4: 4-(tert-Butyl) 7-methyl 2-oxo-1,2,3,5-tetrahydro-4H-benzo[e][1,4]diazepine-4,7-dicarboxylate

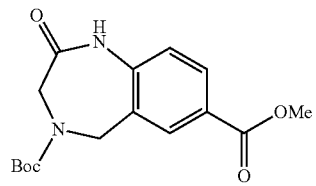 [SMILES: COC(=O)c1ccc2c(c1)CN(C(=O)OC(C)(C)C)CC(=O)N2]

Into a 250-mL round-bottom flask that has been purged and maintained with an inert atmosphere of nitrogen, were placed methyl 4-amino-3-(((tert-butoxycarbonyl)(2-methoxy-2-oxoethyl)amino)methyl)benzoate (1.9 g, 7.5 mmol, 1 equiv), THF (100 mL) and sodium hydride (239 mg, 10 mmol, 1.3 equiv). The resulting solution was stirred for 4 h at room temperature. The reaction mixture was poured into water/ice and extracted with EtOAc (3×150 mL). The combined organic layers was washed with brine (100 mL), dried over anhydrous $Na_2SO_4$, filtered, and concentrated under vacuum. The crude product was recrystallized from diethyl ether to afford the title compound as a white solid (0.5 g, 21% yield). $^1$H-NMR (400 MHz, $CDCl_3$) δ(ppm): 10.34-10.41 (m, 1H), 7.76-7.79 (m, 2H), 7.17-7.20 (m, 1H), 4.27-4.53 (m, 4H), 3.82 (s, 3H), 1.34 (s, 3H), 1.20 (s, 6H).

Step-5: Methyl 2-oxo-2,3,4,5-tetrahydro-1H-benzo[e][1,4]diazepine-7-carboxylate

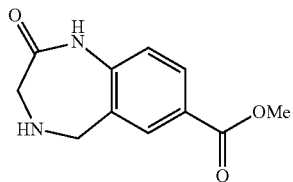 [SMILES: COC(=O)c1ccc2c(c1)CNCC(=O)N2]

Into a 500-mL round-bottom flask that has been purged and maintained with an inert atmosphere of nitrogen, were placed 4-(tert-butyl) 7-methyl 2-oxo-1,2,3,5-tetrahydro-4H-benzo[e][1,4]diazepine-4,7-dicarboxylate (12 g, 37 mmol, 1 equiv) and 4N HCl in dioxane (360 mL). The resulting solution was stirred for 6 h at room temperature. The resulting mixture was concentrated under vacuum and washed with diethyl ether (300 mL) to afford the title compound as the HCl salt as a white solid (9.5 g, 99% yield). MS: (ES, m/z): 221 $[M+H]^+$.

Step-6: Methyl 4-((1H-benzo[d]imidazol-2-yl)methyl)-2-oxo-2,3,4,5-tetrahydro-1H-benzo[e][1,4]diazepine-7-carboxylate

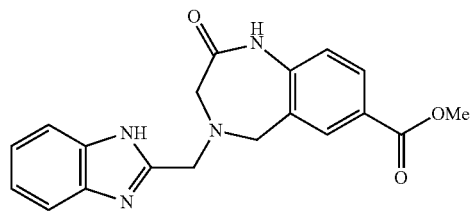 [SMILES: COC(=O)c1ccc2c(c1)CN(Cc1nc3ccccc3[nH]1)CC(=O)N2]

To a suspension of methyl 2-oxo-2,3,4,5-tetrahydro-1H-benzo[e][1,4]diazepine-7-carboxylate hydrochloride (50 mg, 0.195 mmol, 1 equiv) and K$_2$CO$_3$ (56.5 mg, 0.41 mmol, 2.1 equiv) in MeCN (1 mL) was added 2-(chloromethyl)-1H-benzo[d]imidazole (68 mg, 0.41 mmol, 2.1 equiv). The resulting mixture was heated at 55° C. for 2 days. The reaction mixture was partitioned between EtOAc and a saturated aqueous solution of NaHCO$_3$. The layers were separated. The organic layer was washed with water, then with brine, and dried over Na$_2$SO$_4$. The solution was filtered, and concentrated. This crude material was purified by silica gel chromatography (Gradient 0-5% MeOH/CH$_2$Cl$_2$) to afford the title compound as a yellow oil (54.5 mg, 80% yield). MS: (ES, m/z): 351 [M+H]$^+$.

Step-7: 4-((1H-Benzo[d]imidazol-2-yl)methyl)-N-hydroxy-2-oxo-2,3,4,5-tetrahydro-1H-benzo[e][1,4]diazepine-7-carboxamide

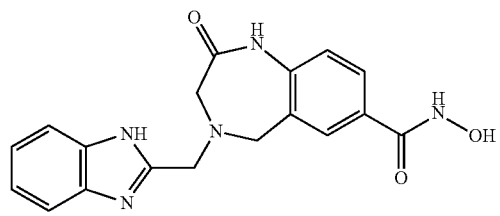 [SMILES: O=C1CN(Cc2nc3ccccc3[nH]2)Cc2cc(C(=O)NO)ccc2N1]

To a solution of methyl 4-((1H-benzo[d]imidazol-2-yl)methyl)-2-oxo-2,3,4,5-tetrahydro-1H-benzo[e][1,4]diazepine-7-carboxylate (54 mg, 0.154 mmol, 1 equiv) in a MeOH/THF (4:1, 2 mL) were added NH$_2$OH (50% in water, 996 µL, 16 mmol, 85 equiv) and aq. 2N NaOH solution (15 µL, 0.31 mmol, 2 equiv). The reaction was stirred at room temperature for 2 h, then was acidified with 2N HCl. The mixture was extracted with EtOAc and the separated organic layer was washed with brine, then dried over anhydrous MgSO$_4$. The solution was filtered, and concentrated. This crude material was purified by Prep-HPLC (Column: XBridge RP C18 OBD, 5 µM, 19×50 mm; Mobile Phase A: Water/0.1% Formic Acid; Mobile Phase B: MeCN/0.1% Formic Acid; Flow rate: 23 mL/min; Gradient: 2% B to 50% B in 7 min) to afford the title compound (10.7 mg, 19% yield). $^1$H-NMR (300 MHz, DMSO-d$_6$) δ(ppm): 12.40 (br s, 1H), 11.12 (br s, 1H), 10.24 (s, 1H), 8.15 (s, 1H), 7.59-7.67 (m, 2H), 7.38-7.56 (m, 2H), 7.07-7.16 (m, 3H), 3.90 (s, 2H), 3.87 (s, 2H), 3.39 (s, 2H). MS: (ES, m/z): 352 [M+H]$^+$.

TABLE 34

The following compound was prepared according to the method of Example 70.

| Structure | Found M + H |
|---|---|
| 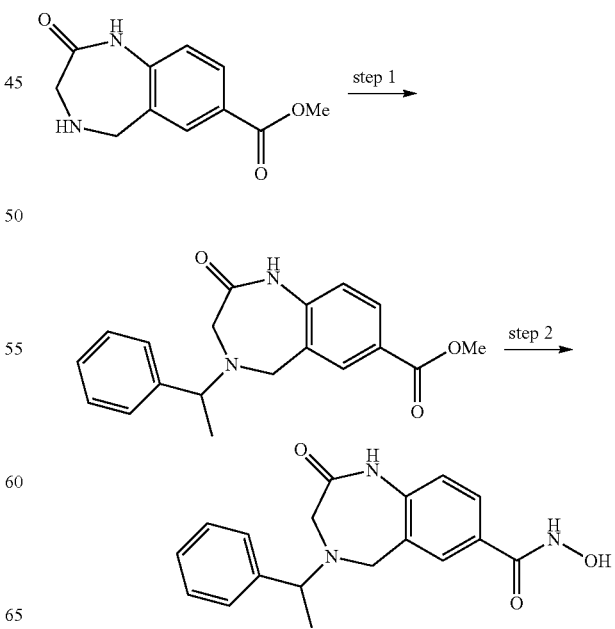 | (ES, m/z): 356 [M + H]$^+$ |

Example 71—Preparation of N-hydroxy-2-oxo-4-(1-phenylethyl)-2,3,4,5-tetrahydro-1H-benzo[e][1,4]diazepine-7-carboxamide

Step-1: Methyl 2-oxo-4-(1-phenylethyl)-2,3,4,5-tetrahydro-1H-benzo[e][1,4]diazepine-7-carboxylate

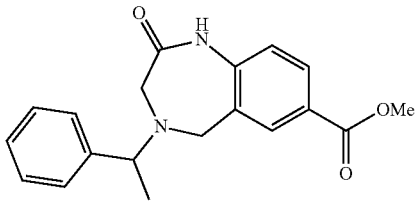 [SMILES: COC(=O)c1ccc2c(c1)CN(C(C)c1ccccc1)CC(=O)N2]

Into a 100-mL round-bottom flask, was placed methyl 2-oxo-2,3,4,5-tetrahydro-1H-1,4-benzodiazepine-7-carboxylate hydrochloride (100 mg, 0.39 mmol, 1 equiv), a solution of (1-bromoethyl)benzene (79 mg, 0.43 mmol, 1.1 equiv) in MeCN (5 mL) and DIEA (252 mg, 1.95 mmol, 5 equiv). The resulting solution was stirred overnight at 50° C. in an oil bath. The resulting mixture was concentrated under vacuum, diluted with H$_2$O (30 mL), and extracted with EtOAc (3×100 mL). The combined organic layers were concentrated and purified by silica gel chromatography (EtOAc/pet. ether, 1:1) to afford the title compound as a yellow solid (110 mg, 87% yield).

Step-2: N-Hydroxy-2-oxo-4-(1-phenylethyl)-2,3,4,5-tetrahydro-H-benzo[e][1,4]diazepine-7-carboxamide

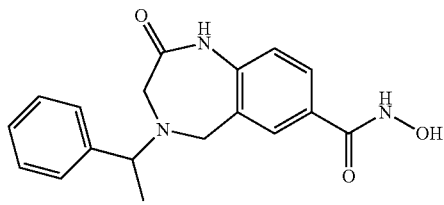 [SMILES: CC(c1ccccc1)N1CC(=O)Nc2ccc(C(=O)NO)cc2C1]

Into a 100-mL round-bottom flask, was placed a solution of methyl 2-oxo-4-(1-phenylethyl)-2,3,4,5-tetrahydro-1H-benzo[e][1,4]diazepine-7-carboxylate (110 mg, 0.34 mmol, 1 equiv) in THF/MeOH (2.5 mL, 4:1), NH$_2$OH (50% in water, 1 mL, 60 equiv), aq. 1N NaOH (0.5 mL, 2 equiv). The resulting solution was stirred for 6 h at room temperature. The crude product was purified by Prep-HPLC (Column: Xbridge RP C18 OBD, 5 μm, 19×50 mm; Mobile Phase A: Water/0.05% TFA; Mobile Phase B: MeCN/0.05% TFA; Flow rate: 30 mL/min; Gradient: 10% B to 53% B in 8 min; Detector, UV 254, 220 nm) to afford the title compound as a light yellow solid (19 mg, 16% yield). $^1$H-NMR (300 MHz, DMSO-d$_6$) δ(ppm): 11.22 (s, 1H), 10.60 (s, 1H), 7.77-7.75 (d, J=6.9 Hz, 2H), 7.45-7.41 (m, 5H), 7.16-7.13 (d, J=8.4 Hz, 1H), 4.16 (s, 3H) 3.52-3.44 (m, 2H), 1.55 (s, 3H). MS: (ES, m/z): 326 [M+H]$^+$.

Example 72—Preparation of N-Hydroxy-4-(4-methoxybenzyl)-2-oxo-2,3,4,5-tetrahydro-1H-benzo[e][1,4]diazepine-7-carboxamide

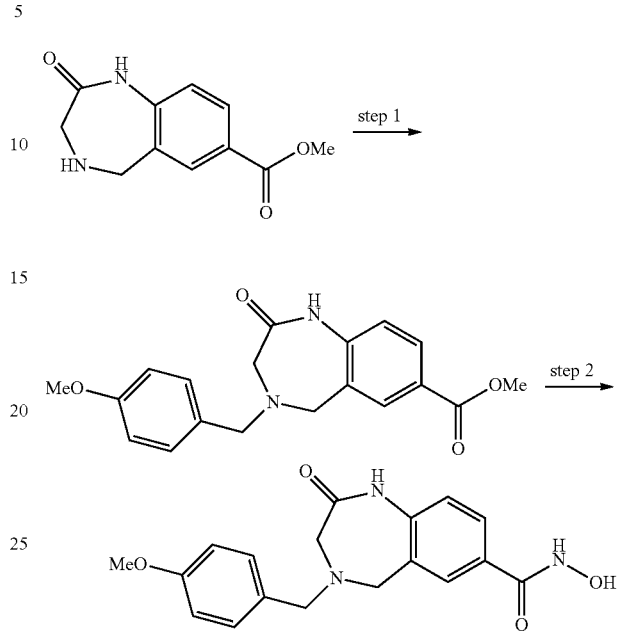

Step-1: Methyl 4-(4-methoxybenzyl)-2-oxo-2,3,4,5-tetrahydro-1H-benzo[e][1,4]diazepine-7-carboxylate

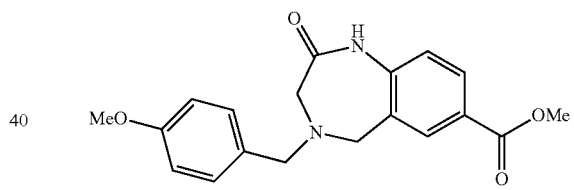

To a suspension of methyl 2-oxo-2,3,4,5-tetrahydro-1H-benzo[e][1,4]diazepine-7-carboxylate hydrochloride (45 mg, 0.175 mmol, 1 equiv) in 1,2-dichloroethane (1.8 mL) were added p-anisaldehyde (32 μL, 0.263 mmol, 1.5 equiv) and Et$_3$N (24 μL, 0.175 mmol, 1 equiv). The reaction mixture was stirred at room temperature for 1 h. Sodium triacetoxyborohydride (93 mg, 0.438 mmol, 2.5 equiv) was added to the reaction mixture and stirred at room temperature overnight. LCMS showed reaction completed. The reaction mixture was partitioned between CH$_2$Cl$_2$ and a saturated aqueous solution of NaHCO$_3$. The layers were separated. The organic layer was washed with brine, and dried over anhydrous Na$_2$SO$_4$. The solution was filtered, and concentrated. This crude material was purified by silica gel chromatography (Gradient 10-100% EtOAc/hexanes) to afford the title compound as a white solid (47.8 mg, 80% yield). MS: (ES, m/z): 341 [M+H]$^+$.

Step-2: N-Hydroxy-4-(4-methoxybenzyl)-2-oxo-2,3,4,5-tetrahydro-1H-benzo[e][1,4]diazepine-7-carboxamide

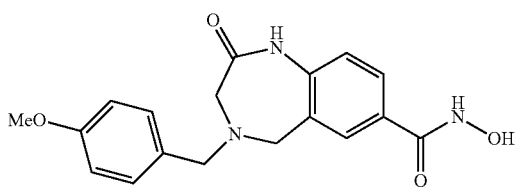 [SMILES: COc1ccc(CN2CC(=O)Nc3ccc(C(=O)NO)cc3C2)cc1]

To a solution of methyl 4-(4-methoxybenzyl)-2-oxo-2,3,4,5-tetrahydro-1H-benzo[e][1,4]diazepine-7-carboxylate (47 mg, 0.138 mmol, 1 equiv) in a MeOH/THF (1.4 mL, ¼) were added an aqueous 50% wt hydroxylamine solution (169 μL, 2.76 mmol, 20 equiv) and aqueous 2N NaOH solution (138 μL, 0.276 mmol, 2 equiv). The reaction was stirred at room temperature for 2 days, then was acidified with 2N HCl. The mixture was concentrated and the residue was purified by Prep-HPLC (Column: Xbridge RP C18 OBD, 5 μm, 19×50 mm; Mobile Phase A: Water/0.1% Formic Acid; Mobile Phase B: MeCN/0.1% Formic Acid; Flow rate: 23 mL/min; Gradient: 5% B to 50% B in 7 min) to afford the title compound as a yellow oil (23 mg, 49% yield). $^1$H-NMR (300 MHz, DMSO-$d_6$) δ(ppm): 11.10 (br s, 1H), 10.18 (s, 1H), 8.11 (s, 1H), 7.57-7.66 (m, 1H), 7.53 (s, 1H), 7.14-7.21 (m, 2H), 7.06 (d, J=8.5 Hz, 1H), 6.86 (br d, J=8.5 Hz, 2H), 3.65-3.75 (m, 5H), 3.56 (s, 2H), 3.22 (s, 2H). MS: (ES, m/z): 342 [M+H]$^+$.

Example 73—Preparation of N-Hydroxy-4-((4-methoxyphenyl)sulfonyl)-2-oxo-2,3,4,5-tetrahydro-1H-benzo[e][1,4]diazepine-7-carboxamide

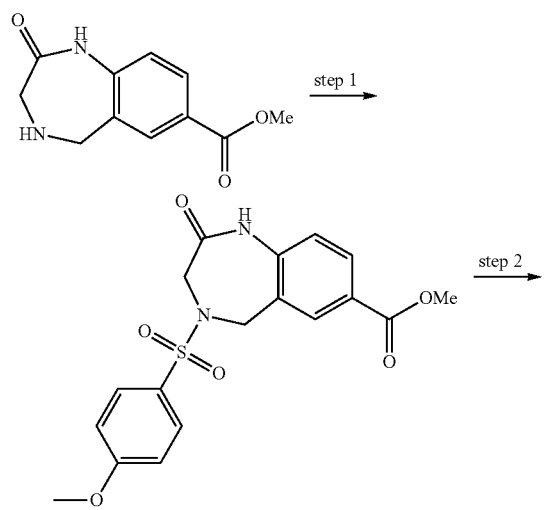

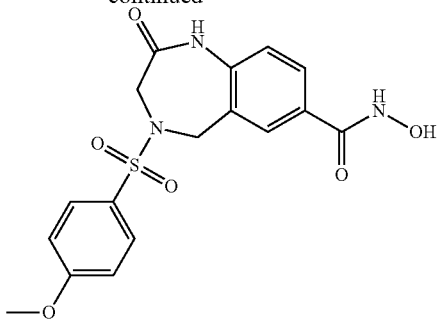

Step-1: Methyl 4-((4-methoxyphenyl)sulfonyl)-2-oxo-2,3,4,5-tetrahydro-1H-benzo[e][1,4]diazepine-7-carboxylate

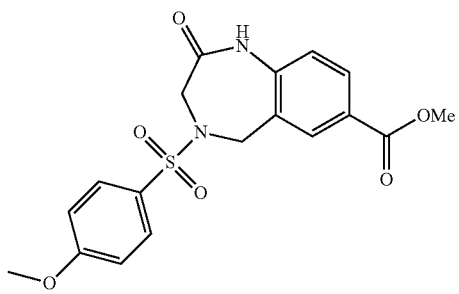 [SMILES: COC(=O)c1ccc2c(c1)CN(S(=O)(=O)c1ccc(OC)cc1)CC(=O)N2]

To a suspension of methyl 2-oxo-2,3,4,5-tetrahydro-1H-benzo[e][1,4]diazepine-7-carboxylate hydrochloride (35 mg, 0.136 mmol, 1 equiv) in THF (1.4 mL) were added DIEA (83 μL, 0.477 mmol, 3.5 equiv) and 4-methoxybenzene-1-sulfonyl chloride (34 mg, 0.164 mmol, 1.2 equiv). The reaction mixture was stirred at room temperature overnight. The reaction mixture was partitioned between EtOAc and a saturated aqueous solution of NaHCO$_3$. The layers were separated. The organic layer was washed with brine, and dried over anhydrous Na$_2$SO$_4$. The solution was filtered, and concentrated to afford the title compound as a white solid (52.7 mg) which was used without further purification. MS: (ES, m/z): 391 [M+H]$^+$.

Step-2: N-Hydroxy-4-((4-methoxyphenyl)sulfonyl)-2-oxo-2,3,4,5-tetrahydro-1H-benzo[e][1,4]diazepine-7-carboxamide

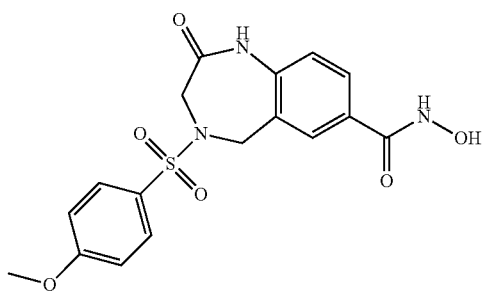 [SMILES: COc1ccc(S(=O)(=O)N2CC(=O)Nc3ccc(C(=O)NO)cc3C2)cc1]

To a solution of methyl 4-((4-methoxyphenyl)sulfonyl)-2-oxo-2,3,4,5-tetrahydro-1H-benzo[e][1,4]diazepine-7-carboxylate (49.4 mg, 0.127 mmol, 1 equiv) in a MeOH/THF (1.3 mL, 1:4) were added NH$_2$OH (50% in water, 155 μL, 2.53 mmol, 20 equiv) and aq. 2N NaOH solution (127 μL, 0.253 mmol, 2 equiv). The reaction was stirred at room temperature for 2 days. The reaction was acidified to pH 6 with 2N HCl and the solution was directly purified by Prep-HPLC (Column: Xbridge RP C18 OBD, 5 μm, 19×50 mm; Mobile Phase A: Water/0.1% Formic Acid; Mobile Phase B: MeCN/0.1% Formic Acid; Flow rate: 20 mL/min; Gradient: 5% B to 70% B in 7 min) to afford the title compound as a white solid (6.3 mg, 13% yield). $^1$H-NMR (300 MHz, DMSO-d$_6$) δ(ppm): 11.12 (br s, 1H), 10.17 (s, 1H), 9.01 (br s, 1H), 7.48-7.64 (m, 4H), 6.79-7 (m, 3H), 4.45 (s, 2H), 4.06 (s, 2H), 3.77 (s, 3H). MS: (ES, m/z): 392 [M+H]$^+$.

Example 74—Preparation of N-Hydroxy-2-oxo-4-phenyl-2,3,4,5-tetrahydro-1H-benzo[e][1,4]diazepine-7-carboxamide

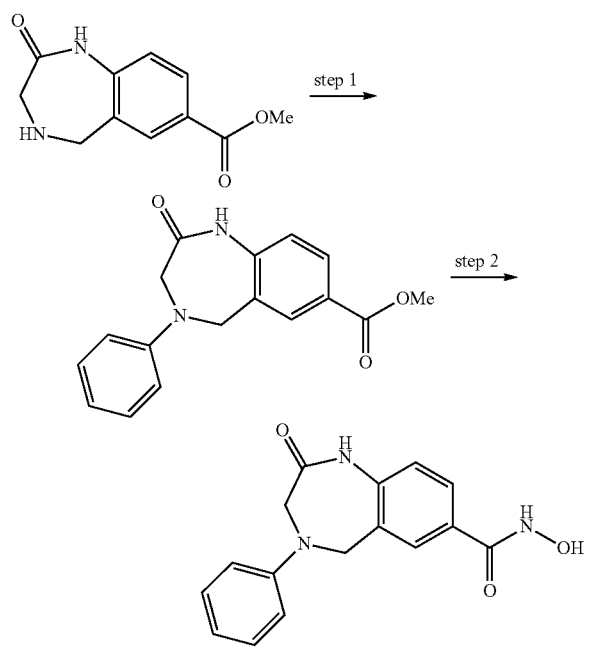

Step-1: Methyl 2-oxo-4-phenyl-2,3,4,5-tetrahydro-1H-benzo[e][1,4]diazepine-7-carboxylate

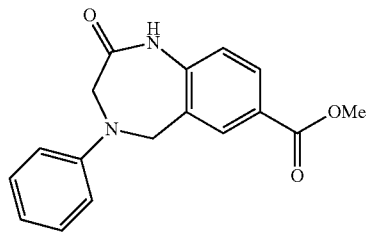 [SMILES: COC(=O)c1ccc2c(c1)CN(c1ccccc1)CC(=O)N2]

A mixture of methyl 2-oxo-2,3,4,5-tetrahydro-1H-benzo[e][1,4]diazepine-7-carboxylate (60 mg, 0.234 mmol, 1 equiv), bromobenzene (0.025 mL, 0.234 mmol, 1 equiv), sodium tert-butoxide (29.2 mg, 0.304 mmol, 1.3 equiv) and XPhos-Pd-G3 (10 mg, 0.012 mmol, 0.05 equiv) in 1,4-dioxane (2 mL) was heated at 80° C. overnight. The reaction was partitioned between water and CH$_2$Cl$_2$. The separated aqueous layer was extracted with CH$_2$Cl$_2$, and the combined organic layers were concentrated to afford the title compound as a pale yellow solid (11.9 mg, 17% yield). MS: (ES, m/z): 297 [M+H]$^+$.

Step-2: N-Hydroxy-2-oxo-4-phenyl-2,3,4,5-tetrahydro-H-benzo[e][1,4]diazepine-7-carboxamide

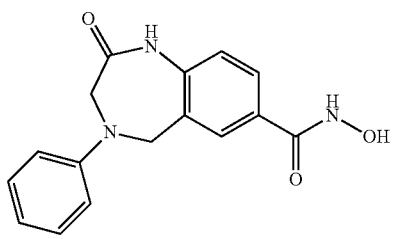 [SMILES: O=C1CN(c2ccccc2)Cc2cc(C(=O)NO)ccc2N1]

To a solution of methyl 2-oxo-4-phenyl-2,3,4,5-tetrahydro-1H-benzo[e][1,4]diazepine-7-carboxylate (11.9 mg, 0.040 mmol) in MeOH (125 μL) and THF (500 μL) was added NH$_2$OH (50% in water, 209 μL, 3.41 mmol, 85 equiv) and aq. 2N NaOH solution (40 μL, 0.080 mmol, 2 equiv). The reaction was stirred at room temperature for 1 h and was directly purified by Prep-HPLC (Column: Xbridge Prep C18 OBD, 5 μm, 19×50 mm; Mobile Phase A: Water/0.1% Formic Acid; Mobile Phase B: MeCN/0.1% Formic Acid; Flow rate: 20 mL/min; Gradient: 5% B to 85% B in 7 min) to afford the title compound (3.3 mg, 28% yield). $^1$H-NMR (300 MHz, DMSO-d$_6$) δ(ppm): 10.02 (s, 1H), 8.25 (s, 1H), 7.72-7.78 (m, 1H), 7.04-7.23 (m, 2H), 6.91-7.04 (m, 1H), 6.79 (m, 2H), 6.56-6.71 (m, 2H), 4.77 (s, 2H), 4.42 (s, 2H). MS: (ES, m/z): 298 [M+H]$^+$.

Example 75—Preparation of N-hydroxy-2-oxo-4-(piperidine-1-carbonyl)-2,3,4,5-tetrahydro-1H-benzo[e][1,4]diazepine-7-carboxamide

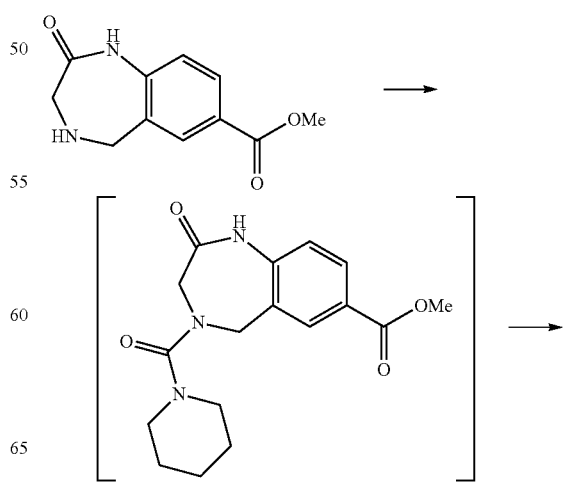

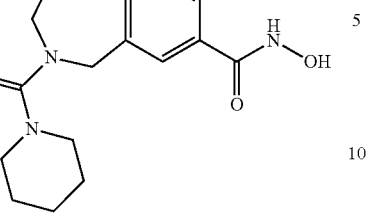

A 2-mL reaction vial was charged with ethyl 2-oxo-2,3,4,5-tetrahydro-1H-benzo[e][1,4]diazepine-7-carboxylate (11 mg, 0.05 mmol), bis(2,5-dioxopyrrolidin-1-yl) carbonate (14 mg, 0.055 mmol), MeCN (500 iμL) and Et₃N (41.8 μL, 0.3 mmol). The vial was sealed and shaken at room temperature for 1 h. The solvent was removed under a stream of nitrogen. DMA (500 μL) and piperidine (neat, 29.6 μL, 0.3 mmol) were added and the vial was shaken at room temperature overnight. The mixture was diluted with brine (500 μL) and extracted with EtOAc (2×600 μL). The combined organic layers was dried under a stream of nitrogen. A solvent mixture of THF/MeOH (3:1, 180 iμL) was added to the vial and it was shaken at 50° C. for 15 min to dissolve the residue. NH₂OH (50% in water, 125 μL) was added followed by aq. 1N NaOH (85 μL) and the vial was sealed and shaken at room temperature overnight. The solvent was evaporated under reduce pressure. The residue was dissolved in DMSO (500 μL), then purified by HPLC to afford the title compound (1.3 mg, 7.8% yield). MS: (ES, m/z): 333 [M+H]⁺.

Example 76—Preparation of N-hydroxy-4-(4-methoxybenzyl)-1-methyl-2-oxo-2,3,4,5-tetrahydro-1H-benzo[e][1,4]diazepine-7-carboxamide

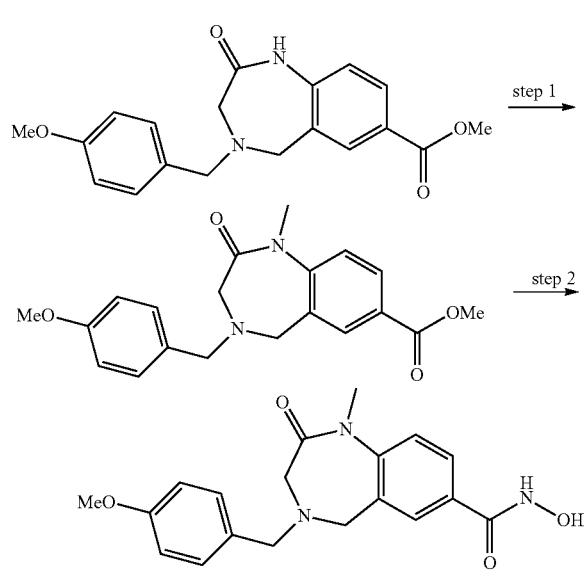

Step-1: Methyl 4-(4-methoxybenzyl)-1-methyl-2-oxo-2,3,4,5-tetrahydro-1H-benzo[e][1,4]diazepine-7-carboxylate

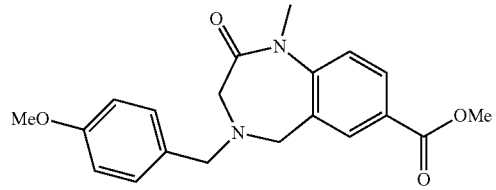 [SMILES: COC(=O)c1ccc2c(c1)CN(Cc1ccc(OC)cc1)CC(=O)N2C]

To a cooled solution of methyl 4-(4-methoxybenzyl)-2-oxo-2,3,4,5-tetrahydro-1H-benzo[e][1,4]diazepine-7-carboxylate (56.5 mg, 0.166 mmol, 1 equiv) in DMF (1.3 mL) was added sodium hydride (10.6 mg, 0.266 mmol, 1.6 equiv). After stirring for 15 minutes in cooling bath, the bath was removed and the reaction was stirred at room temperature for 15 minutes. Iodomethane (11.4 μL, 0.183 mmol, 1.1 equiv) was added and the reaction was stirred at room temperature overnight. To the reaction mixture was added a saturated aqueous solution of NaHCO₃ and water. The resulting solution was extracted with CH₂Cl₂ and the organic layer was washed with brine, dried over anhydrous Na₂SO₄, filtered, and concentrated to afford the title compound (58 mg) which was used without further purification. MS: (ES, m/z): 355 [M+H]⁺.

Step-2: N-Hydroxy-4-(4-methoxybenzyl)-1-methyl-2-oxo-2,3,4,5-tetrahydro-1H-benzo[e][1,4]diazepine-7-carboxamide

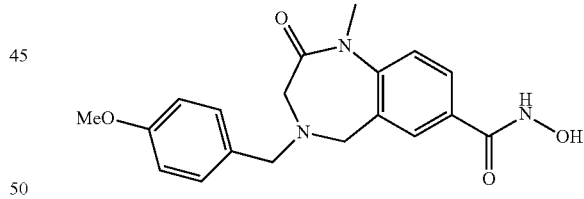

To a solution of methyl 4-(4-methoxybenzyl)-1-methyl-2-oxo-2,3,4,5-tetrahydro-1H-benzo[e][1,4]diazepine-7-carboxylate (58 mg, 0.16 mmol, 1 equiv) in MeOH (300 μL) and THF (1.2 mL) was added NH₂OH (50% in water, 852 μL, 13.9 mmol, 85 equiv) and aq. 2N NaOH solution (164 μL, 0.327 mmol, 2 equiv). The reaction was stirred at room temperature for 2 h and was directly purified by Prep-HPLC (Column: Xbridge RP C18 OBD, 5 μm, 19×50 mm; Mobile Phase A: Water/0.1% Formic Acid; Mobile Phase B: MeCN/0.1% Formic Acid; Flow rate: 20 mL/min; Gradient: 2% B to 50% B in 7 min) to afford the title compound (10.3 mg, 17% yield over 2 steps). ¹H-NMR (300 MHz, DMSO-d₆) δ(ppm): 11.21 (br s, 1H), 9.01 (br s, 1H), 7.71-7.77 (m, 1H), 7.62-7.65 (m, 1H), 7.38 (d, J=8.5 Hz, 1H), 7.21 (d, J=8.5 Hz, 2H), 6.85 (d, J=8.5 Hz, 2H), 3.68 (s, 3H), 3.54 (s, 2H), 3.48 (s, 2H), 3.24 (s, 3H). MS: (ES, m/z): 356 [M+H]⁺.

Example 77—Preparation of N-Hydroxy-4-(4-methoxybenzyl)-2,3,4,5-tetrahydro-1H-benzo[e][1,4]diazepine-7-carboxamide

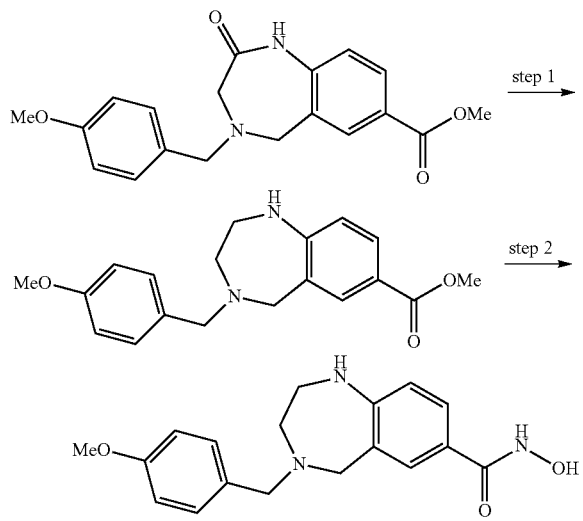

Step-1: Methyl 4-(4-methoxybenzyl)-2,3,4,5-tetrahydro-1H-benzo[e][1,4]diazepine-7-carboxylate

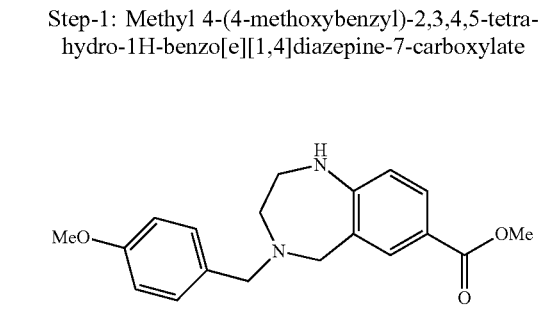

To a suspension of methyl 4-(4-methoxybenzyl)-2-oxo-2,3,4,5-tetrahydro-1H-benzo[e][1,4]diazepine-7-carboxylate (101 mg, 0.298 mmol, 1 equiv) in toluene (3 mL) was added borane-methyl sulfide complex (164 µL, 0.328 mmol, 1.1 equiv). The mixture was heated to reflux for 5 h, then cooled to room temperature. Methanol was added and the reaction was stirred for 10 min at room temperature and then for 15 min at reflux. The reaction mixture was concentrated and purified by silica gel chromatography (Gradient 0-5% MeOH/CH$_2$Cl$_2$) to afford the title compound (83 mg, 85% yield). MS: (ES, m/z): 327 [M+H]$^+$.

Step-2: N-Hydroxy-4-(4-methoxybenzyl)-2,3,4,5-tetrahydro-1H-benzo[e][1,4]diazepine-7-carboxamide

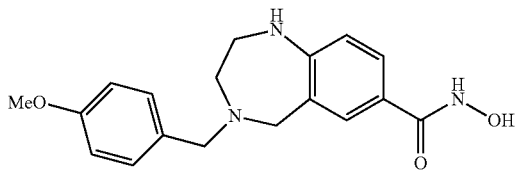 [SMILES: COc1ccc(CN2CCNc3ccc(C(=O)NO)cc3C2)cc1]

To a solution of methyl 4-(4-methoxybenzyl)-2,3,4,5-tetrahydro-1H-benzo[e][1,4]diazepine-7-carboxylate (83 mg, 0.254 mmol, 1 equiv) in MeOH (250 µL) and THF (1 mL) was added NH$_2$OH (50% in water, 1.33 mL, 21.6 mmol, 85 equiv) and aq. 2N NaOH solution (254 µL, 0.509 mmol, 2 equiv). The reaction was stirred at room temperature for 3 h and was directly purified by Prep-HPLC (Column: Xbridge RP C18 OBD, 5 µm, 19×50 mm; Mobile Phase A: Water/0.1% Formic Acid; Mobile Phase B: MeCN/0.1% Formic Acid; Flow rate: 20 mL/min; Gradient: 2% B to 50% B in 7 min) to afford the title compound (11.3 mg, 14% yield). $^1$H-NMR (300 MHz, DMSO-d$_6$) δ(ppm): 8.39 (br s, 1H), 7.52-7.61 (m, 2H), 7.41 (br d, J=8.2 Hz, 2H), 7 (d, J=8.2 Hz, 2H), 6.90 (d, J=8.2 Hz, 1H), 4.20 (br d, J=9.1 Hz, 2H), 3.82 (s, 3H), 3.25-3.42 (m, 4H). MS: (ES, m/z): 328 [M+H]$^+$.

Example 78—Preparation of N-Hydroxy-4-(4-methoxybenzyl)-1-methyl-2,3,4,5-tetrahydro-1H-benzo[e][1,4]diazepine-7-carboxamide

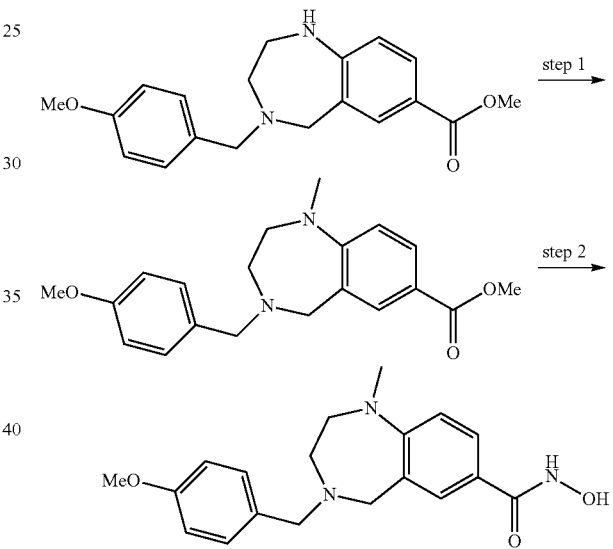

Step-1: Methyl 4-(4-methoxybenzyl)-1-methyl-2,3,4,5-tetrahydro-1H-benzo[e][1,4]diazepine-7-carboxylate

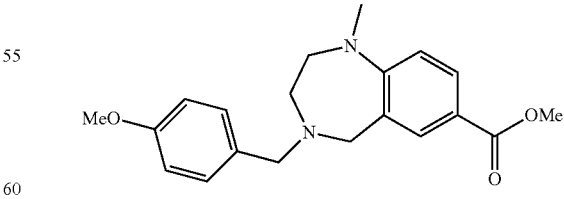

To a solution of methyl 4-(4-methoxybenzyl)-2,3,4,5-tetrahydro-1H-benzo[e][1,4]diazepine-7-carboxylate (60.7 mg, 0.186 mmol, 1 equiv) in MeCN (2 mL) was added Cs$_2$CO$_3$ (60.6 mg, 0.186 mmol, 1 equiv), and methyl iodide (0.014 mL, 0.223 mmol, 1.2 equiv). The reaction was stirred at room temperature for 7 h. Water was added to the reaction and the layers were separated. The aqueous layer was extracted with CH$_2$Cl$_2$. The combined organic layers were dried over anhydrous Na$_2$SO$_4$, filtered, and concentrated. Purification by silica gel chromatography afforded the title compound (34 mg, 54% yield). MS: (ES, m/z): 341 [M+H]$^+$.

Step-2: N-Hydroxy-4-(4-methoxybenzyl)-1-methyl-2,3,4,5-tetrahydro-1H-benzo[e][1,4]diazepine-7-carboxamide

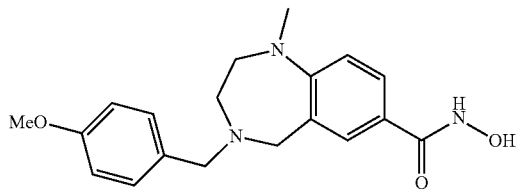 [SMILES: COc1ccc(CN2CCN(C)c3ccc(C(=O)NO)cc3C2)cc1]

To a solution of methyl 4-(4-methoxybenzyl)-1-methyl-2,3,4,5-tetrahydro-1H-benzo[e][1,4]diazepine-7-carboxylate (34.1 mg, 0.100 mmol, 1 equiv) in MeOH (250 μL) and THF (1 mL) was added NH$_2$OH (50% in water, 522 μL, 8.51 mmol, 85 equiv) and aq. 2N NaOH solution (100 μL, 0.2 mmol, 2 equiv). The reaction was stirred at room temperature overnight and concentrated. Purification by Prep-HPLC (Column: Xbridge RP C18 OBD, 5 μm, 19×50 mm; Mobile Phase A: Water/0.05% formic acid; Mobile Phase B: MeCN/0.05% formic acid; Flow rate: 23 mL/min; Gradient: 0% B to 35% B in 8 min; Detector, UV 254, 220 nm) afforded the title compound. MS: (ES, m/z): 342 [M+H]$^+$.

Example 79—Preparation of 2-benzyl-N-hydroxy-3,4-dihydro-2H-benzo[b][1,4,5]oxathiazepine-8-carboxamide 1,1-dioxide

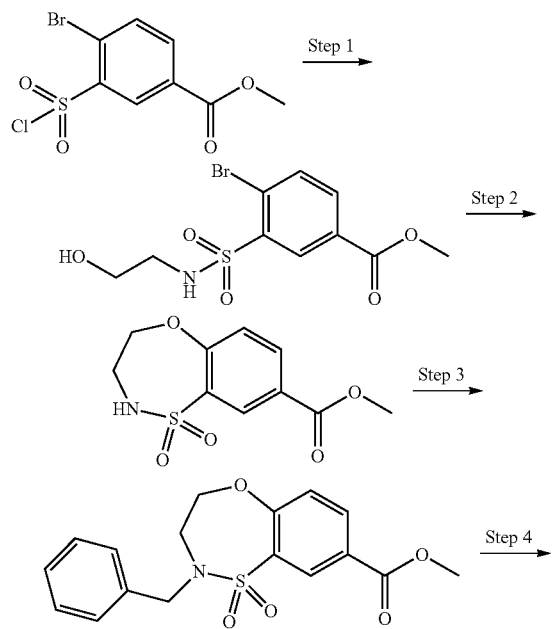

-continued

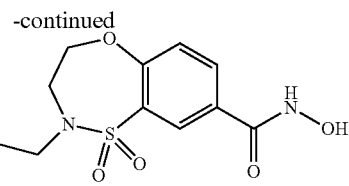

Step-1: Methyl 4-bromo-3-(N-(2-hydroxyethyl)sulfamoyl)benzoate

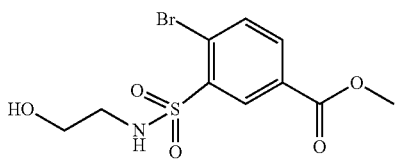 [SMILES: COC(=O)c1ccc(Br)c(S(=O)(=O)NCCO)c1]

Into a 100-mL round-bottom flask, was placed methyl 4-bromo-3-(chlorosulfonyl)benzoate (100 mg, 0.32 mmol, 1 equiv), THF (2 mL), water (0.5 mL), magnesium oxide (0.06 g) and 2-aminoethan-1-ol (22 mg, 0.36 mmol, 1.1 equiv). The resulting mixture was stirred overnight at room temperature concentrated under vacuum. The residue was diluted with H$_2$O (50 mL). The resulting solution was extracted with EtOAc (3×50 mL) and dried over anhydrous sodium sulfate. The solid was filtered out. The filtrate was concentrated under vacuum to afford the title compound as a white solid (57 mg, 53% yield) which was used without further purification. MS: (ES, m/z): 336 [M−H]$^-$.

Step-2: Methyl 3,4-dihydro-2H-benzo[b][1,4,5]oxathiazepine-8-carboxylate 1,1-dioxide

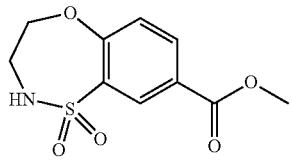 [SMILES: COC(=O)c1ccc2c(c1)S(=O)(=O)NCCO2]

Into a 100-mL round-bottom flask, was placed methyl 4-bromo-3-(N-(2-hydroxyethyl)sulfamoyl)benzoate (350 mg, 1.03 mmol, 1 equiv), MeOH (2 mL), 1-methyl-2-pyrrolidinone (10 mL) and sodium methylate (70 mg, 1.30 mmol, 1.25 equiv). The resulting mixture was stirred 1 h at room temperature. To the above mixture was added CuI (16 mg, 0.08 mmol, 0.08 equiv). The resulting solution was stirred overnight at 110° C. The resulting mixture was washed with H$_2$O (30 mL), extracted with CH$_2$Cl$_2$ (2×30 mL) and dried over anhydrous sodium sulfate. The solid was filtered. The filtrate was concentrated and the residue was purified by silica gel chromatography (EtOAc/pet. ether, 1:3) to afford the title compound as a yellow oil (250 mg, 93% yield). MS: (ES, m/z): 256 [M−H]$^-$.

Step-3: Methyl 2-benzyl-3,4-dihydro-2H-benzo[b][1,4,5]oxathiazepine-8-carboxylate 1,1-dioxide

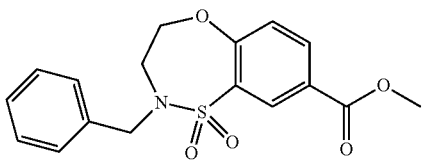 [SMILES: COC(=O)c1ccc2c(c1)S(=O)(=O)N(Cc1ccccc1)CCO2]

Into a 100-mL round-bottom flask, was placed methyl 3,4-dihydro-2H-benzo[b][1,4,5]oxathiazepine-8-carboxylate 1,1-dioxide (50 mg, 0.19 mmol, 1 equiv), DMF (3 mL), sodium hydride (9 mg, 0.38 mmol, 1.9 equiv), (bromomethyl)benzene (48 mg, 0.28 mmol, 1.4 equiv). The resulting mixture was stirred for 2 h at room temperature and then diluted with $H_2O$ (20 mL). The resulting solution was extracted with EtOAc (2×40 mL), washed with $H_2O$ (2×30 mL), and dried over anhydrous sodium sulfate. The solid was filtered out. The filtrate was concentrated under vacuum to afford the title compound as a yellow oil (87 mg) which was used without further purification.

Step-4: 2-Benzyl-N-hydroxy-3,4-dihydro-2H-benzo[b][1,4,5]oxathiazepine-8-carboxamide 1,1-dioxide

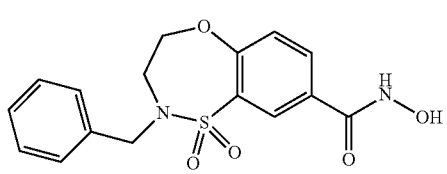 [SMILES: O=C(NO)c1ccc2c(c1)S(=O)(=O)N(Cc1ccccc1)CCO2]

Into a 100-mL round-bottom flask, was placed methyl 2-benzyl-3,4-dihydro-2H-benzo[b][1,4,5]oxathiazepine-8-carboxylate 1,1-dioxide (87 mg, 0.25 mmol, 1 equiv), THF (2 mL), MeOH (0.5 mL), aq. 1N NaOH (0.4 mL) and $NH_2OH$ (50% in water, 800 mg, 24.22 mmol). The resulting solution was stirred for 1 h at room temperature. The pH value of the solution was adjusted to 3 with 1N HCl. The crude product was purified by Prep-HPLC (Column: Xbridge Prep C18 OBD, 5 μm, 19×50 mm; Mobile Phase A: Water/0.3% formic acid; Mobile Phase B: MeCN; Flow rate: 23 mL/min; Gradient: 18% B to 59% B in 6 min, up to 100% B in 0.1 min, hold 0.9 min; Detector, UV 254, 220 nm) to afford the title compound as a white solid (9.6 mg, 11% yield). $^1$H-NMR (400 MHz, DMSO-$d_6$) δ(ppm): 8.18 (d, 1H), 7.80-7.97 (q, 1H), 7.39-7.30 (m, 6H), 4.29-4.27 (t, 2H, J=4.0 Hz), 4.20 (s, 2H), 3.56-3.54 (t, 2H, J=4.4 Hz). MS: (ES, m/z): 349[M+H]$^+$.

Example 80—Preparation of N8-hydroxy-N4-(4-methoxyphenyl)-2,3-dihydrobenzo[f][1,4]oxazepine-4,8(5H)-dicarboxamide

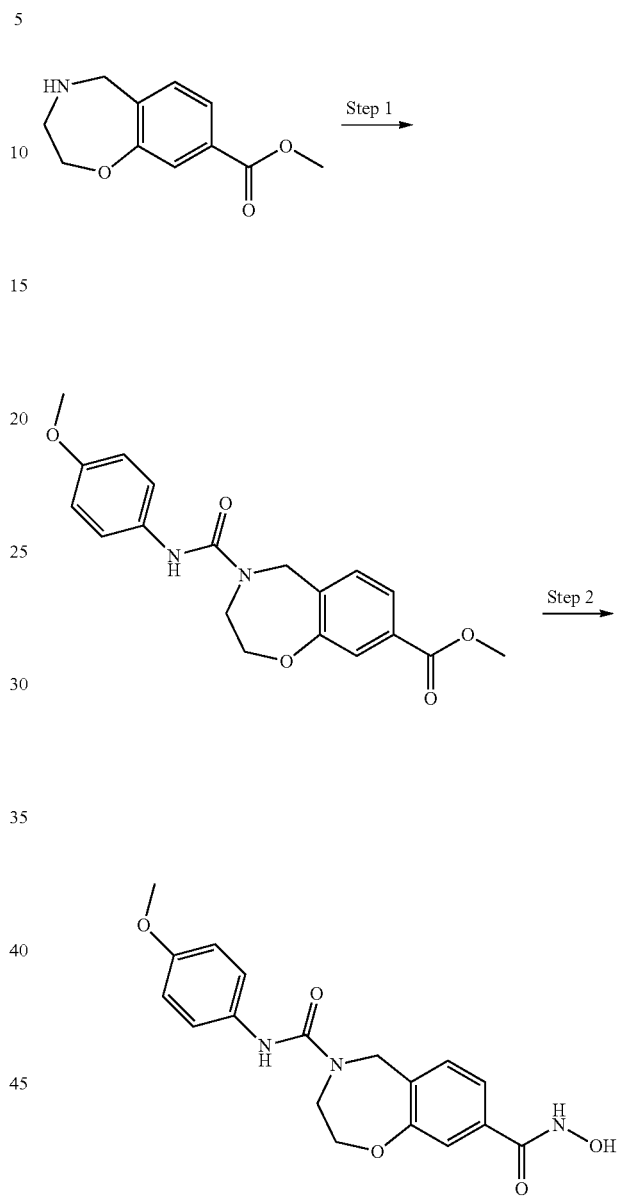

TABLE 35

The following compound was prepared according to the method of Example 79.

| Structure | Found M + H | $^1$H-NMR (400 MHz, DMSO-$d_6$) δ(ppm) |
|---|---|---|
| 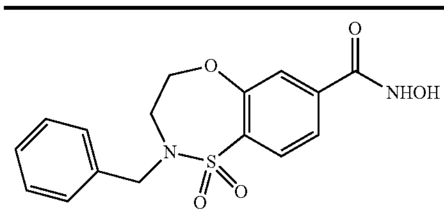 | (ES, m/z): 349 [M + H]$^+$ | 11.40 (s, 1H), 9.30 (s, 1H), 7.86 (d, 1H), 7.72-7.69 (m, 1H), 7.60 (d, 1H), 7.39-7.31 (m, 5H), 4.28-4.18 (m, 4H), 3.55-3.53 (t, 2H, J = 4.0 Hz) |

225

Step-1: Methyl 4-((4-methoxyphenyl)carbamoyl)-2, 3,4,5-tetrahydrobenzo[f][1,4]oxazepine-8-carboxylate

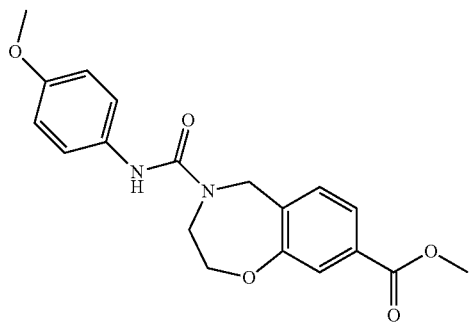 [SMILES: COC(=O)c1ccc2c(c1)OCCN(C(=O)Nc1ccc(OC)cc1)C2]

A 2 mL reaction vial was charged with methyl 2,3,4,5-tetrahydrobenzo[f][1,4]oxazepine-8-carboxylate (0.2 M in 1,2-dichloroethane, 150 µL, 30 µmol) and triethylamine (neat, 10 µL, 71 µmol). 1-Isocyanato-4-methoxybenzene (0.2 M in dioxane, 195 µL, 39 µmol) was added and the vial was sealed and shaken at room temperature overnight. The reaction mixture was diluted with brine (500 µL) and extracted with EtOAc (2×500 µL). The combined organic layers were evaporated to dryness under reduced pressure.

Step-2: N8-Hydroxy-N4-(4-methoxyphenyl)-2,3-dihydrobenzo[f][1,4]oxazepine-4,8(5H)-dicarboxamide

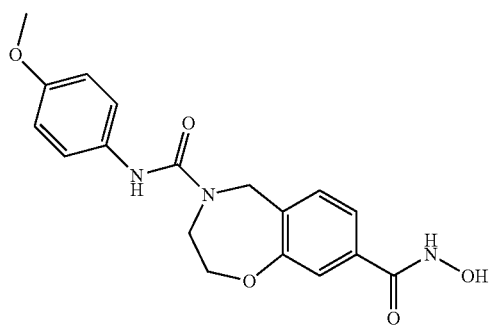 [SMILES: COc1ccc(NC(=O)N2CCOc3cc(C(=O)NO)ccc3C2)cc1]

Mixed solvent of THF/MeOH (3:1, 180 µL) was added to the vial containing methyl 4-((4-methoxyphenyl)carbamoyl)-2,3,4,5-tetrahydrobenzo[f][1,4]oxazepine-8-carboxylate and it was shaken at 50° C. for 15 min to dissolve the residue. NH₂OH (50% in water, 125 µL) was added, followed by aq. 1N NaOH (85 µL) and the vial was sealed and shaken at room temperature overnight. The solvent was evaporated under reduce pressure and the residue was dissolved in DMSO (500 µL), then purified by HPLC to afford the title compound (9.3 mg, 87% yield). MS: (ES, m/z): 358 [M+H]⁺.

226

TABLE 36

The following compound was prepared by the parallel synthesis method of Example 80.

| Structure | Found M + H (ES) |
|---|---|
| 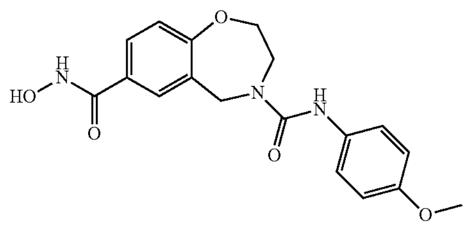 [SMILES: COc1ccc(NC(=O)N2CCOc3ccc(C(=O)NO)cc3C2)cc1] | 358 |
| 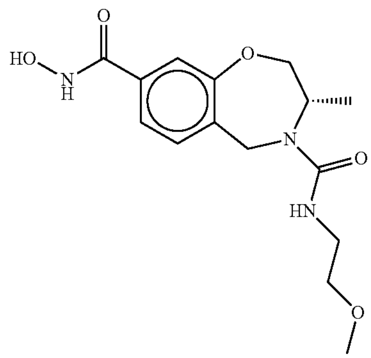 | 324 |
| 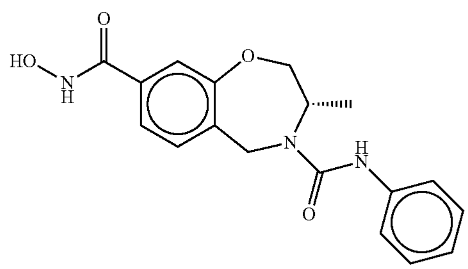 | 342 |

Example 81—Preparation of N-hydroxy-4-((4-methoxyphenyl)sulfonyl)-2,3,4,5-tetrahydrobenzo[f][1,4]oxazepine-8-carboxamide

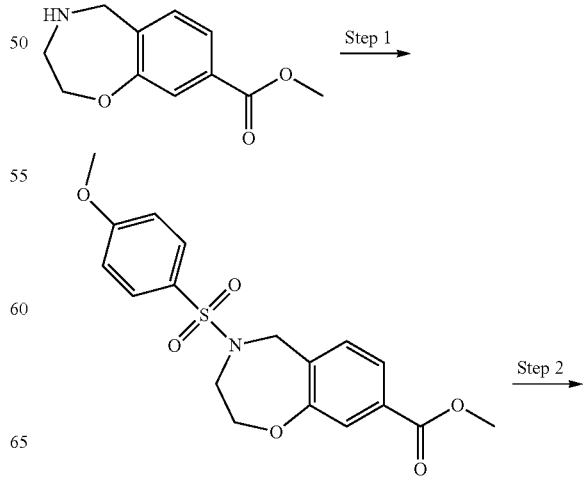

-continued

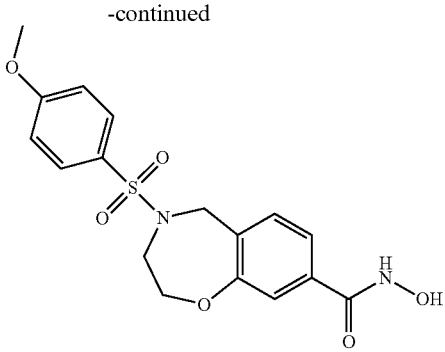

Step-1: Methyl 4-((4-methoxyphenyl)sulfonyl)-2,3,4,5-tetrahydrobenzo[f][1,4]oxazepine-8-carboxylate

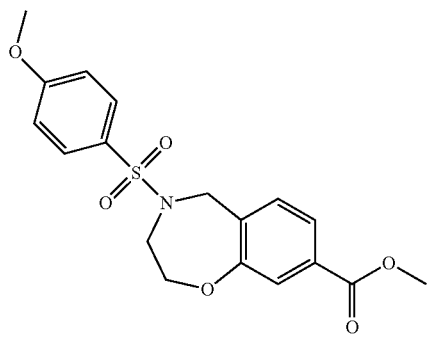 [SMILES: COC(=O)c1ccc2c(c1)OCCN(S(=O)(=O)c1ccc(OC)cc1)C2]

A 2 mL reaction vial was charged with methyl 2,3,4,5-tetrahydrobenzo[f][1,4]oxazepine-8-carboxylate (0.2 M in 1,2-dichloroethane, 150 µL, 30 µmol) and Et$_3$N (neat, 10 µL, 71 µmol). 4-Methoxybenzenesulfonyl chloride (0.2 M in 1,2-dichloroethane, 195 µL, 39 µmol) was added and the vial was sealed and shaken at room temperature overnight. The reaction mixture was diluted with brine (500 µL) and extracted with EtOAc (2×500 µL). The combined organic layers were evaporated to dryness under reduced pressure.

Step-2: N-Hydroxy-4-((4-methoxyphenyl)sulfonyl)-2,3,4,5-tetrahydrobenzo[f][1,4]oxazepine-8-carboxamide

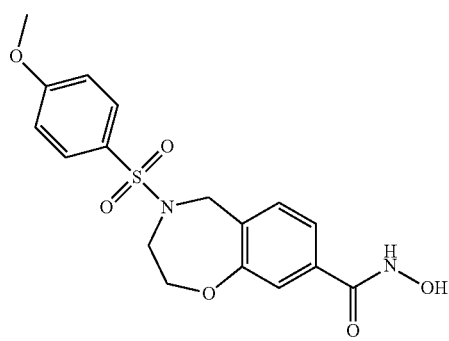 [SMILES: COc1ccc(S(=O)(=O)N2CCOc3cc(C(=O)NO)ccc3C2)cc1]

Mixed solvent of THF/MeOH (3:1, 180 µL) was added to the vial containing methyl 4-((4-methoxyphenyl)sulfonyl)-2,3,4,5-tetrahydrobenzo[f][1,4]oxazepine-8-carboxylate and it was shaken at 50° C. for 15 min to dissolve the residue. NH$_2$OH (50% in water, 125 µL) was added followed by aq. 1N NaOH (85 µL) and the vial was sealed and shaken at room temperature overnight. The solvent was evaporated under reduce pressure and the residue was dissolved in DMSO (500 µL) then purified by HPLC to afford the title compound (9.1 mg, 80% yield). MS: (ES, m/z): 379 [M+H]$^+$.

TABLE 37

The following compound was prepared by the parallel synthesis method of Example 81.

| Structure | Found M + H (ES) |
| --- | --- |
| 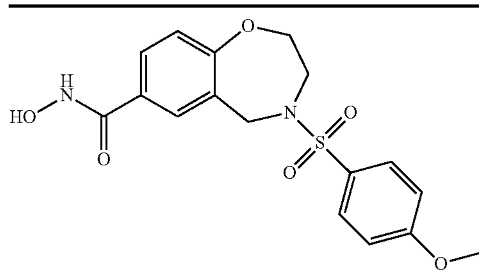 | 379 |
| 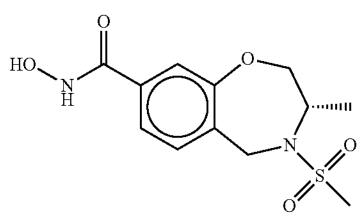 | 301 |
| 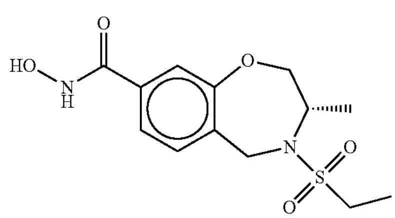 | 315 |
| 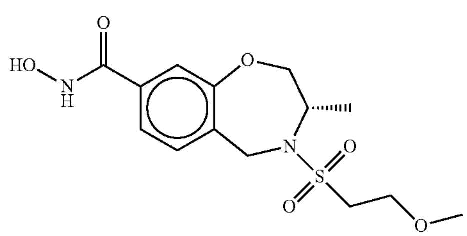 | 345 |
| 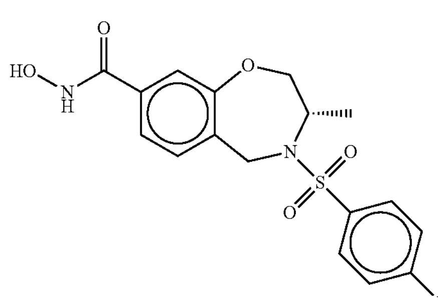 | 381 |

Example 82—Preparation of 4-((1H-benzo[d]imidazol-2-yl)methyl)-N-hydroxy-2,3,4,5-tetrahydrobenzo[f][1,4]oxazepine-8-carboxamide

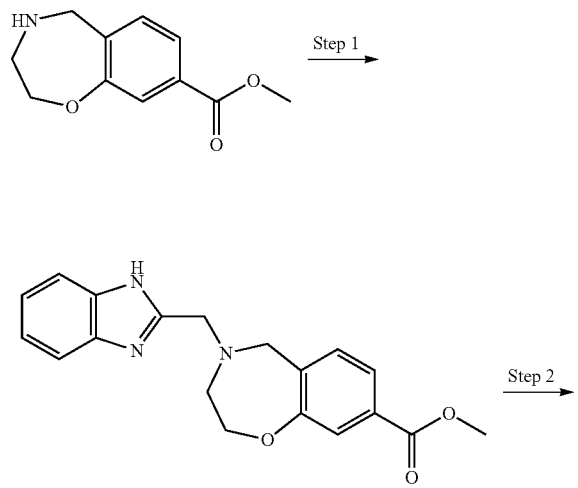

Step-1: Methyl 4-((1H-benzo[d]imidazol-2-yl)methyl)-2,3,4,5-tetrahydrobenzo[f][1,4]oxazepine-8-carboxylate

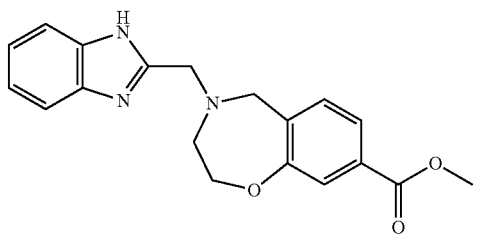 [SMILES: COC(=O)c1ccc2c(c1)OCCN(Cc1nc3ccccc3[nH]1)C2]

A 2 mL reaction vial was charged with methyl 2,3,4,5-tetrahydrobenzo[f][1,4]oxazepine-8-carboxylate (0.2M in N,N-dimethylacetamide, 200 μL, 40 μmol) and 2-(chloromethyl)-1H-benzo[d]imidazole (0.2M in N,N-dimethylacetamide, 200 μL, 40 μmol). Solid K₂CO₃ (22 mg, 160 μmol) was added and the vial was sealed and shaken at room temperature overnight. The reaction mixture was diluted with brine (500 μL) and extracted with EtOAc (2×500 μL). The combined organic layers were evaporated to dryness under reduced pressure.

Step-2: 4-((1H-benzo[d]imidazol-2-yl)methyl)-N-hydroxy-2,3,4,5-tetrahydrobenzo[f][1,4]oxazepine-8-carboxamide

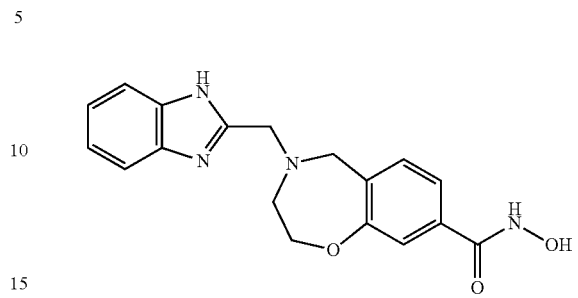

Mixed solvent of THF/MeOH (3:1, 180 μL) was added to the vial containing methyl 4-((1H-benzo[d]imidazol-2-yl)methyl)-2,3,4,5-tetrahydrobenzo[f][1,4]oxazepine-8-carboxylate and it was shaken at 50° C. for 15 min to dissolve the residue. NH₂OH (50% in water, 125 μL) was added followed by aq. 1N NaOH (75 μL) and the vial was sealed and shaken at room temperature overnight. The solvent was evaporated under reduce pressure and the residue was dissolved in DMSO (500 μL) then purified by HPLC to afford the title compound (9.8 mg, 72% yield). MS: (ES, m/z): 339 [M+H]⁺.

TABLE 38

The following compounds were prepared by the parallel synthesis method of Example 82.

| Structure | Found M + H (ES) |
|---|---|
| 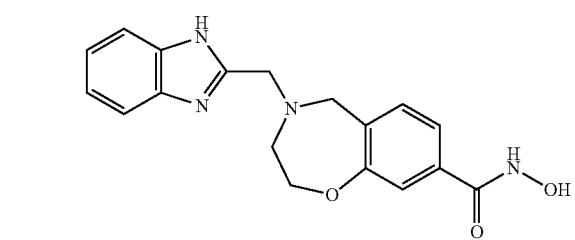 [SMILES: O=C(NO)c1ccc2c(c1)OCCN(Cc1nc3ccccc3[nH]1)C2] | 339 |
| | 397 |
| | 397 |

TABLE 38-continued
The following compounds were prepared by the parallel synthesis method of Example 82.
| Structure | Found M + H (ES) |
|---|---|
|  | 343 |
| 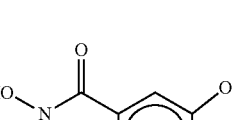 | 343 |
|  | 329 |
| 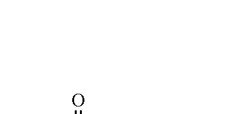 | 329 |
| 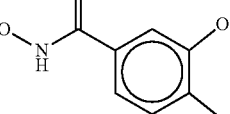 | 295 |
| 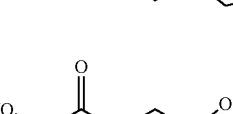 | 345 |
| 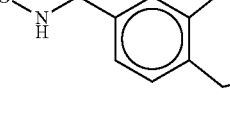 | 350 |
| 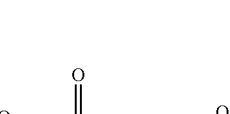 | 321 |
| 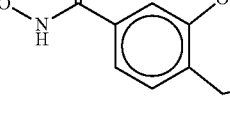 | 251 |
| 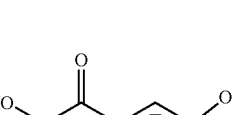 | 265 |
| 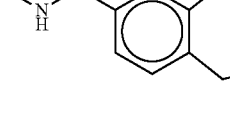 | 279 |
| 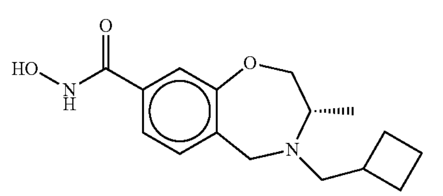 | 291 |
| 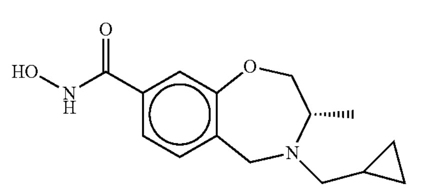 | 277 |

TABLE 38-continued
The following compounds were prepared by the parallel synthesis method of Example 82.
| Structure | Found M + H (ES) |
|---|---|
| 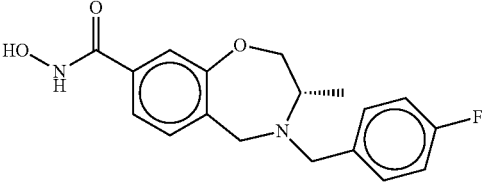 | 331 |
| 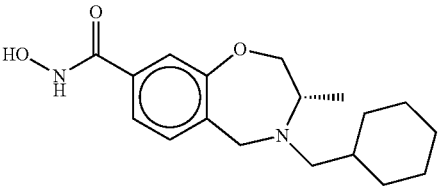 | 319 |
| 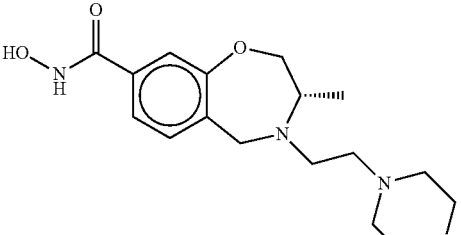 | 336 |
| 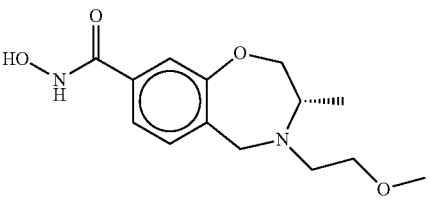 | 281 |
| 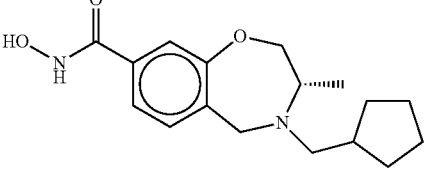 | 305 |
| 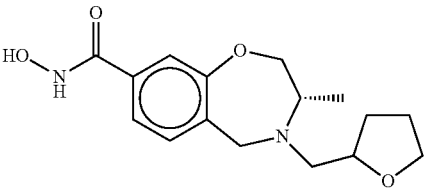 | 307 |
| 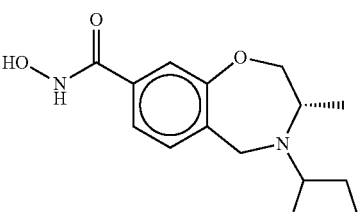 | 291 |
Example 83—Preparation of 4-(1H-benzo[d]imidazol-2-yl)-N-hydroxy-2,3,4,5-tetrahydrobenzo[f][1,4]oxazepine-8-carboxamide
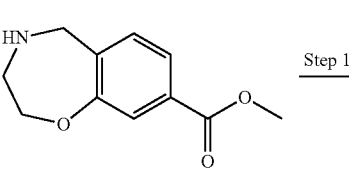 Step 1 →
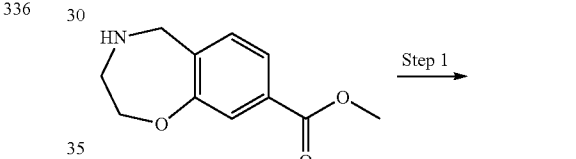 Step 2 →
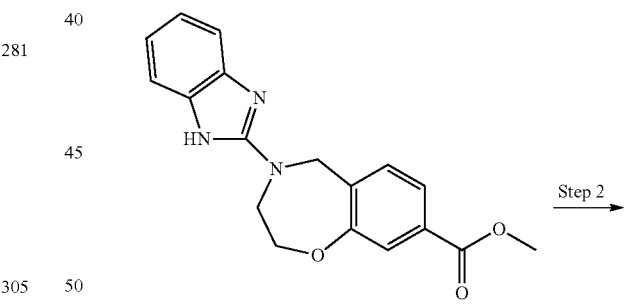

235

Step-1: Methyl 4-(1H-benzo[d]imidazol-2-yl)-2,3,4,5-tetrahydrobenzo[f][1,4]oxazepine-8-carboxylate

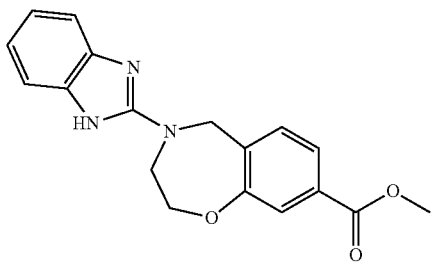 [SMILES: COC(=O)c1ccc2c(c1)OCCN(c1nc3ccccc3[nH]1)C2]

A 2 mL reaction vial was charged with methyl 2,3,4,5-tetrahydrobenzo[f][1,4]oxazepine-8-carboxylate (0.2M in 1-butanol, 200 μL, 40 μmol) and 2-bromo-1H-benzo[d]imidazole (0.2M in 1-butanol, 240 μL, 48 μmol). Solid $KH_2PO_4$ (21.8 mg, 160 μmol) was added and the vial was sealed and shaken at 110° C. overnight. The solvent was removed under reduced pressure and to the residue is added brine (500 μL). The mixture was extracted with EtOAc (2×500 μL) and the combined organic layers were evaporated to dryness under reduced pressure.

Step-2: 4-(1H-benzo[d]imidazol-2-yl)-N-hydroxy-2,3,4,5-tetrahydrobenzo[f][1,4]oxazepine-8-carboxamide

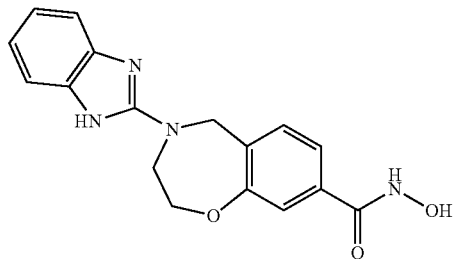 [SMILES: O=C(NO)c1ccc2c(c1)OCCN(c1nc3ccccc3[nH]1)C2]

Mixed solvent of THF/MeOH (3:1, 180 μL) was added to the vial containing methyl 4-(1H-benzo[d]imidazol-2-yl)-2,3,4,5-tetrahydrobnzo[f][1,4]oxazepine-8-carboxylate and it was shaken at 50° C. for 15 min to dissolve the residue. $NH_2OH$ (50% in water, 125 μL) was added followed by aq. 1N NaOH (85 μL) and the vial was sealed and shaken at room temperature overnight. The solvent was evaporated under reduce pressure and the residue was dissolved in DMSO (500 μL) then purified by HPLC to afford the title compound (7.0 mg, 54% yield). MS: (ES, m/z): 325 $[M+H]^+$.

236

TABLE 39

The following compounds were prepared by the parallel synthesis method of Example 83.

| Structure | Found M + H (ES) |
|---|---|
| 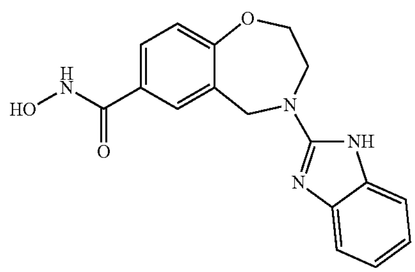 [SMILES: O=C(NO)c1ccc2c(c1)CN(c1nc3ccccc3[nH]1)CCO2] | 325 |
| | 383 |
| | 383 |

Example 84—Preparation of N-hydroxy-4-((5-isopropylpyridin-2-yl)methyl)-2-oxo-2,3,4,5-tetrahydro-1H-benzo[e][1,4]diazepine-7-carboxamide

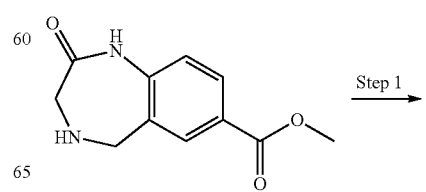
Step 1

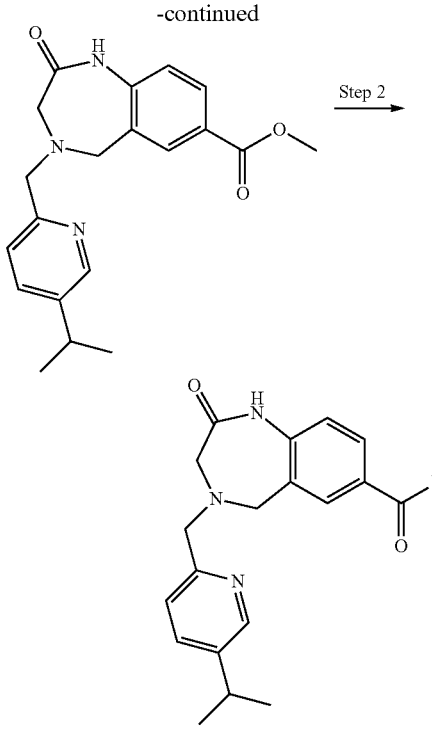

Step-1: Methyl 4-(4-isopropylbenzyl)-2-oxo-2,3,4,5-tetrahydro-H-benzo[e][1,4]diazepine-7-carboxylate A 2 mL reaction vial was charged with methyl 2-oxo-2,3,4,5-tetrahydro-1H-benzo[e][1,4]diazepine-7-carboxylate (0.2 M in N,N-dimethylacetamide, 150 µL, 30 µmol) and 5-isopropylpicolinaldehyde (0.2 M in 1,2-dichloroethane, 225 µL, 45 µmol). The vial was sealed and shaken at room temperature for 1 h. Sodium triacetoxyborohydride (0.2M in 1,2-dichloroethane, 500 µL, 100 µmol) was added and the vial was shaken at room temperature overnight. Half volume of the solvent was removed under reduced pressure. The reaction mixture was diluted with 1N NaOH in brine (500 µL) and extracted with EtOAc (2×500 µL). The combined organic layers were evaporated to dryness under reduced pressure.

Step-2: N-hydroxy-4-((5-isopropylpyridin-2-yl)methyl)-2-oxo-2,3,4,5-tetrahydro-1H-benzo[e][1,4]diazepine-7-carboxamide Mixed solvent of THF/MeOH (3:1, 180 µL) was added to the vial containing methyl 4-(4-isopropylbenzyl)-2-oxo-2,3,4,5-tetrahydro-1H-benzo[e][1,4]diazepine-7-carboxylate and it was shaken at 50° C. for 15 min to dissolve the residue. $NH_2OH$ (50% in water, 125 µL) was added followed by aq. 1N NaOH (85 µL) and the vial was sealed and shaken at room temperature overnight. The solvent was evaporated under reduce pressure and the residue was dissolved in DMSO (500 µL) then purified by HPLC to afford the title compound (1.6 mg, 15% yield). MS: (ES, m/z): 355 $[M+H]^+$.

TABLE 40

The following compounds were prepared by the parallel synthesis method of Example 84.

| Structure | Found M + H (ES) |
|---|---|
|  | 313 |
|  | 313 |
| 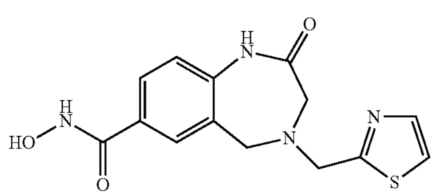 [SMILES: O=C1CN(Cc2nccs2)Cc2cc(C(=O)NO)ccc2N1] | 319 |

TABLE 40-continued

The following compounds were prepared by the parallel synthesis method of Example 84.

| Structure | Found M + H (ES) |
|---|---|
| 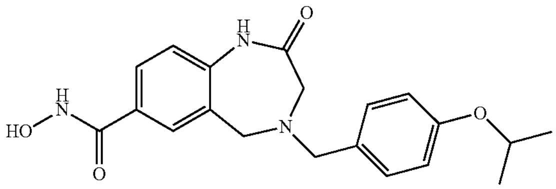 [SMILES: CC(C)Oc1ccc(CN2CC(=O)Nc3ccc(C(=O)NO)cc3C2)cc1] | 370 |
| | 396 |
| | 404 |
| | 404 |
| | 396 |
| | 396 |

TABLE 40-continued

The following compounds were prepared by the parallel synthesis method of Example 84.

| Structure | Found M + H (ES) |
|---|---|
| (structure: hydroxamic acid benzodiazepinone with 4-(pyridin-2-yl)benzyl substituent) | 389 |
| (structure: hydroxamic acid benzodiazepinone with 4-(pyrazol-1-yl)benzyl substituent) | 378 |
| (structure: hydroxamic acid benzodiazepinone with 4-cyanobenzyl substituent) | 337 |
| (structure: hydroxamic acid benzodiazepinone with pyrimidin-5-ylmethyl substituent) | 314 |
| (structure: hydroxamic acid benzodiazepinone with naphthalen-1-ylmethyl substituent) | 362 |
| (structure: hydroxamic acid benzodiazepinone with [2-(3-fluorophenyl)oxazol-4-yl]methyl substituent) | 397 |
| (structure: hydroxamic acid benzodiazepinone with 3-((dimethylamino)methyl)benzyl substituent) | 369 |

TABLE 40-continued

The following compounds were prepared by the parallel synthesis method of Example 84.

| Structure | Found M + H (ES) |
|---|---|
| *benzyl derivative* | 312 |
| *4-isopropylbenzyl derivative* | 354 |
| *4-chlorobenzyl derivative* | 346 |
| *2,5-difluorobenzyl derivative* | 348 |
| *3,5-difluorobenzyl derivative* | 348 |
| *3,5-dichlorobenzyl derivative* | 380 |
| *2-fluoro-4-methoxybenzyl derivative* | 360 |

TABLE 40-continued
The following compounds were prepared by the parallel synthesis method of Example 84.
| Structure | Found M + H (ES) |
|---|---|
| 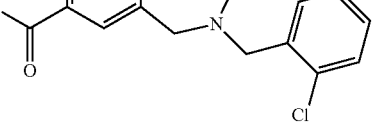 | 346 |
| 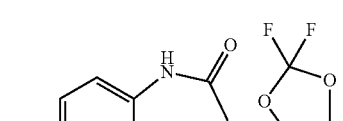 | 392 |
| 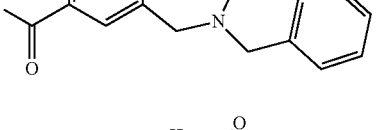 | 313 |
| 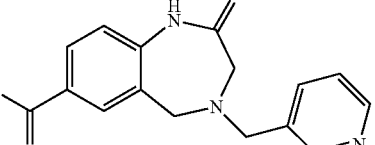 | 316 |
| 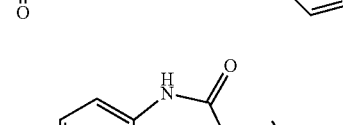 | 361 |
| 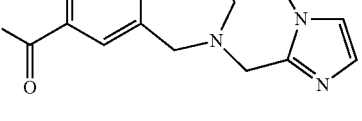 | 352 |
| 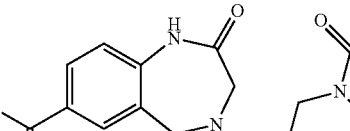 | 276 |

TABLE 40-continued

The following compounds were prepared by the parallel synthesis method of Example 84.

| Structure | Found M + H (ES) |
|---|---|
| 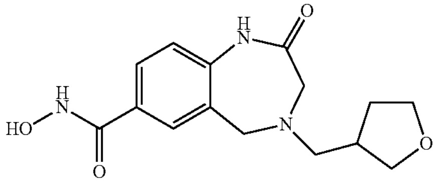 [SMILES: O=C1CN(CC2CCOC2)Cc2cc(C(=O)NO)ccc2N1] | 306 |
| 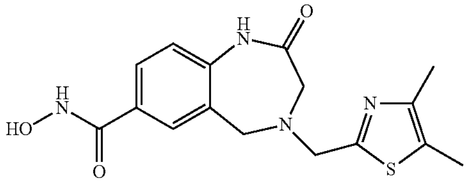 [SMILES: Cc1nc(CN2CC(=O)Nc3ccc(C(=O)NO)cc3C2)sc1C] | 347 |
| 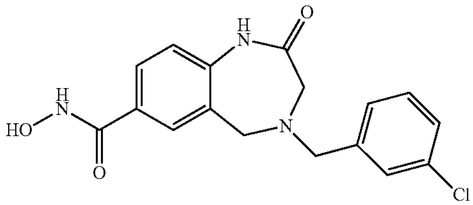 [SMILES: O=C1CN(Cc2cccc(Cl)c2)Cc2cc(C(=O)NO)ccc2N1] | 346 |
| 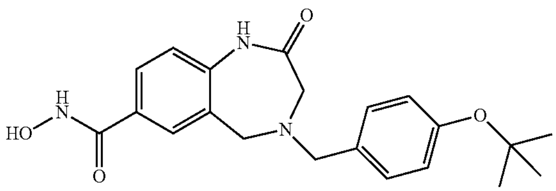 [SMILES: CC(C)(C)Oc1ccc(CN2CC(=O)Nc3ccc(C(=O)NO)cc3C2)cc1] | 384 |
| 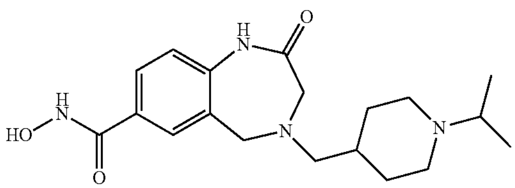 [SMILES: CC(C)N1CCC(CN2CC(=O)Nc3ccc(C(=O)NO)cc3C2)CC1] | 361 |
| 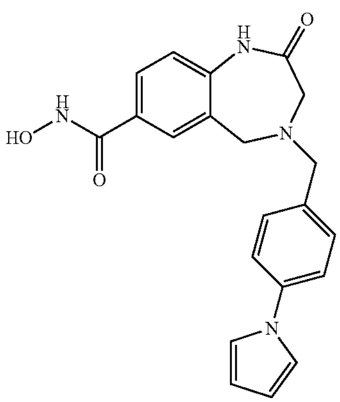 [SMILES: O=C1CN(Cc2ccc(-n3cccc3)cc2)Cc2cc(C(=O)NO)ccc2N1] | 377 |

TABLE 40-continued
The following compounds were prepared by the parallel synthesis method of Example 84.
| Structure | Found M + H (ES) |
|---|---|
| 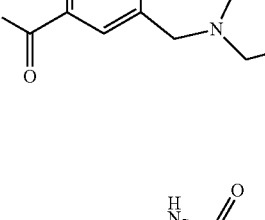 | 362 |
| 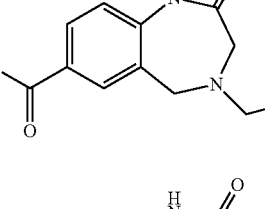 | 398 |
| 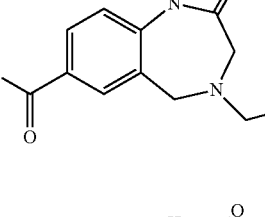 | 352 |
| 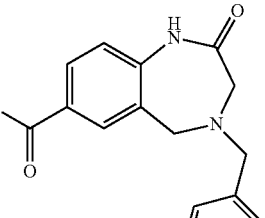 | 395 |
| 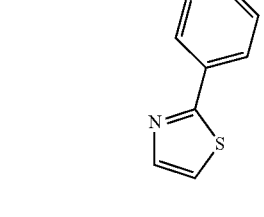 | 330 |
| 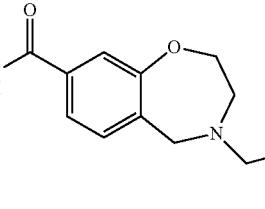 | 330 |

TABLE 40-continued

The following compounds were prepared by the parallel synthesis method of Example 84.

| Structure | Found M + H (ES) |
|---|---|
| (structure) | 330 |
| (structure) | 330 |

Example 85—Preparation of N-hydroxy-4-(2-methylpiperidine-1-carbonyl)-2,3,4,5-tetrahydrobenzo[f][1,4]oxazepine-8-carboxamide

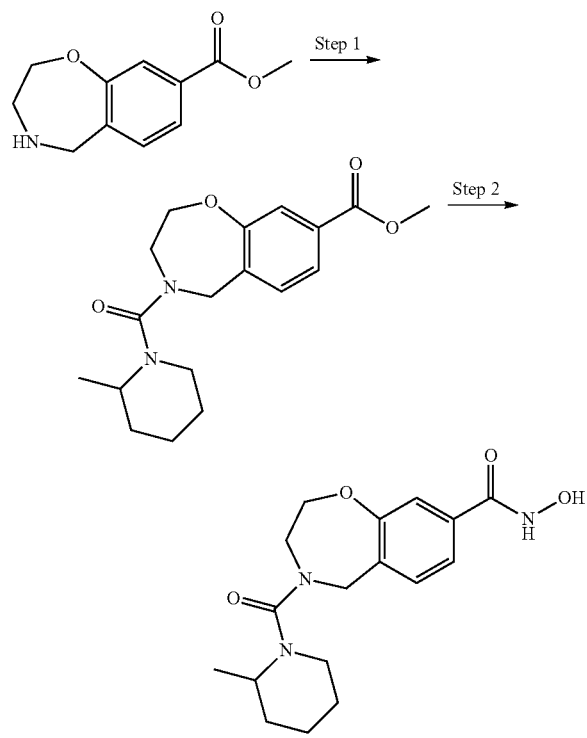

Step-1: Methyl 4-(2-methylpiperidine-1-carbonyl)-2,3,4,5-tetrahydrobenzo[f][1,4]oxazepine-8-carboxylate A 2-mL reaction vial was charged with triphosgene (0.1 M in MeCN, 200 µL, 20 µmol), methyl 2,3,4,5-tetrahydrobenzo[f][1,4]oxazepine-8-carboxylate (0.2 M in MeCN, 250 µL, 50 µmol) and triethylamine (neat, 14 µL, 100 µmol). The mixture was stirred for 20 min. To this mixture was then added 2-methylpiperidine (neat, 24.8 mg, 250 µmol) and the resulting mixture was stirred at room temperature for 2 h, after which time it was diluted with sat aq NaHCO$_3$ (500 µL) and extracted with EtOAc (2×500 µL). The combined organic layers were evaporated to dryness under reduced pressure.

Step-2: N-Hydroxy-4-(2-methylpiperidine-1-carbonyl)-2,3,4,5-tetrahydrobenzo[f][1,4]oxazepine-8-carboxamide Mixed solvent of THF/MeOH (3:1, 180 µL) was added to the vial containing methyl 4-(2-methylpiperidine-1-carbonyl)-2,3,4,5-tetrahydrobenzo[f][1,4]oxazepine-8-carboxylate and it was shaken at 50° C. for 15 min to dissolve the residue. NH$_2$OH (50% in water, 125 µL) was added followed by aq. 1N NaOH (85 µL) and the vial was sealed and shaken at room temperature overnight. The solvent was evaporated under reduce pressure and the residue was dissolved in DMSO (500 µL) then purified by HPLC to afford the title compound (7.1 mg, 42.6% yield). MS: (ES, m/z): 334 [M+H]$^+$.

TABLE 41

The following compounds were prepared by the parallel synthesis method of Example 85.

| Structure | Found M + H (ES) |
|---|---|
| (structure) | 306 |

TABLE 41-continued

The following compounds were prepared by the parallel synthesis method of Example 85.

| Structure | Found M + H (ES) |
|---|---|
| (benzoxazepine-hydroxamide with morpholine-carboxamide) | 322 |
| (benzoxazepine-hydroxamide with 4-methylpiperazine-carboxamide) | 335 |
| (benzoxazepine-hydroxamide with 4-methoxypiperidine-carboxamide) | 350 |
| (benzoxazepine-hydroxamide with isoindoline-carboxamide) | 354 |
| (benzoxazepine-hydroxamide with 3-methylmorpholine-carboxamide) | 336 |
| (methyl-substituted benzoxazepine-hydroxamide with pyrrolidine-carboxamide) | 320 |
| (methyl-substituted benzoxazepine-hydroxamide with morpholine-carboxamide) | 336 |
| (methyl-substituted benzoxazepine-hydroxamide with isoindoline-carboxamide) | 368 |
| (methyl-substituted benzoxazepine-hydroxamide with 4-methylpiperazine-carboxamide) | 349 |
| (methyl-substituted benzoxazepine-hydroxamide with 2-methylpiperidine-carboxamide) | 348 |
| (methyl-substituted benzoxazepine-hydroxamide with 3-methylmorpholine-carboxamide) | 350 |
| (methyl-substituted benzoxazepine-hydroxamide with piperidine-carboxamide) | 334 |

TABLE 41-continued

The following compounds were prepared by the parallel synthesis method of Example 85.

| Structure | Found M + H (ES) |
|---|---|
| 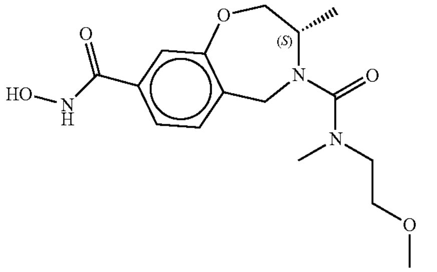 | 338 |
| 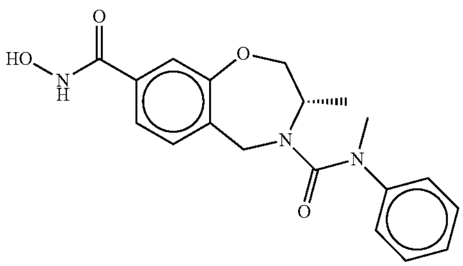 | 356 |

Example 86—Preparation of (S)—N8-hydroxy-N4,N4,3-trimethyl-2,3-dihydrobenzo[f][1,4]oxazepine-4,8(5H)-dicarboxamide

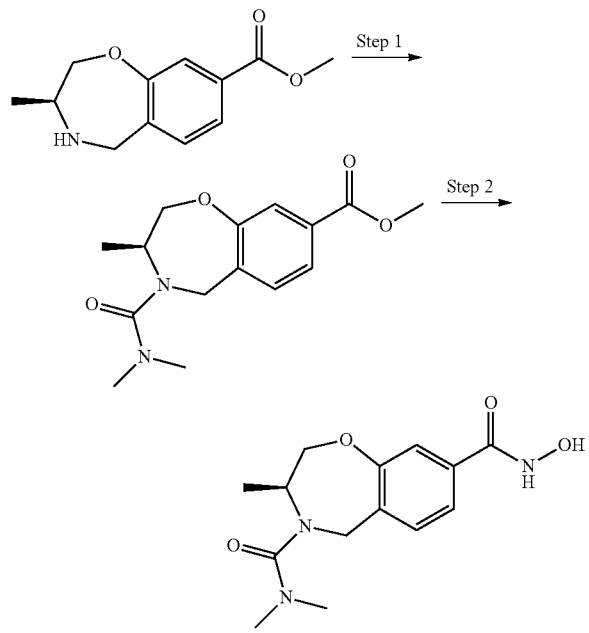

Step-1: Methyl (S)-4-(dimethylcarbamoyl)-3-methyl-2,3,4,5-tetrahydrobenzo[f][1,4]oxazepine-8-carboxylate A 2-mL reaction vial was charged with dimethylcarbamic chloride (0.2M in dichloroethane, 400 μL, 80 μmol), methyl (S)-3-methyl-2,3,4,5-tetrahydrobenzo[f][1,4]oxazepine-8-carboxylate (0.2M in dichloroethane, 200 μL, 40 μmol) and triethylamine (neat, 11 μL, 80 μmol). The reaction was stirred at room temperature for 2 h, after which time it was diluted with brine (500 μL) and extracted with EtOAc (2×500 μL). The combined organic layers were evaporated to dryness under reduced pressure.

Step-2: (S)—N8-hydroxy-N4,N4,3-trimethyl-2,3-dihydrobenzo[f][1,4]oxazepine-4,8(5H)-dicarboxamide Mixed solvent of THF/MeOH (3:1, 180 μL) was added to the vial containing methyl (S)-4-(dimethylcarbamoyl)-3-methyl-2,3,4,5-tetrahydrobenzo[f][1,4]oxazepine-8-carboxylate and it was shaken at 50° C. for 15 min to dissolve the residue. NH$_2$OH (50% in water, 125 μL) was added followed by aq. 1N NaOH (85 μL) and the vial was sealed and shaken at room temperature overnight. The solvent was evaporated under reduce pressure and the residue was dissolved in DMSO (500 μL) then purified by HPLC to afford the title compound. MS: (ES, m/z): 294 [M+H]$^+$.

TABLE 42

The following compound was prepared by the parallel synthesis method of Example 86.

| Structure | Found M + H (ES) |
|---|---|
| 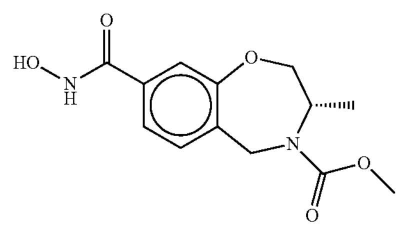 | 281 |

Example 87—Preparation of (S)—N-hydroxy-3-methyl-4-(3-(trifluoromethyl)phenyl)-2,3,4,5-tetrahydrobenzo[f][1,4]oxazepine-8-carboxamide

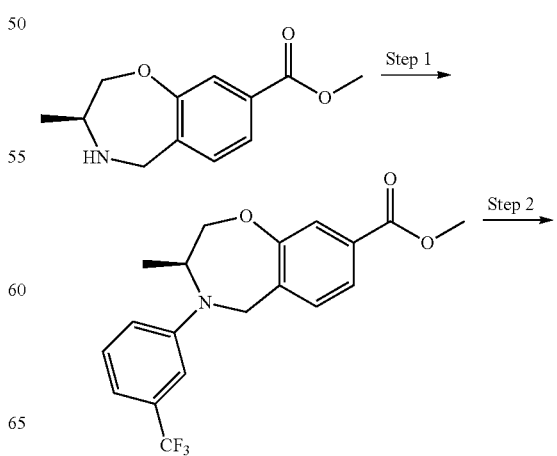

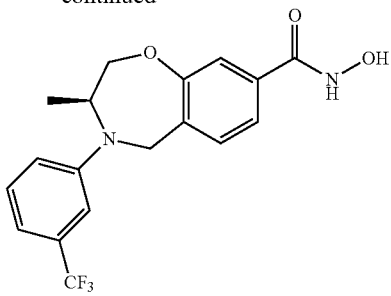

Step-1: Methyl (S)-3-methyl-4-(3-(trifluoromethyl)phenyl)-2,3,4,5-tetrahydrobenzo[f][1,4]oxazepine-8-carboxylate A 2-mL reaction vial was charged with dimethylcarbamic chloride (0.2M in dichloroethane, 400 µL, 80 µmol), methyl (S)-3-methyl-2,3,4,5-tetrahydrobenzo[f][1,4]oxazepine-8-carboxylate (0.2M in dichloroethane, 150 µL, 30 µmol), triethylamine (neat, 12.5 µL, 90 µmol), Cu(OAc)$_2$ (150 µL 0.4M in DMSO, 60 µmol), and (3-(trifluoromethyl)phenyl)boronic acid (300 µL, 0.2M in dichloroethane, 60 µmol). The reaction was stirred at room temperature for 2 days, after which time the solvent was removed under vacuum. The residual solution was diluted with brine (500 µL) and NH$_4$OH (100 µL), then extracted with EtOAc (2×500 µL). The combined organic layers were evaporated to dryness under reduced pressure.

Step-2: (S)—N-Hydroxy-3-methyl-4-(3-(trifluoromethyl)phenyl)-2,3,4,5-tetrahydrobenzo[f][1,4]oxazepine-8-carboxamide Mixed solvent of THF/MeOH (3:1, 180 µL) was added to the vial containing methyl (S)-3-methyl-4-(3-(trifluoromethyl)phenyl)-2,3,4,5-tetrahydrobenzo[f][1,4]oxazepine-8-carboxylate and it was shaken at 50° C. for 15 min to dissolve the residue. NH$_2$OH (50% in water, 125 µL) was added followed by aq. 1N NaOH (85 µL) and the vial was sealed and shaken at room temperature overnight. The solvent was evaporated under reduce pressure and the residue was dissolved in DMSO (500 µL) then purified by HPLC to afford the title compound (0.4 mg, 3.64% yield). MS: (ES, m/z): 367 [M+H]$^+$.

TABLE 43

The following compounds were prepared by the parallel synthesis method of Example 87.

| Structure | Found M + H (ES) |
|---|---|
| 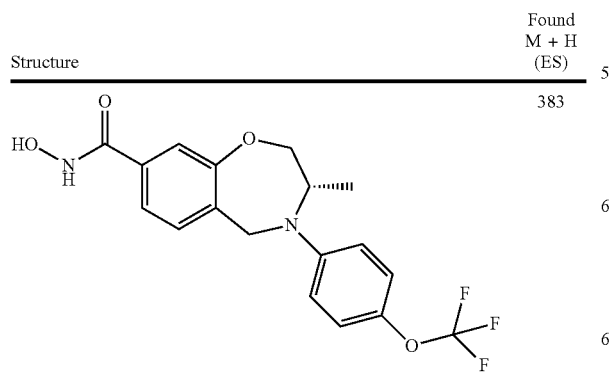 | 383 |

TABLE 43-continued

The following compounds were prepared by the parallel synthesis method of Example 87.

| Structure | Found M + H (ES) |
|---|---|
| 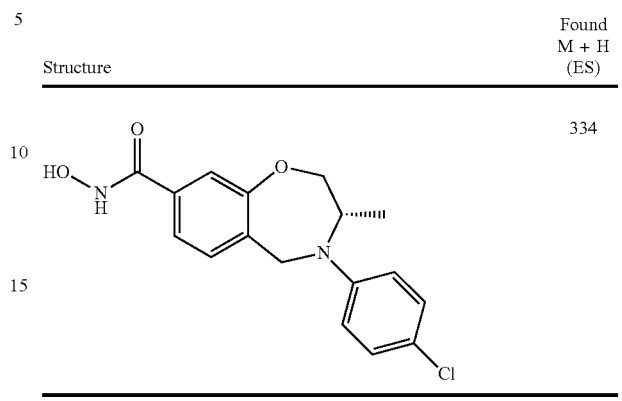 | 334 |

Example 88—Preparation of (S)-4-(2-chlorophenyl)-N-hydroxy-3-methyl-2,3,4,5-tetrahydrobenzo[f][1,4]oxazepine-8-carboxamide

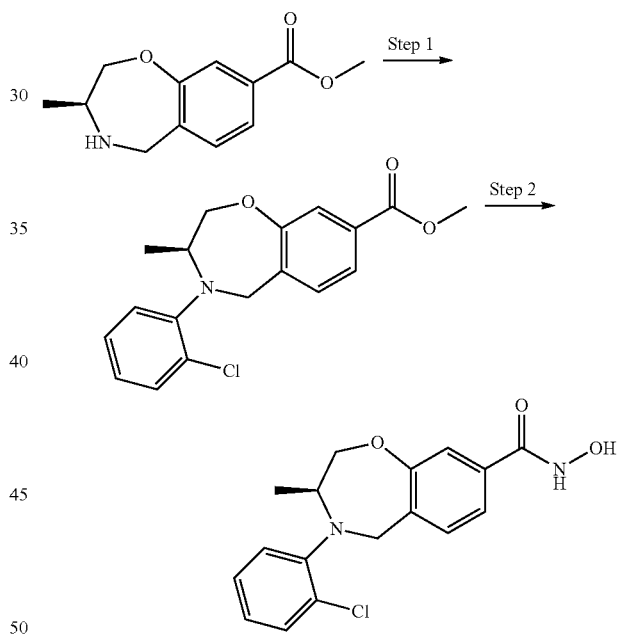

Step-1: Methyl (S)-4-(2-chlorophenyl)-3-methyl-2,3,4,5-tetrahydrobenzo[f][1,4]oxazepine-8-carboxylate Under N$_2$, to a 2-mL reaction vial were charged methyl (S)-3-methyl-2,3,4,5-tetrahydrobenzo[f][1,4]oxazepine-8-carboxylate (0.2M in dioxane, 150 µL, 30 µmol), 1-bromo-2-chlorobenzene (0.2M in toluene, 300 µL, 60 µmol), Xphos Pd G$_2$ (3 mol, 24 mg) and sodium tert-butoxide (60 mol, 5.7 mg), then the vial was sealed and heated at 150° C. in microwave for 90 min. The solvent was removed under vacuum. The residual solution was diluted with brine (500 µL) and extracted with EtOAc (2×500 µL). The combined organic layers were evaporated to dryness under reduced pressure.

Step-2: (S)-4-(2-Chlorophenyl)-N-hydroxy-3-methyl-2,3,4,5-tetrahydrobenzo[f][1,4]oxazepine-8-carboxamide Mixed solvent of THF/MeOH (3:1, 180 μL) was added to the vial containing methyl (S)-4-(2-chlorophenyl)-3-methyl-2,3,4,5-tetrahydrobenzo[f][1,4]oxazepine-8-carboxylate and it was shaken at 50° C. for 15 min to dissolve the residue. NH$_2$OH (50% in water, 125 μL) was added followed by aq. 1N NaOH (85 μL) and the vial was sealed and shaken at room temperature overnight. The solvent was evaporated under reduce pressure and the residue was dissolved in DMSO (500 μL) then purified by HPLC to afford the title compound (0.4 mg, 4.01% yield). MS: (ES, m/z): 334 [M+H]$^+$.

TABLE 44

The following compounds were prepared by the parallel synthesis method of Example 88.

| Structure | Found M + H (ES) |
|---|---|
| (structure shown) | 317 |

Example 89—In Vitro Histone Deacetylase Assay

The enzymatic HDAC6 assay was performed using electrophoretic mobility shift assay. Full length human recombinant HDAC6 protein was expressed in baculoviral system and purified by affinity chromatography. The enzymatic reactions were assembled in 384 well plates in a total volume of 25 μL in a reaction buffer composing: 100 mM HEPES, pH7.5, 25 mM KCl, 0.1% bovine serum albumin, 0.01% Triton X-100, 1% DMSO (from compounds) 2 μM of the fluorescently labeled peptide substrate and enzyme. The enzyme was added at a final concentration of 1 nM. The peptide substrate RHKK(Ac)—NH2 was used. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 μL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide was measured. Activity in each sample was determined as the product to sum ratio (PSR):P/(S+P), where P is the peak height of the product peptide and S is the peak height of the substrate peptide. Percent inhibition (Pinh) is determined using the following equation:

Pinh=(PSR0%−PSRinh)/(PSR0%−PSR100%)*100, where PSRinh is the product sum ratio in the presence of inhibitor, PSR0% is the average product sum ration in the absence of inhibitor and PSR100% is the average product sum ratio in 100%-inhibition control samples. The IC$_{50}$ values of inhibitors were determined by fitting the %-inhibition curves with 4 parameter dose-response model using XLfit 4 software.

As set forth in Table 45, below, IC$_{50}$ values are defined as follows: IC50≤0.1 μM (+++); IC50>0.1 μM and ≤0.5 μM (++); IC50>0.5 μM (+).

TABLE 45

Inhibitory Concentration (IC$_{50}$) Values for Representative Compounds against HDAC6.

| NAME | Activity Range |
|---|---|
| 4-(1,3-benzoxazol-2-yl)-N-hydroxy-2,3,4,5-tetrahydro-1,4-benzoxazepine-8-carboxamide | +++ |
| 4-[1-(cyclohexylmethyl)-1H-1,3-benzodiazol-2-yl]-N-hydroxy-2,3,4,5-tetrahydro-1,4-benzoxazepine-8-carboxamide | ++ |
| 4-(1,3-benzothiazol-2-yl)-N-hydroxy-2,3,4,5-tetrahydro-1,4-benzoxazepine-8-carboxamide | ++ |
| 4-(cyclohexylmethyl)-N-hydroxy-2,3,4,5-tetrahydro-1,4-benzoxazepine-8-carboxamide | ++ |
| N-hydroxy-4-phenyl-2,3,4,5-tetrahydro-1,4-benzoxazepine-8-carboxamide | + |
| 4-[4-cyano-3-(trifluoromethyl)phenyl]-N-hydroxy-2,3,4,5-tetrahydro-1,4-benzoxazepine-8-carboxamide | ++ |
| 4-(3,4-dichlorophenyl)-N-hydroxy-2,3,4,5-tetrahydro-1,4-benzoxazepine-8-carboxamide | ++ |
| N-hydroxy-4-(pyridin-2-yl)-2,3,4,5-tetrahydro-1,4-benzoxazepine-8-carboxamide | ++ |
| N-hydroxy-4-(pyridin-3-yl)-2,3,4,5-tetrahydro-1,4-benzoxazepine-8-carboxamide | ++ |
| N-hydroxy-4-(pyridin-4-yl)-2,3,4,5-tetrahydro-1,4-benzoxazepine-8-carboxamide | + |
| N-hydroxy-4-(4-methylphenyl)-2,3,4,5-tetrahydro-1,4-benzoxazepine-8-carboxamide | ++ |
| N-hydroxy-4-(piperidine-1-carbonyl)-2,3,4,5-tetrahydro-1,4-benzoxazepine-8-carboxamide | +++ |
| 4-methoxyphenyl 8-(hydroxycarbamoyl)-2,3,4,5-tetrahydro-1,4-benzoxazepine-4-carboxylate | +++ |
| cyclohexyl 8-(hydroxycarbamoyl)-2,3,4,5-tetrahydro-1,4-benzoxazepine-4-carboxylate | +++ |

TABLE 45-continued

Inhibitory Concentration (IC$_{50}$) Values for Representative Compounds against HDAC6.

| NAME | Activity Range |
|---|---|
| N-hydroxy-4-(piperidine-1-sulfonyl)-2,3,4,5-tetrahydro-1,4-benzoxazepine-8-carboxamide | +++ |
| N8-hydroxy-N4-methyl-N4-phenyl-2,3,4,5-tetrahydro-1,4-benzoxazepine-4,8-dicarboxamide | + |
| 4-cyclohexyl-N-hydroxy-2,3,4,5-tetrahydro-1,4-benzoxazepine-8-carboxamide | + |
| 4-[2-(dimethylamino)ethyl]-N-hydroxy-2,3,4,5-tetrahydro-1,4-benzoxazepine-8-carboxamide | + |
| N-hydroxy-4-(2-methoxyethyl)-2,3,4,5-tetrahydro-1,4-benzoxazepine-8-carboxamide | ++ |
| N-hydroxy-4-[1-(oxan-4-ylmethyl)-1H-1,3-benzodiazol-2-yl]-2,3,4,5-tetrahydro-1,4-benzoxazepine-8-carboxamide | ++ |
| N-hydroxy-2,3,4,5-tetrahydro-1,4-benzoxazepine-8-carboxamide | ++ |
| N-hydroxy-4-methyl-2,3,4,5-tetrahydro-1,4-benzoxazepine-8-carboxamide | ++ |
| (2R)-N-hydroxy-2-methyl-2,3,4,5-tetrahydro-1,4-benzoxazepine-8-carboxamide | + |
| (2R)-N8-hydroxy-N4-(4-methoxyphenyl)-2-methyl-2,3,4,5-tetrahydro-1,4-benzoxazepine-4,8-dicarboxamide | ++ |
| (2R)-N-hydroxy-4-(4-methoxybenzenesulfonyl)-2-methyl-2,3,4,5-tetrahydro-1,4-benzoxazepine-8-carboxamide | ++ |
| (2R)-N-hydroxy-4-[(4-methoxyphenyl)methyl]-2-methyl-2,3,4,5-tetrahydro-1,4-benzoxazepine-8-carboxamide | ++ |
| (2R)-N-hydroxy-2-methyl-4-phenyl-2,3,4,5-tetrahydro-1,4-benzoxazepine-8-carboxamide | ++ |
| (2R)-N-hydroxy-2,4-dimethyl-2,3,4,5-tetrahydro-1,4-benzoxazepine-8-carboxamide | + |
| (2S)-N-hydroxy-2-methyl-2,3,4,5-tetrahydro-1,4-benzoxazepine-8-carboxamide | ++ |
| (2S)-N8-hydroxy-N4-(4-methoxyphenyl)-2-methyl-2,3,4,5-tetrahydro-1,4-benzoxazepine-4,8-dicarboxamide | +++ |
| (2S)-N-hydroxy-4-(4-methoxybenzenesulfonyl)-2-methyl-2,3,4,5-tetrahydro-1,4-benzoxazepine-8-carboxamide | + |
| (2S)-N-hydroxy-2-methyl-4-phenyl-2,3,4,5-tetrahydro-1,4-benzoxazepine-8-carboxamide | + |
| (2S)-N-hydroxy-2,4-dimethyl-2,3,4,5-tetrahydro-1,4-benzoxazepine-8-carboxamide | + |
| (2S)-N-hydroxy-4-[(4-methoxyphenyl)methyl]-2-methyl-2,3,4,5-tetrahydro-1,4-benzoxazepine-8-carboxamide | ++ |
| N-hydroxy-4-[(4-methoxyphenyl)methyl]-3,3-dimethyl-2,3,4,5-tetrahydro-1,4-benzoxazepine-8-carboxamide | ++ |
| N-hydroxy-3,3-dimethyl-2,3,4,5-tetrahydro-1,4-benzoxazepine-8-carboxamide | +++ |
| N-hydroxy-3,3,4-trimethyl-2,3,4,5-tetrahydro-1,4-benzoxazepine-8-carboxamide | +++ |
| (3R)-N-hydroxy-4-[(4-methoxyphenyl)methyl]-3-(propan-2-yl)-2,3,4,5-tetrahydro-1,4-benzoxazepine-8-carboxamide | +++ |
| (3R)-N-hydroxy-4-phenyl-3-(propan-2-yl)-2,3,4,5-tetrahydro-1,4-benzoxazepine-8-carboxamide | ++ |
| (3R)-N8-hydroxy-N4-(4-methoxyphenyl)-3-(propan-2-yl)-2,3,4,5-tetrahydro-1,4-benzoxazepine-4,8-dicarboxamide | ++ |
| (3R)-N-hydroxy-3-(propan-2-yl)-2,3,4,5-tetrahydro-1,4-benzoxazepine-8-carboxamide | +++ |
| (3R)-N-hydroxy-4-methyl-3-(propan-2-yl)-2,3,4,5-tetrahydro-1,4-benzoxazepine-8-carboxamide | +++ |
| (3S)-N-hydroxy-4-[(4-methoxyphenyl)methyl]-3-(propan-2-yl)-2,3,4,5-tetrahydro-1,4-benzoxazepine-8-carboxamide | +++ |
| (3S)-N-hydroxy-4-phenyl-3-(propan-2-yl)-2,3,4,5-tetrahydro-1,4-benzoxazepine-8-carboxamide | +++ |
| (3S)-N8-hydroxy-N4-(4-methoxyphenyl)-3-(propan-2-yl)-2,3,4,5-tetrahydro-1,4-benzoxazepine-4,8-dicarboxamide | +++ |
| (3S)-N-hydroxy-3-(propan-2-yl)-2,3,4,5-tetrahydro-1,4-benzoxazepine-8-carboxamide | +++ |
| (3S)-N-hydroxy-4-methyl-3-(propan-2-yl)-2,3,4,5-tetrahydro-1,4-benzoxazepine-8-carboxamide | +++ |
| (3R)-N-hydroxy-3-methyl-2,3,4,5-tetrahydro-1,4-benzoxazepine-8-carboxamide | ++ |
| (3R)-N-hydroxy-3,4-dimethyl-2,3,4,5-tetrahydro-1,4-benzoxazepine-8-carboxamide | +++ |
| (3R)-N8-hydroxy-N4-(4-methoxyphenyl)-3-methyl-2,3,4,5-tetrahydro-1,4-benzoxazepine-4,8-dicarboxamide | ++ |
| (3R)-N-hydroxy-4-(4-methoxybenzenesulfonyl)-3-methyl-2,3,4,5-tetrahydro-1,4-benzoxazepine-8-carboxamide | + |
| (3R)-N-hydroxy-4-[(4-methoxyphenyl)methyl]-3-methyl-2,3,4,5-tetrahydro-1,4-benzoxazepine-8-carboxamide | +++ |

TABLE 45-continued

Inhibitory Concentration (IC$_{50}$) Values for
Representative Compounds against HDAC6.

| NAME | Activity Range |
|---|---|
| (3R)-N-hydroxy-3-methyl-4-phenyl-2,3,4,5-tetrahydro-1,4-benzoxazepine-8-carboxamide | ++ |
| (3S)-N8-hydroxy-N4-(4-methoxyphenyl)-3-methyl-2,3,4,5-tetrahydro-1,4-benzoxazepine-4,8-dicarboxamide | +++ |
| (3S)-N-hydroxy-4-(4-methoxybenzenesulfonyl)-3-methyl-2,3,4,5-tetrahydro-1,4-benzoxazepine-8-carboxamide | ++ |
| (3S)-N-hydroxy-4-[(4-methoxyphenyl)methyl]-3-methyl-2,3,4,5-tetrahydro-1,4-benzoxazepine-8-carboxamide | +++ |
| (3S)-N-hydroxy-3-methyl-4-phenyl-2,3,4,5-tetrahydro-1,4-benzoxazepine-8-carboxamide | +++ |
| (3S)-N-hydroxy-3-methyl-2,3,4,5-tetrahydro-1,4-benzoxazepine-8-carboxamide | ++ |
| (3S)-N-hydroxy-3,4-dimethyl-2,3,4,5-tetrahydro-1,4-benzoxazepine-8-carboxamide | ++ |
| (5R/5S)-N-hydroxy-4-[(4-methoxyphenyl)methyl]-5-methyl-2,3,4,5-tetrahydro-1,4-benzoxazepine-7-carboxamide, | + |
| (5S/5R)-N-hydroxy-4-[(4-methoxyphenyl)methyl]-5-methyl-2,3,4,5-tetrahydro-1,4-benzoxazepine-7-carboxamide, | + |
| N8-hydroxy-N4-(4-methoxyphenyl)-2H,3H,4H,5H-pyrido[2,3-f][1,4]oxazepine-4,8-dicarboxamide | +++ |
| N-hydroxy-4-(4-methoxybenzenesulfonyl)-2H,3H,4H,5H-pyrido[2,3-f][1,4]oxazepine-8-carboxamide | ++ |
| N-hydroxy-4-[(4-methoxyphenyl)methyl]-2H,3H,4H,5H-pyrido[2,3-f][1,4]oxazepine-8-carboxamide | ++ |
| N8-hydroxy-N4-(4-methoxyphenyl)-2H,3H,4H,5H-pyrido[3,2-f][1,4]oxazepine-4,8-dicarboxamide | + |
| N-hydroxy-4-(4-methoxybenzenesulfonyl)-2H,3H,4H,5H-pyrido[3,2-f][1,4]oxazepine-8-carboxamide | + |
| N-hydroxy-4-[(4-methoxyphenyl)methyl]-2H,3H,4H,5H-pyrido[3,2-f][1,4]oxazepine-8-carboxamide | + |
| N-hydroxy-4-[(4-methoxyphenyl)methyl]-5-oxo-2,3,4,5-tetrahydro-1,4-benzoxazepine-8-carboxamide | ++ |
| N-hydroxy-4-[2-(4-methoxyphenyl)ethyl]-5-oxo-2,3,4,5-tetrahydro-1,4-benzoxazepine-8-carboxamide | ++ |
| N-hydroxy-4-[(4-methoxyphenyl)methyl]-5-oxo-2,3,4,5-tetrahydro-1,4-benzoxazepine-7-carboxamide | + |
| N-hydroxy-4-[2-(4-methoxyphenyl)ethyl]-5-oxo-2,3,4,5-tetrahydro-1,4-benzoxazepine-7-carboxamide | ++ |
| N-hydroxy-4-[2-(4-methoxyphenyl)ethyl]-2-oxo-2,3,4,5-tetrahydro-1H-1,4-benzodiazepine-8-carboxamide | + |
| 4-(1H-1,3-benzodiazol-2-ylmethyl)-N-hydroxy-2-oxo-2,3,4,5-tetrahydro-1H-1,4-benzodiazepine-8-carboxamide | ++ |
| 4-(1H-1,3-benzodiazol-2-ylmethyl)-N-hydroxy-2-oxo-2,3,4,5-tetrahydro-1H-1,4-benzodiazepine-7-carboxamide | +++ |
| N-hydroxy-4-[2-(4-methoxyphenyl)ethyl]-2-oxo-2,3,4,5-tetrahydro-1H-1,4-benzodiazepine-7-carboxamide | ++ |
| N-hydroxy-2-oxo-4-(1-phenylethyl)-2,3,4,5-tetrahydro-1H-1,4-benzodiazepine-7-carboxamide | +++ |
| N-hydroxy-4-[(4-methoxyphenyl)methyl]-2-oxo-2,3,4,5-tetrahydro-1H-1,4-benzodiazepine-7-carboxamide | ++ |
| N-hydroxy-4-(4-methoxybenzenesulfonyl)-2-oxo-2,3,4,5-tetrahydro-1H-1,4-benzodiazepine-7-carboxamide | + |
| N-hydroxy-2-oxo-4-phenyl-2,3,4,5-tetrahydro-1H-1,4-benzodiazepine-7-carboxamide | + |
| N-hydroxy-4-[(4-methoxyphenyl)methyl]-1-methyl-2-oxo-2,3,4,5-tetrahydro-1H-1,4-benzodiazepine-7-carboxamide | + |
| N-hydroxy-4-[(4-methoxyphenyl)methyl]-2,3,4,5-tetrahydro-1H-1,4-benzodiazepine-7-carboxamide | + |
| N-hydroxy-4-[(4-methoxyphenyl)methyl]-1-methyl-2,3,4,5-tetrahydro-1H-1,4-benzodiazepine-7-carboxamide | + |
| 2-benzyl-N-hydroxy-1,1-dioxo-3,4-dihydro-2H-5,1$\lambda^6$,2-benzoxathiazepine-8-carboxamide | ++ |
| 2-benzyl-N-hydroxy-1,1-dioxo-3,4-dihydro-2H-5,1$\lambda^6$,2-benzoxathiazepine-7-carboxamide | + |
| N8-hydroxy-N4-(4-methoxyphenyl)-2,3,4,5-tetrahydro-1,4-benzoxazepine-4,8-dicarboxamide | ++ |
| N7-hydroxy-N4-(4-methoxyphenyl)-2,3,4,5-tetrahydro-1,4-benzoxazepine-4,7-dicarboxamide | + |
| N-hydroxy-4-(4-methoxybenzenesulfonyl)-2,3,4,5-tetrahydro-1,4-benzoxazepine-8-carboxamide | ++ |
| N-hydroxy-4-(4-methoxybenzenesulfonyl)-2,3,4,5-tetrahydro-1,4-benzoxazepine-7-carboxamide | ++ |
| 4-(1H-1,3-benzodiazol-2-ylmethyl)-N-hydroxy-2,3,4,5-tetrahydro-1,4-benzoxazepine-8-carboxamide | +++ |

TABLE 45-continued

Inhibitory Concentration (IC$_{50}$) Values for Representative Compounds against HDAC6.

| NAME | Activity Range |
|---|---|
| 4-(1H-1,3-benzodiazol-2-ylmethyl)-N-hydroxy-2,3,4,5-tetrahydro-1,4-benzoxazepine-7-carboxamide | + |
| N-hydroxy-4-{[1-(2-methoxyethyl)-1H-1,3-benzodiazol-2-yl]methyl}-2,3,4,5-tetrahydro-1,4-benzoxazepine-8-carboxamide | ++ |
| N-hydroxy-4-{[1-(2-methoxyethyl)-1H-1,3-benzodiazol-2-yl]methyl}-2,3,4,5-tetrahydro-1,4-benzoxazepine-7-carboxamide | + |
| N-hydroxy-4-[2-(4-methoxyphenyl)ethyl]-2,3,4,5-tetrahydro-1,4-benzoxazepine-8-carboxamide | ++ |
| N-hydroxy-4-[2-(4-methoxyphenyl)ethyl]-2,3,4,5-tetrahydro-1,4-benzoxazepine-7-carboxamide | + |
| N-hydroxy-4-[(4-methoxyphenyl)methyl]-2,3,4,5-tetrahydro-1,4-benzoxazepine-8-carboxamide | ++ |
| N-hydroxy-4-[(4-methoxyphenyl)methyl]-2,3,4,5-tetrahydro-1,4-benzoxazepine-7-carboxamide | + |
| 4-(1H-1,3-benzodiazol-2-yl)-N-hydroxy-2,3,4,5-tetrahydro-1,4-benzoxazepine-8-carboxamide | +++ |
| 4-(1H-1,3-benzodiazol-2-yl)-N-hydroxy-2,3,4,5-tetrahydro-1,4-benzoxazepine-7-carboxamide | ++ |
| N-hydroxy-4-[1-(2-methoxyethyl)-1H-1,3-benzodiazol-2-yl]-2,3,4,5-tetrahydro-1,4-benzoxazepine-8-carboxamide | +++ |
| N-hydroxy-4-[1-(2-methoxyethyl)-1H-1,3-benzodiazol-2-yl]-2,3,4,5-tetrahydro-1,4-benzoxazepine-7-carboxamide | ++ |
| N-hydroxy-2-oxo-4-{[5-(propan-2-yl)pyridin-2-yl]methyl}-2,3,4,5-tetrahydro-1H-1,4-benzodiazepine-7-carboxamide | ++ |
| N-hydroxy-2-oxo-4-(pyridin-4-ylmethyl)-2,3,4,5-tetrahydro-1H-1,4-benzodiazepine-7-carboxamide | ++ |
| N-hydroxy-2-oxo-4-(pyridin-2-ylmethyl)-2,3,4,5-tetrahydro-1H-1,4-benzodiazepine-7-carboxamide | + |
| N-hydroxy-2-oxo-4-(1,3-thiazol-2-ylmethyl)-2,3,4,5-tetrahydro-1H-1,4-benzodiazepine-7-carboxamide | + |
| N-hydroxy-2-oxo-4-{[4-(propan-2-yloxy)phenyl]methyl}-2,3,4,5-tetrahydro-1H-1,4-benzodiazepine-7-carboxamide | +++ |
| N-hydroxy-2-oxo-4-{[4-(trifluoromethoxy)phenyl]methyl}-2,3,4,5-tetrahydro-1H-1,4-benzodiazepine-7-carboxamide | ++ |
| N-hydroxy-2-oxo-4-[(3-phenoxyphenyl)methyl]-2,3,4,5-tetrahydro-1H-1,4-benzodiazepine-7-carboxamide | ++ |
| N-hydroxy-2-oxo-4-[(4-phenoxyphenyl)methyl]-2,3,4,5-tetrahydro-1H-1,4-benzodiazepine-7-carboxamide | +++ |
| N-hydroxy-2-oxo-4-{[3-(trifluoromethoxy)phenyl]methyl}-2,3,4,5-tetrahydro-1H-1,4-benzodiazepine-7-carboxamide | ++ |
| N-hydroxy-2-oxo-4-{[2-(trifluoromethoxy)phenyl]methyl}-2,3,4,5-tetrahydro-1H-1,4-benzodiazepine-7-carboxamide | +++ |
| N-hydroxy-2-oxo-4-{[4-(pyridin-2-yl)phenyl]methyl}-2,3,4,5-tetrahydro-1H-1,4-benzodiazepine-7-carboxamide | +++ |
| N-hydroxy-2-oxo-4-{[4-(1H-pyrazol-1-yl)phenyl]methyl}-2,3,4,5-tetrahydro-1H-1,4-benzodiazepine-7-carboxamide | +++ |
| 4-[(4-cyanophenyl)methyl]-N-hydroxy-2-oxo-2,3,4,5-tetrahydro-1H-1,4-benzodiazepine-7-carboxamide | ++ |
| N-hydroxy-2-oxo-4-(pyrimidin-5-ylmethyl)-2,3,4,5-tetrahydro-1H-1,4-benzodiazepine-7-carboxamide | + |
| N-hydroxy-4-(naphthalen-1-ylmethyl)-2-oxo-2,3,4,5-tetrahydro-1H-1,4-benzodiazepine-7-carboxamide | +++ |
| 4-{[2-(3-fluorophenyl)-1,3-oxazol-4-yl]methyl}-N-hydroxy-2-oxo-2,3,4,5-tetrahydro-1H-1,4-benzodiazepine-7-carboxamide | +++ |
| 4-({3-[(dimethylamino)methyl]phenyl}methyl)-N-hydroxy-2-oxo-2,3,4,5-tetrahydro-1H-1,4-benzodiazepine-7-carboxamide | + |
| 4-benzyl-N-hydroxy-2-oxo-2,3,4,5-tetrahydro-1H-1,4-benzodiazepine-7-carboxamide | ++ |
| N-hydroxy-2-oxo-4-{[4-(propan-2-yl)phenyl]methyl}-2,3,4,5-tetrahydro-1H-1,4-benzodiazepine-7-carboxamide | +++ |
| 4-[(4-chlorophenyl)methyl]-N-hydroxy-2-oxo-2,3,4,5-tetrahydro-1H-1,4-benzodiazepine-7-carboxamide | +++ |
| 4-[(2,5-difluorophenyl)methyl]-N-hydroxy-2-oxo-2,3,4,5-tetrahydro-1H-1,4-benzodiazepine-7-carboxamide | ++ |
| 4-[(3,5-difluorophenyl)methyl]-N-hydroxy-2-oxo-2,3,4,5-tetrahydro-1H-1,4-benzodiazepine-7-carboxamide | ++ |
| 4-[(3,5-dichlorophenyl)methyl]-N-hydroxy-2-oxo-2,3,4,5-tetrahydro-1H-1,4-benzodiazepine-7-carboxamide | +++ |
| 4-[(2-fluoro-4-methoxyphenyl)methyl]-N-hydroxy-2-oxo-2,3,4,5-tetrahydro-1H-1,4-benzodiazepine-7-carboxamide | +++ |
| 4-[(2-chlorophenyl)methyl]-N-hydroxy-2-oxo-2,3,4,5-tetrahydro-1H-1,4-benzodiazepine-7-carboxamide | ++ |
| 4-[(2,2-difluoro-2H-1,3-benzodioxol-4-yl)methyl]-N-hydroxy-2-oxo-2,3,4,5-tetrahydro-1H-1,4-benzodiazepine-7-carboxamide | +++ |

TABLE 45-continued

Inhibitory Concentration (IC$_{50}$) Values for Representative Compounds against HDAC6.

| NAME | Activity Range |
|---|---|
| N-hydroxy-2-oxo-4-(pyridin-3-ylmethyl)-2,3,4,5-tetrahydro-1H-1,4-benzodiazepine-7-carboxamide | ++ |
| N-hydroxy-4-[(1-methyl-1H-imidazol-2-yl)methyl]-2-oxo-2,3,4,5-tetrahydro-1H-1,4-benzodiazepine-7-carboxamide | ++ |
| 4-[(1-acetylpiperidin-3-yl)methyl]-N-hydroxy-2-oxo-2,3,4,5-tetrahydro-1H-1,4-benzodiazepine-7-carboxamide | + |
| N-hydroxy-4-{imidazo[1,2-a]pyridin-2-ylmethyl}-2-oxo-2,3,4,5-tetrahydro-1H-1,4-benzodiazepine-7-carboxamide | +++ |
| 4-(cyclopropylmethyl)-N-hydroxy-2-oxo-2,3,4,5-tetrahydro-1H-1,4-benzodiazepine-7-carboxamide | ++ |
| N-hydroxy-2-oxo-4-(oxolan-3-ylmethyl)-2,3,4,5-tetrahydro-1H-1,4-benzodiazepine-7-carboxamide | + |
| 4-[(dimethyl-1,3-thiazol-2-yl)methyl]-N-hydroxy-2-oxo-2,3,4,5-tetrahydro-1H-1,4-benzodiazepine-7-carboxamide | ++ |
| 4-[(3-chlorophenyl)methyl]-N-hydroxy-2-oxo-2,3,4,5-tetrahydro-1H-1,4-benzodiazepine-7-carboxamide | ++ |
| 4-{[4-(tert-butoxy)phenyl]methyl}-N-hydroxy-2-oxo-2,3,4,5-tetrahydro-1H-1,4-benzodiazepine-7-carboxamide | ++ |
| N-hydroxy-2-oxo-4-{[1-(propan-2-yl)piperidin-4-yl]methyl}-2,3,4,5-tetrahydro-1H-1,4-benzodiazepine-7-carboxamide | + |
| N-hydroxy-2-oxo-4-{[4-(1H-pyrrol-1-yl)phenyl]methyl}-2,3,4,5-tetrahydro-1H-1,4-benzodiazepine-7-carboxamide | +++ |
| N-hydroxy-4-(naphthalen-2-ylmethyl)-2-oxo-2,3,4,5-tetrahydro-1H-1,4-benzodiazepine-7-carboxamide | +++ |
| N-hydroxy-4-{[2-(morpholin-4-yl)pyridin-4-yl]methyl}-2-oxo-2,3,4,5-tetrahydro-1H-1,4-benzodiazepine-7-carboxamide | ++ |
| N-hydroxy-4-{imidazo[1,2-a]pyridin-7-ylmethyl}-2-oxo-2,3,4,5-tetrahydro-1H-1,4-benzodiazepine-7-carboxamide | ++ |
| N-hydroxy-2-oxo-4-{[4-(1,3-thiazol-2-yl)phenyl]methyl}-2,3,4,5-tetrahydro-1H-1,4-benzodiazepine-7-carboxamide | +++ |
| N-hydroxy-4-[(6-methoxypyridin-3-yl)methyl]-2,3,4,5-tetrahydro-1,4-benzoxazepine-8-carboxamide | ++ |
| N-hydroxy-4-[(6-methoxypyridin-3-yl)methyl]-2,3,4,5-tetrahydro-1,4-benzoxazepine-7-carboxamide | + |
| N-hydroxy-4-[(5-methoxypyridin-2-yl)methyl]-2,3,4,5-tetrahydro-1,4-benzoxazepine-8-carboxamide | ++ |
| N-hydroxy-4-[(5-methoxypyridin-2-yl)methyl]-2,3,4,5-tetrahydro-1,4-benzoxazepine-7-carboxamide | + |
| (R)-N8-hydroxy-2-isopropyl-N4-(4-methoxyphenyl)-2,3-dihydrobenzo[f][1,4]oxazepine-4,8(5H)-dicarboxamide | + |
| (R)-N8-hydroxy-2-(methoxymethyl)-N4-(4-methoxyphenyl)-2,3-dihydrobenzo[f][1,4]oxazepine-4,8(5H)-dicarboxamide | ++ |
| (S)-N8-hydroxy-2-(methoxymethyl)-N4-(4-methoxyphenyl)-2,3-dihydrobenzo[f][1,4]oxazepine-4,8(5H)-dicarboxamide | ++ |
| (R)-N8-hydroxy-N4-(4-methoxyphenyl)-2-phenyl-2,3-dihydrobenzo[f][1,4]oxazepine-4,8(5H)-dicarboxamide | ++ |
| (S)-N8-hydroxy-N4-(4-methoxyphenyl)-2-phenyl-2,3-dihydrobenzo[f][1,4]oxazepine-4,8(5H)-dicarboxamide | +++ |
| N-hydroxy-4-methyl-4,5-dihydro-2H-spiro[benzo[f][1,4]oxazepine-3,1'-cyclopropane]-8-carboxamide | +++ |
| N-hydroxy-4-phenyl-4,5-dihydro-2H-spiro[benzo[f][1,4]oxazepine-3,1'-cyclopropane]-8-carboxamide | ++ |
| N-hydroxy-4-(4-methoxybenzyl)-4,5-dihydro-2H-spiro[benzo[f][1,4]oxazepine-3,1'-cyclopropane]-8-carboxamide | +++ |
| (S)-3-ethyl-N-hydroxy-4-methyl-2,3,4,5-tetrahydrobenzo[f][1,4]oxazepine-8-carboxamide | +++ |
| (S)-3-ethyl-N-hydroxy-4-(4-methoxybenzyl)-2,3,4,5-tetrahydrobenzo[f][1,4]oxazepine-8-carboxamide | +++ |
| (S)-3-ethyl-N-hydroxy-4-phenyl-2,3,4,5-tetrahydrobenzo[f][1,4]oxazepine-8-carboxamide | +++ |
| (S)-3-ethyl-N-hydroxy-4-(o-tolyl)-2,3,4,5-tetrahydrobenzo[f][1,4]oxazepine-8-carboxamide | +++ |
| (S)-N-hydroxy-3-isopropyl-4-(pyridin-3-yl)-2,3,4,5-tetrahydrobenzo[f][1,4]oxazepine-8-carboxamide | +++ |
| (S)-N-hydroxy-3-isopropyl-4-(pyridin-2-yl)-2,3,4,5-tetrahydrobenzo[f][1,4]oxazepine-8-carboxamide | +++ |
| (S)-N-hydroxy-3-isopropyl-4-(pyridin-4-yl)-2,3,4,5-tetrahydrobenzo[f][1,4]oxazepine-8-carboxamide | + |
| (S)-N-hydroxy-3-methyl-4-(o-tolyl)-2,3,4,5-tetrahydrobenzo[f][1,4]oxazepine-8-carboxamide | +++ |
| (S)-N-hydroxy-4-(2-methoxyphenyl)-3-methyl-2,3,4,5-tetrahydrobenzo[f][1,4]oxazepine-8-carboxamide | +++ |
| (S)-N-hydroxy-3-methyl-4-(pyridin-2-yl)-2,3,4,5-tetrahydrobenzo[f][1,4]oxazepine-8-carboxamide | +++ |

TABLE 45-continued

Inhibitory Concentration (IC$_{50}$) Values for Representative Compounds against HDAC6.

| NAME | Activity Range |
|---|---|
| (S)-N-hydroxy-3-methyl-4-(pyrrolidine-1-carbonyl)-2,3,4,5-tetrahydrobenzo[f][1,4]oxazepine-8-carboxamide | +++ |
| (S)-N-hydroxy-3-methyl-4-(morpholine-4-carbonyl)-2,3,4,5-tetrahydrobenzo[f][1,4]oxazepine-8-carboxamide | +++ |
| (S)-N-hydroxy-4-(isoindoline-2-carbonyl)-3-methyl-2,3,4,5-tetrahydrobenzo[f][1,4]oxazepine-8-carboxamide | +++ |
| (S)-N-hydroxy-4-(4-methoxypiperidine-1-carbonyl)-3-methyl-2,3,4,5-tetrahydrobenzo[f][1,4]oxazepine-8-carboxamide | +++ |
| (S)-N-hydroxy-3-methyl-4-(4-methylpiperazine-1-carbonyl)-2,3,4,5-tetrahydrobenzo[f][1,4]oxazepine-8-carboxamide | ++ |
| (3S)-N-hydroxy-3-methyl-4-(2-methylpiperidine-1-carbonyl)-2,3,4,5-tetrahydrobenzo[f][1,4]oxazepine-8-carboxamide | +++ |
| (3S)-N-hydroxy-3-methyl-4-(3-methylmorpholine-4-carbonyl)-2,3,4,5-tetrahydrobenzo[f][1,4]oxazepine-8-carboxamide | +++ |
| (S)-N-hydroxy-3-methyl-4-(oxetan-3-ylmethyl)-2,3,4,5-tetrahydrobenzo[f][1,4]oxazepine-8-carboxamide | +++ |
| (S)-4-(4-fluorophenyl)-N-hydroxy-3-methyl-2,3,4,5-tetrahydrobenzo[f][1,4]oxazepine-8-carboxamide | +++ |
| (S)-4-(3-fluorophenyl)-N-hydroxy-3-methyl-2,3,4,5-tetrahydrobenzo[f][1,4]oxazepine-8-carboxamide | +++ |
| (S)-N-hydroxy-3-methyl-4-(4-(trifluoromethyl)phenyl)-2,3,4,5-tetrahydrobenzo[f][1,4]oxazepine-8-carboxamide | ++ |
| methyl (S)-8-(hydroxycarbamoyl)-3-methyl-2,3-dihydrobenzo[f][1,4]oxazepine-4(5H)-carboxylate | +++ |
| isopropyl (S)-8-(hydroxycarbamoyl)-3-methyl-2,3-dihydrobenzo[f][1,4]oxazepine-4(5H)-carboxylate | +++ |
| (S)-N-hydroxy-3-methyl-4-(methylsulfonyl)-2,3,4,5-tetrahydrobenzo[f][1,4]oxazepine-8-carboxamide | +++ |
| (S)-4-(ethylsulfonyl)-N-hydroxy-3-methyl-2,3,4,5-tetrahydrobenzo[f][1,4]oxazepine-8-carboxamide | +++ |
| (S)-N8-hydroxy-N4,N4,3-trimethyl-2,3-dihydrobenzo[f][1,4]oxazepine-4,8(5H)-dicarboxamide | +++ |
| (S)-N-hydroxy-4-((2-methoxyethyl)sulfonyl)-3-methyl-2,3,4,5-tetrahydrobenzo[f][1,4]oxazepine-8-carboxamide | ++ |
| (S)-N8-hydroxy-N4-(2-methoxyethyl)-3-methyl-2,3-dihydrobenzo[f][1,4]oxazepine-4,8(5H)-dicarboxamide | +++ |
| (S)-N8-hydroxy-3-methyl-N4-phenyl-2,3-dihydrobenzo[f][1,4]oxazepine-4,8(5H)-dicarboxamide | +++ |
| (S)-N-hydroxy-3-methyl-4-(piperidine-1-carbonyl)-2,3,4,5-tetrahydrobenzo[f][1,4]oxazepine-8-carboxamide | +++ |
| (3S)-N8-hydroxy-N4-(2-methoxyethyl)-N4,3-dimethyl-2,3,7,8-tetrahydrobenzo[f][1,4]oxazepine-4,8(5H)-dicarboxamide | +++ |
| (S)-N-hydroxy-3-methyl-4-(pyridin-3-yl)-2,3,4,5-tetrahydrobenzo[f][1,4]oxazepine-8-carboxamide | +++ |
| (S)-N-hydroxy-3-methyl-4-(pyridin-4-yl)-2,3,4,5-tetrahydrobenzo[f][1,4]oxazepine-8-carboxamide | ++ |
| (S)-N-hydroxy-4-(3-methoxypropyl)-3-methyl-2,3,4,5-tetrahydrobenzo[f][1,4]oxazepine-8-carboxamide | ++ |
| (3S)-4-(1-(4-fluorophenyl)ethyl)-N-hydroxy-3-methyl-2,3,4,5-tetrahydrobenzo[f][1,4]oxazepine-8-carboxamide | ++ |
| (S)-N-hydroxy-3-methyl-4-(3-morpholinopropyl)-2,3,4,5-tetrahydrobenzo[f][1,4]oxazepine-8-carboxamide | ++ |
| (3S)-N-hydroxy-3-methyl-4-(2-(tetrahydrofuran-2-yl)ethyl)-2,3,4,5-tetrahydrobenzo[f][1,4]oxazepine-8-carboxamide | +++ |
| (S)-4-ethyl-N-hydroxy-3-methyl-2,3,4,5-tetrahydrobenzo[f][1,4]oxazepine-8-carboxamide | ++ |
| (S)-N-hydroxy-4-isopropyl-3-methyl-2,3,4,5-tetrahydrobenzo[f][1,4]oxazepine-8-carboxamide | + |
| (S)-N-hydroxy-4-isobutyl-3-methyl-2,3,4,5-tetrahydrobenzo[f][1,4]oxazepine-8-carboxamide | +++ |
| (S)-4-(cyclobutylmethyl)-N-hydroxy-3-methyl-2,3,4,5-tetrahydrobenzo[f][1,4]oxazepine-8-carboxamide | +++ |
| (S)-4-(cyclopropylmethyl)-N-hydroxy-3-methyl-2,3,4,5-tetrahydrobenzo[f][1,4]oxazepine-8-carboxamide | +++ |
| (S)-4-(4-fluorobenzyl)-N-hydroxy-3-methyl-2,3,4,5-tetrahydrobenzo[f][1,4]oxazepine-8-carboxamide | +++ |
| (S)-4-(cyclohexylmethyl)-N-hydroxy-3-methyl-2,3,4,5-tetrahydrobenzo[f][1,4]oxazepine-8-carboxamide | +++ |
| (S)-N-hydroxy-3-methyl-4-(2-morpholinoethyl)-2,3,4,5-tetrahydrobenzo[f][1,4]oxazepine-8-carboxamide | ++ |
| (S)-N-hydroxy-4-(2-methoxyethyl)-3-methyl-2,3,4,5-tetrahydrobenzo[f][1,4]oxazepine-8-carboxamide | +++ |
| (S)-4-(cyclopentylmethyl)-N-hydroxy-3-methyl-2,3,4,5-tetrahydrobenzo[f][1,4]oxazepine-8-carboxamide | +++ |

TABLE 45-continued

Inhibitory Concentration (IC$_{50}$) Values for
Representative Compounds against HDAC6.

| NAME | Activity Range |
|---|---|
| (3S)-N-hydroxy-3-methyl-4-((tetrahydrofuran-2-yl)methyl)-2,3,4,5-tetrahydrobenzo[f][1,4]oxazepine-8-carboxamide | +++ |
| (S)-4-cyclopentyl-N-hydroxy-3-methyl-2,3,4,5-tetrahydrobenzo[f][1,4]oxazepine-8-carboxamide | ++ |
| (S)-4-((4-fluorophenyl)sulfonyl)-N-hydroxy-3-methyl-2,3,4,5-tetrahydrobenzo[f][1,4]oxazepine-8-carboxamide | ++ |
| cyclopentyl (S)-8-(hydroxycarbamoyl)-3-methyl-2,3-dihydrobenzo[f][1,4]oxazepine-4(5H)-carboxylate | +++ |
| cyclohexyl (S)-8-(hydroxycarbamoyl)-3-methyl-2,3-dihydrobenzo[f][1,4]oxazepine-4(5H)-carboxylate | +++ |
| (S)-N8-hydroxy-N4,3-dimethyl-N4-phenyl-2,3-dihydrobenzo[f][1,4]oxazepine-4,8(5H)-dicarboxamide | ++ |
| ethyl (S)-8-(hydroxycarbamoyl)-3-methyl-2,3-dihydrobenzo[f][1,4]oxazepine-4(5H)-carboxylate | +++ |
| cyclobutyl (S)-8-(hydroxycarbamoyl)-3-methyl-2,3-dihydrobenzo[f][1,4]oxazepine-4(5H)-carboxylate | +++ |
| tetrahydro-2H-pyran-4-yl (S)-8-(hydroxycarbamoyl)-3-methyl-2,3-dihydrobenzo[f][1,4]oxazepine-4(5H)-carboxylate | +++ |
| 4-fluorophenyl (S)-8-(hydroxycarbamoyl)-3-methyl-2,3-dihydrobenzo[f][1,4]oxazepine-4(5H)-carboxylate | +++ |
| (S)-N-hydroxy-3-methyl-4-(oxetan-3-yl)-2,3,4,5-tetrahydrobenzo[f][1,4]oxazepine-8-carboxamide | + |
| (R)-N-hydroxy-3-(methoxymethyl)-4-methyl-2,3,4,5-tetrahydrobenzo[f][1,4]oxazepine-8-carboxamide | +++ |
| (R)-N-hydroxy-4-(4-methoxybenzyl)-3-(methoxymethyl)-2,3,4,5-tetrahydrobenzo[f][1,4]oxazepine-8-carboxamide | +++ |
| (R)-N-hydroxy-3-(methoxymethyl)-4-phenyl-2,3,4,5-tetrahydrobenzo[f][1,4]oxazepine-8-carboxamide | ++ |
| (R)-N-hydroxy-3-(methoxymethyl)-4-(o-tolyl)-2,3,4,5-tetrahydrobenzo[f][1,4]oxazepine-8-carboxamide | +++ |
| (S)-N-hydroxy-3-(methoxymethyl)-4-methyl-2,3,4,5-tetrahydrobenzo[f][1,4]oxazepine-8-carboxamide | +++ |
| (S)-N-hydroxy-4-(4-methoxybenzyl)-3-(methoxymethyl)-2,3,4,5-tetrahydrobenzo[f][1,4]oxazepine-8-carboxamide | +++ |
| (S)-N-hydroxy-3-(methoxymethyl)-4-phenyl-2,3,4,5-tetrahydrobenzo[f][1,4]oxazepine-8-carboxamide | +++ |
| (S)-N-hydroxy-3-(methoxymethyl)-4-(o-tolyl)-2,3,4,5-tetrahydrobenzo[f][1,4]oxazepine-8-carboxamide | +++ |
| N-hydroxy-4-(pyrrolidine-1-carbonyl)-2,3,4,5-tetrahydrobenzo[f][1,4]oxazepine-8-carboxamide | +++ |
| N-hydroxy-4-(morpholine-4-carbonyl)-2,3,4,5-tetrahydrobenzo[f][1,4]oxazepine-8-carboxamide | ++ |
| N-hydroxy-4-(4-methylpiperazine-1-carbonyl)-2,3,4,5-tetrahydrobenzo[f][1,4]oxazepine-8-carboxamide | + |
| N-hydroxy-4-(4-methoxypiperidine-1-carbonyl)-2,3,4,5-tetrahydrobenzo[f][1,4]oxazepine-8-carboxamide | ++ |
| N-hydroxy-4-(isoindoline-2-carbonyl)-2,3,4,5-tetrahydrobenzo[f][1,4]oxazepine-8-carboxamide | +++ |
| N-hydroxy-4-(2-methylpiperidine-1-carbonyl)-2,3,4,5-tetrahydrobenzo[f][1,4]oxazepine-8-carboxamide | +++ |
| N-hydroxy-4-(3-methylmorpholine-4-carbonyl)-2,3,4,5-tetrahydrobenzo[f][1,4]oxazepine-8-carboxamide | ++ |
| (R)-N-hydroxy-4-(4-methoxybenzyl)-5-methyl-2,3,4,5-tetrahydrobenzo[f][1,4]oxazepine-8-carboxamide | + |
| (S)-N-hydroxy-4-(4-methoxybenzyl)-5-methyl-2,3,4,5-tetrahydrobenzo[f][1,4]oxazepine-8-carboxamide | ++ |
| (S)-N-hydroxy-3-methyl-4-(3-(trifluoromethyl)phenyl)-2,3,4,5-tetrahydrobenzo[f][1,4]oxazepine-8-carboxamide | ++ |
| (S)-N-hydroxy-3-methyl-4-(4-(trifluoromethoxy)phenyl)-2,3,4,5-tetrahydrobenzo[f][1,4]oxazepine-8-carboxamide | ++ |
| (S)-4-(4-chlorophenyl)-N-hydroxy-3-methyl-2,3,4,5-tetrahydrobenzo[f][1,4]oxazepine-8-carboxamide | +++ |
| (S)-4-(2-chlorophenyl)-N-hydroxy-3-methyl-2,3,4,5-tetrahydrobenzo[f][1,4]oxazepine-8-carboxamide | +++ |
| (S)-4-(2-fluorophenyl)-N-hydroxy-3-methyl-2,3,4,5-tetrahydrobenzo[f][1,4]oxazepine-8-carboxamide | +++ |
| (S)-4-(azetidine-1-carbonyl)-N-hydroxy-3-methyl-2,3,4,5-tetrahydrobenzo[f][1,4]oxazepine-8-carboxamide | +++ |
| (S)-N-hydroxy-4-(3-methoxyazetidine-1-carbonyl)-3-methyl-2,3,4,5-tetrahydrobenzo[f][1,4]oxazepine-8-carboxamide | +++ |
| (3S)-N-hydroxy-4-(3-methoxypyrrolidine-1-carbonyl)-3-methyl-2,3,4,5-tetrahydrobenzo[f][1,4]oxazepine-8-carboxamide | +++ |
| (S)-N8-hydroxy-3-methyl-N4-(pyridin-3-yl)-2,3-dihydrobenzo[f][1,4]oxazepine-4,8(5H)-dicarboxamide | +++ |

TABLE 45-continued

Inhibitory Concentration (IC$_{50}$) Values for Representative Compounds against HDAC6.

| NAME | Activity Range |
|---|---|
| (S)-N4-cyclohexyl-N8-hydroxy-3-methyl-2,3-dihydrobenzo[f][1,4]oxazepine-4,8(5H)-dicarboxamide | +++ |
| (S)-N8-hydroxy-3-methyl-N4-(pyridin-2-yl)-2,3-dihydrobenzo[f][1,4]oxazepine-4,8(5H)-dicarboxamide | +++ |
| (S)-N8-hydroxy-3-methyl-N4-(tetrahydro-2H-pyran-4-yl)-2,3-dihydrobenzo[f][1,4]oxazepine-4,8(5H)-dicarboxamide | +++ |
| (S)-N8-hydroxy-N4,3-dimethyl-N4-(tetrahydro-2H-pyran-4-yl)-2,3-dihydrobenzo[f][1,4]oxazepine-4,8(5H)-dicarboxamide | +++ |
| (S)-N8-hydroxy-3-methyl-N4-(pyridin-4-yl)-2,3-dihydrobenzo[f][1,4]oxazepine-4,8(5H)-dicarboxamide | +++ |
| (S)-4-((1R,5R)-8-oxa-3-azabicyclo[3.2.1]octane-3-carbonyl)-N-hydroxy-3-methyl-2,3,4,5-tetrahydrobenzo[f][1,4]oxazepine-8-carboxamide | +++ |
| (S)-4-((1S,5S)-8-oxa-3-azabicyclo[3.2.1]octane-3-carbonyl)-N-hydroxy-3-methyl-2,3,4,5-tetrahydrobenzo[f][1,4]oxazepine-8-carboxamide | +++ |
| (S)-4-(3,4-dihydro-2H-benzo[b][1,4]oxazine-4-carbonyl)-N-hydroxy-3-methyl-2,3,4,5-tetrahydrobenzo[f][1,4]oxazepine-8-carboxamide | +++ |
| N-hydroxy-2-oxo-4-(piperidine-1-carbonyl)-2,3,4,5-tetrahydro-1H-benzo[e][1,4]diazepine-7-carboxamide | ++ |
| (S)-3-benzyl-N-hydroxy-4-(morpholine-4-carbonyl)-2,3,4,5-tetrahydrobenzo[f][1,4]oxazepine-8-carboxamide | +++ |

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:

1. A compound of Formula I:

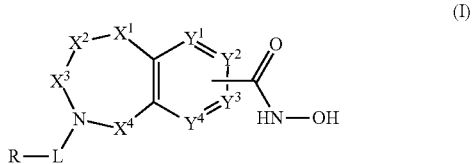

or a pharmaceutically acceptable salt thereof, wherein:
$X^1$ is O;
$X^2$ and $X^4$ are each $CR^1R^2$;
$X^3$ is $CR^1R^2$;
$Y^1$ and $Y^4$ are not bonded to C(O)NHOH and are each $CR^1$;
$Y^2$ and $Y^3$ are each $CR^1$ when not bonded to C(O)NHOH and $Y^2$ and $Y^3$ are C when bonded to —C(O)NHOH;
L is selected from the group consisting of a bond, —(CR$^1$R$^2$)$_n$—, —C(O)O—, —C(O)NR$^3$—, —S(O)$_2$—, —S(O)$_2$NR$^3$—, —S(O)—, and —S(O)NR$^3$—, wherein L is bound to the ring nitrogen through the carbonyl or sulfonyl group;
R is independently selected from the group consisting of —H, —C$_1$-C$_6$ alkyl, —C$_2$-C$_6$ alkenyl, —C$_4$-C$_8$ cycloalkenyl, —C$_2$-C$_6$ alkynyl, —C$_3$-C$_8$ cycloalkyl, —C$_5$-C$_{12}$ spirocycle, heterocyclyl, spiroheterocyclyl, aryl, and heteroaryl containing 1-5 heteroatoms selected from the group consisting of N, S, P, and O, wherein each alkyl, alkenyl, cycloalkenyl, alkynyl, cycloalkyl, spirocycle, heterocyclyl, spiroheterocyclyl, aryl, or heteroaryl is optionally substituted with one or more substituents selected from the group consisting of —OH, halogen, oxo, —NO$_2$, —CN, —R$^1$, —R$^2$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocycle, aryl, and heteroaryl containing 1-5 heteroatoms selected from the group consisting of N, S, P, and O;
each $R^1$ and $R^2$ are independently, and at each occurrence, selected from the group consisting of —H, —R$^3$, —R$^4$, —C$_1$-C$_6$ alkyl, —C$_2$-C$_6$ alkenyl, —C$_4$-C$_8$ cycloalkenyl, —C$_2$-C$_6$ alkynyl, —C$_3$-C$_8$ cycloalkyl, heterocyclyl, aryl, heteroaryl containing 1-5 heteroatoms selected from the group consisting of N, S, P, and O, —OH, halogen, —NO$_2$, —CN, —NHC$_1$-C$_6$ alkyl, —N(C$_1$-C$_6$ alkyl)$_2$, —S(O)$_2$N(C$_1$-C$_6$ alkyl)$_2$, —N(C$_1$-C$_6$ alkyl)S(O)$_2$R$^5$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, and —(CHR$^5$)—NR$^3$R$^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N(R$^3$)$_2$, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocycle, aryl, and heteroaryl containing 1-5 heteroatoms selected from the group consisting of N, S, P, and O;
$R^{1'}$ and $R^{2'}$ are independently, and at each occurrence, selected from the group consisting of —H, —C$_1$-C$_6$ alkyl, —C$_2$-C$_6$ alkenyl, —C$_4$-C$_8$ cycloalkenyl, —C$_2$-C$_6$ alkynyl, —C$_3$-C$_8$ cycloalkyl, heterocyclyl, —OH, halogen, —NO$_2$, —CN, —NHC$_1$-C$_6$ alkyl, —N(C$_1$-C$_6$ alkyl)$_2$, —S(O)$_2$N(C$_1$-C$_6$ alkyl)$_2$, —N(C$_1$-C$_6$ alkyl)S(O)$_2$R$^5$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, and —(CHR$^5$)—NR$^3$R$^4$, wherein each alkyl, alkenyl, cycloalkenyl, alkynyl, cycloalkyl, or heterocyclyl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N (R³)₂, —S(O)₂R⁵, —C(O)R⁵, —CO₂R⁵, —NR³S(O)₂R⁵, —S(O)R⁵, —S(O)NR³R⁴, —NR³S(O)R⁵, heterocycle, aryl, and heteroaryl containing 1-5 heteroatoms selected from the group consisting of N, S, P, and O;

R³ and R⁴ are independently, at each occurrence, selected from the group consisting of —H, —C₁-C₆ alkyl, —C₂-C₆ alkenyl, —C₄-C₈ cycloalkenyl, —C₂-C₆ alkynyl, —C₃-C₈ cycloalkyl, heterocyclyl, aryl, heteroaryl containing 1-5 heteroatoms selected from the group consisting of N, S, P, and O, —S(O)₂N(C₁-C₆ alkyl)₂, —S(O)₂(C₁-C₆ alkyl), —(C₁-C₆ alkyl)S(O)₂R⁵, —C(O)C₁-C₆ alkyl, —CO₂C₁-C₆ alkyl, and —(CHR⁵)—N(C₁-C₆ alkyl)₂, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO₂, oxo, —CN, —R⁵, —O(C₁-C₆ alkyl), —NH(C₁-C₆ alkyl), —N(C₁-C₆ alkyl)₂, —S(O)₂N(C₁-C₆ alkyl)₂, —S(O)₂NH(C₁-C₆ alkyl), —C(O)C₁-C₆ alkyl, —CO₂C₁-C₆ alkyl, —N(C₁-C₆ alkyl)S(O)₂C₁-C₆ alkyl, —S(O)R⁵, —S(O)N(C₁-C₆ alkyl)₂, —N(C₁-C₆ alkyl)S(O)R⁵, heterocycle, aryl, and heteroaryl containing 1-5 heteroatoms selected from the group consisting of N, S, P, and O;

or R³ and R can combine with the nitrogen atom to which they are attached to form a heterocycle, wherein each heterocycle is optionally substituted by —R¹, —R², —R⁴, —OR⁴, or —NR⁴R⁵;

R⁵ is independently, and at each occurrence, selected from the group consisting of —H, —C₁-C₆ alkyl, —C₂-C₆ alkenyl, —C₄-C₈ cycloalkenyl, —C₂-C₆ alkynyl, —C₃-C₈ cycloalkyl, heterocyclyl, aryl, heteroaryl containing 1-5 heteroatoms selected from the group consisting of N, S, P, and O, —OH, halogen, —NO₂, —CN, —NHC₁-C₆ alkyl, —N(C₁-C₆ alkyl)₂, —S(O)₂NH(C₁-C₆ alkyl), —S(O)₂N(C₁-C₆ alkyl)₂, —S(O)₂C₁-C₆ alkyl, —C(O)C₁-C₆ alkyl, —CO₂C₁-C₆ alkyl, —N(C₁-C₆ alkyl)SO₂C₁-C₆ alkyl, —S(O)(C₁-C₆ alkyl), —S(O)N(C₁-C₆ alkyl)₂, —N(C₁-C₆ alkyl)S(O)(C₁-C₆ alkyl), and —(CH₂)ₙN(C₁-C₆ alkyl)₂; and n is independently, and at each occurrence, an integer from 0 to 6.

2. The compound of claim 1, wherein the compound is of the Formula IA:

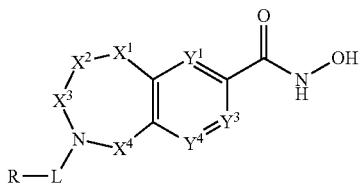

(IA)

or a pharmaceutically acceptable salt thereof.

3. The compound of claim 1, wherein the compound is of the Formula IB

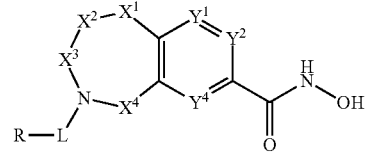

(IB)

or a pharmaceutically acceptable salt thereof.

4. The compound of claim 1 selected from the group consisting of:
4-(benzo[d]oxazol-2-yl)-N-hydroxy-2,3,4,5-tetrahydrobenzo[f][1,4]oxazepine-8-carboxamide;
4-(1-(cyclohexylmethyl)-1H-benzo[d]imidazol-2-yl)-N-hydroxy-2,3,4,5-tetrahydrobenzo[f][1,4]oxazepine-8-carboxamide;
4-(benzo[d]thiazol-2-yl)-N-hydroxy-2,3,4,5-tetrahydrobenzo[f][1,4]oxazepine-8-carboxamide;
4-(cyclohexylmethyl)-N-hydroxy-2,3,4,5-tetrahydrobenzo[f][1,4]oxazepine-8-carboxamide;
N-hydroxy-4-phenyl-2,3,4,5-tetrahydrobenzo[f][1,4]oxazepine-8-carboxamide;
4-(4-cyano-3-(trifluoromethyl)phenyl)-N-hydroxy-2,3,4,5-tetrahydrobenzo[f][1,4]oxazepine-8-carboxamide;
4-(3,4-dichlorophenyl)-N-hydroxy-2,3,4,5-tetrahydrobenzo[f][1,4]oxazepine-8-carboxamide;
N-hydroxy-4-(pyridin-2-yl)-2,3,4,5-tetrahydrobenzo[f][1,4]oxazepine-8-carboxamide;
N-hydroxy-4-(pyridin-3-yl)-2,3,4,5-tetrahydrobenzo[f][1,4]oxazepine-8-carboxamide;
N-hydroxy-4-(pyridin-4-yl)-2,3,4,5-tetrahydrobenzo[f][1,4]oxazepine-8-carboxamide;
N-hydroxy-4-(p-tolyl)-2,3,4,5-tetrahydrobenzo[f][1,4]oxazepine-8-carboxamide;
N-hydroxy-4-(piperidine-1-carbonyl)-2,3,4,5-tetrahydrobenzo[f][1,4]oxazepine-8-carboxamide;
4-methoxyphenyl 8-(hydroxycarbamoyl)-2,3-dihydrobenzo[f][1,4]oxazepine-4(5H)-carboxylate;
cyclohexyl 8-(hydroxycarbamoyl)-2,3-dihydrobenzo[f][1,4]oxazepine-4(5H)-carboxylate;
N-hydroxy-4-(piperidin-1-ylsulfonyl)-2,3,4,5-tetrahydrobenzo[f][1,4]oxazepine-8-carboxamide;
N8-hydroxy-N4-methyl-N4-phenyl-2,3-dihydrobenzo[f][1,4]oxazepine-4,8(5H)-dicarboxamide;
4-cyclohexyl-N-hydroxy-2,3,4,5-tetrahydrobenzo[f][1,4]oxazepine-8-carboxamide;
4-(2-(dimethylamino)ethyl)-N-hydroxy-2,3,4,5-tetrahydrobenzo[f][1,4]oxazepine-8-carboxamide;
N-hydroxy-4-(2-methoxyethyl)-2,3,4,5-tetrahydrobenzo[f][1,4]oxazepine-8-carboxamide;
N-hydroxy-4-(1-((tetrahydro-2H-pyran-4-yl)methyl)-1H-benzo[d]imidazol-2-yl)-2,3,4,5-tetrahydrobenzo[f][1,4]oxazepine-8-carboxamide;
N-hydroxy-2,3,4,5-tetrahydrobenzo[f][1,4]oxazepine-8-carboxamide;
N-hydroxy-4-methyl-2,3,4,5-tetrahydrobenzo[f][1,4]oxazepine-8-carboxamide;
(R)—N-hydroxy-2-methyl-2,3,4,5-tetrahydrobenzo[f][1,4]oxazepine-8-carboxamide;
(R)—N8-hydroxy-N4-(4-methoxyphenyl)-2-methyl-2,3-dihydrobenzo[f][1,4]oxazepine-4,8(5H)-dicarboxamide;
(R)—N-hydroxy-4-((4-methoxyphenyl)sulfonyl)-2-methyl-2,3,4,5-tetrahydrobenzo[f][1,4]oxazepine-8-carboxamide;

(R)—N-hydroxy-4-(4-methoxybenzyl)-2-methyl-2,3,4,5-tetrahydrobenzo[f][1,4]oxazepine-8-carboxamide;
(R)—N-hydroxy-2-methyl-4-phenyl-2,3,4,5-tetrahydrobenzo[f][1,4]oxazepine-8-carboxamide;
(R)—N-hydroxy-2,4-dimethyl-2,3,4,5-tetrahydrobenzo[f][1,4]oxazepine-8-carboxamide;
(S)—N-hydroxy-2-methyl-2,3,4,5-tetrahydrobenzo[f][1,4]oxazepine-8-carboxamide;
(S)—N8-hydroxy-N4-(4-methoxyphenyl)-2-methyl-2,3-dihydrobenzo[f][1,4]oxazepine-4,8(5H)-dicarboxamide;
(S)—N-hydroxy-4-((4-methoxyphenyl)sulfonyl)-2-methyl-2,3,4,5-tetrahydrobenzo[f][1,4]oxazepine-8-carboxamide;
(S)—N-hydroxy-2-methyl-4-phenyl-2,3,4,5-tetrahydrobenzo[f][1,4]oxazepine-8-carboxamide;
(S)—N-hydroxy-2,4-dimethyl-2,3,4,5-tetrahydrobenzo[f][1,4]oxazepine-8-carboxamide;
(S)—N-hydroxy-4-(4-methoxybenzyl)-2-methyl-2,3,4,5-tetrahydrobenzo[f][1,4]oxazepine-8-carboxamide;
N-hydroxy-4-(4-methoxybenzyl)-3,3-dimethyl-2,3,4,5-tetrahydrobenzo[f][1,4]oxazepine-8-carboxamide;
N-hydroxy-3,3-dimethyl-2,3,4,5-tetrahydrobenzo[f][1,4]oxazepine-8-carboxamide;
N-hydroxy-3,3,4-trimethyl-2,3,4,5-tetrahydrobenzo[f][1,4]oxazepine-8-carboxamide;
(R)—N-hydroxy-3-isopropyl-4-(4-methoxybenzyl)-2,3,4,5-tetrahydrobenzo[f][1,4]oxazepine-8-carboxamide;
(R)—N-hydroxy-3-isopropyl-4-phenyl-2,3,4,5-tetrahydrobenzo[f][1,4]oxazepine-8-carboxamide;
(R)—N8-hydroxy-3-isopropyl-N4-(4-methoxyphenyl)-2,3-dihydrobenzo[f][1,4]oxazepine-4,8(5H)-dicarboxamide;
(R)—N-hydroxy-3-isopropyl-2,3,4,5-tetrahydrobenzo[f][1,4]oxazepine-8-carboxamide;
(R)—N-hydroxy-3-isopropyl-4-methyl-2,3,4,5-tetrahydrobenzo[f][1,4]oxazepine-8-carboxamide;
(S)—N-hydroxy-3-isopropyl-4-(4-methoxybenzyl)-2,3,4,5-tetrahydrobenzo[f][1,4]oxazepine-8-carboxamide;
(S)—N-hydroxy-3-isopropyl-4-phenyl-2,3,4,5-tetrahydrobenzo[f][1,4]oxazepine-8-carboxamide;
(S)—N8-hydroxy-3-isopropyl-N4-(4-methoxyphenyl)-2,3-dihydrobenzo[f][1,4]oxazepine-4,8(5H)-dicarboxamide;
(S)—N-hydroxy-3-isopropyl-2,3,4,5-tetrahydrobenzo[f][1,4]oxazepine-8-carboxamide;
(S)—N-hydroxy-3-isopropyl-4-methyl-2,3,4,5-tetrahydrobenzo[f][1,4]oxazepine-8-carboxamide;
(R)—N-hydroxy-3-methyl-2,3,4,5-tetrahydrobenzo[f][1,4]oxazepine-8-carboxamide;
(R)—N-hydroxy-3,4-dimethyl-2,3,4,5-tetrahydrobenzo[f][1,4]oxazepine-8-carboxamide;
(R)—N8-hydroxy-N4-(4-methoxyphenyl)-3-methyl-2,3-dihydrobenzo[f][1,4]oxazepine-4,8(5H)-dicarboxamide;
(R)—N-hydroxy-4-((4-methoxyphenyl)sulfonyl)-3-methyl-2,3,4,5-tetrahydrobenzo[f][1,4]oxazepine-8-carboxamide;
(R)—N-hydroxy-4-(4-methoxybenzyl)-3-methyl-2,3,4,5-tetrahydrobenzo[f][1,4]oxazepine-8-carboxamide;
(R)—N-hydroxy-3-methyl-4-phenyl-2,3,4,5-tetrahydrobenzo[f][1,4]oxazepine-8-carboxamide;
(S)—N8-hydroxy-N4-(4-methoxyphenyl)-3-methyl-2,3-dihydrobenzo[f][1,4]oxazepine-4,8(5H)-dicarboxamide;
(S)—N-hydroxy-4-((4-methoxyphenyl)sulfonyl)-3-methyl-2,3,4,5-tetrahydrobenzo[f][1,4]oxazepine-8-carboxamide;
(S)—N-hydroxy-4-(4-methoxybenzyl)-3-methyl-2,3,4,5-tetrahydrobenzo[f][1,4]oxazepine-8-carboxamide;
(S)—N-hydroxy-3-methyl-4-phenyl-2,3,4,5-tetrahydrobenzo[f][1,4]oxazepine-8-carboxamide;
(S)—N-hydroxy-3-methyl-2,3,4,5-tetrahydrobenzo[f][1,4]oxazepine-8-carboxamide;
(S)—N-hydroxy-3,4-dimethyl-2,3,4,5-tetrahydrobenzo[f][1,4]oxazepine-8-carboxamide;
(R)—N-hydroxy-4-(4-methoxybenzyl)-5-methyl-2,3,4,5-tetrahydrobenzo[f][1,4]oxazepine-7-carboxamide;
(S)—N-hydroxy-4-(4-methoxybenzyl)-5-methyl-2,3,4,5-tetrahydrobenzo[f][1,4]oxazepine-7-carboxamide;
N8-hydroxy-N4-(4-methoxyphenyl)-2,3-dihydrobenzo[f][1,4]oxazepine-4,8(5H)-dicarboxamide;
N7-hydroxy-N4-(4-methoxyphenyl)-2,3-dihydrobenzo[f][1,4]oxazepine-4,7(5H)-dicarboxamide;
N-hydroxy-4-((4-methoxyphenyl)sulfonyl)-2,3,4,5-tetrahydrobenzo[f][1,4]oxazepine-8-carboxamide;
N-hydroxy-4-((4-methoxyphenyl)sulfonyl)-2,3,4,5-tetrahydrobenzo[f][1,4]oxazepine-7-carboxamide;
4-((1H-benzo[d]imidazol-2-yl)methyl)-N-hydroxy-2,3,4,5-tetrahydrobenzo[f][1,4]oxazepine-8-carboxamide;
4-((1H-benzo[d]imidazol-2-yl)methyl)-N-hydroxy-2,3,4,5-tetrahydrobenzo[f][1,4]oxazepine-7-carboxamide;
N-hydroxy-4-((1-(2-methoxyethyl)-1H-benzo[d]imidazol-2-yl)methyl)-2,3,4,5-tetrahydrobenzo[f][1,4]oxazepine-8-carboxamide;
N-hydroxy-4-((1-(2-methoxyethyl)-1H-benzo[d]imidazol-2-yl)methyl)-2,3,4,5-tetrahydrobenzo[f][1,4]oxazepine-7-carboxamide;
N-hydroxy-4-(4-methoxyphenethyl)-2,3,4,5-tetrahydrobenzo[f][1,4]oxazepine-8-carboxamide;
N-hydroxy-4-(4-methoxyphenethyl)-2,3,4,5-tetrahydrobenzo[f][1,4]oxazepine-7-carboxamide;
N-hydroxy-4-(4-methoxybenzyl)-2,3,4,5-tetrahydrobenzo[f][1,4]oxazepine-8-carboxamide;
N-hydroxy-4-(4-methoxybenzyl)-2,3,4,5-tetrahydrobenzo[f][1,4]oxazepine-7-carboxamide;
4-(1H-benzo[d]imidazol-2-yl)-N-hydroxy-2,3,4,5-tetrahydrobenzo[f][1,4]oxazepine-8-carboxamide;
4-(1H-benzo[d]imidazol-2-yl)-N-hydroxy-2,3,4,5-tetrahydrobenzo[f][1,4]oxazepine-7-carboxamide;
N-hydroxy-4-(1-(2-methoxyethyl)-1H-benzo[d]imidazol-2-yl)-2,3,4,5-tetrahydrobenzo[f][1,4]oxazepine-8-carboxamide;
N-hydroxy-4-(1-(2-methoxyethyl)-1H-benzo[d]imidazol-2-yl)-2,3,4,5-tetrahydrobenzo[f][1,4]oxazepine-7-carboxamide;
N-hydroxy-4-((6-methoxypyridin-3-yl)methyl)-2,3,4,5-tetrahydrobenzo[f][1,4]oxazepine-8-carboxamide;
N-hydroxy-4-((6-methoxypyridin-3-yl)methyl)-2,3,4,5-tetrahydrobenzo[f][1,4]oxazepine-7-carboxamide;
N-hydroxy-4-((5-methoxypyridin-2-yl)methyl)-2,3,4,5-tetrahydrobenzo[f][1,4]oxazepine-8-carboxamide;
N-hydroxy-4-((5-methoxypyridin-2-yl)methyl)-2,3,4,5-tetrahydrobenzo[f][1,4]oxazepine-7-carboxamide;
(R)—N8-hydroxy-2-isopropyl-N4-(4-methoxyphenyl)-2,3-dihydrobenzo[f][1,4]oxazepine-4,8(5H)-dicarboxamide;
(R)—N8-hydroxy-2-(methoxymethyl)-N4-(4-methoxyphenyl)-2,3-dihydrobenzo[f][1,4]oxazepine-4,8(5H)-dicarboxamide;

(S)—N8-hydroxy-2-(methoxymethyl)-N4-(4-methoxyphenyl)-2,3-dihydrobenzo[f][1,4]oxazepine-4,8(5H)-dicarboxamide;
(R)—N8-hydroxy-N4-(4-methoxyphenyl)-2-phenyl-2,3-dihydrobenzo[f][1,4]oxazepine-4,8(5H)-dicarboxamide;
(S)—N8-hydroxy-N4-(4-methoxyphenyl)-2-phenyl-2,3-dihydrobenzo[f][1,4]oxazepine-4,8(5H)-dicarboxamide;
(S)-3-ethyl-N-hydroxy-4-methyl-2,3,4,5-tetrahydrobenzo[f][1,4]oxazepine-8-carboxamide;
(S)-3-ethyl-N-hydroxy-4-(4-methoxybenzyl)-2,3,4,5-tetrahydrobenzo[f][1,4]oxazepine-8-carboxamide;
(S)-3-ethyl-N-hydroxy-4-phenyl-2,3,4,5-tetrahydrobenzo[f][1,4]oxazepine-8-carboxamide;
(S)-3-ethyl-N-hydroxy-4-(o-tolyl)-2,3,4,5-tetrahydrobenzo[f][1,4]oxazepine-8-carboxamide;
(S)—N-hydroxy-3-isopropyl-4-(pyridin-3-yl)-2,3,4,5-tetrahydrobenzo[f][1,4]oxazepine-8-carboxamide;
(S)—N-hydroxy-3-isopropyl-4-(pyridin-2-yl)-2,3,4,5-tetrahydrobenzo[f][1,4]oxazepine-8-carboxamide;
(S)—N-hydroxy-3-isopropyl-4-(pyridin-4-yl)-2,3,4,5-tetrahydrobenzo[f][1,4]oxazepine-8-carboxamide;
(S)—N-hydroxy-3-methyl-4-(o-tolyl)-2,3,4,5-tetrahydrobenzo[f][1,4]oxazepine-8-carboxamide;
(S)—N-hydroxy-4-(2-methoxyphenyl)-3-methyl-2,3,4,5-tetrahydrobenzo[f][1,4]oxazepine-8-carboxamide;
(S)—N-hydroxy-3-methyl-4-(pyridin-2-yl)-2,3,4,5-tetrahydrobenzo[f][1,4]oxazepine-8-carboxamide;
(S)—N-hydroxy-3-methyl-4-(pyrrolidine-1-carbonyl)-2,3,4,5-tetrahydrobenzo[f][1,4]oxazepine-8-carboxamide;
(S)—N-hydroxy-3-methyl-4-(morpholine-4-carbonyl)-2,3,4,5-tetrahydrobenzo[f][1,4]oxazepine-8-carboxamide;
(S)—N-hydroxy-4-(isoindoline-2-carbonyl)-3-methyl-2,3,4,5-tetrahydrobenzo[f][1,4]oxazepine-8-carboxamide;
(S)—N-hydroxy-4-(4-methoxypiperidine-1-carbonyl)-3-methyl-2,3,4,5-tetrahydrobenzo[f][1,4]oxazepine-8-carboxamide;
(S)—N-hydroxy-3-methyl-4-(4-methylpiperazine-1-carbonyl)-2,3,4,5-tetrahydrobenzo[f][1,4]oxazepine-8-carboxamide;
(3S)—N-hydroxy-3-methyl-4-(2-methylpiperidine-1-carbonyl)-2,3,4,5-tetrahydrobenzo[f][1,4]oxazepine-8-carboxamide;
(3S)—N-hydroxy-3-methyl-4-(3-methylmorpholine-4-carbonyl)-2,3,4,5-tetrahydrobenzo[f][1,4]oxazepine-8-carboxamide;
(S)—N-hydroxy-3-methyl-4-(oxetan-3-ylmethyl)-2,3,4,5-tetrahydrobenzo[f][1,4]oxazepine-8-carboxamide;
(S)-4-(4-fluorophenyl)-N-hydroxy-3-methyl-2,3,4,5-tetrahydrobenzo[f][1,4]oxazepine-8-carboxamide;
(S)-4-(3-fluorophenyl)-N-hydroxy-3-methyl-2,3,4,5-tetrahydrobenzo[f][1,4]oxazepine-8-carboxamide;
(S)—N-hydroxy-3-methyl-4-(4-(trifluoromethyl)phenyl)-2,3,4,5-tetrahydrobenzo[f][1,4]oxazepine-8-carboxamide;
methyl (S)-8-(hydroxycarbamoyl)-3-methyl-2,3-dihydrobenzo[f][1,4]oxazepine-4(5H)-carboxylate;
isopropyl (S)-8-(hydroxycarbamoyl)-3-methyl-2,3-dihydrobenzo[f][1,4]oxazepine-4(5H)-carboxylate;
(S)—N-hydroxy-3-methyl-4-(methylsulfonyl)-2,3,4,5-tetrahydrobenzo[f][1,4]oxazepine-8-carboxamide;
(S)-4-(ethylsulfonyl)-N-hydroxy-3-methyl-2,3,4,5-tetrahydrobenzo[f][1,4]oxazepine-8-carboxamide;
(S)—N8-hydroxy-N4,N4,3-trimethyl-2,3-dihydrobenzo[f][1,4]oxazepine-4,8(5H)-dicarboxamide;
(S)—N-hydroxy-4-((2-methoxyethyl)sulfonyl)-3-methyl-2,3,4,5-tetrahydrobenzo[f][1,4]oxazepine-8-carboxamide;
(S)—N8-hydroxy-N4-(2-methoxyethyl)-3-methyl-2,3-dihydrobenzo[f][1,4]oxazepine-4,8(5H)-dicarboxamide;
(S)—N8-hydroxy-3-methyl-N4-phenyl-2,3-dihydrobenzo[f][1,4]oxazepine-4,8(5H)-dicarboxamide;
(S)—N-hydroxy-3-methyl-4-(piperidine-1-carbonyl)-2,3,4,5-tetrahydrobenzo[f][1,4]oxazepine-8-carboxamide;
(S)—N8-hydroxy-N4-(2-methoxyethyl)-N4,3-dimethyl-2,3-dihydrobenzo[f][1,4]oxazepine-4,8(5H)-dicarboxamide;
(S)—N-hydroxy-3-methyl-4-(pyridin-3-yl)-2,3,4,5-tetrahydrobenzo[f][1,4]oxazepine-8-carboxamide;
(S)—N-hydroxy-3-methyl-4-(pyridin-4-yl)-2,3,4,5-tetrahydrobenzo[f][1,4]oxazepine-8-carboxamide;
(S)—N-hydroxy-4-(3-methoxypropyl)-3-methyl-2,3,4,5-tetrahydrobenzo[f][1,4]oxazepine-8-carboxamide;
(3S)-4-(1-(4-fluorophenyl)ethyl)-N-hydroxy-3-methyl-2,3,4,5-tetrahydrobenzo[f][1,4]oxazepine-8-carboxamide;
(S)—N-hydroxy-3-methyl-4-(3-morpholinopropyl)-2,3,4,5-tetrahydrobenzo[f][1,4]oxazepine-8-carboxamide;
(3S)—N-hydroxy-3-methyl-4-(2-(tetrahydrofuran-2-yl)ethyl)-2,3,4,5-tetrahydrobenzo[f][1,4]oxazepine-8-carboxamide;
(S)-4-ethyl-N-hydroxy-3-methyl-2,3,4,5-tetrahydrobenzo[f][1,4]oxazepine-8-carboxamide;
(S)—N-hydroxy-4-isopropyl-3-methyl-2,3,4,5-tetrahydrobenzo[f][1,4]oxazepine-8-carboxamide;
(S)—N-hydroxy-4-isobutyl-3-methyl-2,3,4,5-tetrahydrobenzo[f][1,4]oxazepine-8-carboxamide;
(S)-4-(cyclobutylmethyl)-N-hydroxy-3-methyl-2,3,4,5-tetrahydrobenzo[f][1,4]oxazepine-8-carboxamide;
(S)-4-(cyclopropylmethyl)-N-hydroxy-3-methyl-2,3,4,5-tetrahydrobenzo[f][1,4]oxazepine-8-carboxamide;
(S)-4-(4-fluorobenzyl)-N-hydroxy-3-methyl-2,3,4,5-tetrahydrobenzo[f][1,4]oxazepine-8-carboxamide;
(S)-4-(cyclohexylmethyl)-N-hydroxy-3-methyl-2,3,4,5-tetrahydrobenzo[f][1,4]oxazepine-8-carboxamide;
(S)—N-hydroxy-3-methyl-4-(2-morpholinoethyl)-2,3,4,5-tetrahydrobenzo[f][1,4]oxazepine-8-carboxamide;
(S)—N-hydroxy-4-(2-methoxyethyl)-3-methyl-2,3,4,5-tetrahydrobenzo[f][1,4]oxazepine-8-carboxamide;
(S)-4-(cyclopentylmethyl)-N-hydroxy-3-methyl-2,3,4,5-tetrahydrobenzo[f][1,4]oxazepine-8-carboxamide;
(3S)—N-hydroxy-3-methyl-4-((tetrahydrofuran-2-yl)methyl)-2,3,4,5-tetrahydrobenzo[f][1,4]oxazepine-8-carboxamide;
(S)-4-cyclopentyl-N-hydroxy-3-methyl-2,3,4,5-tetrahydrobenzo[f][1,4]oxazepine-8-carboxamide;
(S)-4-((4-fluorophenyl)sulfonyl)-N-hydroxy-3-methyl-2,3,4,5-tetrahydrobenzo[f][1,4]oxazepine-8-carboxamide;
cyclopentyl (S)-8-(hydroxycarbamoyl)-3-methyl-2,3-dihydrobenzo[f][1,4]oxazepine-4(5H)-carboxylate;
cyclohexyl (S)-8-(hydroxycarbamoyl)-3-methyl-2,3-dihydrobenzo[f][1,4]oxazepine-4(5H)-carboxylate;
(S)—N8-hydroxy-N4,3-dimethyl-N4-phenyl-2,3-dihydrobenzo[f][1,4]oxazepine-4,8(5H)-dicarboxamide;
ethyl (S)-8-(hydroxycarbamoyl)-3-methyl-2,3-dihydrobenzo[f][1,4]oxazepine-4(5H)-carboxylate;
cyclobutyl (S)-8-(hydroxycarbamoyl)-3-methyl-2,3-dihydrobenzo[f][1,4]oxazepine-4(5H)-carboxylate;

tetrahydro-2H-pyran-4-yl (S)-8-(hydroxycarbamoyl)-3-methyl-2,3-dihydrobenzo[f][1,4]oxazepine-4(5H)-carboxylate;
4-fluorophenyl (S)-8-(hydroxycarbamoyl)-3-methyl-2,3-dihydrobenzo[f][1,4]oxazepine-4(5H)-carboxylate;
(S)—N-hydroxy-3-methyl-4-(oxetan-3-yl)-2,3,4,5-tetrahydrobenzo[f][1,4]oxazepine-8-carboxamide;
(R)—N-hydroxy-3-(methoxymethyl)-4-methyl-2,3,4,5-tetrahydrobenzo[f][1,4]oxazepine-8-carboxamide;
(R)—N-hydroxy-4-(4-methoxybenzyl)-3-(methoxymethyl)-2,3,4,5-tetrahydrobenzo[f][1,4]oxazepine-8-carboxamide;
(R)—N-hydroxy-3-(methoxymethyl)-4-phenyl-2,3,4,5-tetrahydrobenzo[f][1,4]oxazepine-8-carboxamide;
(R)—N-hydroxy-3-(methoxymethyl)-4-(o-tolyl)-2,3,4,5-tetrahydrobenzo[f][1,4]oxazepine-8-carboxamide;
(S)—N-hydroxy-3-(methoxymethyl)-4-methyl-2,3,4,5-tetrahydrobenzo[f][1,4]oxazepine-8-carboxamide;
(S)—N-hydroxy-4-(4-methoxybenzyl)-3-(methoxymethyl)-2,3,4,5-tetrahydrobenzo[f][1,4]oxazepine-8-carboxamide;
(S)—N-hydroxy-3-(methoxymethyl)-4-phenyl-2,3,4,5-tetrahydrobenzo[f][1,4]oxazepine-8-carboxamide;
(S)—N-hydroxy-3-(methoxymethyl)-4-(o-tolyl)-2,3,4,5-tetrahydrobenzo[f][1,4]oxazepine-8-carboxamid;
N-hydroxy-4-(pyrrolidine-1-carbonyl)-2,3,4,5-tetrahydrobenzo[f][1,4]oxazepine-8-carboxamide;
N-hydroxy-4-(morpholine-4-carbonyl)-2,3,4,5-tetrahydrobenzo[f][1,4]oxazepine-8-carboxamide;
N-hydroxy-4-(4-methylpiperazine-1-carbonyl)-2,3,4,5-tetrahydrobenzo[f][1,4]oxazepine-8-carboxamide;
N-hydroxy-4-(4-methoxypiperidine-1-carbonyl)-2,3,4,5-tetrahydrobenzo[f][1,4]oxazepine-8-carboxamide;
N-hydroxy-4-(isoindoline-2-carbonyl)-2,3,4,5-tetrahydrobenzo[f][1,4]oxazepine-8-carboxamide;
N-hydroxy-4-(2-methylpiperidine-1-carbonyl)-2,3,4,5-tetrahydrobenzo[f][1,4]oxazepine-8-carboxamide;
N-hydroxy-4-(3-methylmorpholine-4-carbonyl)-2,3,4,5-tetrahydrobenzo[f][1,4]oxazepine-8-carboxamide;
(R)—N-hydroxy-4-(4-methoxybenzyl)-5-methyl-2,3,4,5-tetrahydrobenzo[f][1,4]oxazepine-8-carboxamide;
(S)—N-hydroxy-4-(4-methoxybenzyl)-5-methyl-2,3,4,5-tetrahydrobenzo[f][1,4]oxazepine-8-carboxamide;
(S)—N-hydroxy-3-methyl-4-(3-(trifluoromethyl)phenyl)-2,3,4,5-tetrahydrobenzo[f][1,4]oxazepine-8-carboxamide;
(S)—N-hydroxy-3-methyl-4-(4-(trifluoromethoxy)phenyl)-2,3,4,5-tetrahydrobenzo[f][1,4]oxazepine-8-carboxamide;
(S)-4-(4-chlorophenyl)-N-hydroxy-3-methyl-2,3,4,5-tetrahydrobenzo[f][1,4]oxazepine-8-carboxamide;
(S)-4-(2-chlorophenyl)-N-hydroxy-3-methyl-2,3,4,5-tetrahydrobenzo[f][1,4]oxazepine-8-carboxamide;
(S)-4-(2-fluorophenyl)-N-hydroxy-3-methyl-2,3,4,5-tetrahydrobenzo[f][1,4]oxazepine-8-carboxamide;
(S)-4-(azetidine-1-carbonyl)-N-hydroxy-3-methyl-2,3,4,5-tetrahydrobenzo[f][1,4]oxazepine-8-carboxamide;
(S)—N-hydroxy-4-(3-methoxyazetidine-1-carbonyl)-3-methyl-2,3,4,5-tetrahydrobenzo[f][1,4]oxazepine-8-carboxamide;
(3S)—N-hydroxy-4-(3-methoxypyrrolidine-1-carbonyl)-3-methyl-2,3,4,5-tetrahydrobenzo[f][1,4]oxazepine-8-carboxamide;
(S)—N8-hydroxy-3-methyl-N4-(pyridin-3-yl)-2,3-dihydrobenzo[f][1,4]oxazepine-4,8(5H)-dicarboxamide;
(S)—N4-cyclohexyl-N8-hydroxy-3-methyl-2,3-dihydrobenzo[f][1,4]oxazepine-4,8(5H)-dicarboxamide;
(S)—N8-hydroxy-3-methyl-N4-(pyridin-2-yl)-2,3-dihydrobenzo[f][1,4]oxazepine-4,8(5H)-dicarboxamide;
(S)—N8-hydroxy-3-methyl-N4-(tetrahydro-2H-pyran-4-yl)-2,3-dihydrobenzo[f][1,4]oxazepine-4,8(5H)-dicarboxamide;
(S)—N8-hydroxy-N4,3-dimethyl-N4-(tetrahydro-2H-pyran-4-yl)-2,3-dihydrobenzo[f][1,4]oxazepine-4,8(5H)-dicarboxamide;
(S)—N8-hydroxy-3-methyl-N4-(pyridin-4-yl)-2,3-dihydrobenzo[f][1,4]oxazepine-4,8(5H)-dicarboxamide;
(S)-4-((1R,5R)-8-oxa-3-azabicyclo[3.2.1]octane-3-carbonyl)-N-hydroxy-3-methyl-2,3,4,5-tetrahydrobenzo[f][1,4]oxazepine-8-carboxamide;
(S)-4-((1S,5S)-8-oxa-3-azabicyclo[3.2.1]octane-3-carbonyl)-N-hydroxy-3-methyl-2,3,4,5-tetrahydrobenzo[f][1,4]oxazepine-8-carboxamide;
(S)-4-(3,4-dihydro-2H-benzo[b][1,4]oxazine-4-carbonyl)-N-hydroxy-3-methyl-2,3,4,5-tetrahydrobenzo[f][1,4]oxazepine-8-carboxamide; and
(S)-3-benzyl-N-hydroxy-4-(morpholine-4-carbonyl)-2,3,4,5-tetrahydrobenzo[f][1,4]oxazepine-8-carboxamide.

5. The compound of claim 1, selected from the group consisting of:
N8-hydroxy-N4-(tetrahydro-2H-pyran-4-yl)-N4-(3-(trifluoromethyl)phenyl)-2,3-dihydrobenzo[f][1,4]oxazepine-4,8(5H)-dicarboxamide;
(R)—N-hydroxy-4-(morpholine-4-carbonyl)-3-((trifluoromethoxy)methyl)-2,3,4,5-tetrahydrobenzo[f][1,4]oxazepine-8-carboxamide;
(3S)—N-hydroxy-3,5-dimethyl-4-(morpholine-4-carbonyl)-2,3,4,5-tetrahydrobenzo[f][1,4]oxazepine-8-carboxamide; and
(S)-6-fluoro-N-hydroxy-3-methyl-4-(morpholine-4-carbonyl)-2,3,4,5-tetrahydrobenzo[f][1,4]oxazepine-8-carboxamide.

6. A pharmaceutical composition comprising a compound of claim 1 and a pharmaceutically acceptable carrier.

7. The compound of claim 1, wherein the compound is cyclohexyl 8-(hydroxycarbamoyl)-2,3-dihydrobenzo[f][1,4]oxazepine-4(5H)-carboxylate.

8. The compound of claim 1, wherein the compound is 4-(cyclohexylmethyl)-N-hydroxy-2,3,4,5-tetrahydrobenzo[f][1,4]oxazepine-8-carboxamide.

9. The compound of claim 1, wherein the compound is (S)—N-hydroxy-3-methyl-4-((tetrahydrofuran-2-yl)methyl)-2,3,4,5-tetrahydrobenzo[f][1,4]oxazepine-8-carboxamide.

10. A pharmaceutical composition comprising the compound of claim 7, and a pharmaceutically acceptable carrier.

11. A pharmaceutical composition comprising the compound of claim 8, and a pharmaceutically acceptable carrier.

12. A pharmaceutical composition comprising the compound of claim 9, and a pharmaceutically acceptable carrier.

13. The compound of claim 2, wherein the compound is of Formula IA-1a, Formula IA-1b, Formula IA-1c, Formula IA-1d, Formula IA-1e, or Formula IA-1f:

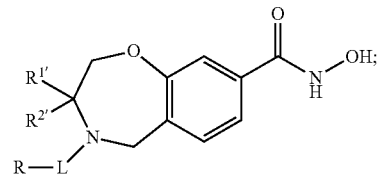

(IA-1a)

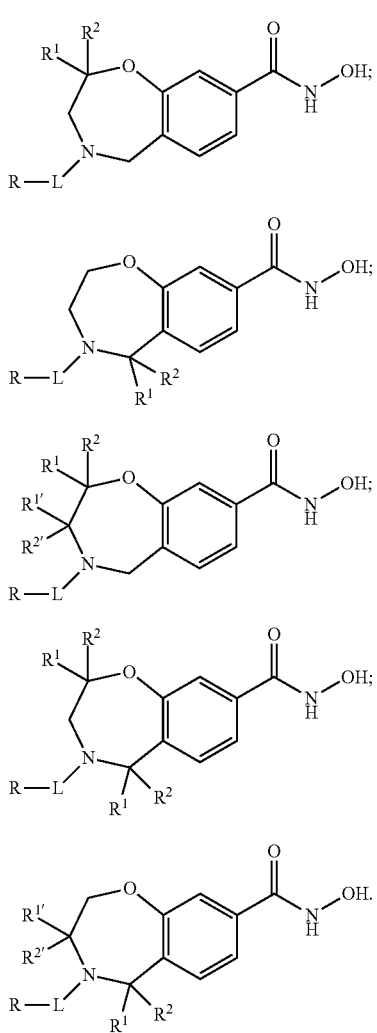

14. The compound of claim 1, wherein at least one of $R^{1'}$ and $R^{2'}$ is —H.

15. The compound of claim 14, wherein one of $R^{1'}$ and $R^{2'}$ is —$C_1$-$C_6$ alkyl, and the other of $R^{1'}$ and $R^{2'}$ is —H.

16. The compound of claim 1, wherein L is —C(O)NR$^3$—.

17. The compound of claim 16, wherein R is an optionally substituted group selected from the group consisting of —$C_1$-$C_6$ alkyl, —$C_3$-$C_8$ cycloalkyl, heterocyclyl, aryl, and heteroaryl.

18. The compound of claim 16, wherein $R^3$ and R combine with the nitrogen atom to which they are attached to form an optionally substituted heterocycle.

19. The compound of claim 18, wherein $R^3$ and R combine with the nitrogen atom to which they are attached to form a heterocycle substituted with —OR$^4$, —NR$^4$R$^5$, or —$C_1$-$C_6$ alkyl.

20. The compound of claim 1, wherein L is a bond.

21. The compound of claim 20, wherein R is an optionally substituted group selected from the group consisting of —$C_1$-$C_6$ alkyl, —$C_3$-$C_8$ cycloalkyl, heterocyclyl, aryl, and heteroaryl.

22. The compound of claim 21, wherein R is —$C_1$-$C_6$ alkyl substituted with an optionally substituted group selected from the group consisting of aryl, heteroaryl, and —$C_3$-$C_8$ cycloalkyl.

23. The compound of claim 1, wherein L is —(CR$^1$R$^2$)$_n$—, —C(O)O—, or —S(O)$_2$—.

24. The compound of claim 23, wherein R is an optionally substituted group selected from the group consisting of —$C_1$-$C_6$ alkyl, —$C_3$-$C_8$ cycloalkyl, heterocyclyl, aryl, and heteroaryl.

25. The compound of claim 15, wherein L is —C(O)NR$^3$—.

26. The compound of claim 25, wherein $R^3$ and R combine with the nitrogen atom to which they are attached to form an optionally substituted heterocycle.

27. The compound of claim 26, wherein $R^3$ and R combine with the nitrogen atom to which they are attached to form a heterocycle substituted with —OR$^4$, —NR$^4$R$^5$, or —$C_1$-$C_6$ alkyl.

28. The compound of claim 27, wherein $R^3$ and R combine with the nitrogen atom to which they are attached to form a piperidinyl ring.

29. The compound of claim 15, wherein L is a bond.

30. The compound of claim 29, wherein R is an optionally substituted group selected from the group consisting of —$C_1$-$C_6$ alkyl, —$C_3$-$C_8$ cycloalkyl, heterocyclyl, aryl, and heteroaryl.

31. The compound of claim 30, wherein R is —$C_1$-$C_6$ alkyl substituted with an optionally substituted group selected from the group consisting of aryl, heteroaryl, and —$C_3$-$C_8$ cycloalkyl.

32. The compound of claim 14, wherein one of $R^1$ and $R^2$ of CR$^1$R$^2$ of $X^4$ is —$C_1$-$C_6$ alkyl or aryl.

33. The compound of claim 32, wherein L is —C(O)NR$^3$—.

34. The compound of claim 33, wherein $R^3$ and R combine with the nitrogen atom to which they are attached to form an optionally substituted heterocycle.

35. The compound of claim 32, wherein L is a bond.

36. The compound of claim 35, wherein R is —$C_1$-$C_6$ alkyl substituted with an optionally substituted group selected from the group consisting of aryl, heteroaryl, and —$C_3$-$C_8$ cycloalkyl.

37. The compound of claim 1, wherein the compound is (S)—N-hydroxy-4-(4-methoxypiperidine-1-carbonyl)-3-methyl-2,3,4,5-tetrahydrobenzo[f][1,4]oxazepine-8-carboxamide.

38. A pharmaceutical composition comprising the compound of claim 37, and a pharmaceutically acceptable carrier.

* * * * *

UNITED STATES PATENT AND TRADEMARK OFFICE
CERTIFICATE OF CORRECTION

PATENT NO.          : 10,214,501 B2
APPLICATION NO.     : 15/013820
DATED               : February 26, 2019
INVENTOR(S)         : Xiaozhang Zheng et al.

Page 1 of 1

It is certified that error appears in the above-identified patent and that said Letters Patent is hereby corrected as shown below:

In the Claims

In Claim 1, Column 274, beginning at Line 43 and ending at Line 44, please delete:
"-$N(C_1-C_6$ alkyl$)S(O)_2C_1-C_6$ alkyl, and –$(CHR^5)$-$NR^3R^4$,"
And insert:
-- -$N(C_1-C_6$ alkyl$)S(O)_2C_1-C_6$ alkyl, and –$(CHR^5)_nNR^3R^4$, --

In Claim 1, Column 274, beginning at Line 62 and ending at Line 63, please delete:
"-$N(C_1-C_6$ alkyl$)S(O)_2C_1-C_6$ alkyl, and –$(CHR^5)$-$NR^3R^4$,"
And insert:
-- -$N(C_1-C_6$ alkyl$)S(O)_2C_1-C_6$ alkyl, and –$(CHR^5)_nNR^3R^4$, --

In Claim 1, Column 275, beginning at Line 15 and ending at Line 16, please delete:
"-$CO_2C_1-C_6$ alkyl, and –$(CHR^5)$-$N(C_1-C_6$ alkyl$)_2$,"
And insert:
-- -$CO_2C_1-C_6$ alkyl, and –$(CHR^5)_nN(C_1-C_6$ alkyl$)_2$, --

In Claim 20, Column 283, Line 59, please delete:
"wherein Lisa bond."
And insert:
-- wherein L is a bond. --

In Claim 35, Column 284, Line 46, please delete:
"wherein Lisa bond."
And insert:
-- wherein L is a bond. --

Signed and Sealed this
Seventh Day of April, 2020

Andrei Iancu
*Director of the United States Patent and Trademark Office*